(12) United States Patent
Mueller et al.

(10) Patent No.: US 11,737,463 B2
(45) Date of Patent: *Aug. 29, 2023

(54) PYRIDINE AND PYRAZINE COMPOUNDS

(71) Applicant: BASF SE, Ludwigshafen am Rhein (DE)

(72) Inventors: Bernd Mueller, Ludwigshafen (DE); Ana Escribano Cuesta, Ludwigshafen (DE); Michael Seet, Ludwigshafen (DE); Antje Wolf, Ludwigshafen (DE); Nadine Riediger, Limburgerhof (DE); Marcus Fehr, Limburgerhof (DE); Erica Cambeis, Ludwigshafen (DE); Jan Klaas Lohmann, Ludwigshafen (DE); Thomas Grote, Ludwigshafen (DE); Wassilios Grammenos, Ludwigshafen (DE); Christian Harald Winter, Ludwigshafen (DE); Violeta Terteryan-Seiser, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 623 days.

This patent is subject to a terminal disclaimer.

(21) Appl. No.: 16/616,888

(22) PCT Filed: May 23, 2018

(86) PCT No.: PCT/EP2018/063453
§ 371 (c)(1),
(2) Date: Nov. 25, 2019

(87) PCT Pub. No.: WO2018/219725
PCT Pub. Date: Dec. 6, 2018

(65) Prior Publication Data
US 2021/0145002 A1    May 20, 2021

(30) Foreign Application Priority Data
May 30, 2017  (EP) .................................... 17173487

(51) Int. Cl.
| C07D 401/12 | (2006.01) |
| A01N 43/653 | (2006.01) |
| A01C 1/06 | (2006.01) |
| A01N 43/40 | (2006.01) |
| A01N 43/56 | (2006.01) |
| A01N 43/60 | (2006.01) |
| C07D 213/65 | (2006.01) |
| C07D 241/18 | (2006.01) |
| C07D 401/14 | (2006.01) |
| C07D 403/12 | (2006.01) |
| C07D 405/12 | (2006.01) |
| C07D 405/14 | (2006.01) |

(52) U.S. Cl.
CPC .............. *A01N 43/653* (2013.01); *A01C 1/06* (2013.01); *A01N 43/40* (2013.01); *A01N 43/56* (2013.01); *A01N 43/60* (2013.01); *C07D 213/65* (2013.01); *C07D 241/18* (2013.01); *C07D 401/12* (2013.01); *C07D 401/14* (2013.01); *C07D 403/12* (2013.01); *C07D 405/12* (2013.01); *C07D 405/14* (2013.01)

(58) Field of Classification Search
CPC ................ C07D 401/12; C07D 241/18; C07D 213/643; A61K 31/497; A61K 31/4965; A61K 31/444; A61K 31/44
USPC .......................... 544/405, 408; 546/300, 261; 514/255.05, 252.1, 335, 351
See application file for complete search history.

(56) References Cited

U.S. PATENT DOCUMENTS

| 4,870,075 A | 9/1989 | Clough et al. |
| 5,939,359 A | 8/1999 | Engel et al. |
| 7,695,728 B2 | 4/2010 | Rheinheimer et al. |
| 10,696,634 B2 * | 6/2020 | Grammenos ........ C07D 213/65 |
| 2003/0004164 A1 | 1/2003 | Bebbington et al. |
| 2004/0157893 A1 | 8/2004 | Bebbington et al. |
| 2010/0093738 A1 | 4/2010 | Muller et al. |

(Continued)

FOREIGN PATENT DOCUMENTS

| CN | 87105790 A | 3/1988 |
| CN | 1159188 A | 9/1997 |

(Continued)

OTHER PUBLICATIONS

Wolff et al., "Burger's Medicinal Chemistry and Drug Discovery," 5th Ed. Part 1, pp. 975-977 (1995). (Year: 1995).*

(Continued)

*Primary Examiner* — Jeffrey H Murray
(74) *Attorney, Agent, or Firm* — Marshall, Gerstein & Borun LLP

(57) ABSTRACT

The present invention relates to compounds of formula I

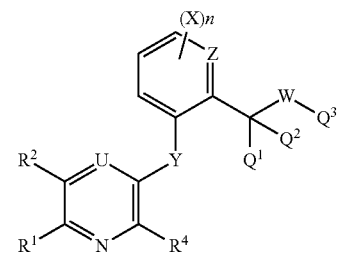

wherein the variables are defined as given in the description and claims. The invention further relates to uses and composition for compounds of formula I.

6 Claims, No Drawings

(56) References Cited

U.S. PATENT DOCUMENTS

2013/0023502 A1 1/2013 Dahmann et al.
2015/0094205 A1 4/2015 Minn et al.

FOREIGN PATENT DOCUMENTS

| EP | 1548007 A1 | | 6/2005 | |
|----|---|---|---|---|
| EP | 2522658 A1 | | 11/2012 | |
| JP | 2010-202530 A | | 9/2010 | |
| JP | 2014-166991 | * | 9/2014 | ........... C07D 215/18 |
| JP | 2014-166991 A | | 9/2014 | |
| KR | 20030061463 A | | 7/2003 | |
| WO | WO-2006/000358 A1 | | 1/2006 | |
| WO | WO-2007/117381 A2 | | 10/2007 | |
| WO | WO-2008/040820 A2 | | 4/2008 | |
| WO | WO-2012/037782 A1 | | 3/2012 | |
| WO | WO-2017/060148 A1 | | 4/2017 | |

OTHER PUBLICATIONS

Banker, et al., (1996), Modern Pharmaceuticals, p. 596. (Year: 1996).*
Betson et al., Three groups good, four groups bad? Atropisomerism in orthoSubstituted diaryl ethers, Angew. Chem. Int. Ed. Engl., 45(35):5803-7 (2006).
European Search Report for EP Application No. 17173487.4, dated Aug. 3, 2017, 3 pages.
Gray et al., Phencyclidine-like effects of tetrahydroisoquinolines and related compounds, J. Med. Chem., 32(6):1242-8 (1989).
International Application No. PCT/EP2018/063453, International Search Report and Written Opinion, dated Jul. 12, 2018.
Kitabatake et al., Facile synthesis and in vitro properties of 1-alkyl- and 1-alkyl-N-propargyl-1,2,3,4-tetrahydroisoquinoline derivatives on PC12 cells, Eur. J. Med. Chem., 44(10):4034-43 (2009).
Taygerly et al., Discovery of INT131: a selective PPAR-gamma modulator that enhances insulin sensitivity, Bioorg. Med. Chem., 21(4):979-92 (2013).

* cited by examiner

PYRIDINE AND PYRAZINE COMPOUNDS

CROSS-REFERENCE TO RELATED APPLICATIONS

This application is a National Stage application of International Application No. PCT/EP2018/063453 filed May 23, 2018. This application also claims priority under 35 U.S.C. § 119 to European Patent Application No. 17173487.4, filed May 30, 2017.

The present invention relates to pyridine and pyrazine compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive pyridine compounds of formula I having favorable fungicidal activity against phytopathogenic fungi.

Accordingly, the present invention relates to the compounds of formula I compounds of the formula I

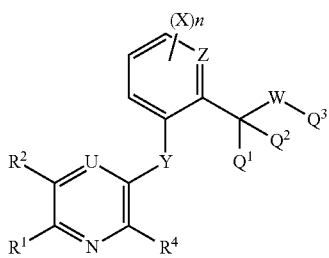

I wherein $R^1$ is in each case independently selected from halogen, OH, $NO_2$, SH, $NH(C_1\text{-}C_4\text{-alkyl})$, $N(C_1\text{-}C_4\text{-alkyl})_2$, $NH(C_2\text{-}C_4\text{-alkenyl})$, $N(C_2\text{-}C_4\text{-alkenyl})_2$, $NH(C_2\text{-}C_4\text{-alkynyl})$, $N(C_2\text{-}C_4\text{-alkynyl})_2$, $NH(C_3\text{-}C_6\text{-cycloalkyl})$, $N(C_3\text{-}C_6\text{-cycloalkyl})_2$, $N(C_1\text{-}C_4\text{-alkyl})(C_2\text{-}C_4\text{-alkenyl})$, $N(C_1\text{-}C_4\text{-alkyl})(C_2\text{-}C_4\text{-alkynyl})$, $N(C_1\text{-}C_4\text{-alkyl})(C_3\text{-}C_6\text{-cycloalkyl})$, $N(C_2\text{-}C_4\text{-alkenyl})(C_2\text{-}C_4\text{-alkynyl})$, $N(C_2\text{-}C_4\text{-alkenyl})(C_3\text{-}C_6\text{-cycloalkyl})$, $N(C_2\text{-}C_4\text{-alkynyl})(C_3\text{-}C_6\text{-cycloalkyl})$, $NH(C(=O)C_1\text{-}C_4\text{-alkyl})$, $N(C(=O)C_1\text{-}C_4\text{-alkyl})$, $NH\text{-}SO_2\text{-}R^x$, $S(O)_m\text{-}C_1\text{-}C_6\text{-alkyl}$, $S(O)_m\text{-aryl}$, $C_1\text{-}C_6\text{-cycloalkylthio}$, $S(O)_m\text{-}C_2\text{-}C_6\text{-alkenyl}$, $S(O)_m\text{-}C_2\text{-}C_6\text{-alkynyl}$, $CH(=O)$, $C(=O)C_1\text{-}C_6\text{-alkyl}$, $C(=O)C_2\text{-}C_6\text{-alkenyl}$, $C(=O)C_2\text{-}C_6\text{-alkynyl}$, $C(=O)C_3\text{-}C_6\text{-cycloalkyl}$, $C(=O)NH(C_1\text{-}C_6\text{-alkyl})$, $C(=O)N(C_1\text{-}C_6\text{-alkyl})_2$, $C(=O)N(C_2\text{-}C_6\text{-alkenyl})_2$, $C(=O)N(C_2\text{-}C_6\text{-alkynyl})_2$, $C(=O)N(C_3\text{-}C_7\text{-cycloalkyl})_2$, $CH(=S)$, $C(=S)C_1\text{-}C_6\text{-alkyl}$, $C(=S)C_2\text{-}C_6\text{-alkenyl}$, $C(=S)C_2\text{-}C_6\text{-alkynyl}$, $C(=S)C_3\text{-}C_6\text{-cycloalkyl}$, $C(=S)O(C_2\text{-}C_6\text{-alkenyl})$, $C(=S)O(C_2\text{-}C_6\text{-alkynyl})$, $C(=S)O(C_3\text{-}C_7\text{-cycloalkyl})$, $C(=S)NH(C_1\text{-}C_6\text{-alkyl})$, $C(=S)NH(C_2\text{-}C_6\text{-alkenyl})$, $C(=S)NH(C_2\text{-}C_6\text{-alkynyl})$, $C(=S)NH(C_3\text{-}C_7\text{-cycloalkyl})$, $C(=S)N(C_1\text{-}C_6\text{-alkyl})_2$, $C(=S)N(C_2\text{-}C_6\text{-alkenyl})_2$, $C(=S)N(C_2\text{-}C_6\text{-alkynyl})_2$, $C(=S)N(C_3\text{-}C_7\text{-cycloalkyl})$, $C_1\text{-}C_6\text{-alkyl}$, $C_1\text{-}C_6\text{-halogenalkyl}$, $C_2\text{-}C_6\text{-alkenyl}$, $C_2\text{-}C_6\text{-alkynyl}$, $OR^Y$, $C_3\text{-}C_6\text{-cycloalkyl}$, five- or six-membered heteroaryl and aryl; wherein the heteroaryl contains one, two or three heteroatoms selected from N, O and S; wherein $R^x$ is $C_1\text{-}C_4\text{-alkyl}$, $C_1\text{-}C_4\text{-halogenalkyl}$, unsubstituted aryl or aryl that is substituted by 1, 2, 3, 4 or 5 substituents $R^{x1}$ independently selected from $C_1\text{-}C_4\text{-alkyl}$, halogen, OH, CN, $C_1\text{-}C_4\text{-halogenalkyl}$, $C_1\text{-}C_4\text{-alkoxy}$ and $C_1\text{-}C_4\text{-halogenalkoxy}$;

$R^Y$ is $C_1\text{-}C_6\text{-alkyl}$, $C_1\text{-}C_6\text{-halogenalkyl}$, $C_2\text{-}C_6\text{-alkenyl}$, $C_2\text{-}C_6\text{-halogenalkenyl}$, $C_2\text{-}C_6\text{-alkynyl}$, $C_2\text{-}C_6\text{-halogenalkynyl}$, $C_3\text{-}C_6\text{-cycloalkyl}$, $C_3\text{-}C_6\text{-halogencycloalkyl}$, phenyl and phenyl-$C_1\text{-}C_6\text{-alkyl}$; wherein the phenyl groups are unsubstituted or carry one, two, three, four or five substituents selected from the group consisting of CN, halogen, OH, $C_1\text{-}C_4\text{-alkyl}$, $C_1\text{-}C_4\text{-halogenalkyl}$, $C_1\text{-}C_4\text{-alkoxy}$ and $C_1\text{-}C_4\text{-halogenalkoxy}$;

wherein the acyclic moieties of $R^1$ are unsubstituted or substituted by groups Ra which independently of one another are selected from:

$R^{1a}$ halogen, OH, CN, $C_1\text{-}C_6\text{-alkoxy}$, $C_3\text{-}C_6\text{-cycloalkyl}$, $C_3\text{-}C_6\text{-halogencycloalkyl}$, $C_1\text{-}C_4\text{-halogenalkoxy}$, $C_1\text{-}C_6\text{-alkylthio}$ and phenoxy, wherein the phenyl group is unsubstituted or substituted by substituents $R^{11a}$ selected from the group consisting of halogen, OH, $C_1\text{-}C_4\text{-alkyl}$, $C_1\text{-}C_4\text{-halogenalkyl}$, $C_1\text{-}C_4\text{-alkoxy}$ and $C_1\text{-}C_4\text{-halogenalkoxy}$;

wherein the carbocyclic, heteroaryl and aryl moieties of $R^1$ are unsubstituted or substituted by groups $R^{1b}$ which independently of one another are selected from:

$R^{1b}$ halogen, OH, CN, $C_1\text{-}C_4\text{-alkyl}$, $C_1\text{-}C_4\text{-alkoxy}$, $C_1\text{-}C_4\text{-halogenalkyl}$, $C_3\text{-}C_6\text{-cycloalkyl}$, $C_3\text{-}C_6\text{-halogencycloalkyl}$, $C_1\text{-}C_4\text{-halogenalkoxy}$ and $C_1\text{-}C_6\text{-alkylthio}$;

and wherein m is 0, 1 and 2;

$R^2$ is in each case independently selected from halogen, OH, $NO_2$, SH, $NH_2$, $NH(C_1\text{-}C_4\text{-alkyl})$, $N(C_1\text{-}C_4\text{-alkyl})_2$, $NH(C_2\text{-}C_4\text{-alkenyl})$, $N(C_2\text{-}C_4\text{-alkenyl})_2$, $NH(C_2\text{-}C_4\text{-alkynyl})$, $N(C_2\text{-}C_4\text{-alkynyl})_2$, $NH(C_3\text{-}C_6\text{-cycloalkyl})$, $N(C_3\text{-}C_6\text{-cycloalkyl})_2$, $N(C_1\text{-}C_4\text{-alkyl})(C_2\text{-}C_4\text{-alkenyl})$, $N(C_1\text{-}C_4\text{-alkyl})(C_2\text{-}C_4\text{-alkynyl})$, $N(C_1\text{-}C_4\text{-alkyl})(C_3\text{-}C_6\text{-cycloalkyl})$, $N(C_2\text{-}C_4\text{-alkenyl})(C_2\text{-}C_4\text{-alkynyl})$, $N(C_2\text{-}C_4\text{-alkenyl})(C_3\text{-}C_6\text{-cycloalkyl})$, $N(C_2\text{-}C_4\text{-alkynyl})(C_3\text{-}C_6\text{-cycloalkyl})$, $NH(C(=O)C_1\text{-}C_4\text{-alkyl})$, $N(C(=O)C_1\text{-}C_4\text{-alkyl})$, $NH\text{-}SO_2\text{-}R^x$, $S(O)_m\text{-}C_1\text{-}C_6\text{-alkyl}$, $S(O)_m\text{-aryl}$, $C_1\text{-}C_6\text{-cycloalkylthio}$, $S(O)_m\text{-}C_2\text{-}C_6\text{-alkenyl}$, $S(O)_m\text{-}C_2\text{-}C_6\text{-alkynyl}$, $CH(=O)$, $C(=O)C_1\text{-}C_6\text{-alkyl}$, $C(=O)C_2\text{-}C_6\text{-alkenyl}$, $C(=O)C_2\text{-}C_6\text{-alkynyl}$, $C(=O)C_3\text{-}C_6\text{-cycloalkyl}$, $C(=O)NH(C_1\text{-}C_6\text{-alkyl})$, $C(=O)N(C_1\text{-}C_6\text{-alkyl})_2$, $C(=O)N(C_2\text{-}C_6\text{-alkenyl})$, $C(=O)N(C_2\text{-}C_6\text{-alkynyl})$, $C(=O)N(C_3\text{-}C_7\text{-cycloalkyl})$, $CH(=S)$, $C(=S)C_1\text{-}C_6\text{-alkyl}$, $C(=S)C_2\text{-}C_6\text{-alkenyl}$, $C(=S)C_2\text{-}C_6\text{-alkynyl}$, $C(=S)C_3\text{-}C_6\text{-cycloalkyl}$, $C(=S)O(C_2\text{-}C_6\text{-alkenyl})$, $C(=S)O(C_2\text{-}C_6\text{-alkynyl})$, $C(=S)O(C_3\text{-}C_7\text{-cycloalkyl})$, $C(=S)NH(C_1\text{-}C_6\text{-alkyl})$, $C(=S)NH(C_2\text{-}C_6\text{-alkenyl})$, $C(=S)NH(C_2\text{-}C_6\text{-alkynyl})$, $C(=S)NH(C_3\text{-}C_7\text{-cycloalkyl})$, $C(=S)N(C_1\text{-}C_6\text{-alkyl})_2$, $C(=S)N(C_2\text{-}C_6\text{-alkenyl})$, $C(=S)N(C_2\text{-}C_6\text{-alkynyl})$, $C(=S)N(C_3\text{-}C_7\text{-cycloalkyl})$, $C_1\text{-}C_6\text{-alkyl}$, $C_1\text{-}C_6\text{-halogenalkyl}$, $C_2\text{-}C_6\text{-alkenyl}$, $C_2\text{-}C_6\text{-alkynyl}$, $OR^Y$, $C_3\text{-}C_6\text{-cycloalkyl}$, five- or six-membered heteroaryl and aryl; wherein the heteroaryl contains one, two or three heteroatoms selected from N, O and S; wherein $R^x$ is defined as above;

$R^Y$ is defined as above;

wherein the acyclic moieties of $R^2$ are unsubstituted or substituted by groups $R^{2a}$ which independently of one another are selected from:

$R^{2a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or substituted by substituents $R^{21a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the carbocyclic, heteroaryl and aryl moieties of $R^2$ are unsubstituted or substituted by groups $R^{2b}$ which independently of one another are selected from:

$R^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio; and U is N or $CR^3$;

$R^3$ is selected from H, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; wherein $R^x$ is defined as above;

and wherein the aliphatic moieties of $R^3$ are unsubstituted or substituted with identical or different groups $R^{3a}$ which independently of one another are selected from:

$R^{3a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenoxy group is unsubstituted or carries 1, 2, 3, 4 or 5 substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from:

$R^{3b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$R^4$ is selected from H, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; wherein $R^x$ is defined as above;

and wherein the aliphatic moieties of $R^4$ are unsubstituted or substituted with identical or different groups $R^{4a}$ which independently of one another are selected from:

$R^{4a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenoxy group is unsubstituted or carries 1, 2, 3, 4 or 5 substituents $R^{41a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

and wherein the cycloalkyl, heteroaryl and aryl moieties of $R^4$ are unsubstituted or substituted with 1, 2, 3, 4, 5 or up to the maximum number of identical or different groups $R^4$ which independently of one another are selected from:

$R^{4b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

Y is O or $S(O)_m$, wherein m is defined as above;

Z is N or $CR^5$;

$R^5$ is independently selected from H, halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl), $NH$—$SO_2$—$R^x$, $CH(=O)$, $C(=O)C_1$-$C_6$-alkyl, $C(=O)NH(C_1$-$C_6$-alkyl), $CR'=NOR''$, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, $S(O)_m$—$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein R' and R'' are independently unsubstituted or substituted by R''' which is independently selected from halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl; wherein m and $R^x$ is as defined above;

and wherein the aliphatic moieties of $R^5$ are not further substituted or carry 1, 2, 3 or up to the maximum possible number of identical or different groups $R^{5a}$ which independently of one another are selected from:

$R^{5a}$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl, phenyl and phenoxy group is unsubstituted or unsubstituted or substituted with $R^{51a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the alicyclic, phenyl, heterocyclic and heteroaryl moieties of $R^5$ are unsubstituted or substituted with identical or different groups $R^{5b}$ which independently of one another are selected from:

$R^{5b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;

X is independently selected from halogen, OH, CN, $NO_2$, SH, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl), $NH$—$SO_2$—$R^x$, $CH(=O)$, $C(=O)C_1$-$C_6$-alkyl, $C(=O)NH(C_1$-$C_6$-alkyl), $CR'=NOR''$, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, $S(O)m$-$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; wherein m, R', R'' and $R^x$ is as defined above;

and wherein the aliphatic moieties of X are not further substituted or carry 1, 2, 3 or up to the maximum possible number of identical or different groups $X^a$ which independently of one another are selected from:

$X^a$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl, phenyl and phenoxy group is unsubstituted or unsubstituted or substituted with $X^{1a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the alicyclic, phenyl, heterocyclic and heteroaryl moieties of X are unsubstituted or substituted with identical or different groups $X^b$ which independently of one another are selected from:

$X^b$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;

n is 0, 1, or 2;

$Q^1$ is selected from CN, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, three-, four-, five- or six-membered saturated or partially unsaturated heterocycle, five- or six-membered heteroaryl and aryl; wherein the heterocycle and heteroaryl contains one, two or three heteroatoms selected from N, O and S;

wherein the aliphatic moieties of $Q^1$ are unsubstituted or substituted with identical or different groups $Q^{1a}$ which independently of one another are selected from:

$Q^{1a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $Q^{1a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heterocyclic, heteroaryl and aryl moieties of $Q^1$ are unsubstituted or substituted with 1, 2, 3, 4, 5 or up to the maximum number of identical or different groups $Q^{1b}$ which independently of one another are selected from:

$Q^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$Q^2$ is selected from H, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, three-, four-, five- or six-membered saturated or partially unsaturated heterocycle, five- or six-membered heteroaryl and aryl; wherein the heterocycle and heteroaryl contains one, two or three heteroatoms selected from N, O and S;

wherein the aliphatic moieties of $Q^2$ are unsubstituted or substituted with identical or different groups $Q^{2a}$ which independently of one another are selected from:

$Q^{2a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or substituted with 1, 2, 3, 4 or 5 substituents $Q^{12}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heterocyclic, heteroaryl and aryl moieties of $Q^2$ are unsubstituted or substituted with 1, 2, 3, 4, 5 or up to the maximum number of identical or different groups $Q^{2b}$ which independently of one another are selected from: $Q^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$Q^1$ and $Q^2$ together with the carbon atom to which they are bound form a three- to seven-membered saturated or partially unsaturated carbo-, or heterocycle wherein the ring may further contain 1, 2, 3 or 4 heteroatoms selected from N—$R^N$, O and S, wherein $R^N$ is selected from H, $C_1$-$C_4$-alkyl and $SO_2R^Q$; wherein $R^Q$ is selected from $C_1$-$C_4$-alkyl, $C_1$-$C_4$-halogenalkyl, unsubstituted aryl or heteroaryl that is substituted by 1, 2, 3, 4 or 5 substituents $R^{Q1}$ independently selected from $C_1$-$C_4$-alkyl;

and wherein S may be in the form of its oxide SO or $SO_2$; and wherein in each case one or two $CH_2$ groups of the carbo- or heterocycle may be replaced by a group independently selected from C(=O) and C(=S);

and wherein the ring is unsubstituted or substituted with 1, 2, 3, 4, 5 or up to the maximum number of identical or different groups $R^{QR}$ which independently of one another are selected from:

$Q^R$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

W is O, $S(O)_m$ or $NQ^4$ m is defined as above;

$Q^3$ is selected from substituted $C_1$-$C_{15}$-alkyl, $C_1$-$C_{15}$-halogenalkyl, $C_2$-$C_{15}$-alkenyl, $C_2$-$C_{15}$-halogenalkenyl, $C_2$-$C_{15}$-alkynyl, $C_3$-$C_7$-cycloalkyl, $S(O)_m$—$C_1$-$C_{15}$-alkyl, $S(O)_m$—$C_1$-$C_{15}$-alkoxy, $S(O)_m$-aryl, $S(O)_m$—$C_2$-$C_{15}$-alkenyl, $S(O)_m$—$C_2$-$C_{15}$-alkynyl, C(=O)$C_1$-$C_{15}$-alkyl, C(=O)$C_1$-$C_{15}$-halogenalkyl, C(=O)$C_2$-$C_{15}$-alkenyl, C(=O)$C_2$-$C_{15}$-alkynyl, C(=O)$C_3$-$C_7$-cycloalkyl, C(=O)aryl, C(=O)NH($C_1$-$C_{15}$-alkyl), C(=O)N($C_1$-$C_{15}$-alkyl)$_2$, C(=O)NH($C_2$-$C_{15}$-alkenyl), C(=O)N($C_2$-$C_{15}$-alkenyl), C(=O)NH($C_2$-$C_{15}$-alkynyl), C(=O)N($C_2$-$C_{15}$-alkynyl), C(=O)NH($C_3$-$C_7$-cycloalkyl), C(=O)N($C_3$-$C_7$-cycloalkyl), C(=S)$C_1$-$C_{15}$-alkyl, C(=S)$C_2$-$C_{15}$-alkenyl, C(=S)$C_2$-$C_{15}$-alkynyl, C(=S)$C_3$-$C_6$-cycloalkyl, C(=S)aryl, C(=S)O($C_1$-$C_{15}$-alkyl), C(=S)O($C_2$-$C_{15}$-alkenyl), C(=S)O($C_2$-$C_{15}$-alkynyl), C(=S)O($C_3$-$C_7$-cycloalkyl), C(=S)NH($C_1$-$C_{15}$-alkyl), C(=S)NH($C_2$-$C_{15}$-alkenyl), C(=S)NH($C_2$-$C_{15}$-alkynyl), C(=S)NH($C_3$-$C_7$-cycloalkyl), C(=S)N($C_1$-$C_{15}$-alkyl)$_2$, C(=S)N($C_2$-$C_{15}$-alkenyl), C(=S)N($C_2$-$C_{15}$-alkynyl), C(=S)N($C_3$-$C_7$-cycloalkyl)$_2$, $C_3$-$C_6$-cycloalkyl, three-, four-, five- or six-membered saturated or partially unsaturated heterocycle, five- or six-membered heteroaryl, and aryl; wherein the heterocycle and heteroaryl contains one, two or three heteroatoms selected from N, O and S; wherein in each case one or two $CH_2$ groups of the carbocycle and heterocycle may be replaced by a group independently selected from C(=O) and C(=S)

wherein the aliphatic moieties of $Q^3$ except for substituted $C_1$-$C_{15}$-alkyl moieties are unsubstituted or substituted with identical or different groups $Q^{3a}$ which independently of one another are selected from:

$Q^{3a}$ halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-halogenalkylthio, S(O)m-$C_1$-$C_6$-alkyl, $S(O)_m$—$C_1$-$C_6$-halogenalkyl, $S(O)_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", $C_1$-$C_6$-alkoxy $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy and heteryloxy; wherein in each case one or two $CH_2$ groups of the carbocycle and heterocycle may be replaced by a group independently selected from C(=O) and C(=S); wherein the heterocycle or heteroaryl contains one, two or three heteroatoms selected from N, O and S; wherein the carbocyclic, heterocyclic, aryl, phenoxy, and heteroaryl groups are unsubstituted or substituted with 1, 2, 3, 4 or 5 substituents $Q^{31a}$ selected from the group consisting of halogen, OH, CN, $NO_2$, SH, $NH_2$, NH($C_1$-$C_4$-alkyl), $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_6\text{-alkylthio}$, $S(O)_m-C_1-C_6\text{-alkyl}$, $C_1-C_4\text{-alkyl}$, $C_1-C_4\text{-halogenalkyl}$, $C_1-C_4\text{-alkoxy}$, $C_1-C_4\text{-halogenalkoxy}$, $CR'=NOR''$, phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{31a}$ selected from the group consisting of halogen, OH, $C_1-C_4\text{-alkyl}$, $C_1-C_4\text{-halogenalkyl}$, $C_1-C_4\text{-alkoxy}$, CN, $CR'=NOR''$ and $C_1-C_4\text{-halogenalkoxy}$; and wherein m, $R^x$, R' and R'' is defined as above;

wherein the carbocycle, heterocycle, heteroaryl and aryl moieties of $Q^3$ are unsubstituted or substituted with 1, 2, 3, 4, 5 or up to the maximum number of identical or different groups $Q^{3b}$ which independently of one another are selected from:

$Q^{3b}$ halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$ $C_1-C_4\text{-alkyl}$, $C_1-C_6\text{-alkoxy}$, $C_3-C_6\text{-cycloalkyl}$, $C_3-C_6\text{-halogencycloalkyl}$, $C_1-C_4\text{-halogenalkoxy}$, $C_1-C_6\text{-alkylthio}$, $S(O)_m-C_1-C_6\text{-alkyl}$, $C_1-C_4\text{-alkoxy-}C_1-C_4\text{-alkyl}$, phenyl, phenoxy and five- to ten- membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{31b}$ selected from the group consisting of halogen, OH, $C_1-C_4\text{-alkyl}$, $C_1-C_4\text{-halogenalkyl}$, $C_1-C_4\text{-alkoxy}$, $C_1-C_4\text{-halogenalkoxy}$, $CR'=NOR''$; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311b}$ selected from the group consisting of halogen, OH, $C_1-C_4\text{-alkyl}$, $C_1-C_4\text{-halogenalkyl}$, $C_1-C_4\text{-alkoxy}$, CN, $CR'=NOR''$ and $C_1-C_4\text{-halogenalkoxy}$; and wherein R' and R'' are defined as above;

wherein the substituted $C_1-C_{15}$-alkyl moieties of $Q^3$ carry one, two, three or up to the maximum possible number of identical or different groups $Q^{3c}$, respectively, which independently of one another are selected from:

$Q^{3c}$ halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_4\text{-alkoxy}$, $C_1-C_4\text{-halogenalkoxy}$, $C_3-C_6\text{-halogencycloalkyl}$, $C_1-C_6\text{-alkylthio}$, $C_1-C_6\text{-halogenalkylthio}$, $S(O)m-C_1-C_6\text{-alkyl}$, $S(O)_m-C_1-C_6\text{-halogenalkyl}$, $S(O)_m$-aryl, $CH(=O)$, $C(=O)C_1-C_6\text{-alkyl}$, $C(=O)O(C_1-C_6\text{-alkyl})$, $C(=O)NH(C_1-C_6\text{-alkyl})$, $C(=O)N(C_1-C_6\text{-alkyl})_2$, $CR'=NOR''$, a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from $C(=O)$ and $C(=S)$; wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_6\text{-alkylthio}$, $C_1-C_4\text{-alkyl}$, $C_1-C_4\text{-halogenalkyl}$, $C_1-C_4\text{-alkoxy}$, $C_1-C_4\text{-halogenalkyl}$, $S(O)_m-C_1-C_6\text{-alkyl}$ and $CR'=NOR''$; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311c}$ selected from the group consisting of halogen, OH, $C_1-C_4\text{-alkyl}$, $C_1-C_4\text{-halogenalkyl}$, $C_1-C_4\text{-alkoxy}$, CN, $CR'=NOR''$ and $C_1-C_4\text{-halogenalkoxy}$; and wherein R' and R'' is defined as above; wherein m, $R^x$, R' and R'' is as defined above;

$Q^4$ is selected from hydrogen, OH, $CH(=O)$, $C(=O)C_1-C_6\text{-alkyl}$, $C(=O)C_2-C_6\text{-alkenyl}$, $C(=O)C_2-C_6\text{-alkynyl}$, $C(=O)C_3-C_6\text{-cycloalkyl}$, $C(=O)O(C_1-C_6\text{-alkyl})$, $C(=O)O(C_2-C_6\text{-alkenyl})$, $C(=O)O(C_2-C_6\text{-alkynyl})$, $C(=O)O(C_3-C_6\text{-cycloalkyl})$, $C(=O)NH(C_1-C_6\text{-alkyl})$, $C(=O)NH(C_2-C_6\text{-alkenyl})$, $C(=O)NH(C_2-C_6\text{-alkynyl})$, $C(=O)NH(C_3-C_6\text{-cycloalkyl})$, $C(=O)N(C_1-C_6\text{-alkyl})_2$, $C(=O)N(C_2-C_6\text{-alkenyl})$, $C(=O)N(C_2-C_6\text{-alkynyl})$, $C(=O)N(C_3-C_6\text{-cycloalkyl})$, $CH(=S)$, $C(=S)C_1-C_6\text{-alkyl}$, $C(=S)C_2-C_6\text{-alkenyl}$, $C(=S)C_2-C_6\text{-alkynyl}$, $C(=S)C_3-C_6\text{-cycloalkyl}$, $C(=S)O(C_1-C_6\text{-alkyl})$, $C(=S)O(C_2-C_6\text{-alkenyl})$, $C(=S)O(C_2-C_6\text{-alkynyl})$, $C(=S)O(C_3-C_6\text{-cycloalkyl})$, $C(=S)NH(C_1-C_6\text{-alkyl})$, $C(=S)NH(C_2-C_6\text{-alkenyl})$, $C(=S)NH(C_2-C_6\text{-alkynyl})$, $C(=S)NH(C_3-C_6\text{-cycloalkyl})$, $C(=S)N(C_1-C_6\text{-alkyl})_2$, $C(=S)N(C_2-C_6\text{-alkenyl})$, $C(=S)N(C_2-C_6\text{-alkynyl})$, $C(=S)N(C_3-C_6\text{-cycloalkyl})_2$, $C_1-C_6\text{-alkyl}$, $C_1-C_4\text{-halogenalkyl}$, $C_3-C_6\text{-cycloalkyl}$, $C_3-C_6\text{-halogencycloalkyl}$, $C_1-C_4\text{-alkoxy}$, $C_1-C_4\text{-halogenalkoxy}$, $OR^Y$, $C_1-C_6\text{-alkylthio}$, $C_1-C_6\text{-halogenalkylthio}$, $C_2-C_6\text{-alkenyl}$, $C_2-C_6\text{-halogenalkenyl}$, $C_2-C_6\text{-alkynyl}$, $C_2-C_6\text{-halogenalkynyl}$, $S(O)_m-C_1-C_6\text{-alkyl}$, $S(O)_m-C_1-C_6\text{-halogenalkyl}$, $S(O)_m-C_1-C_6\text{-alkoxy}$, $S(O)_m-C_2-C_6\text{-alkenyl}$, $S(O)_m-C_2-C_6\text{-alkynyl}$, $S(O)_m$ aryl, $SO_2-NH(C_1-C_6\text{-alkyl})$, $SO_2-NH(C_1-C_6\text{-halogenalkyl})$, $SO_2-NH\text{-aryl}$, $\text{tri-}(C_1-C_6\text{ alkyl})\text{silyl}$ and $\text{di-}(C_1-C_6\text{ alkoxy})\text{phosphoryl})$, five- or six-membered heteroaryl and aryl; wherein the heteroaryl contains one, two or three heteroatoms selected from N, O and S; wherein the aryl groups are unsubstituted or carry one, two, three, four or five substituents selected from the group consisting of CN, halogen, OH, $C_1-C_4\text{-alkyl}$, $C_1-C_4\text{-halogenalkyl}$, $C_1-C_4\text{-alkoxy}$ and $C_1-C_4\text{-halogenalkoxy}$;

$R^Y$ is defined as above;

wherein the acyclic moieties of $Q^4$ are not further substituted or carry one, two, three or up to the maximum possible number of identical or different groups Q which independently of one another are selected from:

$Q^{4a}$ halogen, OH, CN, $C_1-C_6\text{-alkoxy}$, $C_3-C_6\text{-cycloalkyl}$, $C_3-C_6\text{-cycloalkenyl}$, $C_3-C_6\text{-halogencycloalkyl}$, $C_3-C_6\text{-halogencycloalkenyl}$, $C_1-C_4\text{-halogenalkoxy}$, $C_1-C_6\text{-alkylthio}$, five- or six-membered heteroaryl, phenyl and phenoxy, wherein the heteroaryl, phenyl and phenoxy group is unsubstituted or carries one, two, three, four or five substituents $Q^{4a'}$ selected from the group consisting of halogen, OH, $C_1-C_4\text{-alkyl}$, $C_1-C_4\text{-halogenalkyl}$, $C_1-C_4\text{-alkoxy}$ and $C_1-C_4\text{-halogenalkoxy}$;

wherein the alicyclic, phenyl, heterocyclic and heteroaryl moieties of $Q^4$ are not further substituted or carry one, two, three, four, five or up to the maximum number of identical or different groups $Q^{4b}$ which independently of one another are selected from:

$Q^{4b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

and wherein m is defined as above;

with the proviso that if

U is $CR^3$

W cannot be O or $S(O)_m$ and of an agriculturally acceptable salt thereof. and of the compositions for combating phytopathogenic fungi.

The numbering of the ring members in the compounds of the present invention is as given in formula I above:

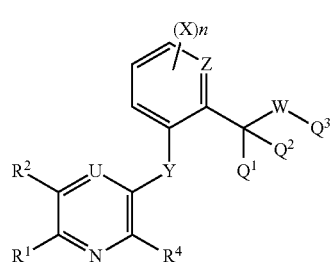

Compounds of type I can be prepared by reacting compounds of type II with a suitable electrophile $Q^3$-LG in an organic solvent, preferably NMP or a halocarbon and in the presence of a base at temperatures between −20 and 100° C., most preferably between 0 and 40° C. LG represents a suitable leaving group, preferably a halogen or a sulfonate.

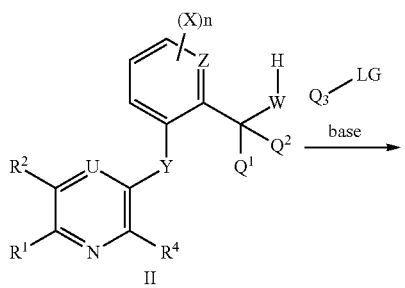

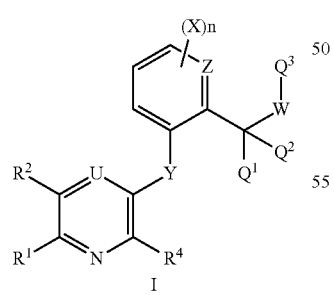

Alternatively compounds I may be obtained by reacting compounds II* with compounds Q3-W—H under conditions described for the reaction between compounds and Q3-LG yielding compounds I.

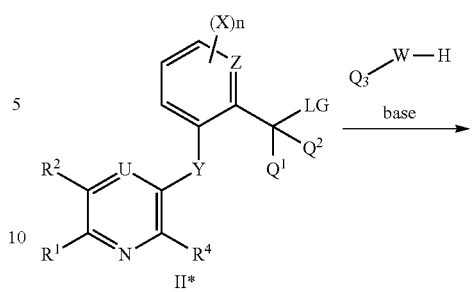

Compounds of type I-1 can also be obtained by reacting compounds II** with compounds Q3*-CN under conditions described for the reaction between compounds II and Q3-LG yielding compounds I-I

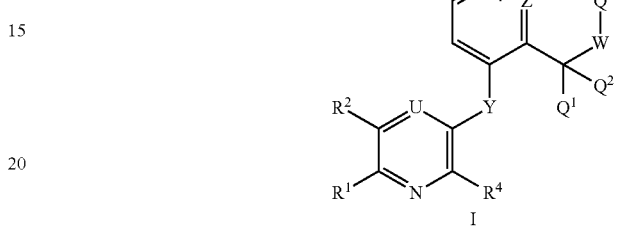

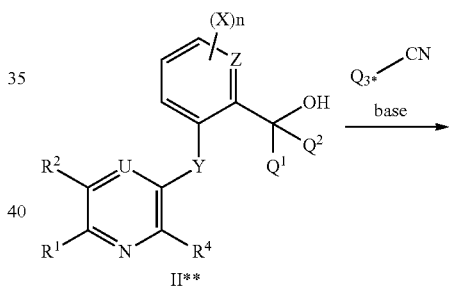

Compounds of type I-2 can be obtained via reaction with a reactive group $Q^4$-LG. Reactive groups are preferably $C_1$-$C_8$-alkyl halides, $C_2$-$C_6$-alkenyl halides, $C_2$-$C_6$-alkynyl halides, benzyl halides, aldehydes, ester, acid chlorides, amides, sulfates, silyl halides or phosphates, e.g. carboxylic acid (LG=OH), aldehydes (LG=H), acid chloride (LG=Cl), amides (LG=NMe$_2$) or phosphates (LH=OCH$_3$).

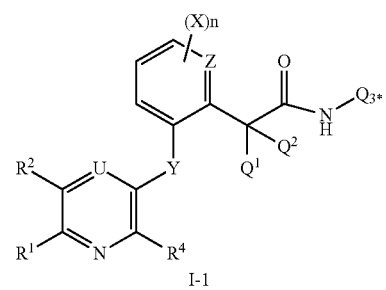

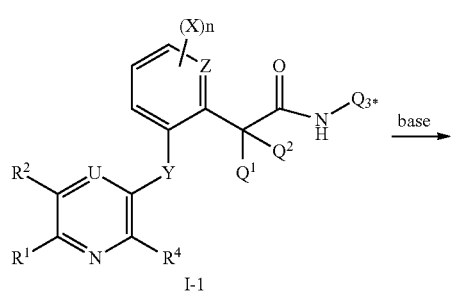

I-1

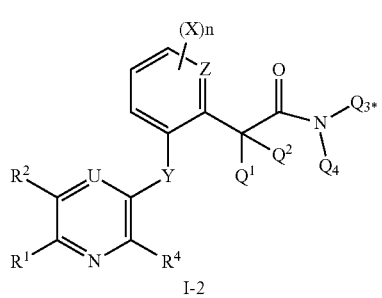

I-2

Typically the reaction is performed in a range between 0° C. and ambient temperature in the presence of a reactive group and organic base. Suitable base preferably $NEt_3$, pyridine NaOH, TEBAC, $K_2CO_3$, $NaCO_3$ or KOH. Most preferably solvents are THF, DMF, DMSO, MeOH or water (see for example, Journal of Medicinal Chemistry, 1989, 32(6), 1242-1248; European Journal of Medicinal Chemistry, 2009, 44(10), 4034-4043).

Compounds of type II may be accessed as described for example in JP2010/202530 or Angewandte Chemie, International Edition, 45(35), 5803-5807; 2006 and as outlined below. Compounds of type III (where Hal is a halogen, most preferably Br or I) can be metallated by treatment with an appropriate organometallic reagent [M] in an ethereal solvent at low temperatures. Preferably, an organolithium or organomagnesium compound is used and the reaction is best performed in THF and between −78° C. and 0° C. The intermediary organometallic species can be trapped with carbonyl, thiocarbonyl or imines compounds of type IV to furnish compounds of type II after aqueous workup. Compounds of type IV are readily available either from commercial suppliers or through methods obvious to a person skilled in the art.

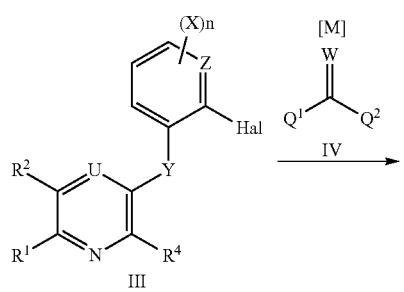

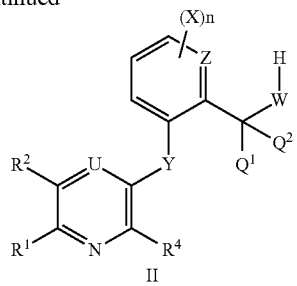

II

To access compounds of type III, it may be preferred to react compounds V in a nucleophilic aromatic substitution with compounds of type VI which are either commercially available or can be prepared following procedures that are obvious to a skilled person. LG represents a suitable leaving group, with special preference given to fluoride (for precedents see e.g. WO2007/117381, WO2012/037782, or Bioorganic & Medicinal Chemistry, 21(4), 979-992; 2013). The reaction is best carried out at temperatures between 0 and 100° C., preferably between room temperature and 80° C. Furthermore, it may be appropriate to perform the reaction in an organic solvent, preferably, but not limited to DMF or NMP and in the presence of a base, preferably, but not limited to potassium carbonate or sodium hydride.

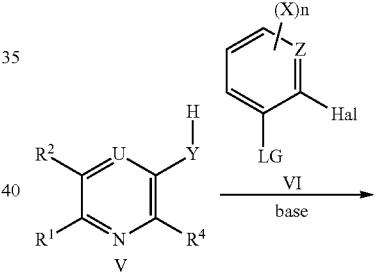

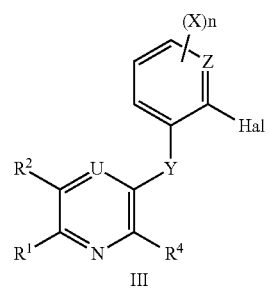

III

Alternatively compounds III can be synthesized reacting compounds V* and VI* applying conditions already described for the reaction of compounds V with compounds VI

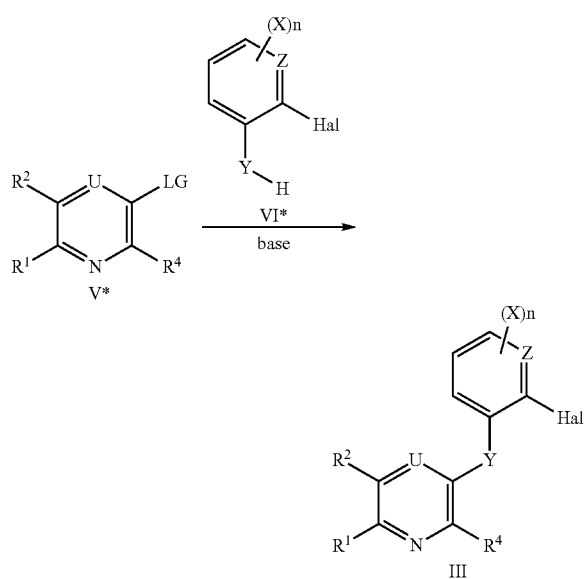

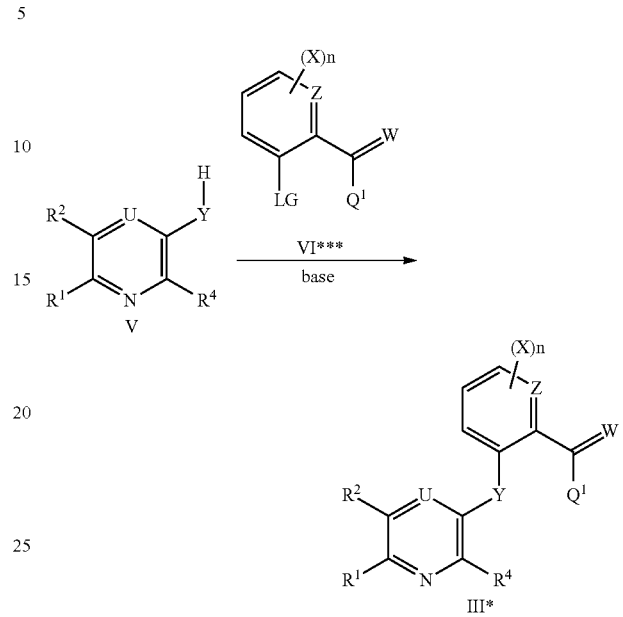

Alternatively compounds III* can be accessed by reacting compounds V* with compounds VI** applying conditions already described for the reaction of V* with VI* yielding compounds III*. Compounds III* can subsequently be converted to compounds II using methods already described for the reaction of compounds III with compounds IV yielding compounds II

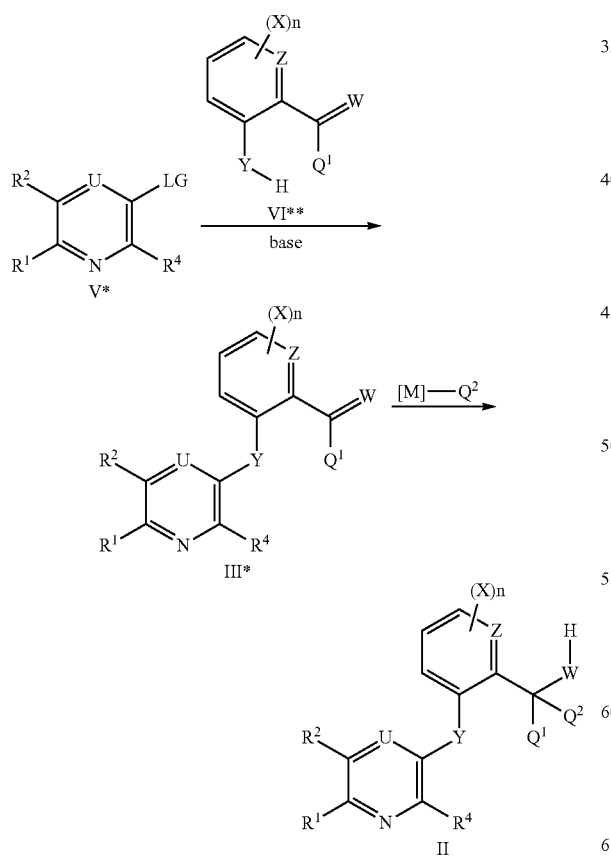

Additionally compounds III* can be accessed by reacting compounds V with compounds V*** applying conditions already described for the reaction of V* with VI* yielding compounds III*.

Compounds of type V can be prepared from nitro compounds of type VII in a two-step sequence that has been previously described (for examples see Journal of Medicinal Chemistry, 35(20), 3667-71; 1992, WO2005/123668, or US20060293364). The first step seeks to achieve a chemoselective reduction of the nitro group to its amino congener by employing a suitable reducing agent, such as iron, zinc, or hydrogen in the presence of a transition metal catalyst such as palladium. Preferably, the reduction is performed in an organic solvent, more preferably in an alcoholic solvent, if appropriate at elevated temperatures and/or increased pressure. The respective amino compounds can be transformed into compounds of type V through a Sandmeyer reaction by reacting them first with a suitable nitrite source at low temperatures, preferably but not limited to sodium nitrite or t-BuONO. For the preparation of compounds in which Y is oxygen, the intermediary diazonium salt may be treated with a suitable acid, for example, but not limited to HCl or $HBF_4$. It may be appropriate to increase the temperature upon addition of the acid. Compounds in which Y is S can be accessed by reacting said diazonium salt with a suitable sulfur source, preferably a alkali xanthate such as potassium xanthate, followed by base-mediated cleavage of the thioester. A precedent can be found for example in Journal of Medicinal Chemistry, 36(8), 953-66; 1993.

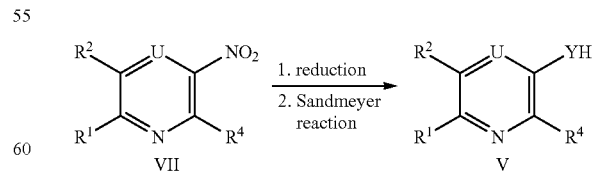

A person skilled in the art will realize that compounds of type VII are either commercially available or be able to prepare said compounds following standard procedures.

The N-oxides may be prepared from the inventive compounds according to conventional oxidation methods, e. g.

by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-halogenalkyl" refers to an alkyl group having 1 or 6 carbon atoms as defined above, wherein some or all of the hydrogen atoms in these groups may be replaced by halogen atoms as mentioned above. Examples are "$C_1$-$C_2$-halogenalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_1$-$C_4$-alkoxy-$C_1$-$C_4$-alkyl" refers to alkyl having 1 to 4 carbon atoms (as defined above), where According to one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), where According to one hydrogen atom of the alkyl radical is replaced by a $C_1$-$C_6$-alkoxy group (as defined above).

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_1$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methyl, propoxy, 2-methylpropoxy or 1,1-dimethylethoxy.

The term "$C_1$-$C_6$-halogenalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-halogenalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chlorothoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoro, propoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "$C_2$-$C_6$-alkenyloxy" refers to a straight-chain or branched alkenyl group having 2 to 6 carbon atoms which is bonded via an oxygen, at any position in the alkenyl group. Examples are "$C_2$-$C_4$-alkenyloxy" groups.

The term "$C_2$-$C_6$-alkynyloxy" refers to a straight-chain or branched alkynyl group having 2 to 6 carbon atoms which is bonded via an oxygen, at any position in the alkynyl group. Examples are "$C_2$-$C_4$-alkynyloxy" groups.

The term "$C_3$-$C_6$-cycloalkyl" refers to monocyclic saturated hydrocarbon radicals having 3 to 6 carbon ring members, such as cyclopropyl, cyclobutyl, cyclopentyl, cyclohexyl. Accordingly, a saturated three-, four-, five-, six-, seven-, eight-, nine or ten-membered carbocyclyl or carbocycle is a "$C_3$-$C_{10}$-cycloalkyl".

The term "$C_3$-$C_6$-cycloalkenyl" refers to a monocyclic partially unsaturated 3-, 4- 5- or 6-membered carbocycle having 3 to 6 carbon ring members and at least one double bond, such as cyclopentenyl, cyclopentadienyl, cyclohexadienyl. Accordingly, a partially unsaturated three-, four-, five-, six-, seven-, eight-, nine or ten-membered carbocyclyl or carbocycle is a "$C_3$-$C_{10}$-cycloalkenyl".

The term "$C_3$-$C_8$-cycloalkyl-$C_1$-$C_4$-alkyl" refers to alkyl having 1 to 4 carbon atoms (as defined above), where According to one hydrogen atom of the alkyl radical is replaced by a cycloalkyl radical having 3 to 8 carbon atoms (as defined above).

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-halogenalkylthio" as used herein refers to straight-chain or branched halogenalkyl group having 1 to 6 carbon atoms (as defined above) bonded through a sulfur atom, at any position in the halogenalkyl group.

The term "C(=O)—$C_1$-$C_6$-alkyl" refers to a radical which is attached through the carbon atom of the group C(=O) as indicated by the number valence of the carbon atom. The number of valence of carbon is 4, that of nitrogen is 3. Likewise the following terms are to be construed: NH($C_1$-$C_4$-alkyl), N($C_1$-$C_4$-alkyl)$_2$, NH($C_3$-$C_6$-cycloalkyl), N($C_3$-$C_6$-cycloalkyl)$_2$, C(=O)—NH($C_1$-$C_6$-alkyl), C(=O)—N($C_1$-$C_6$-alkyl)$_2$.

The term "saturated or partially unsaturated three-, four-, five-, six-, seven-, eight-, nine or ten-membered heterocyclyl or heterocycle, wherein the heterocyclyl or heterocycle contains 1, 2, 3 or 4 heteroatoms selected from N, O and S" is to be understood as meaning both saturated and partially unsaturated heterocycles, wherein the ring member atoms of the heterocycle include besides carbon atoms 1, 2, 3 or 4 heteroatoms independently selected from the group of O, N and S. For example:

a 3- or 4-membered saturated heterocycle which contains 1 or 2 heteroatoms from the group consisting of O, N and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of O, N and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-iso-thiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "substituted" refers to substituted with 1, 2, 3 or up to the maximum possible number of substituents.

The term "5- or 6-membered heteroaryl" or "5- or 6-membered heteroaromatic" refers to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

$R^1$ is in each case independently selected from halogen, OH, $NO_2$, SH, $NH(C_1$-$C_4$-alkyl), $N(C_1$-$C_4$-alkyl)$_2$, $NH(C_2$-$C_4$-alkenyl), $N(C_2$-$C_4$-alkenyl)$_2$, $NH(C_2$-$C_4$-alkynyl), $N(C_2$-$C_4$-alkynyl)$_2$, $NH(C_3$-$C_6$-cycloalkyl), $N(C_3$-$C_6$-cycloalkyl)$_2$, $N(C_2$-$C_4$-alkyl)($C_2$-$C_4$-alkenyl), $N(C_2$-$C_4$-alkyl)($C_2$-$C_4$-alkynyl), $N(C_2$-$C_4$-alkyl)($C_3$-$C_6$-cycloalkyl), $N(C_2$-$C_4$-alkenyl)($C_2$-$C_4$-alkynyl), $N(C_2$-$C_4$-alkenyl)($C_3$-$C_6$-cycloalkyl), $N(C_2$-$C_4$-alkynyl)($C_3$-$C_6$-cycloalkyl), $NH(C(=O)C_1$-$C_4$-alkyl), $N(C(=O)C_1$-$C_4$-alkyl), $NH$—$SO_2$—$R^x$, $S(O)_m$—$C_1$-$C_6$-alkyl, $S(O)_m$-aryl, $C_1$-$C_6$-cycloalkylthio, $S(O)_m$—$C_2$-$C_6$-alkenyl, $S(O)_m$—$C_2$-$C_6$-alkynyl, $CH(=O)$, $C(=O)C_1$-$C_6$-alkyl, $C(=O)C_2$-$C_6$-alkenyl, $C(=O)C_2$-$C_6$-alkynyl, $C(=O)C_3$-$C_6$-cycloalkyl, $C(=O)NH(C_1$-$C_6$-alkyl), $C(=O)N(C_1$-$C_6$-alkyl)$_2$, $C(=O)N(C_2$-$C_6$-alkenyl), $C(=O)N(C_2$-$C_6$-alkynyl), $C(=O)N(C_3$-$C_7$-cycloalkyl), $CH(=S)$, $C(=S)C_1$-$C_6$-alkyl, $C(=S)C_2$-$C_6$-alkenyl, $C(=S)C_2$-$C_6$-alkynyl, $C(=S)C_3$-$C_6$-cycloalkyl, $(=S)O(C_2$-$C_6$-alkenyl), $C(=S)O(C_2$-$C_6$-alkynyl), $C(=S)O(C_3$-$C_7$-cycloalkyl), $C(=S)NH(C_1$-$C_6$-alkyl), $C(=S)NH(C_2$-$C_6$-alkenyl), $C(=S)NH(C_2$-$C_6$-alkynyl), $C(=S)NH(C_3$-$C_7$-cycloalkyl), $C(=S)N(C_1$-$C_6$-alkyl)$_2$, $C(=S)N(C_2$-$C_6$-alkenyl), $C(=S)N(C_2$-$C_6$-alkynyl), $C(=S)N(C_3$-$C_7$-cycloalkyl), $C_1$-$C_6$-alkyl, $C_2$-$C_6$-alkenyl, $C_2$-$C_6$-alkynyl, $OR^Y$, $C_3$-$C_6$-cycloalkyl, five- or six-membered heteroaryl and aryl; wherein the heteroaryl contains one, two or three heteroatoms selected from N, O and S; wherein $R^x$ is $C_1$-$C_4$-alkyl, $C_1$-$C_4$-halogenalkyl, unsubstituted aryl or aryl that is substituted by 1, 2, 3, 4 or 5 substituents $R^{x1}$ independently selected from $C_1$-$C_4$-alkyl, halogen, OH, CN, $C_1$-$C_4$-halogenalkyl, $C_1$-$C_4$-alkoxy and $C_1$-$C_4$-halogenalkoxy;

$R^Y$ is $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_3$-$C_6$-cycloalkyl, $C_3$-$C_6$-halogencycloalkyl; phenyl and phenyl-$C_1$-$C_6$-alkyl; wherein the phenyl group is unsubstituted or substituted with substituents selected from the group consisting of halogen, CN, OH, $C_1$-$C_6$-alkyl, $C_1$-$C_6$-halogenalkyl, $C_1$-$C_6$-alkoxy and $C_1$-$C_6$-halogenalkoxy;

wherein the acyclic moieties of $R^1$ are unsubstituted or substituted with groups Ra which independently of one another are selected from:

$R^{1a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenoxy group is unsubstituted or substituted with substituents $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the carbocycle, heteroaryl and aryl moieties of $R^1$ are unsubstituted or substituted with groups $R^{1a}$ which independently of one another are selected from:

$R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

and wherein m is 0, 1 and 2.

According to one embodiment of formula I, $R^1$ is selected from the group consisting of halogen, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl and $C_3$-$C_6$-halogencycloalkyl.

According to still another embodiment of formula I, $R^1$ is halogen, in particular F, Cl, Br or I, more specifically F, Cl or Br, in particular F or Cl.

According to still another embodiment of formula I, $R^1$ is F.

According to still another embodiment of formula I, $R^1$ is Cl.

According to still another embodiment of formula I, $R^1$ is Br.

According to still another embodiment of formula I, $R^1$ is OH.

According to still another embodiment of formula I, $R^1$ is $NO_2$.

According to still another embodiment of formula I, $R^1$ is SH.

According to still another embodiment of formula I, $R^1$ is, $NH(C_1$-$C_4$-alkyl), in particular $NH(CH_3)$, $NH(C_2H_5)$.

According to still another embodiment of formula I, R is, $N(C_1$-$C_4$-alkyl)$_2$, in particular $NH(CH_3)_2$, $NH(C_2H_5)_2$.

According to still another embodiment of formula I, $R^1$ is, $NH(C_2$-$C_4$-alkenyl), in particular $NH(CH=CH_2)$, $NH(CH_2CH=CH_2)$.

According to still another embodiment of formula I, $R^1$ is, $N(C_2$-$C_4$-alkenyl)$_2$, in particular $N(CH=CH_2)_2$, $N(CH_2CH=CH_2)_2$.

According to still another embodiment of formula I, $R^1$ is, $NH(C_2$-$C_4$-alkynyl), in particular $NH(C≡CH)$, $NH(CH_2C≡CH)$.

According to still another embodiment of formula I, $R^1$ is, $N(C_2$-$C_4$-alkynyl)$_2$, in particular $N(C≡CH)_2$, $N(CH_2C≡CH)_2$.

According to still another embodiment of formula I, $R^1$ is, $NH(C_3$-$C_6$-cycloalkyl), in particular $NH(C_3H)$, $NH(C_4H_9)$.

According to still another embodiment of formula I, $R^1$ is, $N(C_3$-$C_6$-cycloalkyl)$_2$, in particular $N(C_3H_7)_2$, $N(C_4H_9)_2$.

According to still another embodiment of formula I, R is $N(C_1$-$C_4$-alkyl)($C_2$-$C_4$-alkenyl), in particular $N(CH_3)(CH=CH_2)$, $N(CH_3)(CH_2CH=CH_2)$, $N(C_2H_5)(CH=CH_2)$, $N(C_2H_5)(CH_2CH=CH_2)$.

According to still another embodiment of formula I, R is $N(C_1$-$C_4$-alkyl)($C_2$-$C_4$-alkynyl), in particular $N(CH_3)(C≡CH)$, $N(CH_3)(CH_2C≡CH)$, $N(C_2H_5)(C≡CH)$, $N(C_2H_5)(CH_2C≡CH)$.

According to still another embodiment of formula I, R is $N(C_1$-$C_4$-alkyl)($C_3$-$C_6$-cycloalkyl), in particular $N(CH_3)(C_3H_7)$, $N(CH_3)(C_4H_9)$, $N(C_2H_5)(C_3H_7)$, $N(CH_3)(C_4H_9)$.

According to still another embodiment of formula I, R is $N(C_2$-$C_4$-alkenyl)($C_2$-$C_4$-alkynyl), in particular $N(CH=CH_2)(C≡CH)$, $N(CH_2CH=CH_2)(CH_2C≡CH)$, $N(CH=CH_2)(C≡CH)$, $N(CH_2CH=CH_2)(CH_2C≡CH)$.

According to still another embodiment of formula I, R is $N(C_2\text{-}C_4\text{-alkenyl})(C_3\text{-}C_6\text{-cycloalkyl})$, in particular $N(CH=CH_2)(C_3H_7)$, $N(CH_2CH=CH_2)(C_4H_9)$, $N(CH=CH_2)(C_3H_7)$, $N(CH_2CH=CH_2)(C_4H_9)$.

According to still another embodiment of formula I, R is $N(C_2\text{-}C_4\text{-alkynyl})(C_3\text{-}C_6\text{-cycloalkyl})$, in particular $N(C\equiv CH)(C_3H)$, $N(CH_2C\equiv CH)(C_4H_9)$, $N(C\equiv CH)(C_3H)$, $N(CH_2C\equiv CH)(C_4H_9)$.

According to still another embodiment of formula I, $R^1$ is, $NH(C(=O)(C_1\text{-}C_4\text{-alkyl})$, in particular $NH(C(=O)(CH_3))$, $NH(C(=O)(C_2H_5))$.

According to still another embodiment of formula I, $R^1$ is $N(C(=O)(C_1\text{-}C_4\text{-alkyl})_2$, in particular $N(C(=O)(CH_3)_2$, $N(C(=O)(C_2H_5)_2$.

According to a further specific embodiment of formula I, $R^1$ is $NH\text{—}SO_2\text{—}R^x$ such as $NH\text{—}SO_2\text{—}CH_3$, $NH\text{—}SO_2\text{—}CH_2\text{—}CH_3$, $NH\text{—}SO_2\text{—}CF_3$, $NH\text{—}SO_2\text{-Ts}$.

According to still another embodiment of formula I, $R^1$ is $S(O)m\text{-}C_1\text{-}C_6\text{-alkyl}$ such as $SCH_3$, $S(=O)CH_3$, $S(O)_2CH_3$.

According to still another embodiment of formula I, $R^1$ is $S(O)m\text{-aryl}$ such as S-phenyl, $S(=O)$ phenyl, $S(O)_2\text{phenyl}$.

According to still another embodiment of formula I, $R^1$ is $S(O)m\text{-}C_2\text{-}C_6\text{-alkenyl}$ such as $SCH=CH_2$, $S(=O)CH=CH_2$, $S(O)_2CH=CH_2$, $SCH_2CH=CH_2$, $S(=O)CH_2CH=CH_2$, $S(O)_2CH_2CH=CH_2$.

According to still another embodiment of formula I, $R^1$ is $S(O)m\text{-}C_2\text{-}C_6\text{-alkynyl}$ such as $SC\equiv CH$, $S(=O)C\equiv CH$, $S(O)_2C\equiv CH$, $SCH_2C\equiv CH$, $S(=O)CH_2C\equiv CH$, $S(O)_2CH_2C\equiv CH$.

According to a further specific embodiment of formula I, $R^1$ is $CH(=O)$.

According to a further specific embodiment of formula I, R is $C(=O)C_1\text{-}C_6\text{-alkyl}$, $C(=O)O(C_1\text{-}C_6\text{-alkyl})$, $C(=O)NH(C_1\text{-}C_6\text{-alkyl})$ or $C(=O)N(C_1\text{-}C_6\text{-alkyl})_2$, wherein alkyl is $CH_3$, $C_2H_5$, n-propyl, i-propyl, n-butyl, i-butyl, tert-butyl, n-pentyl or i-pentyl.

According to a further specific embodiment of formula I, R is $C(=O)C_2\text{-}C_6\text{-alkenyl}$, $C(=O)O(C_2\text{-}C_6\text{-alkenyl})$, $(=O)NH(C_2\text{-}C_6\text{-alkenyl})$ or $C(=O)N(C_2\text{-}C_6\text{-alkenyl})_2$, wherein alkenyl is $CH=CH_2$, $CH_2CH=CH_2$.

According to a further specific embodiment of formula I, R is $C(=O)C_2\text{-}C_6\text{-alkynyl}$, $C(=O)O(C_2\text{-}C_6\text{-alkynyl})$, $C(=O)NH(C_2\text{-}C_6\text{-alkynyl})$ or $C(=O)N(C_2\text{-}C_6\text{-alkynyl})_2$, wherein alkynyl is $C\equiv CH$, $CH_2C\equiv CH$.

According to a further specific embodiment of formula I, R is $C(=O)C_3\text{-}C_6\text{-cycloalkyl}$, $C(=O)O(C_3\text{-}C_6\text{-cycloalkyl})$, $C(=O)NH(C_3\text{-}C_6\text{-cycloalkyl})$ or $C(=O)N(C_3\text{-}C_7\text{-cycloalkyl})_2$, wherein cycloalkyl is cyclopropyl $(C_3H_7)$ or cyclobutyl $(C_4H_9)$.

According to a further specific embodiment of formula I, $R^1$ is $CH(=S)$.

According to a further specific embodiment of formula I, R is $C(=S)C_1\text{-}C_6\text{-alkyl}$, $C(=S)OC_1\text{-}C_6\text{-alkyl}$, $C(=S)NH(C_1\text{-}C_6\text{-alkyl})$ or $C(=S)NH(C_1\text{-}C_6\text{-alkyl})$, wherein alkyl is $CH_3$, $C_2H_5$, n-propyl, i-propyl, n-butyl, i-butyl, tert-butyl, n-pentyl or i-pentyl.

According to a further specific embodiment of formula I, R is $C(=S)C_2\text{-}C_6\text{-alkenyl}$, $C(=S)OC_2\text{-}C_6\text{-alkenyl}$, $C(=S)NH(C_2\text{-}C_6\text{-alkenyl})$ or $C(=S)N(C_2\text{-}C_6\text{-alkenyl})_2$, wherein alkenyl is $CH=CH_2$, $CH_2CH=CH_2$.

According to a further specific embodiment of formula I, R is $C(=S)C_2\text{-}C_6\text{-alkynyl}$, $C(=S)O(C_2\text{-}C_6\text{-alkynyl})$, $C(=S)NH(C_2\text{-}C_6\text{-alkynyl})$ or $C(=S)N(C_2\text{-}C_6\text{-alkynyl})_2$, wherein alkynyl is $C\equiv CH$, $CH_2C\equiv CH$.

According to a further specific embodiment of formula I, $R^1$ is $C(=S)C_3\text{-}C_6\text{-cycloalkyl}$, $C(=S)O(C_3\text{-}C_7\text{-cycloalkyl})$, $C(=S)NH(C_3\text{-}C_7\text{-cycloalkyl})$ or, $C(=S)N(C_3\text{-}C_7\text{-cycloalkyl})_2$, wherein cycloalkyl is cyclopropyl $(C_3H_7)$ or cyclobutyl $(C_4H_9)$.

According to still another embodiment of formula I, $R^1$ is $C_1\text{-}C_6\text{-alkyl}$, in particular $C_1\text{-}C_4\text{-alkyl}$, such as $CH_3$. or $C_{25}$, in particular $CH_3$ or $CH_2CH_3$.

According to still another embodiment of formula I, $R^1$ is $C_1\text{-}C_6\text{-halogenalkyl}$, in particular $C_1\text{-}C_4\text{-halogenalkyl}$, such as $CF_3$, $CCl_3$, $FCH_2$, $ClCH_2$, $F_2CH$, $C_2CH$, $CF_3CH_2$, $CCl_3CH_2$ or $CF_2CHF_2$.

According to still a further embodiment of formula I, $R^1$ is $C_2\text{-}C_6\text{-alkenyl}$, in particular $C_2\text{-}C_4\text{-alkenyl}$, such as $CH=CH_2$, $C(CH_3)=CH_2$, $CH_2CH=CH_2$.

According to a further specific embodiment of formula I, $R^1$ is $C_2\text{-}C_6\text{-halogenalkenyl}$, in particular $C_2\text{-}C_4\text{-halogenalkenyl}$, more specifically $C_2\text{-}C_3\text{-halogenalkenyl}$ such as $CH=CHF$, $CH=CHCl$, $CH=CF_2$, $CH=CCl_2$, $CH_2CH=CHF$, $CH_2CH=CHCl$, $CH_2CH=CF_2$, $CH_2CH=CCl_2$, $CF_2CH=CF_2$, $CCl_2CH=CCl_2$, $CF_2CF=CF_2$, $CCl_2CCl=CCl_2$.

According to still a further embodiment of formula I, R is $C_2\text{-}C_6\text{-alkynyl}$ or $C_2\text{-}C_6\text{-halogenalkynyl}$, in particular $C_2\text{-}C_4\text{-alkynyl}$ or $C_2\text{-}C_4\text{-halogenalkynyl}$, such as $C\equiv CH$, $CH_2C\equiv CH$, $C\equiv CCl$, $CH_2C\equiv CCl$, or $CCl_2C\equiv CCl$.

According to a further specific embodiment of formula I, $R^1$ is OR wherein R is $C_1\text{-}C_6\text{-alkyl}$, $C_1\text{-}C_6\text{-halogenalkyl}$, $C_2\text{-}C_6\text{-alkenyl}$, $C_2\text{-}C_6\text{-halogenalkenyl}$, $C_2\text{-}C_6\text{-alkynyl}$, $C_2\text{-}C_6\text{-halogenalkynyl}$, $C_3\text{-}C_6\text{-cycloalkyl}$, $C_3\text{-}C_6\text{-halogencycloalkyl}$.

According to a further specific embodiment of formula I, $R^1$ is $OR^Y$ wherein $R^Y$ is $C_1\text{-}C_6\text{-alkyl}$, in particular $C_1\text{-}C_4\text{-alkyl}$, more specifically $C_1\text{-}C_2\text{-alkoxy}$. $R^1$ is such as $OCH_3$ or $OCH_2CH_3$.

According to a further specific embodiment of formula I, $R^1$ is OR wherein R is $C_1\text{-}C_6\text{-halogenalkyl}$, in particular $C_1\text{-}C_4\text{-halogenalkyl}$, more specifically $C_1\text{-}C_2\text{-halogenalkyl}$. $R^1$ is such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment of formula I, $R^1$ is OR wherein R $C_2\text{-}C_6\text{-alkenyl}$, in particular $C_2\text{-}C_4\text{-alkenyl}$, more specifically $C_1\text{-}C_2\text{-alkenyl}$. $R^1$ is such as $OCH=CH_2$, $OCH_2CH=CH_2$.

According to a further specific embodiment of formula I, $R^1$ is $OR^Y$, wherein R $C_2\text{-}C_6\text{-halogenalkenyl}$, in particular $C_2\text{-}C_4\text{-halogenalkenyl}$, more specifically $C_1\text{-}C_2\text{-halogenalkenyl}$.

According to a further specific embodiment of formula I, $R^1$ is OR wherein R $C_2\text{-}C_6\text{-alkynyl}$, in particular $C_2\text{-}C_6\text{-alkynyl}$, in particular $C_2\text{-}C_4\text{-alkynyl}$, more specifically $C_1\text{-}C_2\text{-alkynyl}$. $R^1$ is such as $OC\equiv CH$, According to a further specific embodiment of formula I, $R^1$ is $OR^Y$, wherein R $C_2\text{-}C_6\text{-halogenalkynyl}$, in particular $C_2\text{-}C_6\text{-halogenalkynyl}$, in particular $C_2\text{-}C_4\text{-halogenalkynyl}$, more specifically $C_1\text{-}C_2\text{-halogenalkynyl}$. $R^1$ is such as $OC\equiv CCl$, $OCH_2C\equiv CCl$, or $OCCl_2C\equiv CCl$.

According to still another embodiment of formula I, $R^1$ is OR wherein R $C_3\text{-}C_6\text{-cycloalkenyl}$, in particular cyclopropenyl.

According to still another embodiment of formula I, $R^1$ is $C_3\text{-}C_6\text{-cycloalkyl}$, in particular cyclopropyl.

According to still another embodiment of formula I, $R^1$ is $C_3\text{-}C_6\text{-halogencycloalkyl}$. In a special embodiment $R^{1b}$ is fully or partially halogenated cyclopropyl, such as 1-F-cyclopropyl, 1-Cl-cyclopropyl, $1,1\text{-}F_2$-cyclopropyl, $1,1\text{-}Cl_2$-cyclopropyl.

According to still another embodiment of formula I, $R^1$ is phenyl-$C_1\text{-}C_6\text{-alkyl}$, such as phenyl-$CH_2$, wherein the phenyl moiety in each case is unsubstituted or substituted by one, two or three identical or different groups $R^{1b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, Cl, Br, $CH_3$, $OCH_3$, $CF_3$ and $OCF_3$.

According to still another embodiment of formula I, $R^1$ is aryl, in particular phenyl, wherein the aryl or phenyl moiety in each case is unsubstituted or substituted with identical or different groups $R^{1b}$ which independently of one another are selected from CN, halogen, $C_1$-$C_2$-alkyl, $C_1$-$C_2$-alkoxy, $C_1$-$C_2$-halogenalkyl and $C_1$-$C_2$-halogenalkoxy, in particular CN, F, C, Br, $CH_3$, $OCH_3$, $CHF_2$, $OCHF_2$, $CF_3$ and $OCF_3$. According to one embodiment, $R^1$ is unsubstituted phenyl. According to another embodiment, $R^1$ is phenyl, that is substituted with one, two or three, in particular one, halogen, in particular selected from F, Cl and Br, more specifically selected from F and Cl.

According to still another embodiment of formula I, $R^1$ is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $R^1$ is a 6-membered heteroaryl such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to still another embodiment of formula I, $R^1$ is in each case independently selected from halogen, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl and $C_3$-$C_6$-halogencycloalkyl, wherein the acyclic moieties of $R^1$ are unsubstituted or substituted with identical or different groups $R^{1a}$ as defined and preferably defined herein, and wherein the carbocyclic, phenyl and heteroaryl moieties of $R^1$ are unsubstituted or substituted with identical or different groups $R^{1b}$ as defined and preferably defined herein.

According to still another embodiment of formula I, $R^1$ is in each case independently selected from halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy; wherein the acyclic moieties of $R^1$ are unsubstituted or substituted with identical or different groups $R^{1a}$ as defined and preferably defined herein.

According to still another embodiment of formula I, $R^1$ is in each case independently selected from halogen, $C_1$-$C_6$-alkyl, $C_1$-$C_6$-halogenalkyl, $C_2$-$C_6$-alkynyl, $OR^Y$, $C_3$-$C_6$-cycloalkyl; wherein R is $C_1$-$C_6$-alkyl, $C_1$-$C_6$-halogenalkyl, $C_2$-$C_6$-alkenyl or $C_2$-$C_6$-alkynyl.

$R^{1a}$ are the possible substituents for the acyclic moieties of $R^1$.

According to one embodiment $R^{1a}$ is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenyl group is unsubstituted or substituted with substituents $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to one embodiment $R^{1a}$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $R^{1a}$ is independently selected from F, Cl, Br, I, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to still another embodiment of formula I, $R^{1a}$ is independently halogen, in particular selected from F, Cl, Br and I, more specifically F, Cl and Br.

$R^{1b}$ are the possible substituents for the carbocyclic, heteroaryl and phenyl moieties of $R^1$. $R^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-akylthio.

According to one embodiment thereof $R^{1b}$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, R is independently selected from F, Cl, CN, $CH_3$, $OCH_3$ and halogenmethoxy.

Particularly preferred embodiments of $R^1$ according to the invention are in Table P1 below, wherein each line of lines P1-1 to P1-40 corresponds to one particular embodiment of the invention, wherein P1-1 to P1-40 are also in any combination with one another a preferred embodiment of the present invention. The connection point to the carbon atom, to which $R^1$ is bound is marked with "#" in the drawings.

TABLE P1

| No. | $R^1$ |
|---|---|
| P1-1 | $CH_3$ |
| P1-2 | $CH_2F$ |
| P1-3 | $CHF_2$ |
| P1-4 | $CF_3$ |
| P1-5 | $C_2H_5$ |
| P1-6 | $CH(CH_3)_2$ |
| P1-7 | $CH_2CH_2CH_3$ |
| P1-8 | $CH_2CH_2CH_2CH_3$ |
| P1-9 | $CH_2CH(CH_3)_2$ |
| P1-10 | $C(CH_3)_3$ |
| P1-11 | $CH_2CH_2CH_2CH_2CH_3$ |
| P1-12 | $CH=CH_2$ |
| P1-13 | $CH_2CH=CH_2$ |
| P1-14 | $C\equiv CH$ |
| P1-15 | $CH_2C\equiv CH$ |
| P1-16 | $CH_2CH_2CH(CH_3)_2$ |
| P1-17 | OH |
| P1-18 | $OCH_3$ |
| P1-19 | $OCHF_2$ |
| P1-20 | $OC_2H_5$ |
| P1-21 | F |
| P1-22 | Cl |
| P1-23 | Br |
| P1-24 | $NO_2$ |
| P1-25 | $CO-NH_2$ |
| P1-26 | $CO-NH(CH_3)$ |
| P1-27 | $CO-N(CH_3)_2$ |
| P1-28 | $HNCH_3$ |
| P1-29 | $HNC_2H_5$ |
| P1-30 | $(CH_3)_2N$ |
| P1-31 | $SO_2H$ |
| P1-32 | $SO_2-CH_3$ |
| P1-33 | $SO-CH_3$ |
| P1-34 | $S-CH_3$ |
| P1-35 |  |

TABLE P1-continued

| No. | R¹ |
|---|---|
| P1-36 | #—◇ (cyclobutyl) |
| P1-37 | #—⬠ (cyclopentyl) |
| P1-38 | #—⬡ (cyclohexyl) |
| P1-39 | #—C₆H₅ (phenyl) |
| P1-40 | #—pyridyl |

$R^2$ is in each case independently selected from halogen, OH, $NO_2$, SH, $NH_2$, $NH(C_1-C_4\text{-alkyl})$, $N(C_1-C_4\text{-alkyl})_2$, $NH(C_2-C_4\text{-alkenyl})$, $N(C_2-C_4\text{-alkenyl})_2$, $NH(C_2-C_4\text{-alkynyl})$, $N(C_2-C_4\text{-alkynyl})_2$, $NH(C_3-C_6\text{-cycloalkyl})$, $N(C_3-C_6\text{-cycloalkyl})_2$, $N(C_2-C_4\text{-alkyl})(C_2-C_4\text{-alkenyl})$, $N(C_2-C_4\text{-alkyl})(C_2-C_4\text{-alkynyl})$, $N(C_2-C_4\text{-alkyl})(C_3-C_6\text{-cycloalkyl})$, $N(C_2-C_4\text{-alkenyl})(C_2-C_4\text{-alkynyl})$, $N(C_2-C_4\text{-alkenyl})(C_3-C_6\text{-cycloalkyl})$, $N(C_2-C_4\text{-alkynyl})(C_3-C_6\text{-cycloalkyl})$, $NH(C(=O)C_1-C_4\text{-alkyl})$, $N(C(=O)C_1-C_4\text{-alkyl})_2$, $NH-SO_2-R^x$, $S(O)_m-C_1-C_6\text{-alkyl}$, $S(O)_m\text{-aryl}$, $C_1-C_6\text{-cycloalkylthio}$, $S(O)_m-C_2-C_6\text{-alkenyl}$, $S(O)_m-C_2-C_6\text{-alkynyl}$, $CH(=O)$, $C(=O)C_1-C_6\text{-alkyl}$, $C(=O)C_2-C_6\text{-alkenyl}$, $C(=O)C_2-C_6\text{-alkynyl}$, $C(=O)C_3-C_6\text{-cyclpalkyl}$, $C(=O)NH(C_1-C_6\text{-alkyl})$, $C(=O)N(C_1-C_6\text{-alkyl})_2$, $C(=O)N(C_2-C_6\text{-alkenyl})_2$, $C(=O)N(C_2-C_6\text{-alkynyl})_2$, $C(=O)N(C_3-C_7\text{-cycloalkyl})_2$, $CH(=S)$, $C(=S)C_1-C_6\text{-alkyl}$, $C(=S)C_2-C_6\text{-alkenyl}$, $C(=S)C_2-C_6\text{-alkynyl}$, $C(=S)C_3-C_6\text{-cyclpalkyl}$, $C(=S)O(C_2-C_6\text{-alkenyl})$, $C(=S)O(C_2-C_6\text{-alkynyl})$, $C(=S)O(C_3-C_7\text{-cycloalkyl})$, $C(=S)NH(C_1-C_6\text{-alkyl})$, $C(=S)NH(C_2-C_6\text{-alkenyl})$, $C(=S)NH(C_2-C_6\text{-alkynyl})$, $C(=S)NH(C_3-C_7\text{-cycloalkyl})$, $C(=S)N(C_1-C_6\text{-alkyl})_2$, $C(=S)N(C_2-C_6\text{-alkenyl})_2$, $C(=S)N(C_2-C_6\text{-alkynyl})_2$, $C(=S)N(C_3-C_7\text{-cycloalkyl})_2$, $C_1-C_6\text{-alkyl}$, $C_2-C_6\text{-alkenyl}$, $C_2-C_6\text{-alkynyl}$, $OR^Y$, $C_3-C_6\text{-cycloalkyl}$, five- or six-membered heteroaryl and aryl; wherein the heteroaryl contains one, two or three heteroatoms selected from N, O and S; wherein
$R^x$ is as defined above;
$R^Y$ is as defined above;
wherein the acyclic moieties of $R^2$ are unsubstituted or substituted with groups $R^{2a}$ which independently of one another are selected from:
$R^{2a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, aryl and phenoxy, wherein the aryl and phenyl group is unsubstituted or substituted with substituents $R^{21a}$ selected from the group consisting of halogen, OH, $C_1-C_4$-alkyl, $C_1-C_4$-halogenalkyl, $C_1-C_4$-alkoxy and $C_1-C_4$-halogenalkoxy;
wherein the carbocyclic, heteroaryl and aryl moieties of $R^2$ are unsubstituted or substituted with groups $R^{2b}$ which independently of one another are selected from:
$R^{2b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy and $C_1-C_6$-alkylthio.

According to one embodiment of formula I, $R^2$ is selected from the group consisting of halogen, $C_1-C_6$-alkyl, $C_1-C_6$-halogenalkyl, $C_2-C_6$-alkenyl, $C_2-C_6$-halogenalkenyl, $C_2-C_6$-alkynyl, $C_2-C_6$-halogenalkynyl, $C_1-C_6$-alkoxy, $C_1-C_6$-halogenalkoxy and $OR^Y$.

$R^2$ is selected from the group consisting of halogen, $C_1-C_6$-alkyl, $C_1-C_6$-halogenalkyl, $C_2-C_6$-alkenyl, $C_2-C_6$-halogenalkenyl, $C_2-C_6$-alkynyl, $C_2-C_6$-halogenalkynyl, $C_1-C_6$-alkoxy, $C_1-C_6$-halogenalkoxy and $C_3-C_6$-halogencycloalkyl.

According to still another embodiment of formula I, $R^2$ is halogen, in particular F, Cl, Br or I, more specifically F, Cl or Br, in particular F or Cl.

According to still another embodiment of formula I, $R^2$ is F.

According to still another embodiment of formula I, $R^2$ is Cl.

According to still another embodiment of formula I, $R^2$ is Br.

According to still another embodiment of formula I, $R^2$ is OH.

According to still another embodiment of formula I, $R^2$ is $NO_2$.

According to still another embodiment of formula I, $R^2$ is SH.

According to still another embodiment of formula I, $R^2$ is $NH_2$.

According to still another embodiment of formula I, $R^2$ is, $NH(C_1-C_4\text{-alkyl})$, in particular $NH(CH_3)$, $NH(C_2H_5)$.

According to still another embodiment of formula I, $R^2$ is $N(C_1-C_4\text{-alkyl})_2$, in particular $NH(CH_3)_2$, $NH(C_2H_5)_2$.

According to still another embodiment of formula I, $R^2$ is $NH(C_2-C_4\text{-alkenyl})$, in particular $NH(CH=CH_2)$, $NH(CH_2CH=CH_2)$.

According to still another embodiment of formula I, $R^2$ is $N(C_2-C_4\text{-alkenyl})_2$, in particular $N(CH=CH_2)_2$, $N(CH_2CH=CH_2)_2$.

According to still another embodiment of formula I, $R^2$ is, $NH(C_2-C_4\text{-alkynyl})$, in particular $NH(C\equiv CH)$, $NH(CH_2C\equiv CH)$.

According to still another embodiment of formula I, $R^2$ is, $N(C_2-C_4\text{-alkynyl})_2$, in particular $N(C\equiv CH)_2$, $N(CH_2C\equiv CH)_2$.

According to still another embodiment of formula I, $R^2$ is, $NH(C_3-C_6\text{-cycloalkyl})$, in particular $NH(C_3H)$, $NH(C_4H_9)$.

According to still another embodiment of formula I, $R^2$ is, $N(C_3-C_6\text{-cycloalkyl})_2$, in particular $N(C_3H_7)_2$, $N(C_4H_9)_2$.

According to still another embodiment of formula I, $R^2$ is $N(C_1-C_4\text{-alkyl})(C_2-C_4\text{-alkenyl})$, in particular $N(CH_3)(CH=CH_2)$, $N(CH_3)(CH_2CH=CH_2)$, $N(C_2H_5)(CH=CH_2)$, $N(C_2H_5)(CH_2CH=CH_2)$.

According to still another embodiment of formula I, $R^2$ is $N(C_1-C_4\text{-alkyl})(C_2-C_4\text{-alkynyl})$, in particular $N(CH_3)(C\equiv CH)$, $N(CH_3)(CH_2C\equiv CH)$, $N(C_2H_5)(C\equiv CH)$, $N(C_2H_5)(CH_2C\equiv CH)$.

According to still another embodiment of formula I, $R^2$ is $N(C_1-C_4\text{-alkyl})(C_3-C_6\text{-cycloalkyl})$, in particular $N(CH_3)(C_3H_7)$, $N(CH_3)(C_4H_9)$, $N(C_2H_5)(C_3H_7)$, $N(CH_3)(C_4H_9)$.

According to still another embodiment of formula I, $R^2$ is $N(C_2-C_4\text{-alkenyl})(C_2-C_4\text{-alkynyl})$, in particular $N(CH=CH_2)(C\equiv CH)$, $N(CH_2CH=CH_2)(CH_2C\equiv CH)$, $N(CH=CH_2)(C\equiv CH)$, $N(CH_2CH=CH_2)(CH_2C\equiv CH)$.

According to still another embodiment of formula I, $R^2$ is $N(C_2-C_4\text{-alkenyl})(C_3-C_6\text{-cycloalkyl})$, in particular $N(CH=CH_2)(C_3H_7)$, $N(CH_2CH=CH_2)(C_4H_9)$, $N(CH=CH_2)(C_3H_7)$, $N(CH_2CH=CH_2)(C_4H_9)$.

According to still another embodiment of formula I, $R^2$ is $N(C_2\text{-}C_4\text{-alkynyl})(C_3\text{-}C_6\text{-cycloalkyl})$, in particular $N(C{\equiv}CH)(C_3H)$, $N(CH_2C{\equiv}CH)(C_4H_9)$, $N(C{\equiv}CH)(C_3H_7)$, $N(CH_2C{\equiv}CH)(C_4H_9)$.

According to still another embodiment of formula I, $R^2$ is, $NH(C({=}O)(C_1\text{-}C_4\text{-alkyl})$, in particular $NH(C({=}O)(CH_3))$, $NH(C({=}O)(C_2H_5))$.

According to still another embodiment of formula I, $R^2$ is $N(C({=}O)(C_1\text{-}C_4\text{-alkyl})_2$, in particular $N(C({=}O)(CH_3))_2$, $N(C({=}O)(C_2H_5))_2$.

According to a further specific embodiment of formula I, $R^2$ is $NH\text{—}SO_2\text{—}R^x$ such as $NH\text{—}SO_2\text{—}CH_3$, $NH\text{—}SO_2\text{—}CH_2\text{—}CH_3$, $NH\text{—}SO_2\text{—}CF_3$, $NH\text{—}SO_2\text{-Ts}$.

According to still another embodiment of formula I, $R^2$ is $S(O)m\text{-}C_1\text{-}C_6\text{-alkyl}$ such as $SCH_3$, $S({=}O)CH_3$, $S(O)_2CH_3$.

According to still another embodiment of formula I, $R^2$ is $S(O)m$-aryl such as S-phenyl, $S({=}O)$ phenyl, $S(O)_2$phenyl.

According to still another embodiment of formula I, $R^2$ is $S(O)m\text{-}C_2\text{-}C_6\text{-alkenyl}$ such as $SCH{=}CH_2$, $S({=}O)CH{=}CH_2$, $S(O)_2CH{=}CH_2$, $SCH_2CH{=}CH_2$, $S({=}O)CH_2CH{=}CH_2$, $S(O)_2CH_2CH{=}CH_2$.

According to still another embodiment of formula I, $R^2$ is $S(O)m\text{-}C_2\text{-}C_6\text{-alkynyl}$ such as $SC{\equiv}CH$, $S({=}O)C{\equiv}CH$, $S(O)_2C{\equiv}CH$, $SCH_2C{\equiv}CH$, $S({=}O)CH_2C{\equiv}CH$, $S(O)_2CH_2C{\equiv}CH$.

According to a further specific embodiment of formula I, $R^2$ is $CH({=}O)$.

According to a further specific embodiment of formula I, $R^2$ is $C({=}O)C_1\text{-}C_6\text{-alkyl}$, $C({=}O)O(C_1\text{-}C_6\text{-alkyl})$, $C({=}O)NH(C_1\text{-}C_6\text{-alkyl})$ or $C({=}O)N(C_1\text{-}C_6\text{-alkyl})_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $R^2$ is $C({=}O)C_2\text{-}C_6\text{-alkenyl}$, $C({=}O)O(C_2\text{-}C_6\text{-alkenyl})$, $C({=}O)NH(C_2\text{-}C_6\text{-alkenyl})$ or $C({=}O)N(C_2\text{-}C_6\text{-alkenyl})_2$, wherein alkenyl is $CH{=}CH_2$, $C(CH_3){=}CH_2$, $CH_2CH{=}CH_2$.

According to a further specific embodiment of formula I, $R^2$ is $C({=}O)C_2\text{-}C_6\text{-alkynyl}$, $C({=}O)O(C_2\text{-}C_6\text{-alkynyl})$, $C({=}O)NH(C_2\text{-}C_6\text{-alkynyl})$ or $C({=}O)N(C_2\text{-}C_6\text{-alkynyl})_2$), wherein alkynyl is $C{\equiv}CH$, $CH_2C{\equiv}CH$, According to a further specific embodiment of formula I, $R^2$ is $C({=}O)C_3\text{-}C_6\text{-cycloalkyl}$, $C({=}O)O(C_3\text{-}C_6\text{-cycloalkyl})$, $C({=}O)NH(C_3\text{-}C_6\text{-cycloalkyl})$ or $C({=}O)N(C_3\text{-}C_7\text{-cycloalkyl})_2$, wherein cycloalkyl is cyclopropyl $(C_3H_7)$ or cyclobutyl $(C_4H_9)$.

According to a further specific embodiment of formula I, $R^2$ is $CH({=}S)$.

According to a further specific embodiment of formula I, $R^2$ is $C({=}S)C_1\text{-}C_6\text{-alkyl}$, $C({=}S)OC_1\text{-}C_6\text{-alkyl}$, $C({=}S)NH(C_1\text{-}C_6\text{-alkyl})$ or $C({=}S)NH(C_1\text{-}C_6\text{-alkyl})$, wherein alkyl is $CH_3$, $C_2H$, n-propyl, i-propyl, n-butyl, i-butyl, tert-butyl, n-pentyl or i-pentyl.

According to a further specific embodiment of formula I, $R^2$ is $C({=}S)C_2\text{-}C_6\text{-alkenyl}$, $C({=}S)OC_2\text{-}C_6\text{-alkenyl}$, $C({=}S)NH(C_2\text{-}C_6\text{-alkenyl})$ or $C({=}S)N(C_2\text{-}C_6\text{-alkenyl})_2$, wherein alkenyl is $CH{=}CH_2$, $CH_2CH{=}CH_2$.

According to a further specific embodiment of formula I, $R^2$ is $C({=}S)C_2\text{-}C_6\text{-alkynyl}$, $C({=}S)O(C_2\text{-}C_6\text{-alkynyl})$, $C({=}S)NH(C_2\text{-}C_6\text{-alkynyl})$ or $C({=}S)N(C_2\text{-}C_6\text{-alkynyl})$, wherein alkynyl is $C{\equiv}CH$, $CH_2C{\equiv}CH$.

According to a further specific embodiment of formula I, $R^2$ is $C({=}S)C_3\text{-}C_6\text{-cycloalkyl}$, $C({=}S)O(C_3\text{-}C_7\text{-cycloalkyl})$, $C({=}S)NH(C_3\text{-}C_7\text{-cycloalkyl})$ or $C({=}S)N(C_3\text{-}C_7\text{-cycloalkyl})_2$, wherein cycloalkyl is cyclopropyl $(C_3H_7)$ or cyclobutyl $(C_4H_9)$.

According to still another embodiment of formula I, $R^2$ is $C_1\text{-}C_6\text{-alkyl}$, in particular $C_1\text{-}C_4\text{-alkyl}$, such as $CH_3$. or $C_2H_5$, in particular $CH_3$ or $CH_2CH_3$.

According to still another embodiment of formula I, $R^2$ is $C_1\text{-}C_6\text{-halogenalkyl}$, in particular $C_1\text{-}C_4\text{-halogenalkyl}$, such as $CF_3$, $CCl_3$, $FCH_2$, $ClCH_2$, $F_2CH$, $C_2CH$, $CF_3CH_2$, $CCl_3CH_2$ or $CF_2CHF_2$.

According to still a further embodiment of formula I, $R^2$ is $C_2\text{-}C_6\text{-alkenyl}$, in particular $C_2\text{-}C_4\text{-alkenyl}$, such as $CH{=}CH_2$.

According to a further embodiment of formula I, $R^2$ is $C_2\text{-}C_6\text{-halogenalkenyl}$, in particular $C_2\text{-}C_4\text{-halogenalkenyl}$, more specifically $C_2\text{-}C_3\text{-halogenalkenyl}$ such as $CH{=}CHF$, $CH{=}CHCl$, $CH{=}CF_2$, $CH{=}CCl_2$, $CH_2CH{=}CHF$, $CH_2CH{=}CHCl$, $CH_2CH{=}CF_2$, $CH_2CH{=}CCl_2$, $CF_2CH{=}CF_2$, $CCl_2CH{=}CCl_2$, $CF_2CF{=}CF_2$, $CCl_2CCl{=}CCl_2$.

According to still a further embodiment of formula I, $R^2$ is $C_2\text{-}C_6\text{-alkynyl}$ or $C_2\text{-}C_6\text{-halogenalkynyl}$, in particular $C_2\text{-}C_4\text{-alkynyl}$ or $C_2\text{-}C_4\text{-halogenalkynyl}$, such as $C{\equiv}CH$, $CH_2$, $C{\equiv}CH$, $C{\equiv}CCl$, $CH_2C{\equiv}CCl$, or $CCl_2C{\equiv}CCl$.

According to a further specific embodiment of formula I, $R^2$ is $OR$ wherein $R$ is $C_1\text{-}C_6\text{-alkyl}$, $C_1\text{-}C_6\text{-halogenalkyl}$, $C_2\text{-}C_6\text{-alkenyl}$, $C_2\text{-}C_6\text{-halogenalkenyl}$, $C_2\text{-}C_6\text{-alkynyl}$, $C_2\text{-}C_6\text{-halogenalkynyl}$, $C_3\text{-}C_6\text{-cycloalkyl}$, $C_3\text{-}C_6\text{-halogencycloalkyl}$.

According to a further specific embodiment of formula I, $R^2$ is $OR$ wherein $R$ is $C_1\text{-}C_6\text{-alkyl}$, in particular $C_1\text{-}C_4\text{-alkyl}$, more specifically $C_1\text{-}C_2\text{-alkoxy}$. $R^2$ is such as $OCH_3$ or $OCH_2CH_3$.

According to a further specific embodiment of formula I, $R^2$ is $OR$ wherein $R$ is $C_1\text{-}C_6\text{-halogenalkyl}$, in particular $C_1\text{-}C_4\text{-halogenalkyl}$, more specifically $C_1\text{-}C_2\text{-halogenalkyl}$. $R^2$ is such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment of formula I, $R^2$ is $OR$ wherein $R$ $C_2\text{-}C_6\text{-alkenyl}$, in particular $C_2\text{-}C_4\text{-alkenyl}$, more specifically $C_1\text{-}C_2\text{-alkenyl}$. $R^2$ is such as $OCH{=}CH_2$, $OCH_2CH{=}CH_2$.

According to a further specific embodiment of formula I, $R^2$ is $OR$ wherein $R$ $C_2\text{-}C_6\text{-alkynyl}$, in particular $C_2\text{-}C_6\text{-alkynyl}$, in particular $C_2\text{-}C_4\text{-alkynyl}$, more specifically $C_1\text{-}C_2\text{-alkynyl}$. $R^2$ is such as $OC{\equiv}CH$, $OC{\equiv}CCl$, $OCH_2C{\equiv}CCl$, or $OCCl_2C{\equiv}CCl$ According to still another embodiment of formula $R^2$ is $OR$ wherein $R$ is $C_3\text{-}C_6\text{-cycloalkyl}$, in particular cyclopropyl.

According to still another embodiment of formula I, $R^2$ is $OR^Y$ wherein $R^Y$ is $C_3\text{-}C_6\text{-halogencycloalkyl}$. In a special embodiment $R^1$ is fully or partially halogenated cyclopropyl.

According to still another embodiment of formula I, $R^2$ is $OR$ wherein $R$ $C_3\text{-}C_6\text{-cycloalkenyl}$, in particular cyclopropenyl.

According to still another embodiment of formula I, $R^2$ is $C_3\text{-}C_6\text{-cycloalkyl}$, in particular cyclopropyl.

According to still another embodiment of formula I, $R^2$ is $C_3\text{-}C_6\text{-halogencycloalkyl}$. In a special embodiment $R^{2b}$ is fully or partially halogenated cyclopropyl, such as 1-F-cyclopropyl, 1-Cl-cyclopropyl, 1,1-$F_2$-cyclopropyl, 1,1-$Cl_2$-cyclopropyl According to still another embodiment of formula I, $R^2$ is phenyl-$C_1\text{-}C_6\text{-alkyl}$, such as phenyl-$CH_2$, wherein the phenyl moiety in each case is unsubstituted or substituted by one, two or three identical or different groups $R^{2b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, Cl, Br, $CH_3$, $OCH_3$, $CF_3$ and $OCF_3$.

According to still another embodiment of formula I, $R^2$ is aryl, in particular phenyl, wherein the aryl or phenyl moiety in each case is unsubstituted or substituted with identical or different groups $R^{2b}$ which independently of one another are selected from CN, halogen, $C_1$-$C_2$-alkyl, $C_1$-$C_2$-alkoxy, $C_1$-$C_2$-halogenalkyl and $C_1$-$C_2$-halogenalkoxy, in particular CN, F, C, Br, $CH_3$, $OCH_3$, $CHF_2$, $OCHF_2$, $CF_3$ and $OCF_3$. According to one embodiment, $R^2$ is unsubstituted phenyl. According to another embodiment, $R^2$ is phenyl, that is substituted with one, two or three, in particular one, halogen, in particular selected from F, Cl and Br, more specifically selected from F and Cl.

According to still another embodiment of formula I, $R^2$ is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $R^9$ is a 6-membered heteroaryl such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to still another embodiment of formula I, $R^2$ is in each case independently selected from halogen, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl and $C_3$-$C_6$-halogencycloalkyl, wherein the acyclic moieties of $R^2$ are unsubstituted or substituted with identical or different groups $R^{2a}$ as defined and preferably defined herein, and wherein the carbocyclic, phenyl and heteroaryl moieties of $R^2$ are unsubstituted or substituted with identical or different groups $R^{2b}$ as defined and preferably defined herein.

According to still another embodiment of formula I, $R^2$ is in each case independently selected from halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy; wherein the acyclic moieties of $R^2$ are unsubstituted or substituted with identical or different groups $R^{2a}$ as defined and preferably defined herein.

According to still another embodiment of formula I, $R^2$ is in each case independently selected from CN, halogen, $C_1$-$C_6$-alkyl, $C_1$-$C_6$-halogenalkyl, $C_2$-$C_6$-alkynyl, $OR^Y$, $C_3$-$C_6$-cycloalkyl; wherein $R^Y$ is $C_1$-$C_6$-alkyl, $C_1$-$C_6$-halogenalkyl, $C_2$-$C_6$-alkenyl or $C_2$-$C_6$-alkynyl.

$R^{2a}$ are the possible substituents for the acyclic moieties of $R^2$.

According to one embodiment $R^{2a}$ is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, aryl and phenoxy, wherein the aryl and phenyl group is unsubstituted or substituted with substituents $R^{21a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to one embodiment $R^{2a}$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $R^{2a}$ is independently selected from F, C, Br, I, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to still another embodiment of formula I, $R^{2a}$ is independently halogen, in particular selected from F, Cl, Br and I, more specifically F, Cl and Br.

$R^2$ are the possible substituents for the carbocyclic, heteroaryl and phenyl moieties of $R^2$. $R^{2b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment thereof $R^{2b}$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, $R^{2b}$ is independently selected from F, Cl, CN, $CH_3$, $OCH_3$ and halogenmethoxy.

Particularly preferred embodiments of $R^2$ according to the invention are in Table P2 below, wherein each line of lines P2-1 to P2-41 corresponds to one particular embodiment of the invention, wherein P2-1 to P2-41 are also in any combination with one another a preferred embodiment of the present invention. The connection point to the carbon atom, to which $R^2$ is bound is marked with "#" in the drawings.

TABLE P2

| No. | $R^1$ |
|---|---|
| P2-1 | $CH_3$ |
| P2-2 | $CH_2F$ |
| P2-3 | $CHF_2$ |
| P2-4 | $CF_3$ |
| P2-5 | $C_2H_5$ |
| P2-6 | $CH(CH_3)_2$ |
| P2-7 | $CH_2CH_2CH_3$ |
| P2-8 | $CH_2CH_2CH_2CH_3$ |
| P2-9 | $CH_2CH(CH_3)_2$ |
| P2-10 | $C(CH_3)_3$ |
| P2-11 | $CH_2CH_2CH_2CH_2CH_3$ |
| P2-12 | $CH=CH_2$ |
| P2-13 | $CH_2CH=CH_2$ |
| P2-14 | $C\equiv CH$ |
| P2-15 | $CH_2C\equiv CH$ |
| P2-16 | $CH_2CH_2CH(CH_3)_2$ |
| P2-17 | OH |
| P2-18 | $OCH_3$ |
| P2-19 | $OCHF_2$ |
| P2-20 | $OC_2H_5$ |
| P2-21 | F |
| P2-22 | Cl |
| P2-23 | Br |
| P2-24 | $NO_2$ |
| P2-25 | $NH_2$ |
| P2-26 | CO—$NH_2$ |
| P2-27 | CO—NH($CH_3$) |
| P2-28 | CO—N($CH_3$)$_2$ |
| P2-29 | HN$CH_3$ |
| P2-30 | HN$C_2H_5$ |
| P2-31 | $(CH_3)_2$N |
| P2-32 | $SO_2$H |
| P2-33 | $SO_2$—$CH_3$ |
| P2-34 | SO—$CH_3$ |
| P2-35 | S—$CH_3$ |
| P2-36 | #—△ |
| P2-37 | #—◇ |

TABLE P2-continued

| No. | $R^1$ |
|---|---|
| P2-38 | #—cyclopentyl |
| P2-39 | #—cyclohexyl |
| P2-40 | #—phenyl |
| P2-41 | #—pyridin-4-yl |

U according to the invention is N or $CR^3$.

According to one embodiment of formula I, U is N.

According to another embodiment of formula I, U is $CR^3$.

$R^3$ according to the invention is in each case independently selected from hydrogen, halogen, OH, CN, $NO_2$, SH, $NH_2$, $NH(C_1-C_4$-alkyl), $N(C_1-C_4$-alkyl$)_2$, $NH-SO_2-R^x$, $C_1-C_6$-alkyl, $C_2-C_6$-alkenyl, $C_2-C_6$-alkynyl, $C_1-C_6$-alkoxy, $C_3-C_6$-cycloalkyl, five- or six-membered heteroaryl and aryl; wherein the heteroaryl contains one, two or three heteroatoms selected from N, O and S; and wherein $R^x$ is $C_1-C_4$-alkyl, $C_1-C_4$-halogenalkyl, unsubstituted aryl or aryl that is substituted with one, two, three, four or five substituents $R^{x3}$ independently selected from $C_1-C_4$-alkyl, halogen, OH, CN, $C_1-C_4$-halogenalkyl, $C_1-C_4$-alkoxy and $C_1-C_4$-halogenalkoxy;

wherein the acyclic moieties of $R^3$ are unsubstituted or substituted with identical or different groups $R^{3a}$ which independently of one another are selected from:

$R^{3a}$ halogen, OH, CN, $C_1-C_6$-alkoxy, $C_3-C_6$-cycloalkyl, $C_3-C_6$-halogencycloalky, $C_1-C_4$-halogenalkoxy, $C_1-C_6$-alkylthio, aryl and phenoxy, wherein the aryl and phenoxy group is unsubstituted or substituted with $R^{31a}$ selected from the group consisting of halogen, OH, $C_1-C_4$-alkyl, $C_1-C_4$-halogenalkyl, $C_1-C_4$-alkoxy and $C_1-C_4$-halogenalkoxy;

wherein the carbocyclic, heteroaryl and aryl moieties of $R^3$ are unsubstituted or substituted with identical or different groups $R^{3b}$ which independently of one another are selected from:

$R^{3b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalky, $C_1-C_4$-halogenalkoxy and $C_1-C_6$-alkylthio.

For every $R^3$ that is present in the inventive compounds, the following embodiments and preferences apply independently of the meaning of the other $R^3$ that may be present in the ring.

According to one embodiment of formula I, $R^3$ is H, halogen or $C_1-C_6$-alkyl, in particular H, $CH_3$, Et, F, C, more specifically H, $CH_3$, F or Cl most preferred H, F or Cl.

According to another of formula I, $R^3$ is halogen, in particular Br, F or C, more specifically F or Cl.

According to another embodiment of formula I, $R^3$ is F

According to another embodiment of formula I, $R^3$ is Cl

According to another embodiment of formula I, $R^3$ is Br.

According to still another embodiment of formula I, $R^3$ is hydrogen.

According to still another embodiment of formula I, $R^3$ is OH.

According to still another embodiment of formula I, $R^3$ is CN.

According to still another embodiment of formula I, $R^3$ is $NO_2$.

According to still another embodiment of formula I, $R^3$ is SH.

In a further specific embodiment $R^3$ is $NH_2$, $NH(C_1-C_4$-alkyl), $N(C_1-C_4$-alkyl$)_2$ or $NH-SO_2-R^x$, wherein $R^x$ is $C_1-C_4$-alkyl, $C_1-C_4$-halogenalkyl, unsubstituted phenoxy or aryl that is substituted with one, two, three, four or five substituents $R^{x3}$ independently selected from $C_1-C_4$-alkyl, halogen, OH, CN, $C_1-C_4$-halogenalkyl, $C_1-C_4$-alkoxy, or $C_1-C_4$-halogenalkoxy. In particular $C_1-C_4$-alkyl, such as $NHCH_3$ and $N(CH_3)_2$. In particular $R^x$ is $C_1-C_4$-alkyl, and phenyl that is substituted with one $CH_3$, more specifically $SO_2-R^x$ is $CH_3$ and tosyl group ("Ts").

According to still another embodiment of formula I, $R^3$ is $C_1-C_6$-alkyl, in particular $C_1-C_4$-alkyl, such as $CH_3$ or $CH_2CH_3$.

According to still another embodiment of formula I, $R^3$ is $C_1-C_6$-halogenalkyl, in particular $C_1-C_4$-halogenalkyl, such as $CF_3$, $CHF_2$, $CH_2F$, $CCl_3$, $CHCl_2$, $CH_2Cl$, $CF_3CH_2$, $CCl_3CH_2$ or $CF_2CHF_2$.

According to still a further embodiment, $R^3$ is $C_2-C_6$-alkenyl or $C_2-C_6$-halogenalkenyl, in particular $C_2-C_4$-alkenyl or $C_2-C_4$-halogenalkenyl, such as $CH=CH_2$, $CH=CCl_2$, $CH=CF_2$, $CCl=CCl_2$, $CF=CF_2$, $CH=CH_2$, $CH_2CH=CCl_2$, $CH_2CH=CF_2$, $CH_2CCl=CCl_2$, $CH_2CF=CF_2$, $CCl_2CH=CCl_2$, $CF_2CH=CF_2$, $CCl_2CCl=CCl_2$, or $CF_2CF=CF_2$.

According to still a further embodiment, $R^3$ is $C_2-C_6$-alkynyl or $C_2-C_6$-halogenalkynyl, in particular $C_2-C_4$-alkynyl or $C_2-C_4$-halogenalkynyl, such as $C\equiv CH$, $C\equiv CCl$, $C\equiv CF$, $CH_2C\equiv CH$, $CH_2C\equiv CCl$, or $CH_2C\equiv CF$.

According to still another embodiment of formula I, $R^3$ is $C_1-C_6$-alkoxy, in particular $C_1-C_4$-alkoxy, more specifically $C_1-C_2$-alkoxy such as $OCH_3$ or $OCH_2CH_3$.

According to still another embodiment of formula I, $R^3$ is $C_1-C_6$-halogenalkoxy, in particular $C_1-C_4$-halogenalkoxy, more specifically $C_1-C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

In a further specific embodiment $R^3$ is $C_3-C_6$-cycloalkyl, in particular cyclopropyl.

In a further specific embodiment, $R^3$ is $C_3-C_6$-cycloalkyl, for example cyclopropyl, substituted with one, two, three or up to the maximum possible number of identical or different groups $R^{3b}$ as defined and preferably herein.

According to still another embodiment of formula I, $R^3$ is $C_3-C_6$-halogencycloalkyl. In a special embodiment $R^3$ is fully or partially halogenated cyclopropyl.

According to still another embodiment of formula I, $R^3$ is unsubstituted aryl or aryl that is substituted with one, two, three or four $R^{3b}$, as defined herein. In particular, $R^3$ is unsubstituted phenyl or phenyl that is substituted with one, two, three or four $R^{3b}$, as defined herein.

According to still another embodiment of formula I, $R^3$ is unsubstituted 5- or 6-membered heteroaryl. According to still a further embodiment, $R^3$ is 5- or 6-membered heteroaryl that is substituted with one, two or three $R^{3b}$, as defined herein.

According to still another embodiment of formula I, $R^3$ is in each case independently selected from hydrogen, halogen, OH, CN, $NO_2$, SH, $NH_2$, $NH(C_1-C_4$-alkyl), $N(C_1-C_4$-alkyl$)_2$, $NH-SO_2-R^x$, $C_1-C_6$-alkyl, $C_2-C_6$-alkenyl, $C_2-C_6$- alkynyl, $C_1$-$C_6$-alkoxy and $C_3$-$C_6$-cycloalkyl; wherein the acyclic moieties of $R^3$ are not further substituted or carry one, two, three, four or five identical or different groups $R^{3a}$ as defined below and wherein the cycloalkyl moieties of $R^3$ are not further substituted or carry one, two, three, four or five identical or different groups $R^{3b}$ as defined below.

According to still another embodiment of formula I, $R^3$ is independently selected from hydrogen, halogen, CN, OH, $C_1$-$C_6$-alkyl, $C_1$-$C_6$-alkoxy, $C_6$-alkenyl, $C_2$-$C_6$-alkynyl, $C_3$-$C_6$-cycloalkyl, wherein the acyclic and cyclic moieties of $R^3$ are unsubstituted or substituted by halogen.

According to still another embodiment of formula I, $R^3$ is independently selected from hydrogen, halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from H, F, C, Br, CN, OH, $C_1$-$C_4$-alkyl, $C_1$-$C_4$-halogenalkyl, $C_1$-$C_4$-alkoxy and $C_1$-$C_4$-halogenalkoxy.

According to still another embodiment of formula I, $R^3$ is independently selected from H, CN, halogen or $C_1$-$C_6$-alkyl, in particular H, CN, $CH_3$, Et, F, Cl, more specifically H, CN, $CH_3$, F or C most preferred H, $CH_3$, F or Cl.

$R^{3a}$ are the possible substituents for the acyclic moieties of $R^3$.

$R^{3a}$ according to the invention is independently selected from halogen, OH, CN, $C_1$-$C_6$-alkoxy, $C_3$-$C_6$-cycloalkyl, $C_3$-$C_6$-halogencycloalky, $C_1$-$C_4$-halogenalkoxy, $C_1$-$C_6$-alkylthio, aryl and phenoxy, wherein the aryl and phenoxy group is unsubstituted or substituted with $R^{33a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $R^{3a}$ is independently selected from halogen, OH, CN, $C_1$-$C_2$-alkoxy, $C_3$-$C_6$-cycloalkyl, $C_3$-$C_6$-halogencycloalky and $C_1$-$C_2$-halogenalkoxy. Specifically, $R^{3a}$ is independently selected from F, C, OH, CN, $C_1$-$C_2$-alkoxy, cyclopropyl, 1-F-cyclopropyl, 1-Cl-cyclopropyl, 1,1-$F_2$-cyclopropyl, 1,1-$C_2$-cyclopropyl and $C_1$-$C_2$-halogenalkoxy.

According to one embodiment $R^{3a}$ is independently selected from halogen, such as F, Cl, Br and I, more specifically F, Cl and Br.

According to still another embodiment of formula I, $R^{3a}$ is independently selected from OH, $C_3$-$C_6$-cycloalkyl, $C_3$-$C_6$-halogencycloalky and $C_1$-$C_2$-halogenalkoxy. Specifically, $R^{3a}$ is independently selected from OH, cyclopropyl and $C_1$-$C_2$-halogenalkoxy.

According to still another embodiment of formula I, $R^{3a}$ is independently selected from aryl and phenoxy, wherein the aryl and phenoxy group is unsubstituted or substituted with $R^{33a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

$R^{3b}$ are the possible substituents for the carbocyclic, heteroaryl and aryl moieties of $R^3$.

$R^{3b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalky, $C_1$-$C_4$-halogenalkoxy and $C_1$-$C_6$-alkylthio;

According to one embodiment thereof $R^{3b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{3b}$ is independently selected from F, C, Br, OH, CN, $CH_3$, $OCH_3$, $CHF_2$, $OCHF_2$, cyclopropyl, 1-F-cyclopropyl, 1-Cl-cyclopropyl 1,1-$F_2$-cyclopropyl, 1,1-$CO_2$-cyclopropyl, $OCF_3$, and $OCHF_2$.

According to still another embodiment thereof $R^{3b}$ is independently selected from halogen, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^3$ is independently selected from halogen, OH, $CH_3$, $OCH_3$, CN, $CHF_2$, $OCHF_2$, $OCF_3$, $OCH_3$, cyclopropyl, 1-F-cyclopropyl, 1-Cl-cyclopropyl, 1,1-$F_2$-cyclopropyl, 1,1-$Cl_2$-cyclopropyl and halogenmethoxy, more specifically independently selected from F, C, OH, $CH_3$, $OCH_3$, $CHF_2$, $OCH_3$, cyclopropyl, 1-F-cyclopropyl, 1-Cl-cyclopropyl, 1,1-$F_2$-cyclopropyl, 1,1-$C_2$-cyclopropyl, $OCHF_2$ and $OCF_3$.

Particularly preferred embodiments of $R^3$ according to the invention are in Table P3 below, wherein each line of lines P3-1 to P3-16 corresponds to one particular embodiment of the invention. Thereby, for every $R^3$ that is present in the inventive compounds, these specific embodiments and preferences apply independently of the meaning of any other $R^3$ that may be present in the ring:

TABLE P3

| No. | $R^3$ |
|---|---|
| P3-1 | H |
| P3-2 | Cl |
| P3-3 | F |
| P3-4 | Br |
| P3-5 | OH |
| P3-6 | CN |
| P3-7 | $NO_2$ |
| P3-8 | $CH_3$ |
| P3-9 | $CH_2CH_3$ |
| P3-10 | $CF_3$ |
| P3-11 | $CHF_2$ |
| P3-12 | $OCH_3$ |
| P3-13 | $OCH_2CH_3$ |
| P3-14 | $OCF_3$ |
| P3-15 | $OCHF_2$ |
| P3-16 | NH-Ts |

$R^4$ according to the invention is in each case independently selected from hydrogen, halogen, OH, CN, $NO_2$, SH, $NH_2$, $NH(C_1$-$C_4$-alkyl), $N(C_1$-$C_4$-alkyl)$_2$, NH—$SO_2$—$R^x$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; and wherein $R^x$ is $C_1$-$C_4$-alkyl, $C_1$-$C_4$-halogenalkyl, unsubstituted aryl or aryl that is substituted with one, two, three, four or five substituents $R^{x4}$ independently selected from $C_1$-$C_4$-alkyl, halogen, OH, CN, $C_1$-$C_4$-halogenalkyl, $C_1$-$C_4$-alkoxy and $C_1$-$C_4$-halogenalkoxy;

wherein the acyclic moieties of $R^4$ are unsubstituted or substituted with identical or different groups $R^{4a}$ which independently of one another are selected from:

$R^{4a}$ halogen, OH, CN, $C_1$-$C_6$-alkoxy, $C_3$-$C_6$-cycloalkyl, $C_3$-$C_6$-halogencycloalky, $C_1$-$C_4$-halogenalkoxy, $C_1$-$C_6$-alkylthio, aryl and phenoxy, wherein the aryl and phenoxy group is unsubstituted or substituted with $R^{41a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the carbocyclic, heteroaryl and aryl moieties of $R^4$ are unsubstituted or substituted with identical or different groups $R^{4b}$ which independently of one another are selected from:

$R^{4b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalky, $C_1$-$C_4$-halogenalkoxy and $C_1$-$C_6$-alkylthio.

For every $R^4$ that is present in the inventive compounds, the following embodiments and preferences apply independently of the meaning of the other $R^4$ that may be present in the ring.

According to one embodiment of formula I, $R^4$ is H, halogen or $C_1$-$C_6$-alkyl, in particular H, $CH_3$, Et, F, C, more specifically H, $CH_3$, F or Cl most preferred H, F or Cl.

According to another of formula I, $R^4$ is halogen, in particular Br, F or C, more specifically F or Cl.

According to another embodiment of formula I, $R^4$ is F

According to another embodiment of formula I, $R^4$ is Cl

According to another embodiment of formula I, $R^4$ is Br.

According to still another embodiment of formula I, $R^4$ is hydrogen.

According to still another embodiment of formula I, $R^4$ is OH.

According to still another embodiment of formula I, $R^4$ is CN.

According to still another embodiment of formula I, $R^4$ is $NO_2$.

According to still another embodiment of formula I, $R^4$ is SH.

In a further specific embodiment $R^4$ is $NH_2$, $NH_2$, $NH(C_1$-$C_4$-alkyl), $N(C_1$-$C_4$-alkyl)$_2$ or $NH$—$SO_2$—$R^x$, wherein $R^x$ is $C_1$-$C_4$-alkyl, $C_1$-$C_4$-halogenalkyl, unsubstituted phenoxy or aryl that is substituted with one, two, three, four or five substituents $R^{x4}$ independently selected from $C_1$-$C_4$-alkyl, halogen, OH, CN, $C_1$-$C_4$-halogenalkyl, $C_1$-$C_4$-alkoxy, or $C_1$-$C_4$-halogenalkoxy. In particular $C_1$-$C_4$-alkyl, such as $NHCH_3$ and $N(CH_3)_2$. In particular $R^x$ is $C_1$-$C_4$-alkyl, and phenyl that is substituted with one $CH_3$, more specifically $SO_2$—$R^x$ is $CH_3$ and tosyl group ("Ts").

According to still another embodiment of formula I, $R^4$ is $C_1$-$C_6$-alkyl, in particular $C_1$-$C_4$-alkyl, such as $CH_3$ or $CH_2CH_3$.

According to still another embodiment of formula I, $R^4$ is $C_1$-$C_6$-halogenalkyl, in particular $C_1$-$C_4$-halogenalkyl, such as $CF_3$, $CHF_2$, $CH_2F$, $CCl_3$, $CHCl_2$, $CH_2Cl$, $CF_3CH_2$, $CCl_3CH_2$ or $CF_2CHF_2$.

According to still a further embodiment, $R^4$ is $C_2$-$C_6$-alkenyl or $C_2$-$C_6$-halogenalkenyl, in particular $C_2$-$C_4$-alkenyl or $C_2$-$C_4$-halogenalkenyl, such as $CH$=$CH_2$, $CH$=$CCl_2$, $CH$=$CF_2$, $CCl$=$CCl_2$, $CF$=$CF_2$, $CH$=$CH_2$, $CH_2CH$=$CCl_2$, $CH_2CH$=$CF_2$, $CH_2CCl$=$CCl_2$, $CH_2CF$=$CF_2$, $CCl_2CH$=$CCl_2$, $CF_2CH$=$CF_2$, $CCl_2CCl$=$CCl_2$, or $CF_2CF$=$CF_2$.

According to still a further embodiment, $R^4$ is $C_2$-$C_6$-alkynyl or $C_2$-$C_6$-halogenalkynyl, in particular $C_2$-$C_4$-alkynyl or $C_2$-$C_4$-halogenalkynyl, such as $C$≡$CH$, $C$≡$CCl$, $C$≡$CF$. $CH_2C$≡$CH$, $CH_2C$≡$CCl$, or $CH_2C$≡$CF$.

According to still another embodiment of formula I, $R^4$ is $C_1$-$C_6$-alkoxy, in particular $C_1$-$C_4$-alkoxy, more specifically $C_1$-$C_2$-alkoxy such as $OCH_3$ or $OCH_2CH_3$.

According to still another embodiment of formula I, $R^4$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

In a further specific embodiment $R^4$ is $C_3$-$C_6$-cycloalkyl, in particular cyclopropyl.

In a further specific embodiment, $R^4$ is $C_3$-$C_6$-cycloalkyl, for example cyclopropyl, substituted with one, two, three or up to the maximum possible number of identical or different groups $R^{4b}$ as defined and preferably herein.

According to still another embodiment of formula I, $R^4$ is $C_3$-$C_6$-halogencycloalkyl. In a special embodiment $R^4$ is fully or partially halogenated cyclopropyl.

According to still another embodiment of formula I, $R^4$ is unsubstituted aryl or aryl that is substituted with one, two, three or four $R^{4b}$, as defined herein. In particular, $R^4$ is unsubstituted phenyl or phenyl that is substituted with one, two, three or four $R^{4b}$, as defined herein.

According to still another embodiment of formula I, $R^4$ is unsubstituted 5- or 6-membered heteroaryl. According to still a further embodiment, $R^4$ is 5- or 6-membered heteroaryl that is substituted with one, two or three $R^{4b}$, as defined herein.

According to still another embodiment of formula I, $R^4$ is in each case independently selected from hydrogen, halogen, OH, CN, $NO_2$, SH, $NH_2$, $NH(C_1$-$C_4$-alkyl), $N(C_1$-$C_4$-alkyl)$_2$, $NH$—$SO_2$—$R^x$, $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl; wherein the acyclic moieties of $R^4$ are not further substituted or carry one, two, three, four or five identical or different groups $R^4$ as defined below and wherein the cycloalkyl moieties of $R^4$ are not further substituted or carry one, two, three, four or five identical or different groups $R^{4b}$ as defined below.

According to still another embodiment of formula I, $R^4$ is independently selected from hydrogen, halogen, CN, OH, $C_1$-$C_6$-alkyl, $C_1$-$C_6$-alkoxy, $C_6$-alkenyl, $C_2$-$C_6$-alkynyl, $C_3$-$C_6$-cycloalkyl, wherein the acyclic and cyclic moieties of $R^4$ are unsubstituted or substituted by halogen.

According to still another embodiment of formula I, $R^4$ is independently selected from hydrogen, halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from H, F, Cl, Br, CN, OH, $C_1$-$C_4$-alkyl, $C_1$-$C_4$-halogenalkyl, $C_1$-$C_4$-alkoxy and $C_1$-$C_4$-halogenalkoxy.

According to still another embodiment of formula I, $R^4$ is independently selected from H, CN, halogen or $C_1$-$C_6$-alkyl, in particular H, CN, $CH_3$, Et, F, Cl, more specifically H, CN, $CH_3$, F or C most preferred H, $CH_3$, F or Cl.

$R^{4a}$ are the possible substituents for the acyclic moieties of $R^4$.

$R^{4a}$ according to the invention is independently selected from halogen, OH, CN, $C_1$-$C_6$-alkoxy, $C_3$-$C_6$-cycloalkyl, $C_3$-$C_6$-halogencycloalky, $C_1$-$C_4$-halogenalkoxy, $C_1$-$C_6$-alkylthio, aryl and phenoxy, wherein the aryl and phenoxy group is unsubstituted or substituted with $R^{44a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $R^{4a}$ is independently selected from halogen, OH, CN, $C_1$-$C_2$-alkoxy, $C_3$-$C_6$-cycloalkyl, $C_3$-$C_6$-halogencycloalky and $C_1$-$C_2$-halogenalkoxy. Specifically, $R^{4a}$ is independently selected from F, C, OH, CN, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to one embodiment $R^{4a}$ is independently selected from halogen, such as F, Cl, Br and I, more specifically F, Cl and Br.

According to still another embodiment of formula I, $R^{4a}$ is independently selected from OH, $C_3$-$C_6$-cycloalkyl, $C_3$-$C_6$-halogencycloalky and $C_1$-$C_2$-halogenalkoxy. Specifically, $R^{4a}$ is independently selected from OH, cyclopropyl and $C_1$-$C_2$-halogenalkoxy.

According to still another embodiment of formula I, $R^{4a}$ is independently selected from aryl and phenoxy, wherein the aryl and phenoxy group is unsubstituted or substituted with $R^{44a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

$R^{4b}$ are the possible substituents for the carbocyclic, heteroaryl and aryl moieties of $R^4$.

$R^4$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalky, $C_1$-$C_4$-halogenalkoxy and $C_1$-$C_6$-alkylthio;

According to one embodiment thereof $R^4$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^4$ is independently selected from F, C, Br, OH, CN, $CH_3$, $OCH_3$, $CHF_2$, $OCHF_2$, cyclopropyl, 1-F-cyclopropyl, 1-Cl-cyclopropyl 1,1-$F_2$-cyclopropyl, 1,1-$CO_2$-cyclopropyl, $OCF_3$, and $OCHF_2$.

According to still another embodiment thereof $R^{4b}$ is independently selected from halogen, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^4$ is independently selected from halogen, OH, $CH_3$, $OCH_3$, CN, $CHF_2$, $OCHF_2$, $OCF_3$, $OCH_3$, cyclopropyl, 1-F-cyclopropyl, 1-Cl-cyclopropyl, 1,1-$F_2$-cyclopropyl, 1,1-$Cl_2$-cyclopropyl and halogenmethoxy, more specifically independently selected from F, C, OH, $CH_3$, $OCH_3$, $CHF_2$, $OCH_3$ cyclopropyl, 1-F-cyclopropyl, 1-Cl-cyclopropyl, 1,1-$F_2$-cyclopropyl, 1,1-$C_2$-cyclopropyl, $OCHF_2$ and $OCF_3$.

Particularly preferred embodiments of $R^4$ according to the invention are in Table P4 below, wherein each line of lines P4-1 to P4-16 corresponds to one particular embodiment of the invention. Thereby, for every $R^4$ that is present in the inventive compounds, these specific embodiments and preferences apply independently of the meaning of any other $R^4$ that may be present in the ring:

TABLE P4

"Ts" in the table stands for the tosylgroup $SO_2$-(p-$CH_3$)phenyl.

| No. | $R^4$ |
|---|---|
| P4-1 | H |
| P4-2 | Cl |
| P4-3 | F |
| P4-4 | Br |
| P4-5 | OH |
| P4-6 | CN |
| P4-7 | $NO_2$ |
| P4-8 | $CH_3$ |
| P4-9 | $CH_2CH_3$ |
| P4-10 | $CF_3$ |
| P4-11 | $CHF_2$ |
| P4-12 | $OCH_3$ |
| P4-13 | $OCH_2CH_3$ |
| P4-14 | $OCF_3$ |
| P4-15 | $OCHF_2$ |
| P4-16 | NH-Ts |

Y according to the invention is O or $S(O)_m$, wherein m is 0, 1 or 2.

According to one embodiment of formula I, Y is O.
According to another embodiment of formula I, Y is S.
According to another embodiment of formula I, Y is SO.
According to another embodiment of formula I, Y is $SO_2$.
Z according to the invention is N or $CR^5$.

Z according to the invention is N
Z according to the invention is $CR^5$.

$R^5$ according to the invention is in each case independently selected from is are independently selected from H, halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, CH(=O), C(=O)$C_1$-$C_6$-alkyl, C(=O)NH($C_1$-$C_6$-alkyl), CR'=NOR", $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, S(O)m-$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein R' and R" are independently unsubstituted or substituted by R''' which is independently selected from halogen, OH, CN, $NO_2$, SH, $NH_2$, NH($C_1$-$C_4$-alkyl), N($C_1$-$C_4$-alkyl)$_2$, NH—$SO_2$—$R^x$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl; wherein m is 0, 1 and 2;

$R^x$ is $C_1$-$C_4$-alkyl, $C_1$-$C_4$-halogenalkyl, unsubstituted aryl or aryl that is substituted with one, two, three, four or five substituents $R^5$ independently selected from $C_1$-$C_4$-alkyl, halogen, OH, CN, $C_1$-$C_4$-halogenalkyl, $C_1$-$C_4$-alkoxy and $C_1$-$C_4$-halogenalkoxy;

and wherein the aliphatic moieties of $R^5$ are not further substituted or carry 1, 2, 3 or up to the maximum possible number of identical or different groups $R^{5a}$ which independently of one another are selected from:

$R^{5a}$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl, phenyl and phenoxy group is unsubstituted or unsubstituted or substituted with $R^{51a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the alicyclic, phenyl, heterocyclic and heteroaryl moieties of $R^5$ are unsubstituted or substituted with identical or different groups $R^{5b}$ which independently of one another are selected from:

$R^{5b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;

According to one specific embodiment, $R^5$ is H.
According to one specific embodiment, $R^5$ is halogen, in particular F, C, Br or I, more specifically F, Cl or Br, in particular F or Cl.
According to still another embodiment of formula I, $R^5$ is F.
According to still another embodiment of formula I, $R^5$ is Cl.
According to still another embodiment of formula I, $R^5$ is Br.
According to a further specific embodiment, $R^5$ is OH.
According to a further specific embodiment, $R^5$ is CN.
According to a further specific embodiment, $R^5$ is $NO_2$.
According to still another embodiment of formula I, $R^5$ is SH.
According to still another embodiment of formula I, $R^5$ is $NH_2$.
According to still another embodiment of formula I, R is, NH($C_1$-$C_4$-alkyl), N($C_1$-$C_4$-alkyl)$_2$, NH(C(=O)($C_1$-$C_4$-alkyl), N(C(=O)(C$_1$-C$_4$-alkyl)$_2$, wherein C$_1$-C$_4$-alkyl is CH$_3$, C$_2$H$_5$, n-propyl, i-propyl, n-butyl, i-butyl, tert-butyl, n-pentyl or i-pentyl.

According to a further specific embodiment of formula I, R$^5$ is NH—SO$_2$—R$^x$ such as NH—SO$_2$—CH$_3$, NH—SO$_2$—CH$_2$—CH$_3$, NH—SO$_2$—CF$_3$ or NH—SO$_2$-Ts.

According to a further specific embodiment of formula I, R$^5$ is CH(=O), C(=O)C$_1$-C$_6$-alkyl, C(=O)O(C$_1$-C$_6$-alkyl) or C(=O)NH(C$_1$-C$_6$-alkyl), wherein alkyl is CH$_3$, C$_2$H$_5$, n-propyl, i-propyl, n-butyl, i-butyl, tert-butyl, n-pentyl or i-pentyl.

According to a further specific embodiment of formula I, R$^5$ is CR'=NOR" such as C(CH$_3$)=NOCH$_3$, C(CH$_3$)=NOCH$_2$CH$_3$ or C(CH$_3$)=NOCF$_3$.

According to a further specific embodiment, R$^5$ is C$_1$-C$_6$-alkyl, in particular C$_1$-C$_4$-alkyl, such as CH$_3$, C$_2$H$_5$, n-propyl, i-propyl, n-butyl, i-butyl, tert-butyl, n-pentyl or i-pentyl, in particular CH$_3$.

According to a further specific embodiment, R$^5$ is C$_1$-C$_6$-halogenalkyl, in particular C$_1$-C$_4$-halogenalkyl, such as CF$_3$, CCl$_3$, FCH$_2$, ClCH$_2$, F$_2$CH, C$_2$CH, CF$_3$CH$_2$, CCl$_3$CH$_2$ or CF$_2$CHF$_2$.

According to still a further embodiment, R$^5$ is C$_2$-C$_6$-alkenyl, in particular C$_2$-C$_4$-alkenyl, such as CH=CH$_2$ or CH$_2$, CH=CH$_2$.

According to still another embodiment of formula I R$^5$ is C$_3$-C$_6$-cycloalkyl, in particular cyclopropyl.

According to still another embodiment of formula I, R$^5$ is C$_3$-C$_6$-halogencycloalkyl. In a special embodiment R$^1$ is fully or partially halogenated cyclopropyl.

According to still a further embodiment, R$^5$ is C$_3$-C$_6$-cycloalkyl-C$_2$-C$_6$-alkenyl, in particular C$_3$-C$_6$-cycloalkyl-C$_2$-C$_4$-alkenyl, more specifically C$_3$-C$_6$-cycloalkyl-C$_2$-C$_3$-alkenyl, such as C$_3$H$_5$—CH=CH$_2$.

According to a further specific embodiment, R$^5$ is C$_2$-C$_6$-halogenalkenyl, in particular C$_2$-C$_4$-halogenalkenyl, more specifically C$_2$-C$_3$-halogenalkenyl such as CH=CHF, CH=CHCl, CH=CF$_2$, CH=CCl$_2$, CH$_2$CH=CHF, CH$_2$CH=CHCl, CH$_2$CH=CF$_2$, CH$_2$CH=CCl$_2$, CH$_2$CF=CF$_2$, CH$_2$CCl=CCl$_2$, CF$_2$CF=CF$_2$ or CCl$_2$CCl=CCl$_2$.

According to still a further embodiment, R$^5$ is C$_2$-C$_6$-alkynyl, in particular C$_2$-C$_4$-alkynyl, more specifically C$_2$-C$_3$-alkynyl, such as C≡CH.

According to still a further embodiment, R$^5$ is C$_2$-C$_6$-halogenalkynyl, in particular C$_2$-C$_4$-halogenalkynyl, more specifically C$_2$-C$_3$-halogenalkynyl.

According to a further specific embodiment, R$^5$ is C$_1$-C$_6$-alkoxy, in particular C$_1$-C$_4$-alkoxy, more specifically C$_1$-C$_2$-alkoxy such as OCH$_3$ or OCH$_2$CH$_3$.

According to a further specific embodiment, R$^5$ is C$_1$-C$_6$-halogenalkoxy, in particular C$_1$-C$_4$-halogenalkoxy, more specifically C$_1$-C$_2$-halogenalkoxy such as OCF$_3$, OCHF$_2$, OCH$_2$F, OCCl$_3$, OCHCl$_2$, OCH$_2$Cl and OCF$_2$CHF$_2$, in particular OCF$_3$, OCHF$_2$ and OCF$_2$CHF$_2$.

According to a further specific embodiment of formula I, R$^5$ is C$_2$-C$_6$-alkenyloxy, in particular C$_2$-C$_4$-alkenyloxy, more specifically C$_1$-C$_2$-alkenyloxy such as OCH=CH$_2$, OCH$_2$CH=CH$_2$.

According to a further specific embodiment of formula I, R$^5$ is C$_2$-C$_6$-alkynyloxy, in particular C$_2$-C$_4$-alkynyloxy, more specifically C$_1$-C$_2$-alkynyloxy such as OC≡CH According to a further specific embodiment of formula I, R$^5$ is S(O)$_m$—C$_1$-C$_6$-alkyl, wherein alkyl is CH$_3$, C$_2$H$_5$, n-propyl, i-propyl, n-butyl, i-butyl, tert-butyl, n-pentyl or i-pentyl and m is 1, 2 or 3.

According to a further specific embodiment of formula I, R$^5$ is S(O)$_m$—C$_1$-C$_6$-halogenalkyl, wherein halogenalkyl is CF$_3$ or CHF$_2$ and m is 1, 2 or 3.

According to still another embodiment of formula I, R$^5$ is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents R$^{5b}$ as defined below. According to one embodiment thereof, the heterocycle is unsubstituted.

According to still another embodiment of formula I, R$^5$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents R$^{5b}$ as defined below. According to one embodiment thereof, the heterocycle is unsubstituted.

According to still another embodiment of formula I, in the embodiments of R$^5$ described above, the heterocycle contains preferably one, two or three, more specifically one or two heteroatoms selected from N, O and S. More specifically, the heterocycle contains one heteroatom selected from N, O and S. In particular, the heterocycle contains one or two, in particular one O.

According to one embodiment, R$^5$ is a 4-membered saturated heterocycle which contains 1 or 2 heteroatoms, in particular 1 heteroatom, from the group consisting of N, O and S, as ring members.

According to one embodiment, the heterocycle contains one O as heteroatom. For example, the formed heterocycle is oxetane. According to one embodiment thereof, the heterocycle is unsubstituted, i.e. it does not carry any substituent R$^{5b}$. According to still another embodiment of formula I, it is substituted by R$^5$.

According to still another embodiment of formula I, R$^5$ is a 5-membered saturated heterocycle which contains 1, 2 or 3, in particular 1 or 2, heteroatoms from the group consisting of N, O and S, as ring members. According to one embodiment, the heterocycle contains one O as heteroatom.

According to one embodiment thereof, the heterocycle is unsubstituted, i.e. it does not carry any substituent R$^{5b}$. According to still another embodiment of formula I, it is substituted by R$^{5b}$.

According to still another embodiment of formula I, R$^5$ is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent R$^{5b}$. According to still another embodiment of formula I, it is substituted by R$^{5b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent R$^5$. According to still another embodiment of formula I, it is substituted by R$^5$.

According to still another embodiment of formula I, R$^5$ is phenyl-C$_1$-C$_6$-alkyl, such as phenyl-CH$_2$, wherein the phenyl moiety in each case is unsubstituted or substituted by one, two or three identical or different groups R$^{5b}$ which independently of one another are selected from halogen, C$_1$-C$_2$-alkyl, C$_1$-C$_2$-alkoxy, C$_1$-C$_2$-halogenalkyl and C$_1$-C$_2$-halogenalkoxy, in particular CN, F, Cl, Br, CH$_3$, OCH$_3$, CHF$_2$, CF$_3$, OCHF$_2$, and OCF$_3$.

According to still a further specific embodiment, $R^5$ is unsubstituted phenyl or phenyl that is substituted by one, two, three or four $R^{5b}$, as defined and preferably herein. In particular, $R^5$ is unsubstituted phenyl or phenyl that is substituted by one, two, three or four $R^{5b}$, as defined herein. In one embodiment $R^5$ is unsubstituted phenyl.

According to still another embodiment of formula I, $R^5$ is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $R^5$ is a 6-membered heteroaryl, such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to one further embodiment, $R^5$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy, $C_3$-$C_6$-cycloalkyl, $S(O)_m$—$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the acyclic moieties of $R^5$ are not further substituted or carry one, two, three or up to the maximum possible number of identical or different groups $R^{5a}$ as defined and preferably defined herein, and wherein the heterocyclic, alicyclic, phenyl and heteroaryl moieties of $R^5$ are not further substituted or carry one, two, three, four, five or up to the maximum number of identical or different groups $R^{5b}$ as defined and preferably defined herein.

According to one further embodiment, $R^5$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl, $S(O)_m$—$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the acyclic moieties of $R^5$ are not further substituted or carry one, two, three or up to the maximum possible number of identical or different groups $R^{5a}$ as defined and preferably defined herein, and wherein the heterocyclic, alicyclic, phenyl and heteroaryl moieties of $R^5$ are not further substituted or carry one, two, three, four, five or up to the maximum number of identical or different groups $R^{5b}$ as defined and preferably defined herein. According to one specific embodiment, the acyclic and cyclic moieties of $R^5$ are not further substituted, according to another embodiment, the acyclic moieties of $R^5$ carry one, two, three or four identical or different groups $R^{5a}$ as defined and preferably defined herein.

According to a further embodiment, $R^5$ is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy, $C_3$-$C_6$-cycloalkyl and $S(O)_m$—$C_1$-$C_6$-alkyl, wherein the acyclic moieties of $R^5$ are not further substituted or carry one, two, three or up to the maximum possible number of identical or different groups $R^{5a}$ as defined and preferably defined herein, and wherein the cycloalkyl moieties of $R^5$ are not further substituted or carry one, two, three, four, five or up to the maximum number of identical or different groups $R^{5b}$ as defined and preferably defined herein.

According to a further embodiment, $R^5$ is in each case independently selected from halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl and $S(O)_m$—$C_1$-$C_6$-alkyl, wherein the acyclic moieties of $R^5$ are not further substituted or carry one, two, three or up to the maximum possible number of identical or different groups $R^{5a}$ as defined and preferably defined herein, and wherein the cycloalkyl moieties of $R^5$ are not further substituted or carry one, two, three, four, five or up to the maximum number of identical or different groups $R^{5b}$ as defined and preferably defined herein. According to one specific embodiment, the acyclic and cyclic moieties of $R^5$ are not further substituted, according to another embodiment, the acyclic moieties of $R^5$ carry one, two, three or four identical or different groups $R^{5a}$ as defined and preferably defined herein.

According to still a further embodiment, $R^5$ is in each case independently selected from halogen, $C_1$-$C_6$-alkyl and $C_1$-$C_6$-alkoxy, wherein the acyclic moieties of $R^5$ are not further substituted or carry one, two, three or up to the maximum possible number of identical or different groups $R^{5a}$ defined and preferably defined herein.

According to still a further embodiment, $R^5$ is in each case independently selected from CN, halogen, $C_1$-$C_6$-alkyl, $C_1$-$C_6$-halogenalkyl, $C_1$-$C_6$-alkoxy and $C_1$-$C_6$-halogenalkoxy, wherein the acyclic moieties of $R^5$ are not further substituted or carry one, two, three or up to the maximum possible number of identical or different groups $R^{5a}$ defined and preferably defined herein. According to one specific embodiment, the acyclic and cyclic moieties of $R^5$ are not further substituted, according to another embodiment, the acyclic moieties of $R^5$ carry one, two, three or four identical or different groups $R^{5a}$ as defined and preferably defined herein.

According to still a further embodiment, $R^5$ is in each case independently selected from halogen, $C_1$-$C_6$-alkyl, $C_1$-$C_6$-halogenalkyl, $C_1$-$C_6$-alkoxy, $C_1$-$C_6$-halogenalkoxy or CN.

$R^{5a}$ are the possible substituents for the acyclic moieties of $R^5$. $R^{5a}$ is independently selected from halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl and phenyl group is unsubstituted or carries one, two, three, four or five substituents $R^{5a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to one embodiment $R^{5a}$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $R^{5a}$ is independently selected from F, C, Br, I, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to a further embodiment, $R^{5a}$ is independently halogen, in particular selected from F, Cl, Br and I, more specifically F, Cl and Br.

$R^{5b}$ are the possible substituents for the cycloalkyl, heterocycle, heteroaryl and phenyl moieties of $R^5$. $R^{5b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment thereof $R^{5b}$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, $R^{5b}$ is independently selected from F, Cl, CN, $CH_3$, $OCH_3$ and halogenmethoxy.

Particularly preferred embodiments of $R^5$ according to the invention are in Table P5 below, wherein each line of lines P5-1 to P5-34 corresponds to one particular embodiment of the invention, wherein P5-1 to P5-34 are also in any combination with one another a preferred embodiment of the present invention:

TABLE P5

| No. | $R^5$ |
|---|---|
| P5-1 | H |
| P5-2 | Cl |
| P5-3 | F |
| P5-4 | Br |
| P5-5 | OH |
| P5-6 | CN |
| P5-7 | $NO_2$ |
| P5-8 | $CH_3$ |
| P5-9 | $CH_2CH_3$ |
| P5-10 | cPr |
| P5-11 | $CF_3$ |
| P5-12 | $CHF_2$ |
| P5-13 | $CH_2F$ |
| P5-14 | $CCl_3$ |
| P5-15 | $CHCl_2$ |
| P5-16 | $CH_2Cl$ |
| P5-17 | $CH_2CF_{23}$ |
| P5-18 | $CH_2CCl_3$ |
| P5-19 | $CHF_2CF_2$ |
| P5-20 | $OCH_3$ |
| P5-21 | $OCH_2CH_3$ |
| P5-22 | $OCF_3$ |
| P5-23 | $OCHF_2$ |
| P5-24 | $OCH_2F$ |
| P5-25 | $OCF_2CHF_2$ |
| P5-26 | $OCCl_3$ |
| P5-27 | $OCHCl_2$ |
| P5-28 | $OCH_2Cl$ |
| P5-29 | CCH |
| P5-30 | OC≡CH |
| P5-31 | $CH=CH_2$ |
| P5-32 | $OCH=CH_2$ |
| P5-33 | $OCH_2CH=CH_2$ |
| P5-34 | $S(O)_2$—$CH_3$ | n according to the invention is 0, 1, or 2.
According to one specific embodiment, n is 0.
According to one specific embodiment, n is 1.
According to one specific embodiment, n is 2.

X according to the invention is in each case independently selected from halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, NH—$SO_2$—$R^x$, CH(=O), C(=O)$C_1$-$C_6$-alkyl, C(=O)NH($C_1$-$C_6$-alkyl), CR'=NOR", $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_2$-$C_6$-alkenyloxy, $C_2$-$C_6$-alkynyloxy, $C_3$-$C_6$-cycloalkyl, $C_3$-$C_6$-cycloalkenyl, S(O)m-$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein R' and R" are independently unsubstituted or substituted by R'" which is independently selected from halogen, OH, CN, $NO_2$, SH, $NH_2$, $NH(C_1$-$C_4$-alkyl), $N(C_1$-$C_4$-alkyl)$_2$, NH—$SO_2$—$R^x$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl.

and wherein the aliphatic moieties of X are not further substituted or carry 1, 2, 3 or up to the maximum possible number of identical or different groups $X^a$ which independently of one another are selected from:

$X^a$ halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl, phenyl and phenoxy group is unsubstituted or unsubstituted or substituted with $X^a$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the alicyclic, phenyl, heterocyclic and heteroaryl moieties of X are unsubstituted or substituted with identical or different groups $X^b$ which independently of one another are selected from:

$X^b$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy, and $C_1$-$C_6$-alkylthio;

According to one specific embodiment, X is halogen, in particular F, C, Br or I, more specifically F, Cl or Br, in particular F or Cl.

According to still another embodiment of formula I, X is F.

According to still another embodiment of formula I, X is Cl.

According to still another embodiment of formula I, X is Br.

According to a further specific embodiment, X is OH.
According to a further specific embodiment, X is CN.
According to a further specific embodiment, X is $NO_2$.
According to still another embodiment of formula I, X is SH.

According to still another embodiment of formula I, X is $NH_2$.

According to still another embodiment of formula I, X is, $NH(C_1$-$C_4$-alkyl), $N(C_1$-$C_4$-alkyl)$_2$. $NH(C(=O)(C_1$-$C_4$-alkyl), $N(C(=O)(C_1$-$C_4$-alkyl)$_2$, wherein $C_1$-$C_4$-alkyl is $CH_3$, $C_2H_5$, n-propyl, i-propyl, n-butyl, i-butyl, tert-butyl, n-pentyl or i-pentyl.

According to a further specific embodiment of formula I, X is NH—$SO_2$—$R^x$ such as NH—$SO_2$—$CH_3$, NH—$SO_2$—$CH_2$—$CH_3$, NH—$SO_2$—$CF_3$ or NH—$SO_2$-Ts.

According to a further specific embodiment of formula I, X is CH(=O), C(=O)$C_1$-$C_6$-alkyl, C(=O)O($C_1$-$C_6$-alkyl) or C(=O)NH($C_1$-$C_6$-alkyl), wherein alkyl is $CH_3$, $C_2H_5$, n-propyl, i-propyl, n-butyl, i-butyl, tert-butyl, n-pentyl or i-pentyl.

According to a further specific embodiment of formula I, X is CR'=NOR" such as C($CH_3$)=$NOCH_3$, C($CH_3$)=$NOCH_2CH_3$ or C($CH_3$)=$NOCF_3$.

According to a further specific embodiment, X is $C_1$-$C_6$-alkyl, in particular $C_1$-$C_4$-alkyl, such as $CH_3$, $C_2H_5$, n-propyl, i-propyl, n-butyl, i-butyl, tert-butyl, n-pentyl or i-pentyl, in particular $CH_3$.

According to a further specific embodiment, X is $C_1$-$C_6$-halogenalkyl, in particular $C_1$-$C_4$-halogenalkyl, such as $CF_3$, $CCl_3$, $FCH_2$, $ClCH_2$, $F_2CH$, $C_2CH$, $CF_3CH_2$, $CCl_3CH_2$ or $CF_2CHF_2$.

According to still a further embodiment, X is $C_2$-$C_6$-alkenyl, in particular $C_2$-$C_4$-alkenyl, such as CH=$CH_2$ or $CH_2$, CH=$CH_2$.

According to still another embodiment of formula I X is $C_3$-$C_6$-cycloalkyl, in particular cyclopropyl.

According to still another embodiment of formula I, X is $C_3$-$C_6$-halogencycloalkyl. In a special embodiment $R^1$ is fully or partially halogenated cyclopropyl.

According to still a further embodiment, X is $C_3$-$C_6$-cycloalkyl-$C_2$-$C_6$-alkenyl, in particular $C_3$-$C_6$-cycloalkyl-$C_2$-$C_4$-alkenyl, more specifically $C_3$-$C_6$-cycloalkyl-$C_2$-$C_3$-alkenyl, such as $C_3H_5$—CH=$CH_2$.

According to a further specific embodiment, X is $C_2$-$C_6$-halogenalkenyl, in particular $C_2$-$C_4$-halogenalkenyl, more specifically $C_2$-$C_3$-halogenalkenyl such as CH=CHF, CH=CHCl, CH=$CF_2$, CH=$CCl_2$, $CH_2$CH=CHF, $CH_2$CH=CHCl, $CH_2$CH=$CF_2$, $CH_2$CH=$CCl_2$. $CH_2$CF=$CF_2$, $CH_2$CCl=$CCl_2$.

$CF_2$CF=$CF_2$ or $CCl_2$CCl=$CCl_2$.

According to still a further embodiment, X is $C_2$-$C_6$-alkynyl, in particular $C_2$-$C_4$-alkynyl, more specifically $C_2$-$C_3$-alkynyl, such as C≡CH.

According to still a further embodiment, X is $C_2$-$C_6$-halogenalkynyl, in particular $C_2$-$C_4$-halogenalkynyl, more specifically $C_2$-$C_3$-halogenalkynyl.

According to a further specific embodiment, X is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, X is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$, $OCH_2Cl$ and $OCF_2CHF_2$, in particular $OCF_3$, $OCHF_2$ and $OCF_2CHF_2$.

According to a further specific embodiment of formula I, X is $C_2$-$C_6$-alkenyloxy, in particular $C_2$-$C_4$-alkenyloxy, more specifically $C_1$-$C_2$-alkenyloxy such as OCH=$CH_2$, $OCH_2$CH=$CH_2$.

According to a further specific embodiment of formula I, X is $C_2$-$C_6$-alkynyloxy, in particular $C_2$-$C_4$-alkynyloxy, more specifically $C_1$-$C_2$-alkynyloxy such as OC≡CH According to a further specific embodiment of formula I, X is $S(O)_m$—$C_1$-$C_6$-alkyl, wherein alkyl is $CH_3$, $C_2H_5$, n-propyl, i-propyl, n-butyl, i-butyl, tert-butyl, n-pentyl or i-pentyl and m is 1, 2 or 3.

According to a further specific embodiment of formula I, X is $S(O)_m$—$C_1$-$C_6$-halogenalkyl, wherein halogenalkyl is $CF_3$ or $CHF_2$ and m is 1, 2 or 3.

According to still another embodiment of formula I, X is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $X^b$ as defined below. According to one embodiment thereof, the heterocycle is unsubstituted.

According to still another embodiment of formula I, X is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $X^b$ as defined below. According to one embodiment thereof, the heterocycle is unsubstituted.

According to still another embodiment of formula I, in the embodiments of X described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one embodiment, X is a 4-membered saturated heterocycle which contains 1 or 2 heteroatoms, in particular 1 heteroatom, from the group consisting of N, O and S, as ring members.

According to one embodiment, the heterocycle contains one O as heteroatom. For example, the formed heterocycle is oxetane. According to one embodiment thereof, the heterocycle is unsubstituted, i.e. it does not carry any substituent $X^b$. According to still another embodiment of formula I, it is substituted by $X^b$.

According to still another embodiment of formula I, X is a 5-membered saturated heterocycle which contains 1, 2 or 3, in particular 1 or 2, heteroatoms from the group consisting of N, O and S, as ring members. According to one embodiment, the heterocycle contains one O as heteroatom.

According to one embodiment thereof, the heterocycle is unsubstituted, i.e. it does not carry any substituent $X^b$. According to still another embodiment of formula I, it is substituted by $X^b$.

According to still another embodiment of formula I, X is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $X^b$. According to still another embodiment of formula I, it is substituted by $X^b$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $X^b$. According to still another embodiment of formula I, it is substituted by $X^b$.

According to still another embodiment of formula I, X is phenyl-$C_1$-$C_6$-alkyl, such as phenyl-$CH_2$, wherein the phenyl moiety in each case is unsubstituted or substituted by one, two or three identical or different groups $X^b$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular CN, F, Cl, Br, $CH_3$, $OCH_3$, $CHF_2$, $CF_3$, $OCHF_2$, and $OCF_3$.

According to still a further specific embodiment, X is unsubstituted phenyl or phenyl that is substituted by one, two, three or four $X^b$, as defined and preferably herein. In particular, X is unsubstituted phenyl or phenyl that is substituted by one, two, three or four $X^b$, as defined herein. In one embodiment X is unsubstituted phenyl.

According to still another embodiment of formula I, X is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, X is a 6-membered heteroaryl, such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to one further embodiment, X is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy, $C_3$-$C_6$-cycloalkyl, $S(O)_m$—$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the acyclic moieties of X are not further substituted or carry one, two, three or up to the maximum possible number of identical or different groups $X^a$ as defined and preferably defined herein, and wherein the heterocyclic, alicyclic, phenyl and heteroaryl moieties of X are not further substituted or carry one, two, three, four, five or up to the maximum number of identical or different groups $X^b$ as defined and preferably defined herein.

According to one further embodiment, X is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl, $S(O)_m$—$C_1$-$C_6$-alkyl, three-, four-, five- or six-membered saturated or partially unsaturated heterocycle, five- or six-membered heteroaryl and phenyl; wherein the heterocycle or heteroaryl contains one, two or three heteroatoms selected from N, O and S; and wherein the acyclic moieties of X are not further substituted or carry one, two, three or up to the maximum possible number of identical or different groups $X^a$ as defined and preferably defined herein, and wherein the heterocyclic, alicyclic, phenyl and heteroaryl moieties of X are not further substituted or carry one, two, three, four, five or up to the maximum number of identical or different groups $X^b$ as defined and preferably defined herein. According to one specific embodiment, the acyclic and cyclic moieties of X are not further substituted, according to another embodiment, the acyclic moieties of X carry one, two, three or four identical or different groups $X^a$ as defined and preferably defined herein.

According to a further embodiment, X is in each case independently selected from halogen, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy, $C_3$-$C_6$-cycloalkyl and $S(O)_m$—$C_1$-$C_6$-alkyl, wherein the acyclic moieties of X are not further substituted or carry one, two, three or up to the maximum possible number of identical or different groups $X^a$ as defined and preferably defined herein, and wherein the cycloalkyl moieties of X are not further substituted or carry one, two, three, four, five or up to the maximum number of identical or different groups $X^b$ as defined and preferably defined herein.

According to a further embodiment, X is in each case independently selected from halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy, $C_3$-$C_6$-cycloalkyl and $S(O)_m$—$C_1$-$C_6$-alkyl, wherein the acyclic moieties of X are not further substituted or carry one, two, three or up to the maximum possible number of identical or different groups $X^a$ as defined and preferably defined herein, and wherein the cycloalkyl moieties of X are not further substituted or carry one, two, three, four, five or up to the maximum number of identical or different groups $X^b$ as defined and preferably defined herein. According to one specific embodiment, the acyclic and cyclic moieties of X are not further substituted, according to another embodiment, the acyclic moieties of X carry one, two, three or four identical or different groups $X^a$ as defined and preferably defined herein.

According to still a further embodiment, X is in each case independently selected from halogen, $C_1$-$C_6$-alkyl and $C_1$-$C_6$-alkoxy, wherein the acyclic moieties of X are not further substituted or carry one, two, three or up to the maximum possible number of identical or different groups $X^a$ defined and preferably defined herein.

According to still a further embodiment, X is in each case independently selected from CN, halogen, $C_1$-$C_6$-alkyl, $C_1$-$C_6$-halogenalkyl, $C_1$-$C_6$-alkoxy and $C_1$-$C_6$-halogenalkoxy, wherein the acyclic moieties of X are not further substituted or carry one, two, three or up to the maximum possible number of identical or different groups $X^a$ defined and preferably defined herein. According to one specific embodiment, the acyclic and cyclic moieties of X are not further substituted, according to another embodiment, the acyclic moieties of X carry one, two, three or four identical or different groups $X^a$ as defined and preferably defined herein.

According to still a further embodiment, X is in each case independently selected from halogen, $C_1$-$C_6$-alkyl, $C_1$-$C_6$-halogenalkyl, $C_1$-$C_6$-alkoxy, $C_1$-$C_6$-halogenalkoxy or CN.

$X^a$ are the possible substituents for the acyclic moieties of X. $X^a$ is independently selected from halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, phenyl and phenoxy, wherein the heteroaryl and phenyl group is unsubstituted or carries one, two, three, four or five substituents $X^{a'}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to one embodiment $X^a$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $X^a$ is independently selected from F, C, Br, I, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to a further embodiment, $X^a$ is independently halogen, in particular selected from F, Cl, Br and I, more specifically F, Cl and Br.

$X^b$ are the possible substituents for the cycloalkyl, heterocycle, heteroaryl and phenyl moieties of X. $X^b$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment thereof $X^b$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, $X^b$ is independently selected from F, Cl, CN, $CH_3$, $OCH_3$ and halogenmethoxy.

Particularly preferred embodiments of X according to the invention are in Table PX below, wherein each line of lines PX-1 to PX-33 corresponds to one particular embodiment of the invention, wherein PX-1 to PX-33 are also in any combination with one another a preferred embodiment of the present invention:

TABLE PX

| No. | X |
|---|---|
| PX-1 | Cl |
| PX-2 | F |
| PX-3 | Br |
| PX-4 | OH |
| PX-5 | CN |
| PX-6 | $NO_2$ |
| PX-7 | $CH_3$ |

TABLE PX-continued

| No. | X |
|---|---|
| PX-8 | $CH_2CH_3$ |
| PX-9 | cPr |
| PX-10 | $CF_3$ |
| PX-11 | $CHF_2$ |
| PX-12 | $CH_2F$ |
| PX-13 | $CCl_3$ |
| PX-14 | $CHCl_2$ |
| PX-15 | $CH_2Cl$ |
| PX-16 | $CH_2CF_{23}$ |
| PX-17 | $CH_2CCl_3$ |
| PX-18 | $CHF_2CF_2$ |
| PX-19 | $OCH_3$ |
| PX-20 | $OCH_2CH_3$ |
| PX-21 | $OCF_3$ |
| PX-22 | $OCHF_2$ |
| PX-23 | $OCH_2F$ |
| PX-24 | $OCF_2CHF_2$ |
| PX-25 | $OCCl_3$ |
| PX-26 | $OCHCl_2$ |
| PX-27 | $OCH_2Cl$ |
| PX-28 | CCH |
| PX-29 | OC≡CH |
| PX-30 | $CH=CH_2$ |
| PX-31 | $OCH=CH_2$ |
| PX-32 | $OCH_2CH=CH_2$ |
| PX-33 | $S(O)_2—CH_3$ |

$Q^1$ according to the invention is in each case independently selected from CN, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, three-, four-, five- or six-membered saturated or partially unsaturated heterocycle, five- or six-membered heteroaryl and aryl; wherein the heterocycle and heteroaryl contains one, two or three heteroatoms selected from N, O and S; wherein the aliphatic moieties of $Q^1$ are unsubstituted or substituted with identical or different groups $Q^{1a}$ which independently of one another are selected from:

$Q^{1a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $Q^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heterocycle, heteroaryl and aryl moieties of $Q^1$ are unsubstituted or substituted with 1, 2, 3, 4, 5 or up to the maximum number of identical or different groups $Q^{1b}$ which independently of one another are selected from:

$Q^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to a further specific embodiment, $Q^1$ is $C_1$-$C_6$-alkyl, in particular $C_1$-$C_4$-alkyl, such as $CH_3$ or $CH_2CH_3$ According to a further specific embodiment, $Q^1$ is CN.

According to one specific embodiment, $Q^1$ is halogen, in particular F, Cl, Br or I, more specifically F, Cl or Br, in particular F or Cl.

According to still another embodiment of formula I, $Q^1$ is F.

According to still another embodiment of formula I, $Q^1$ is Cl.

According to a further specific embodiment, $Q^1$ is $C_1$-$C_6$-alkyl, in particular C-alkyl, substituted by phenyl which carries 1, 2 or 3 halogen.

According to a further specific embodiment, $Q^1$ is $C_1$-$C_6$-alkyl, in particular C-alkyl, substituted by phenyl which carries 1, 2 or 3 $C_1$-$C_4$-alkoxy groups.

According to a further specific embodiment, $Q^1$ is $C_1$-$C_6$-alkyl, in particular C-alkyl, substituted by phenyl which is carries 1, 2 or 3 $C_1$-$C_4$-alkyl groups.

According to a further specific embodiment, $Q^1$ is $C_1$-$C_6$-alkyl, in particular C-alkyl, substituted by phenyl which is carries 1, 2 or 3 $C_1$-$C_4$-halogenalkyl groups.

According to a further specific embodiment, $Q^1$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $Q^1$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $Q^1$ is $C_2$-$C_6$-alkynyl or $C_2$-$C_6$-halogenalkynyl, in particular $C_2$-$C_4$-alkynyl or $C_2$-$C_4$-halogenalkynyl, such as C≡CH.

According to a further specific embodiment $Q^1$ is $C_3$-$C_6$-cycloalkyl, in particular cyclopropyl.

In a further specific embodiment, $Q^1$ is $C_3$-$C_6$-cycloalkyl, for example cyclopropyl, substituted by one, two, three or up to the maximum possible number of identical or different groups $Q^{1b}$ as defined and preferably herein.

According to a specific embodiment $Q^1$ is $C_3$-$C_6$-halogencycloalkyl. In a special embodiment $Q^1$ is fully or partially halogenated cyclopropyl.

According to a specific embodiment $Q^1$ is three-, four-, five- or six-membered saturated or partially unsaturated heterocycle, According to still another embodiment of formula I, $Q^1$ is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^{1b}$ as defined below. According to one embodiment thereof, the heterocycle is unsubstituted.

According to still another embodiment of formula I, $Q^1$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^1$ as defined below. According to one embodiment thereof, the heterocycle is unsubstituted.

According to still another embodiment of formula I, in the embodiments of $Q^1$ described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one embodiment, $Q^1$ is a 4-membered saturated heterocycle which contains 1 or 2 heteroatoms, in particular 1 heteroatom, from the group consisting of N, O and S, as ring members.

According to one embodiment, the heterocycle contains one O as heteroatom. For example, the formed heterocycle is oxetane. According to one embodiment thereof, the heterocycle is unsubstituted, i.e. it does not carry any substituent $Q^1$. According to still another embodiment of formula I, it is substituted by $Q^{1b}$.

According to still another embodiment of formula I, $Q^1$ is a 5-membered saturated heterocycle which contains 1, 2 or 3, in particular 1 or 2, heteroatoms from the group consisting of N, O and S, as ring members. According to one embodiment, the heterocycle contains one O as heteroatom. According to one embodiment thereof, the heterocycle is unsubstituted, i.e. it does not carry any substituent $Q^{1b}$. According to still another embodiment of formula I, it is substituted by $Q^{1b}$.

According to still a further specific embodiment, $Q^1$ is unsubstituted aryl or aryl that is substituted by one, two, three or four $Q^{1b}$, as defined herein. In particular, $Q^1$ is unsubstituted phenyl or phenyl that is substituted by one, two, three or four $Q^{1b}$, as defined herein.

According to still a further specific embodiment, $Q^1$ is unsubstituted 5- or 6-membered heteroaryl. According to still a further embodiment, $Q^1$ is 5- or 6-membered heteroaryl that is substituted by one, two or three $Q^{1b}$, as defined herein.

According to still a further specific embodiment, $Q^1$ is unsubstituted 5- or 6-membered heterocycle. According to still a further embodiment, $Q^1$ is 5- or 6-membered heterocycle that is substituted by one, two or three $Q^{1b}$, as defined herein.

According to one further embodiment $Q^1$ according to the invention is in each case independently selected from CN, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, five- or six-membered heteroaryl, aryl and benzyl; wherein the heteroaryl contains one, two or three heteroatoms selected from N, O and S; wherein $Q^{1a}$ is selected from halogen, $C_1$-$C_6$-alkoxy, $C_3$-$C_6$-halogencycloalkyl, phenyl that is unsubstituted or substituted by 1, 2, 3, 4 or 5 substituents $Q^{11a}$ independently selected from $C_1$-$C_4$-alkyl; and wherein the cycloalkyl moieties of $Q^1$ are not further substituted or carry one, two, three, four or five identical or different groups $Q^{1b}$ as defined below.

According to a further embodiment, $Q^1$ is independently selected from CN, halogen, $C_1$-$C_6$-alkyl, $C_1$-$C_6$-halogenalkyl, in particular independently selected from hydrogen, $C_1$-$C_4$-alkyl and $C_1$-$C_4$-halogenalkyl.

$Q^{1a}$ are the possible substituents for the aliphatic moieties of $Q^1$.

$Q^{1a}$ according to the invention is independently selected from halogen, $C_1$-$C_6$-alkoxy, $C_3$-$C_6$-halogencycloalkyl, and phenyl, wherein the phenyl group is unsubstituted or carries one, two, three, four or five substituents $Q^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $Q^{1a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{1a}$ is independently selected from F, C, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $Q^{1a}$ is independently selected from halogen, such as F, Cl, Br and I, more specifically F, Cl and Br.

According to a further embodiment, $Q^{1a}$ is independently selected from OH, $C_3$-$C_6$-cycloalkyl, $C_3$-$C_6$-halogencycloalkyl and $C_1$-$C_2$-halogenalkoxy. Specifically, $Q^{1a}$ is independently selected from OH, cyclopropyl and $C_1$-$C_2$-halogenalkoxy.

$Q^{1b}$ are the possible substituents for the cycloalkyl, heteroaryl and aryl moieties of $Q^1$.

$Q^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $Q^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{1b}$ is independently selected from F, C, OH, CN, $CH_3$, $OCH_3$ cyclopropyl, 1-F-cyclopropyl, 1-Cl-cyclopropyl and halogenmethoxy.

According to a further embodiment thereof $Q^{1b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy.

Specifically, $Q^{1b}$ is independently selected from OH, $CH_3$, $OCH_3$ cyclopropyl, 1-F-cyclopropyl, 1-Cl-cyclopropyl and halogenmethoxy, more specifically independently selected from OH, $CH_3$, $OCH_3$ cyclopropyl, 1-F-cyclopropyl, 1-Cl-cyclopropyl and $OCHF_2$.

Particularly preferred embodiments of $Q^1$ according to the invention are in Table Q1 below, wherein each line of lines Q1-1 to Q1-39 corresponds to one particular embodiment of the invention, wherein Q1-1 to Q1-39 are also in any combination with one another a preferred embodiment of the present invention:

TABLE Q1

| No. | Q1 |
| --- | --- |
| Q1-1 | F |
| Q1-2 | Cl |
| Q1-3 | CN |
| Q1-4 | $CH_3$ |
| Q1-5 | $CH_2CH_3$ |
| Q1-6 | iPr |
| Q1-7 | cPr |
| Q1-8 | $CF_3$ |
| Q1-9 | $CHF_2$ |
| Q1-10 | $CH_2F$ |
| Q1-11 | $CCl_3$ |
| Q1-12 | $CHCl_2$ |
| Q1-13 | $CH_2Cl$ |
| Q1-14 | $CH_2CF_3$ |
| Q1-15 | $CH_2CCl_3$ |
| Q1-16 | $CHF_2CF_2$ |
| Q1-17 | $OCH_3$ |
| Q1-18 | $OCH_2CH_3$ |
| Q1-19 | $OCF_3$ |
| Q1-20 | $OCHF_2$ |
| Q1-21 | $OCH_2F$ |
| Q1-22 | $OCF_2CHF_2$ |
| Q1-23 | $OCCl_3$ |
| Q1-24 | $OCHCl_2$ |
| Q1-25 | $OCH_2Cl$ |
| Q1-26 | CCH |
| Q1-27 | OC≡CH |
| Q1-28 | CH=$CH_2$ |
| Q1-29 | $CH_2$CH=$CH_2$ |
| Q1-30 | OCH=$CH_2$ |
| Q1-31 | $OCH_2$CH=$CH_2$ |
| Q1-32 | Ph |
| Q1-33 | $CH_2$Ph |
| Q1-34 | 3-py |
| Q1-35 | 2-py |
| Q1-36 | 4-py |
| Q1-37 | 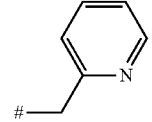 |
| Q1-38 | 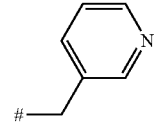 |

TABLE Q1-continued

| No. | Q1 |
| --- | --- |
| Q1-39 | 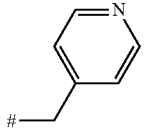 |

$Q^2$ according to the invention is in each case independently selected from hydrogen, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, three-, four-, five- or six-membered saturated or partially unsaturated heterocycle, five- or six-membered heteroaryl and aryl; wherein the heterocycle and heteroaryl contains one, two or three heteroatoms selected from N, O and S; wherein the aliphatic moieties of $Q^2$ are unsubstituted or substituted with identical or different groups $Q^{2a}$ which independently of one another are selected from:

$Q^{2a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $Q^{22a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heterocycle, heteroaryl and aryl moieties of $Q^2$ are unsubstituted or substituted with 1, 2, 3, 4, 5 or up to the maximum number of identical or different groups $Q^{2b}$ which independently of one another are selected from:

$Q^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one specific embodiment, $Q^2$ is halogen, in particular F, Cl, Br or I, more specifically F, Cl or Br, in particular F or Cl.

According to still another embodiment of formula I, $Q^2$ is F.

According to still another embodiment of formula I, $Q^2$ is Cl.

According to a further specific embodiment, $Q^2$ is $C_1$-$C_6$-alkyl, in particular $C_1$-$C_4$-alkyl, such as $CH_3$ or $CH_2CH_3$ According to a further specific embodiment, $Q^2$ is $C_1$-$C_6$-alkyl, in particular $C_1$-alkyl, substituted by phenyl which is unsubstituted.

According to a further specific embodiment, $Q^2$ is $C_1$-$C_6$-alkyl, in particular $C_1$-alkyl, substituted by phenyl which carries 1, 2 or 3 halogen.

According to a further specific embodiment, $Q^2$ is $C_1$-$C_6$-alkyl, in particular $C_1$-alkyl, substituted by phenyl which is carries 1, 2 or 3 $C_1$-$C_4$-alkoxy groups.

According to a further specific embodiment, $Q^2$ is $C_1$-$C_6$-alkyl, in particular $C_1$-alkyl, substituted by phenyl which carries 1, 2 or 3 $C_1$-$C_4$-alkyl groups.

According to a further specific embodiment, $Q^2$ is $C_1$-$C_6$-alkyl, in particular $C_1$-alkyl, substituted by phenyl which carries 1, 2 or 3 $C_1$-$C_4$-halogenalkyl groups.

According to a further specific embodiment, $Q^2$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further specific embodiment, $Q^2$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $Q^2$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment $Q^2$ is $C_3$-$C_6$-cycloalkyl, in particular cyclopropyl.

In a further specific embodiment, $Q^2$ is $C_3$-$C_6$-cycloalkyl, for example cyclopropyl, substituted by one, two, three or up to the maximum possible number of identical or different groups $Q^{2b}$ as defined and preferably herein.

According to a specific embodiment $Q^2$ is $C_3$-$C_6$-halogencycloalkyl. In a special embodiment $Q^2$ is fully or partially halogenated cyclopropyl.

According to a specific embodiment $Q^2$ is three-, four-, five- or six-membered saturated or partially unsaturated heterocycle, According to still another embodiment of formula I, $Q^2$ is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^{2b}$ as defined below. According to one embodiment thereof, the heterocycle is unsubstituted.

According to still another embodiment of formula I, $Q^2$ is a saturated three-, four-, five-, six-, seven-, eight-, nine- or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^{2b}$ as defined below. According to one embodiment thereof, the heterocycle is unsubstituted.

According to still another embodiment of formula I, in the embodiments of $Q^2$ described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one embodiment, $Q^2$ is a 4-membered saturated heterocycle which contains 1 or 2 heteroatoms, in particular 1 heteroatom, from the group consisting of N, O and S, as ring members.

According to one embodiment, the heterocycle contains one O as heteroatom. For example, the formed heterocycle is oxetane. According to one embodiment thereof, the heterocycle is unsubstituted, i.e. it does not carry any substituent $Q^{2b}$. According to still another embodiment of formula I, it is substituted by $Q^{2b}$.

According to still another embodiment of formula I, $Q^2$ is a 5-membered saturated heterocycle which contains 1, 2 or 3, in particular 1 or 2, heteroatoms from the group consisting of N, O and S, as ring members. According to one embodiment, the heterocycle contains one O as heteroatom.

According to one embodiment thereof, the heterocycle is unsubstituted, i.e. it does not carry any substituent $Q^{2b}$. According to still another embodiment of formula I, it is substituted by $Q^{2b}$.

According to still a further specific embodiment, $Q^2$ is unsubstituted aryl or aryl that is substituted by one, two, three or four $Q^{2b}$, as defined herein. In particular, $Q^2$ is unsubstituted phenyl or phenyl that is substituted by one, two, three or four $Q^{2b}$, as defined herein.

According to still a further specific embodiment, $Q^2$ is unsubstituted 5- or 6-membered heteroaryl. According to still a further embodiment, $Q^2$ is 5- or 6-membered heteroaryl that is substituted by one, two or three $Q^{2b}$, as defined herein.

According to still a further specific embodiment, $Q^2$ is unsubstituted 5- or 6-membered heterocycle. According to still a further embodiment, $Q^2$ is 5- or 6-membered heterocycle that is substituted by one, two or three $Q^{2b}$, as defined herein.

According to one further embodiment $Q^2$ according to the invention is in each case independently selected from hydrogen, halogen, $C_1$-$C_6$-alkyl, $C_1$-$C_6$-halogenalkyl, $C_2$-$C_6$-alkenyl, $C_2$-$C_6$-alkynyl, $C_3$-$C_6$-cycloalkyl, five- or six-membered heteroaryl, aryl and benzyl; wherein the heteroaryl contains one, two or three heteroatoms selected from N, O and S; wherein $Q^{2a}$ is selected from halogen, $C_1$-$C_6$-alkoxy, $C_3$-$C_6$-halogencycloalkyl, phenyl that is unsubstituted or substituted by 1, 2, 3, 4 or 5 substituents $Q^{22a}$ independently selected from $C_1$-$C_4$-alkyl; and wherein the aliphatic moieties of $Q^2$ are unsubstituted or substituted with identical or different groups $Q^{2a}$ as defined below and wherein the cycloalkyl moieties of $Q^2$ are not further substituted or carry one, two, three, four or five identical or different groups $Q^{2b}$ as defined below.

According to a further embodiment, $Q^2$ is independently selected from hydrogen, halogen $C_1$-$C_6$-alkyl, $C_1$-$C_6$-halogenalkyl, in particular independently selected from hydrogen, $C_1$-$C_4$-alkyl and $C_1$-$C_4$-halogenalkyl.

$Q^{2a}$ are the possible substituents for the aliphatic moieties of $Q^2$.

$Q^{2a}$ according to the invention is independently selected from halogen, $C_1$-$C_6$-alkoxy, $C_3$-$C_6$-halogencycloalkyl, and phenyl, wherein the phenyl group is unsubstituted or carries one, two, three, four or five substituents $R^{42a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $Q^{2a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{2a}$ is independently selected from F, C, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $Q^{2a}$ is independently selected from halogen, such as F, C, Br and I, more specifically F, Cl and Br.

According to a further embodiment, $Q^{2a}$ is independently selected from OH, $C_3$-$C_6$-cycloalkyl, $C_3$-$C_6$-halogencycloalkyl and $C_1$-$C_2$-halogenalkoxy. Specifically, $Q^{2a}$ is independently selected from OH, cyclopropyl and $C_1$-$C_2$-halogenalkoxy.

$Q^{2b}$ are the possible substituents for the cycloalkyl, heteroaryl and aryl moieties of $Q^2$.

$Q^{2b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $Q^{2b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{2b}$ is independently selected from F, C, OH, CN, $CH_3$, $OCH_3$, cyclopropyl, 1-F-cyclopropyl, 1-Cl-cyclopropyl and halogenmethoxy.

According to a further embodiment thereof $Q^{2b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy.

Specifically, $Q^{2b}$ is independently selected from OH, $CH_3$, $OCH_3$ cyclopropyl, 1-F-cyclopropyl, 1-Cl-cyclopropyl and halogenmethoxy, more specifically independently selected from OH, $CH_3$, $OCH_3$ cyclopropyl, 1-F-cyclopropyl, 1-Cl-cyclopropyl and $OCHF_2$.

Particularly preferred embodiments of $Q^2$ according to the invention are in Table Q1 below, wherein each line of lines Q2-1 to Q2-39 corresponds to one particular embodiment of the invention, wherein Q2-1 to Q2-39 are also in any combination with one another a preferred embodiment of the present invention:

TABLE Q2

| No. | Q1 |
|---|---|
| Q2-1 | H |
| Q2-2 | F |
| Q2-3 | Cl |
| Q2-4 | $CH_3$ |
| Q2-5 | $CH_2CH_3$ |
| Q2-6 | iPr |
| Q2-7 | cPr |
| Q2-8 | $CF_3$ |
| Q2-9 | $CHF_2$ |
| Q2-10 | $CH_2F$ |
| Q2-11 | $CCl_3$ |
| Q2-12 | $CHCl_2$ |
| Q2-13 | $CH_2Cl$ |
| Q2-14 | $CH_2CF_3$ |
| Q2-15 | $CH_2CCl_3$ |
| Q2-16 | $CHF_2CF_2$ |
| Q2-17 | $OCH_3$ |
| Q2-18 | $OCH_2CH_3$ |
| Q2-19 | $OCF_3$ |
| Q2-20 | $OCHF_2$ |
| Q2-21 | $OCH_2F$ |
| Q2-22 | $OCF_2CHF_2$ |
| Q2-23 | $OCCl_3$ |
| Q2-24 | $OCHCl_2$ |
| Q2-25 | $OCH_2Cl$ |
| Q2-26 | CCH |
| Q2-27 | OC≡CH |
| Q2-28 | $CH=CH_2$ |
| Q2-29 | $CH_2CH=CH_2$ |
| Q2-30 | $OCH=CH_2$ |
| Q2-31 | $OCH_2CH=CH_2$ |
| Q2-32 | Ph |
| Q2-33 | $CH_2Ph$ |
| Q2-34 | 3-py |
| Q2-35 | 2-py |
| Q2-36 | 4-py |
| Q2-37 | 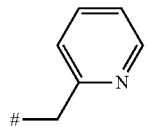 |
| Q2-38 | 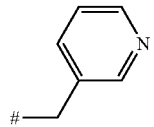 |
| Q2-39 | 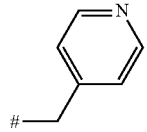 |

$Q^1$ and $Q^2$ according to the present invention form, together with the carbon atom to which they are bound form a three- to seven-membered saturated or partially unsaturated carbo- or heterocycle, wherein the ring may further contain 1, 2, 3 or 4 heteroatoms selected from N—R$^N$, O and S, wherein R$^N$ is selected from H, C$_1$-C$_4$-alkyl and SO$_2$R$^Q$; wherein R$^Q$ is selected from C$_1$-C$_4$-alkyl, C$_1$-C$_4$-halogenalkyl, unsubstituted aryl or heteroaryl that is substituted by 1, 2, 3, 4 or 5 substituents R$^1$ independently selected from C$_1$-C$_4$-alkyl; and wherein S may be in the form of its oxide SO or SO$_2$; and wherein in each case one or two CH$_2$ groups of the carbo- or heterocycle may be replaced by a group independently selected from C(=O) and C(=S);

and wherein the ring is unsubstituted or substituted with 1, 2, 3, 4, 5 or up to the maximum number of identical or different groups R$^{QR}$ which independently of one another are selected from:

Q$^R$ halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl, C$_1$-C$_4$-halogenalkoxy and C$_1$-C$_6$-alkylthio.

According to one embodiment, the carbocycle formed by Q$^1$ and Q$^2$ is saturated.

According to a further embodiment, the carbocycle formed by Q$^1$ and Q$^2$ is a saturated unsubstituted or substituted carbocycle. According to one embodiment, this saturated carbocycle is unsubstituted. According to a further embodiment, the saturated carbocycle carries one, two, three or four substituents Q$^{QR}$. In one further particular embodiment, said carbocycle is cyclopropane. In one further particular embodiment, said carbocycle is cyclobutane. In one further particular embodiment, said carbocycle is cyclohexane. In one further particular embodiment, said carbocycle is cyclopentane. In one further particular embodiment, said carbocycle is cyclopropane substituted by halogene or C$_1$-C$_4$-alkyl. In one further particular embodiment, said carbocycle is cyclobutane substituted by halogene or C$_1$-C$_4$-alkyl. In one further particular embodiment, said carbocycle is cyclohexane substituted by halogene or C$_1$-C$_4$-alkyl. In one further particular embodiment, said carbocycle is cyclopentane substituted by halogene or C$_1$-C$_4$-alkyl.

According to a further embodiment, the unsubstituted or substituted and saturated or partially unsaturated heterocycle is three-, four-, five- or six-membered and contains one, two or three, more particularly one or two, heteroatoms selected from NH, NR$^N$, O, S, S(=O) and S(=O)$_2$, wherein R$^N$ is as defined above or preferably selected from C$_1$-C$_2$-alkyl, C$_1$-C$_2$-halogenalkyl and SO$_2$Ph, wherein Ph is unsubstituted phenyl or phenyl that is substituted by one C$_1$-C$_2$-alkyl. In one further particular embodiment, said heterocycle is four- or six-membered.

According to a further embodiment, the heterocycle formed by Q$^1$ and Q$^2$ contains one, two or three, more specifically one or two, heteroatoms selected from NH and NR$^N$, wherein R$^N$ is as defined and preferably defined below, more particularly selected from C$_1$-C$_2$-alkyl, C$_1$-C$_2$-halogenalkyl and SO$_2$Ph, wherein Ph is unsubstituted phenyl or phenyl that is substituted by one methyl.

In one embodiment thereof, it contains one or two heteroatoms NH, in particular one NH. In another embodiment, it contains one or two heteroatoms NR$^N$, in particular one NR$^N$, wherein R$^N$ in each case is as defined and preferably defined above.

According to a further embodiment, the heterocycle formed by Q$^1$ and Q$^2$ contains one, two or three, more specifically one or two, in particular one, heteroatom(s) selected from S, S(=O) and S(=O)$_2$. In one embodiment thereof, it contains one or two heteroatoms S, in particular one S. In another embodiment, it contains one or two heteroatoms S(=O), in particular one S(=O). In still another embodiment, it contains one or two heteroatoms S(=O)$_2$, in particular one S(=O)$_2$.

According to a further embodiment, the heterocycle formed by Q$^1$ and Q$^2$ contains one or two heteroatoms O. In one embodiment thereof, it contains one heteroatom O. In another embodiment, it contains two heteroatoms O.

According to a further embodiment, the heterocycle formed by Q$^1$ and Q$^2$ is unsubstituted, i.e. it does not carry any substituent Q$^{QR}$. According to a further embodiment, it carries one, two, three or four Q$^R$.

According to one particular embodiment, Q$^1$ and Q$^2$ together form a 4-membered saturated heterocycle which contains 1 or 2 heteroatoms, in particular 1 heteroatom, from the group consisting of NH, NR$^N$, O, S, S(=O) and S(=O)$_2$, as ring members, wherein R$^N$ is defined and preferably defined above. In one embodiment, the heterocycle contains one O as heteroatom. For example, the formed heterocycle is oxetane. According to one embodiment thereof, the heterocycle is unsubstituted, i.e. it does not carry any substituent Q$^{QR}$. According to a further embodiment, it carries one, two, three or four Q$^R$.

According to a further particular embodiment, Q$^1$ and Q$^2$ together form a 5-membered saturated heterocycle which contains 1, 2 or 3, in particular 1 or 2, heteroatoms from the group consisting of NH, NR$^N$, O, S, S(=O) and S(=O)$_2$, as ring members, wherein R$^N$ is as defined and preferably defined above. According to one embodiment thereof, the heterocycle is unsubstituted, i.e. it does not carry any substituent Q$^{QR}$. According to a further embodiment, it carries one, two, three or four Q$^R$.

According to a further particular embodiment, Q$^1$ and Q$^2$ together form a 6-membered saturated heterocycle which contains 1, 2 or 3, in particular 1 or 2, heteroatoms from the group consisting of NH, NR$^N$, O, S, S(=O) and S(=O)$_2$, as ring members, wherein R$^N$ is as defined and preferably defined below. According to one embodiment thereof, the heterocycle is unsubstituted, i.e. it does not carry any substituent Q$^{QR}$. According to a further embodiment, it carries one, two, three or four Q$^R$. According to one specific embodiment thereof, said 6-membered saturated heterocycle contains 1 or 2 heteroatoms selected from NH and NR$^N$. According to a further specific embodiment thereof, said 6-membered saturated heterocycle contains 1 or 2 heteroatoms 0.

According to a further specific embodiment thereof, said 6-membered saturated heterocycle contains 1 or 2 heteroatoms selected from S, S(=O) and S(=O)$_2$. According to one embodiment thereof, the respective 6-membered heterocycle is unsubstituted, i.e. it does not carry any substituent Q$^{QR}$. According to a further embodiment, it carries one, two, three or four Q$^R$.

According to a further particular embodiment, Q$^1$ and Q$^2$ together form a three- to six-membered saturated or partially unsaturated carbo-, or heterocycle.

Q$^{QR}$ are the possible substituents for the heterocycle formed by Q$^1$ and Q$^2$ and are independently selected from halogen, OH, CN, NO$_2$, SH, NH$_2$, C$_1$-C$_6$-alkyl, C$_1$-C$_6$-halogenalkyl, C$_1$-C$_6$-alkoxy, C$_1$-C$_6$-halogenalkoxy, C$_1$-C$_6$-alkylthio, C$_1$-C$_6$-halogenalkylthio, C$_1$-C$_4$-alkoxy-C$_1$-C$_4$-alkyl, phenyl and phenoxy, wherein the phenyl groups are unsubstituted or carry one, two, three, four or five substituents Q$^R$ selected from the group consisting of halogen, OH, C$_1$-C$_4$-alkyl, C$_1$-C$_4$-halogenalkyl, C$_1$-C$_4$-alkoxy and C$_1$-C$_4$-halogenalkoxy; and wherein in each case one or two CH$_2$ groups of the carbo- or heterocycle may be replaced by a group independently selected from C(=O) and C(=S).

In one preferred embodiment, $Q^{QR}$ is in each case independently selected from halogen, OH, CN, SH, $C_1$-$C_6$-alkyl, $C_1$-$C_6$-halogenalkyl, $C_1$-$C_6$-alkoxy, $C_1$-$C_6$-halogenalkoxy and $C_1$-$C_6$-alkylthio. In one further preferred embodiment, $Q^{QR}$ is in each case independently selected from halogen, $C_1$-$C_6$-alkyl and $C_1$-$C_6$-halogenalkyl. In one further particular embodiment, $Q^{QR}$ is in each case independently selected from $C_1$-$C_6$-alkyl, such as methyl and ethyl.

$R^N$ is the substituent of the heteroatom $NR^N$ that is contained in the heterocycle formed by $Q^2$ and $Q^3$ in some of the inventive compounds. $R^N$ is selected from $C_1$-$C_4$-alkyl, $C_1$-$C_4$-halogenalk and $SO_2Ph$, wherein Ph is unsubstituted phenyl or phenyl that is substituted by one, two or three substituents selected from $C_1$-$C_4$-alkyl. In one preferred embodiment, $R^N$ is in each case independently selected from $C_1$-$C_2$-alkyl, $C_1$-$C_2$-halogenalkyl and $SO_2Ph$, wherein Ph is unsubstituted phenyl or phenyl that is substituted by one methyl substituents. In one particular embodiment, $R^N$ is in each case independently selected from $C_1$-$C_2$-alkyl, more particularly methyl. In one particular embodiment, $R^N$ is in each case independently selected from $SO_2Ph$, wherein Ph is unsubstituted phenyl or phenyl that is substituted by one methyl.

Particularly preferred embodiments of the heterocycles formed $Q^1$ and $Q^2$ and according to the invention are in Table Q12 below, wherein each line of lines Q12-1 to Q12-15 corresponds to one particular embodiment of the invention, wherein Q12-1 to Q12-15 are also in any combination with one another a preferred embodiment of the present invention. The carbon atom, to which $Q^1$ and $Q^2$ are bound is marked with # in the drawings.

TABLE Q12

| No. | heterocycle formed by $Q^1$ and $Q^2$ |
|---|---|
| Q12-1 |  |
| Q12-2 |  |
| Q12-3 |  |
| Q12-4 |  |
| Q12-5 | 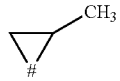 |
| Q12-6 | 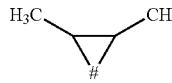 |
| Q12-7 | 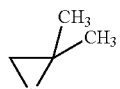 |
| Q12-8 | 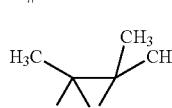 |

TABLE Q12-continued

| No. | heterocycle formed by $Q^1$ and $Q^2$ |
|---|---|
| Q12-9 | 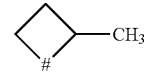 |
| Q12-10 |  |
| Q12-11 |  |
| Q12-12 |  |
| Q12-13 |  |
| Q12-14 |  |
| Q12-15 |  |

W according to the invention is O, $S(O)_m$ or $NQ^4$; wherein m is 0, 1 or 2.

According to one embodiment of formula I, W is O.
According to another embodiment of formula I, W is S.
According to another embodiment of formula I, W is SO.
According to another embodiment of formula I, W is $SO_2$.
According to another embodiment of formula I, U is $CR^3$ and W is $NQ^4$
According to one most preferred embodiment of formula I, U is N and W is O.
According to one further most preferred embodiment of formula I, U is N and W is S
According to one further most preferred embodiment of formula I, U is N and W is SO.
According to one further most preferred embodiment of formula I, U is N and W is $SO_2$.
According to one further most preferred embodiment of formula I, U is N and W is $NQ^4$.

$Q^3$ according to the invention is selected from substituted $C_1$-$C_{15}$-alkyl, $C_2$-$C_{15}$-alkenyl, $C_2$-$C_{15}$-halogenalkenyl, $C_2$-$C_{15}$-alkynyl, $C_3$-$C_7$-cycloalkyl, $S(O)_m$—$C_1$-$C_{15}$-alkyl, $S(O)_m$—$C_1$-$C_{15}$-alkoxy, $S(O)_m$-aryl, $S(O)_m$—$C_2$-$C_{15}$-alkenyl, $S(O)_m$—$C_2$-$C_{15}$-alkynyl, $C(=O)C_1$-$C_{15}$-alkyl, $C(=O)C_1$-$C_{15}$-halogenalkyl, $C(=O)C_2$-$C_{15}$-alkenyl, $C(=O)C_2$-$C_{15}$-alkynyl, $C(=O)C_3$-$C_7$-cycloalkyl, $C(=O)$ aryl, $C(=O)NH(C_1$-$C_{15}$-alkyl), $C(=O)N(C_1$-$C_{15}$-alkyl)$_2$, $C(=O)NH(C_2$-$C_{15}$-alkenyl), $C(=O)N(C_2$-$C_{15}$-alkenyl), $C(=O)NH(C_2$-$C_{15}$-alkynyl), $C(=O)N(C_2$-$C_{15}$-alkynyl), $C(=O)NH(C_3$-$C_7$-cycloalkyl), $C(=O)N(C_3$-$C_7$-cycloalkyl), $C(=S)C_1$-$C_{15}$-alkyl, $C(=S)C_2$-$C_{15}$-alkenyl, $C(=S)C_2$-$C_{15}$-alkynyl, $C(=S)C_3$-$C_6$-cycloalkyl, $C(=S)O(C_1$-$C_{15}$-alkyl), $C(=S)O(C_2$-$C_{15}$-alkenyl), $C(=S)O(C_2$-$C_{15}$-alkynyl), $C(=S)O(C_3$-$C_7$-cycloalkyl), $C(=S)NH(C_1$-$C_{15}$- alkyl), C(=S)NH($C_2$-$C_{15}$-alkenyl), C(=S)NH($C_2$-$C_{15}$-alkynyl), C(=S)NH($C_3$-$C_7$-cycloalkyl), C(=S)N($C_1$-$C_{15}$-alkyl)$_2$, C(=S)N($C_2$-$C_{15}$-alkenyl), C(=S)N($C_2$-$C_{15}$-alkynyl)$_2$, C(=S)N($C_3$-$C_7$-cycloalkyl), $C_3$-$C_6$-cycloalkyl, three-, four-, five- or six-membered saturated or partially unsaturated heterocycle, five- or six-membered heteroaryl and aryl; wherein the heteroaryl contains one, two or three heteroatoms selected from N, O and S; wherein in each case one or two $CH_2$ groups of the carbocycle and heterocycle may be replaced by a group independently selected from C(=O) and C(=S)

wherein the aliphatic moieties of $Q^3$ except for substituted $C_1$-$C_{15}$-alkyl moieties are unsubstituted or substituted with identical or different groups $Q^{3a}$ which independently of one another are selected from:

$Q^{3a}$ halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-halogenalkylthio, S(O)m-$C_1$-$C_6$-alkyl, S(O)$_m$—$C_1$-$C_6$-halogenalkyl, S(O)$_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein in each case one or two $CH_2$ groups of the carbocycle and heterocycle may be replaced by a group independently selected from C(=O) and C(=S); wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{31a}$ selected from the group consisting of halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-alkylthio, S(O)$_m$—$C_1$-$C_6$-alkyl, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311a}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy; and wherein m, $R^x$, R' and R" is defined as above;

wherein the carbocycle, heterocycle, heteroaryl and aryl moieties of $Q^3$ are unsubstituted or substituted with 1, 2, 3, 4, 5 or up to the maximum number of identical or different groups $Q^{3b}$ which independently of one another are selected from:

$Q^{3b}$ halogen, OH, CN, $C_1$-$C_4$-alkyl, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{31b}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311b}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy; and wherein R' and R" are defined as above.

wherein the substituted $C_1$-$C_{15}$-alkyl moieties of $Q^3$ carry one, two, three or up to the maximum possible number of identical or different groups $Q^{3c}$, respectively, which independently of one another are selected from:

$Q^{3c}$ halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, S(O)m-$C_1$-$C_6$-alkyl, S(O)$_m$—$C_1$-$C_6$-halogenalkyl, S(O)$_m$,-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from C(=O) and C(=S); wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, S(O)$_m$—$C_1$-$C_6$-alkyl and CR'=NOR"; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl), NH—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and S(O)$_m$—$C_1$-$C_6$-alkyl; wherein m, $R^x$, R' and R" is as defined above;

According to still another embodiment of formula I, $Q^3$ is $C_1$-$C_{15}$-halogenalkyl, in particular $C_1$-$C_7$-halogenalkyl, such as $CF_3$, $CCl_3$, $FCH_2$, $ClCH_2$, $F_2CH$, $Cl_2CH$, $CF_3CH_2$, $CCl_3CH_2$ or $CF_2CHF_2$.

According to still a further embodiment of formula I, $Q^3$ is $C_2$-$C_{15}$-alkenyl, in particular $C_2$-$C_7$-alkenyl, such as CH=$CH_2$, C($CH_3$)=$CH_2$, $CH_2$CH=$CH_2$.

According to a further specific embodiment of formula I, $Q^3$ is $C_2$-$C_{15}$-alkenyl, in particular $C_2$-$C_7$-alkenyl, more specifically $C_2$-$C_4$-alkenyl such as CH=$CH_2$, $CH_2$CH=$CH_2$ or $CH_2$, $CH_2$CH=$CH_2$ According to a further specific embodiment of formula I, $Q^3$ is $C_2$-$C_{15}$-halogenalkenyl, in particular $C_2$-$C_7$-halogenalkenyl, more specifically $C_2$-$C_3$-halogenalkenyl such as CH=CHF, CH=CHCl, CH=$CF_2$, CH=$CCl_2$, $CH_2$CH=CHF, $CH_2$CH=CHCl, $CH_2$CH=$CF_2$, $CH_2$CH=$CCl_2$, $CF_2$CH=$CF_2$, $CCl_2$CH=$CCl_2$, $CF_2$CF=$CF_2$, $CCl_2$CCl=$CCl_2$.

According to still a further embodiment of formula I, $Q^3$ is $C_2$-$C_{15}$-alkynyl or $C_2$-$C_{15}$-halogenalkynyl, in particular $C_2$-$C_4$-alkynyl or $C_2$-$C_4$-halogenalkynyl, such as C≡CH, $CH_2$C≡CH.

According to still another embodiment of formula I $Q^3$ is $C_3$-$C_7$-cycloalkyl, in particular cyclopropyl.

According to still another embodiment of formula I, $Q^3$ is $C_3$-$C_7$-halogencycloalkyl. In a special embodiment $R^{3b}$ is fully or partially halogenated cyclopropyl, such as 1-F-cyclopropyl, 1-Cl-cyclopropyl, 1,1-$F_2$-cyclopropyl, 1,1-$Cl_2$-cyclopropyl.

According to still another embodiment of formula I, $Q^3$ is S(O)m-$C_1$-$C_{15}$-alkyl such as $SCH_3$, S(=O)$CH_3$, S(O)$_2CH_3$.

According to still another embodiment of formula I, $Q^3$ is S(O)m-$C_1$-$C_{15}$-halogenalkyl such as $SCF_3$, S(=O)$CF_3$, S(O)$_2CF_3$, $SCHF_2$, S(=O)$CHF_2$, S(O)$_2CHF_2$.

According to still another embodiment of formula I, $Q^3$ is S(O)m-$C_1$-$C_{15}$-alkoxy such as S($OCH_3$), S(=O)($OCH_3$), S(O)$_2$($OCH_3$).

According to still another embodiment of formula I, $Q^3$ is S(O)m-aryl such as S-phenyl, S(=O) phenyl, S(O)$_2$phenyl, wherein the phenyl group is unsubstituted or carries one, two, three, four or five substituents $R^{78a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

According to still another embodiment of formula I, $Q^3$ is S(O)n-$C_2$-$C_6$-alkenyl such as SCH=$CH_2$, S(=O)CH=$CH_2$, S(O)$_2$CH=$CH_2$, $SCH_2$CH=$CH_2$, S(=O)$CH_2$CH=$CH_2$, S(O)$_2CH_2$CH=$CH_2$.

According to still another embodiment of formula I, $Q^3$ is S(O)n-$C_2$-$C_6$-alkynyl such as SC≡CH, S(=O)C≡CH, S(O)$_2$C≡CH, $SCH_2$C≡CH, S(=O)$CH_2$C≡CH, S(O)$_2$$CH_2$C≡CH.

According to a further specific embodiment of formula I, $Q^3$ is C(=O)$C_1$-$C_{15}$-alkyl, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is C(=O)$C_1$-$C_{15}$-halogenalkyl, wherein halogenalkyl is $CF_3$, $CCl_3$, $FCH_2$, $ClCH_2$, $F_2$CH, $C_2$CH, $CF_3CH_2$, $CCl_3CH_2$ or $CF_2CHF_2$.

According to a further specific embodiment of formula I, $Q^3$ is C(=O)$C_2$-$C_{15}$-alkenyl, wherein alkenyl is CH=$CH_2$, $CH_2$CH=$CH_2$.

According to a further specific embodiment of formula I, $Q^3$ is C(=O)$C_2$-$C_{15}$-alkynyl, wherein alkynyl is C≡CH, $CH_2$C≡CH.

According to a further specific embodiment of formula I, $Q^3$ is C(=O)$C_3$-$C_7$-cycloalkyl, wherein cycloalkyl is cyclopropyl ($C_3H_7$) or cyclobutyl ($C_4H_9$).

According to a further specific embodiment of formula I, $Q^3$ is C(=O)aryl, wherein the phenyl group is unsubstituted or carries one, two, three, four or five substituents $R^{78a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

According to a further specific embodiment of formula I, $Q^3$ is C(=O)NH($C_1$-$C_{15}$-alkyl) or C(=O)N($C_1$-$C_{15}$-alkyl)$_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is C(=O)NH($C_2$-$C_{15}$-alkenyl) or C(=O)N($C_2$-$C_{15}$-alkenyl)$_2$), wherein alkenyl is CH=$CH_2$, $CH_2$CH=$CH_2$.

According to a further specific embodiment of formula I, $Q^3$ is C(=O)NH($C_2$-$C_{15}$-alkynyl) or C(=O)N($C_2$-$C_{15}$-alkynyl)$_2$, wherein alkynyl is C≡CH, $CH_2$C≡CH.

According to a further specific embodiment of formula I, $Q^3$ is C(=O)NH($C_3$-$C_7$-cycloalkyl) or C(=O)N($C_3$-$C_7$-cycloalkyl)$_2$, wherein cycloalkyl is cyclopropyl ($C_3H_7$) or cyclobutyl ($C_4H_9$).

According to a further specific embodiment of formula I, $Q^3$ is C(=S)$C_1$-$C_{15}$-alkyl, C(=S)O($C_1$-$C_{15}$-alkyl), C(=S)NH($C_1$-$C_5$-alkyl) or C(=S)N($C_1$-$C_{15}$-alkyl)$_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is C(=S)$C_2$-$C_{15}$-alkenyl, C(=S)O($C_2$-$C_{15}$-alkenyl), C(=S)NH($C_2$-$C_{15}$-alkenyl) or C(=S)N($C_2$-$C_{15}$-alkenyl)$_2$, wherein alkenyl is CH=$CH_2$, $CH_2$CH=$CH_2$.

According to a further specific embodiment of formula I, $Q^3$ is C(=S)O($C_2$-$C_{15}$-alkynyl), C(=S)NH($C_2$-$C_{15}$-alkynyl) or C(=S)N($C_2$-$C_{15}$-alkynyl), wherein alkynyl is C≡CH, $CH_2$C≡CH.

According to a further specific embodiment of formula I, $Q^3$ is C(=S)$C_3$-$C_7$-cycloalkyl, C(=S)O($C_3$-$C_7$-cycloalkyl) or C(=S)N($C_3$-$C_7$-cycloalkyl)$_2$, wherein cycloalkyl is cyclopropyl ($C_3H_7$) or cyclobutyl ($C_4H_9$).

According to still another embodiment of formula I, $Q^3$ is a partially unsaturated three-, four-, five-, six-, seven-, eight-, nine-, or ten-membered carbocycle, in particular three-, four-, five- or six-membered, wherein the carbocycle is unsubstituted or substituted by substituents $Q^{3b}$ as defined below. According to one embodiment thereof, the carbocycle is unsubstituted.

According to still another embodiment of formula I, $Q^3$ is a partially unsaturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $Q^{3b}$ as defined below. According to one embodiment thereof, the carbocycle or heterocycle is unsubstituted.

According to still a further embodiment, $Q^3$ is a saturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $Q^{3b}$ as defined below. According to one embodiment thereof, the carbocycle or heterocycle is unsubstituted.

According to still another embodiment of formula I, $Q^3$ is a saturated three-, four-, five-, six-, seven-, eight-, nine-, or ten-membered carbocycle, in particular three-, four-, five- or six-membered, wherein the carbocycle is unsubstituted or substituted by substituents $Q^{3b}$ as defined below. According to one embodiment thereof, the carbocycle is unsubstituted.

According to one embodiment, $Q^3$ is a 3-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^3$ is a 3-membered saturated carbocycle, which is unsubstituted such as cyclopropyl.

According to one embodiment, $Q^3$ is a 3-membered saturated carbocycle, which is substituted by halogen, more specifically by F, such as $C_3H_3F_2$.

According to one embodiment, $Q^3$ is a 3-membered saturated carbocycle, which is substituted by halogen. More specifically by C, such as $C_3H_3Cl_2$.

According to one embodiment, $Q^3$ is a 4-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^3$ is a 5-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^3$ is a 6-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to still another embodiment of formula I, $Q^3$ is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $R^{4b}$ as defined below. According to one embodiment thereof, the heterocycle is unsubstituted.

According to still another embodiment of formula I, $Q^3$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $R^{4b}$ as defined below. According to one embodiment thereof, the heterocycle is unsubstituted.

According to still another embodiment of formula I, in the embodiments of $Q^3$ described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one embodiment, $Q^3$ is a 4-membered saturated heterocycle which contains 1 or 2 heteroatoms, in particular 1 heteroatom, from the group consisting of N, O and S, as ring members. According to one embodiment, the heterocycle contains one O as heteroatom. For example, the formed heterocycle is oxetane. According to one embodiment thereof, the heterocycle is unsubstituted, i.e. it does not carry any substituent $Q^{3b}$. According to still another embodiment of formula I, it is substituted by $Q^{3b}$.

According to still another embodiment of formula I, $Q^3$ is a 5-membered saturated heterocycle which contains 1, 2 or 3, in particular 1 or 2, heteroatoms from the group consisting of N, O and S, as ring members. According to one embodiment, the heterocycle contains one O as heteroatom. According to one embodiment thereof, the heterocycle is unsubstituted, i.e. it does not carry any substituent $Q^{3b}$. According to still another embodiment of formula I, it is substituted by $Q^{3b}$.

According to still another embodiment of formula I, $Q^3$ is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $Q^{3b}$. According to still another embodiment of formula I, it is substituted by $Q^{3b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $Q^{3b}$. According to still another embodiment of formula I, it is substituted by $Q^{3b}$.

According to still another embodiment of formula I, $Q^3$ is aryl, in particular phenyl, wherein the aryl or phenyl moiety in each case is unsubstituted or substituted by identical or different groups $R^{3b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, Cl, Br, $CH_3$, $OCH_3$, $CF_3$ and $OCF_3$. According to one embodiment, $Q^3$ is unsubstituted phenyl. According to another embodiment, $Q^3$ is phenyl, that is substituted by one, two or three, in particular one, halogen, in particular selected from F, Cl and Br, more specifically selected from F and Cl.

According to still another embodiment of formula I, $Q^3$ is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $Q^3$ is a 6-membered heteroaryl such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to still another embodiment of formula I, $Q^3$ is in each case independently selected from substituted $C_1$-$C_{15}$-alkyl, $C_2$-$C_{15}$-alkenyl, $C_2$-$C_{15}$-halogenalkenyl, $C_2$-$C_{15}$-alkynyl, $C_3$-$C_7$-cycloalkyl, $C(=O)C_1$-$C_{15}$-alkyl, $C(=O)C_1$-$C_{15}$-halogenalkyl, $C(=O)$aryl, three-, four-, five- or six-membered saturated or partially unsaturated heterocycle, five- or six-membered heteroaryl, and aryl; wherein the heterocycle and heteroaryl contains one, two or three heteroatoms selected from N, O and S; wherein in each case one or two $CH_2$ groups of the carbocycle and heterocycle may be replaced by a group independently selected from $C(=O)$ and $C(=S)$; wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein.

According to still another embodiment of formula I, $Q^3$ is in each case independently selected from substituted $C_1$-$C_6$-alkyl, $C_2$-$C_6$-alkenyl, $C_2$-$C_6$-alkynyl, and $C_3$-$C_6$-cycloalkyl, wherein in each case one or two $CH_2$ groups of the carbocycle and heterocycle may be replaced by a group independently selected from $C(=O)$ and $C(=S)$; wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein.

According to still another embodiment of formula I, $Q^3$ is in each case independently selected from $C(=O)C_1$-$C_6$- alkyl, C(=O)O($C_1$-$C_6$-alkyl) and C(=O)NH($C_1$-$C_6$-alkyl), C(=O)N($C_1$-$C_6$-alkyl), C(=O)$C_2$-$C_6$-alkenyl, C(=O)O ($C_2$-$C_6$-alkenyl), C(=O)NH($C_2$-$C_6$-alkenyl), C(=O)N($C_2$-$C_6$-alkenyl), C(=O)$C_2$-$C_6$-alkynyl, C(=O)O($C_2$-$C_6$-alkynyl), C(=O)NH($C_2$-$C_6$-alkynyl), C(=O)N($C_2$-$C_6$-alkynyl)$_2$C(=O)$C_3$-$C_6$-cycloalkyl, C(=O)O($C_3$-$C_6$-cycloalkyl), C(=O)NH($C_3$-$C_6$-cycloalkyl) and C(=O)N($C_3$-$C_6$-cycloalkyl)$_2$, wherein in each case one or two $CH_2$ groups of the carbocycle and heterocycle may be replaced by a group independently selected from C(=O) and C(=S); wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein.

According to still another embodiment of formula I, $Q^3$ is in each case independently selected from C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, C(=O)$C_2$-$C_6$-alkenyl, C(=O)O ($C_2$-$C_6$-alkenyl), C(=O)NH($C_2$-$C_6$-alkenyl), C(=O)N($C_2$-$C_6$-alkenyl)$_2$; wherein in each case one or two $CH_2$ groups of the carbocycle and heterocycle may be replaced by a group independently selected from C(=O) and C(=S); wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein.

According to still another embodiment of formula I, $Q^3$ is in each case independently selected from $SO_2$—NH($C_1$-$C_6$-alkyl), $SO_2$—NH($C_1$-$C_6$-halogenalkyl), $SO_2$—NHphenyl; wherein in each case one or two $CH_2$ groups of the carbocycle and heterocycle may be replaced by a group independently selected from C(=O) and C(=S); wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein.

According to still another embodiment of formula I, $Q^3$ is in each case independently selected from substituted $C_1$-$C_6$-alkyl, C(=O)$C_1$-$C_6$-alkyl, C(=O)O($C_1$-$C_6$-alkyl), S(O)m-$C_1$-$C_6$-alkyl, S(O)$_m$aryl; wherein in each case one or two $CH_2$ groups of the carbocycle and heterocycle may be replaced by a group independently selected from C(=O) and C(=S); wherein the acyclic moieties of $Q^3$ except for substituted $C_1$-$C_{15}$-alkyl moieties are unsubstituted or substituted with identical or different groups $Q^{3a}$ as defined and preferably defined herein; wherein the carbocyclic, phenyl and heteroaryl moieties of $Q^3$ are unsubstituted or substituted with identical or different groups $Q^{3b}$ as defined and preferably defined herein; and wherein the substituted $C_1$-$C_{15}$-alkyl moieties of $Q^3$ are or substituted with identical or different groups $Q^{3c}$ as defined and preferably defined herein. According to still another embodiment of formula I, $Q^3$ is in each case independently selected from substituted $C_1$-$C_{15}$-alkyl, $C_2$-$C_{15}$-alkenyl, $C_2$-$C_{15}$-halogenalkenyl, $C_2$-$C_{15}$-alkynyl, C(=O)$C_1$-$C_{15}$-alkyl, C(=O)$C_1$-$C_{15}$-halogenalkyl, wherein the acyclic moieties of $Q^3$ except for substituted $C_1$-$C_{15}$-alkyl moieties are unsubstituted or substituted with identical or different groups $Q^{3a}$ as defined and preferably defined herein; and wherein the substituted $C_1$-$C_{15}$-alkyl moieties of $Q^3$ are or substituted with identical or different groups $Q^{3c}$ as defined and preferably defined herein.

$Q^{3a}$ are the possible substituents for the aliphatic moieties of $Q^3$ except for substituted $C_1$-$C_{15}$-alkyl moieties.

According to one embodiment $Q^{3a}$ is independently selected from halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-halogenalkylthio, S(O)m-$C_1$-$C_6$-alkyl, S(O)$_m$—$C_1$-$C_6$-halogenalkyl, S(O)$_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", $C_1$-$C_6$-alkoxy $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy and heteryloxy; wherein in each case one or two $CH_2$ groups of the carbocycle and heterocycle may be replaced by a group independently selected from C(=O) and C(=S); wherein the heterocycle or heteroaryl contains one, two or three heteroatoms selected from N, O and S; wherein the carbocyclic, heterocyclic, aryl, phenoxy, and heteroaryl groups are unsubstituted or substituted with 1, 2, 3, 4 or 5 substituents $Q^{31a}$ selected from the group consisting of halogen, OH, CN, $NO_2$, SH, $NH_2$, NH($C_1$-$C_4$-alkyl), N($C_1$-$C_4$-alkyl)$_2$, NH(C(=O)$C_1$-$C_4$-alkyl), N(C(=O)$C_1$-$C_4$-alkyl)$_2$, NH—$SO_2$—$R^x$, $C_1$-$C_6$-alkylthio, S(O)$_m$—$C_1$-$C_6$-alkyl, $C_1$-$C_4$-alkyl, $C_1$-$C_4$-halogenalkyl, $C_1$-$C_4$-alkoxy, $C_1$-$C_4$-halogenalkoxy, CR'=NOR", phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311a}$ selected from the group consisting of halogen, OH, CN, $C_1$-$C_4$-alkyl, $C_1$-$C_4$-halogenalkyl, $C_1$-$C_4$-alkoxy, CN, CR'=NOR" and $C_1$-$C_4$-halogenalkoxy; and wherein m, $R^x$, R' and R" is defined as above;

According to one preferred embodiment, $Q^{3a}$ is in each case independently selected from halogen, OH, CN, $NO_2$, $NH_2$, NH($C_1$-$C_4$-alkyl), N($C_1$-$C_4$-alkyl)$_2$, NH—$SO_2$—$R^x$, CH(=O), C(=O)$C_1$-$C_6$-alkyl, C(=O)O($C_1$-$C_6$-alkyl), C(=O)NH($C_1$-$C_6$-alkyl) or CR'=NOR".

According to one preferred embodiment, $Q^{3a}$ is in each case independently selected from OH, CN, CH(=O), C(=O)$C_1$-$C_6$-alkyl, C(=O)O($C_1$-$C_6$-alkyl), C(=O)NH ($C_1$-$C_6$-alkyl) such as CN, CHO, C(O)O($CH_3$), $CO_2$NH ($CH_3$) or $CO_2$N($CH_3$)$_2$.

According to one preferred embodiment, $Q^{3a}$ is in each case independently selected from, S(O)$_2$—$C_1$-$C_6$-alkyl, S(O)$_2$—$C_1$-$C_6$-halogenalkyl, S(O)$_2$-aryl, such as $SCH_3$, $SO_2CH_3$, $SO_2$Ph.

According to one preferred embodiment, $Q^{3a}$ is in each case independently selected from NH($C_1$-$C_4$-alkyl), N($C_1$-$C_4$-alkyl)$_2$, NH—$SO_2$—$R^x$, such as NH($CH_3$) N($CH_3$)$_2$, $NHSO_2CH_3$, $NHSO_2CF_3$ or $NHSO_2$Ph.

According to one preferred embodiment, $Q^{3a}$ is in each case independently selected from $C_3$-$C_6$-cycloalkyl, $C_3$-$C_6$-halogencycloalkyl, such as cyclopropyl or fully or partially halogenated cyclopropyl.

According to one preferred embodiment, $Q^{3a}$ is in each case independently selected from $C_1$-$C_6$-alkoxy, $C_1$-$C_6$-halogenalkoxy, such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to one preferred embodiment, $Q^{3a}$ is in each case independently selected from heterocycle, wherein the heterocycle is a saturated, two $CH_2$ groups are replaced by $C(=O)$ and contains one N as a ring member.

According to one preferred embodiment, $Q^{3a}$ is in each case independently selected from aryl, wherein the aryl is substituted by halogen selected from the group consisting of F, C, Br, $CH_3$, $CHF_2$, $OCH_3$, $OCHF_2$, $OCF_3$, CN or $SO_2CH_3$.

According to one preferred embodiment, $Q^{3a}$ is in each case independently selected from halogen, OH, CN, $C_3$-$C_6$-cycloalkyl, $C_3$-$C_6$-halogencycloalkyl and heterocycle, wherein the heterocyclocycle is a saturated and contains one N as a ring member.

According to one preferred embodiment, $Q^{3a}$ is in each case independently selected from halogen, OH, CN, $C_3$-$C_6$-cycloalkyl, $C_3$-$C_6$-halogencycloalkyl and heterocycle, wherein the heterocycle is a saturated, one $CH_2$ group is replaced by $C(=O)$ and contains one N as a ring member.

According to one preferred embodiment, $Q^{3a}$ is in each case independently selected from halogen, OH, CN, $C_3$-$C_6$-cycloalkyl, $C_3$-$C_6$-halogencycloalkyl and heterocycle, wherein the heretocyclocycle is a saturated, two $CH_2$ groups are replaced by $C(=O)$ and contains one N as a ring member.

According to one preferred embodiment, $Q^{3a}$ is in each case independently selected from halogen, OH, CN, $C_1$-$C_6$-alkoxy, $C_1$-$C_6$-halogenalkoxy, phenyl, aryl or heteroaryl; wherein the aryl and heteroaryl is substituted by halogen selected from the group consisting of F, C, Br, $CH_3$, $CHF_2$, $OCH_3$, $OCHF_2$, $OCF_3$, CN or $SO_2CH_3$.

According to one further preferred embodiment, $Q^{3a}$ is in each case independently selected from halogen, phenyl, halogenphenyl and heteroaryl, wherein the halogenphenyl is substituted by halogen selected from the group consisting of F, Cl and Br, in particular selected from F and Cl.

According to one further preferred embodiment, $Q^{3a}$ is in each case independently selected from halogen, CN, $C_3$-$C_6$-cycloalkyl, $C_3$-$C_6$-halogencycloalkyl, $C_1$-$C_6$-alkoxy, $C_1$-$C_4$-halogenalkoxy, $C_1$-$C_6$-alkylthio, $C_1$-$C_6$-halogenalkylthio, phenyl, wherein the phenyl is substituted by halogen selected from the group consisting of F, C and Br or by $C_1$-$C_4$-alkyl, $C_1$-$C_4$-halogenalkyl, $C_1$-$C_4$-alkoxy and $C_1$-$C_4$-halogenalkoxy.

According to one further preferred embodiment, $Q^{3a}$ is in each case independently selected from halogen and phenyl wherein the phenyl is substituted by halogen selected from the group consisting of F, Cl and Br, in particular selected from F and Cl.

According to still another embodiment of formula I, $Q^{3a}$ is a partially unsaturated three-, four-, five-, six-, seven-, eight-, nine-, or ten-membered carbocycle, in particular three-, four-, five- or six-membered, wherein the carbocycle is unsubstituted or substituted by substituents $Q^{3b}$ as defined below. According to one embodiment thereof, the carbocycle is unsubstituted.

According to still another embodiment of formula I, $Q^{3a}$ is a partially unsaturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $Q^{3b}$ as defined below. According to one embodiment thereof, the carbocycle or heterocycle is unsubstituted.

According to still a further embodiment, $Q^{3a}$ is a saturated three-, four-, five-, six-, seven-, eight-, nine-, or ten-membered carbocycle or heterocycle, in particular three-, four-, five- or six-membered, wherein the heterocycle contains one, two, three or four heteroatoms selected from N, O and S, and wherein the carbocycle and heterocycle are unsubstituted or substituted with substituents $Q^{3b}$ as defined below. According to one embodiment thereof, the carbocycle or heterocycle is unsubstituted.

According to still another embodiment of formula I, $Q^{3a}$ is a saturated three-, four-, five-, six-, seven-, eight-, nine-, or ten-membered carbocycle, in particular three-, four-, five- or six-membered, wherein the carbocycle is unsubstituted or substituted by substituents $Q^{3b}$ as defined below. According to one embodiment thereof, the carbocycle is unsubstituted.

According to one embodiment, $Q^{3a}$ is a 3-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^{3a}$ is a 3-membered saturated carbocycle, which is unsubstituted such as cyclopropyl.

According to one embodiment, $Q^{3a}$ is a 3-membered saturated carbocycle, which is substituted by halogen, more specifically by F, such as $C_3H_3F_2$.

According to one embodiment, $Q^{3a}$ is a 3-membered saturated carbocycle, which is substituted by halogen. More specifically by C, such as $C_3H_3Cl_2$.

According to one embodiment, $Q^{3a}$ is a 4-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^{3a}$ is a 5-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^{3a}$ is a 6-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to still another embodiment of formula I, $Q^{3a}$ is a partially unsaturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^{3b}$ as defined below. According to one embodiment thereof, the heterocycle is unsubstituted.

According to still another embodiment of formula I, $Q^{3a}$ is a saturated three-, four-, five-, six-, seven-, eight-, nine-, or ten-membered heterocycle, in particular three-, four-, five- or six-membered, wherein the heterocycle contains one, two, three or four heteroatoms selected from N, O and S, and wherein the heterocycle is unsubstituted or substituted by substituents $Q^{3b}$ as defined below. According to one embodiment thereof, the heterocycle is unsubstituted.

According to still another embodiment of formula I, in the embodiments of $Q^{3a}$ described above, the heterocycle contains preferably one, two or three, more specifically one or two heteroatoms selected from N, O and S. More specifically, the hetereocycle contains one heteroatom selected from N, O and S. In particular, the heterocycle contains one or two, in particular one O.

According to one embodiment, $Q^{3a}$ is a 4-membered saturated heterocycle which contains 1 or 2 heteroatoms, in particular 1 heteroatom, from the group consisting of N, O and S, as ring members. According to one embodiment, the heterocycle contains one O as heteroatom. For example, the formed heterocycle is oxetane. According to one embodiment thereof, the heterocycle is unsubstituted, i.e. it does not carry any substituent $Q^{3b}$. According to still another embodiment of formula I, it is substituted by $Q^{3b}$.

According to still another embodiment of formula I, $Q^{3a}$ is a 5-membered saturated heterocycle which contains 1, 2 or 3, in particular 1 or 2, heteroatoms from the group consisting of N, O and S, as ring members. According to one embodiment, the heterocycle contains one O as heteroatom. According to one embodiment thereof, the heterocycle is unsubstituted, i.e. it does not carry any substituent $Q^{3b}$. According to still another embodiment of formula I, it is substituted by $Q^{3b}$.

According to still another embodiment of formula I, $Q^{3a}$ is a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $Q^{3b}$. According to still another embodiment of formula I, it is substituted by $Q^{3b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $Q^{3b}$. According to still another embodiment of formula I, it is substituted by $Q^{3b}$.

$Q^{3b}$ are the possible substituents for the carbocycle, heterocycle, heteroaryl and aryl moieties of $Q^3$.

$Q^{3b}$ according to the invention is independently selected from halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_4\text{-alkyl}$, $C_1-C_6\text{-alkoxy}$, $C_3-C_6\text{-cycloalkyl}$, $C_3-C_6\text{-halogencycloalkyl}$, $C_1-C_4\text{-alkoxy}$, $C_1-C_4\text{-halogenalkoxy}$, $C_1-C_6\text{-alkylthio}$, $S(O)_m-C_1-C_6\text{-alkyl}$, $C_1-C_4\text{-alkoxy-}C_1-C_4\text{-alkyl}$, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{31b}$ selected from the group consisting of halogen, OH, $C_1-C_4\text{-alkyl}$, $C_1-C_4\text{-halogenalkyl}$, $C_1-C_4\text{-alkoxy}$, $C_1-C_4\text{-halogenalkoxy}$, $CR'=NOR''$; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{311b}$ selected from the group consisting of halogen, OH, $C_1-C_4\text{-alkyl}$, $C_1-C_4\text{-halogenalkyl}$, $C_1-C_4\text{-alkoxy}$, CN, $CR'=NOR''$ and $C_1-C_4\text{-halogenalkoxy}$; and wherein R', R'' and $R^x$ are defined as above;

According to one embodiment thereof $Q^{3b}$ is independently selected from halogen, CN, $C_1-C_4\text{-alkyl}$, $C_1-C_4\text{-alkoxy}$, $C_1-C_4\text{-halogenalkyl}$ and $C_1-C_4\text{-halogenalkoxy}$, in particular halogen, $C_1-C_4\text{-alkyl}$ and $C_1-C_4\text{-alkoxy}$. Specifically, $Q^{3b}$ is independently selected from F, Cl, CN, $CH_3$, $CHF_2$, $CF_3OCH_3$ and halogenmethoxy.

According to one preferred embodiment, $Q^{3b}$ is in each case independently selected from halogen, OH, CN, SH, $C_1-C_6\text{-alkyl}$, $C_1-C_6\text{-halogenalkyl}$, $C_1-C_6\text{-alkoxy}$, $C_1-C_6\text{-halogenalkoxy}$, $C_1-C_6\text{-alkylthio}$ and $S(O)_m-C_1-C_6\text{-alkyl}$. According to one further preferred embodiment, $Q^{3b}$ is in each case independently selected from halogen, $C_1-C_6\text{-alkoxy}$, $C_1-C_6\text{-halogenalkyl}$, $C_1-C_6\text{-halogenalkoxy}$ and $S(O)_m-C_1-C_6\text{-alkyl}$. According to one further particular embodiment, $Q^{3b}$ is in each case independently selected from halogen such as Cl, Br, F. According to one further particular embodiment, $Q^{3b}$ is in each case independently selected from $C_1-C_6\text{-alkyl}$, such as methyl and ethyl. According to one further particular embodiment, $Q^{3b}$ is in each case independently selected from halogen, such as F, Cl and Br. According to one further particular embodiment, $Q^{3b}$ is in each case independently selected from $C_1-C_6\text{-alkoxy}$, such as $OCH_3$. According to one further particular embodiment, $Q^{3b}$ is in each case independently selected from $C_1-C_4\text{-halogenalkoxy}$, such as $OCHF_2$ and $OCF_3$. According to one further particular embodiment, $Q^{3b}$ is in each case independently selected from $S(O)_m-C_1-C_6\text{-alkyl}$ such as $SO_2CH_3$.

$Q^{3c}$ are the possible substituents for the substituted $C_1-C_{15}\text{-alkyl}$ moieties of $Q^3$.

$Q^{3c}$ according to the invention is independently selected from halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_4\text{-alkoxy}$, $C_1-C_4\text{-halogenalkoxy}$, $C_3-C_6\text{-halogencycloalkyl}$, $C_1-C_6\text{-alkylthio}$, $C_1-C_6\text{-halogenalkylthio}$, $S(O)m-C_1-C_6\text{-alkyl}$, $S(O)_m-C_1-C_6\text{-halogenalkyl}$, $S(O)_m\text{-aryl}$, $CH(=O)$, $C(=O)C_1-C_6\text{-alkyl}$, $C(=O)O(C_1-C_6\text{-alkyl})$, $C(=O)NH(C_1-C_6\text{-alkyl})$, $C(=O)N(C_1-C_6\text{-alkyl})_2$, $CR'=NOR''$, a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from $C(=O)$ and $C(=S)$; wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_6\text{-alkylthio}$, $C_1-C_4\text{-alkyl}$, $C_1-C_4\text{-halogenalkyl}$, $C_1-C_4\text{-alkoxy}$, $C_1-C_4\text{-halogenalkoxy}$, $S(O)_m-C_1-C_6\text{-alkyl}$ and $CR'=NOR''$; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, NH, $NH(C_1-C_4\text{-alkyl})$, $N(C_1-C_4\text{-alkyl})_2$, $NH(C(=O)C_1-C_4\text{-alkyl})$, $N(C(=O)C_1-C_4\text{-alkyl})_2$, $NH-SO_2-R^x$, $C_1-C_6\text{-alkylthio}$, $C_1-C_4\text{-alkyl}$, $C_1-C_4\text{-halogenalkyl}$, $C_1-C_4\text{-alkoxy}$, $C_1-C_4\text{-halogenalkoxy}$ and $S(O)_m-C_1-C_6\text{-alkyl}$; wherein m, $R^x$, R' and R'' is as defined above;

According to still another embodiment of formula I, $Q^3$ is $C_1-C_6\text{-alkyl}$ such as $CH_3$, $C_2H_5$, n-propyl, i-propyl, n-butyl, i-butyl, tert-butyl, n-pentyl or i-pentyl which is substituted by at least one group $R^{4c}$, which independently of one another are selected from:

halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl), $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, $S(O)_m$—$C_1$-$C_6$-alkyl, $S(O)_m$—$C_1$-$C_6$-halogenalkyl, $S(O)_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from C(=O) and C(=S); wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, NH, N H($C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and CR'=NOR"; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is $CH_3$ which is substituted by at least one group $Q^{3c}$, which independently of one another are selected from: halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, S(O)m-$C_1$-$C_6$-alkyl, $S(O)_m$—$C_1$-$C_6$-halogenalkyl, $S(O)_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from C(=O) and C(=S); wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and CR'=NOR"; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is Et which is substituted by at least one group $Q^{3c}$, which independently of one another are selected from: halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, S(O)m-$C_1$-$C_6$-alkyl, $S(O)_m$—$C_1$-$C_6$-halogenalkyl, $S(O)_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from C(=O) and C(=S); wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and CR'=NOR"; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, NH, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is Pr which is substituted by at least one group $Q^{3c}$, which independently of one another are selected from: halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, S(O)m-$C_1$-$C_6$-alkyl, $S(O)_m$—$C_1$-$C_6$-halogenalkyl, $S(O)_m$-aryl, CH(=O), C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl)$_2$, CR'=NOR", a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from C(=O) and C(=S); wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1$-

$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and $CR'=NOR''$; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is iPr which is substituted by at least one group $Q^{3c}$, which independently of one another are selected from: halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, $S(O)m$-$C_1$-$C_6$-alkyl, $S(O)_m$—$C_1$-$C_6$-halogenalkyl, $S(O)_m$-aryl, $CH(=O)$, $C(=O)C_1$-$C_6$-alkyl, $C(=O)O(C_1$-$C_6$-alkyl), $C(=O)NH(C_1$-$C_6$-alkyl), $C(=O)N(C_1$-$C_6$-alkyl)$_2$, $CR'=NOR''$, a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from $C(=O)$ and $C(=S)$; wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and $CR'=NOR''$; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is butyl which is substituted by at least one group $Q^{3c}$, which independently of one another are selected from: halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_4$-alkoxy, $C_1$-$C_4$-halogenalkoxy, $C_3$-$C_6$-halogencycloalkyl, $C_1$-$C_6$-alkylthio, $C_1$-$C_6$-halogenalkylthio, $S(O)m$-$C_1$-$C_6$-alkyl, $S(O)_m$—$C_1$-$C_6$-halogenalkyl, $S(O)_m$-aryl, $CH(=O)$, $C(=O)C_1$-$C_6$-alkyl, $C(=O)O(C_1$-$C_6$-alkyl), $C(=O)NH(C_1$-$C_6$-alkyl), $C(=O)N(C_1$-$C_6$-alkyl)$_2$, $CR'=NOR''$, a saturated or partially unsaturated three-, four-, five-, six-, seven-, eight-, nine-, or ten-membered carbocycle or heterocycle, aryl and five-, six- or ten-membered heteroaryl, heterocycloxy, heteryloxy; wherein in each case one or two $CH_2$ groups of the carbocycle and heterocycle may be replaced by a group independently selected from $C(=O)$ and $C(=S)$; wherein the heterocycle and heteroaryl contain independently one, two, three or four heteroatoms selected from N, O and S; wherein the carbocyclic, heterocyclic, aryl, phenoxy and heteroaryl groups are independently unsubstituted or carry one, two, three, four or five substituents $Q^{31c}$ selected from the group consisting of s halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy, $S(O)_m$—$C_1$-$C_6$-alkyl and $CR'=NOR''$; phenyl, phenoxy and five- to ten-membered heterocycle and heteroaryl; wherein the heterocycle or heteroaryl contains one, two or three heteroatoms selected from N, O and S; and wherein the carbocyclic, heterocyclic, phenyl, phenoxy, heterocycle and heteroaryl groups are unsubstituted or substituted with 1, 2, 3, 4 or 5 substituents $Q^{311c}$ selected from the group consisting of halogen, OH, CN, $NO_2$, SH, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $C_1$-$C_6$-alkylthio, $C_1$-$C_4$-alkyl, $C_1$-$C_4$-halogenalkyl, $C_1$-$C_4$-alkoxy, $C_1$-$C_4$-halogenalkoxy and $S(O)_m$—$C_1$-$C_6$-alkyl;

According to still another embodiment of formula I, $Q^3$ is $CH_2CN$.

According to still another embodiment of formula I, $Q^3$ is $CH_2OH$.

According to a further specific embodiment of formula I, $Q^3$ is $C_1$-$C_{15}$-alkyl-$C_1$-$C_6$-alkoxy, in particular $C_1$-$C_7$-alkyl-$C_1$-$C_4$-alkoxy, more specifically $C_1$-$C_4$-alkyl-$C_1$-$C_2$-alkoxy such as $CH_2OCH_3$, $CH_2CH_2OCH_3 CH_2CH_2O$ $CH_2CH_3$, $CH_2CH_2$, $CH_2OCH_3CH_2CH_2$, $CH_2O$ $CH_2CH_3$, According to a further specific embodiment of formula I, $Q^3$ is $C_1$-$C_{15}$-alkyl-$C_1$-$C_6$-halogenalkoxy, in particular $C_1$-$C_7$-alkyl-$C_1$-$C_4$-halogenalkoxy, more specifically $C_1$-$C_4$-alkyl-$C_1$-$C_2$-halogenalkoxy such as $CH_2OCF_3$, $CH_2CH_2OCF_3$, $CH_2OCHF_2$, $CH_2OCH_2F$, $CH_2OCCl_3$, $CH_2OCHCl_2$ or $CH_2OCH_2Cl$, in particular $CH_2OCF_3$, $CH_2OCHF_2$, $CH_2OCCl_3$ or $CH_2OCHCl_2$.

According to a further specific embodiment of formula I, $Q^3$ is $C_1$-$C_{15}$-alkyl-$C_1$-$C_6$-halogenalkylthio, in particular $C_1$-$C_{15}$-alkyl-$C_1$-$C_4$-halogenalkylthio, more specifically $C_1$-$C_4$-alkyl-$C_1$-$C_2$-halogenalkylthio such as $CH_2SCF_3$, $CH_2SCHF_2$, $CH_2SCH_2F$, $CH_2SCCl_3$, $CH_2SCHCl_2$ or $CH_2SCH_2Cl$, in particular $CH_2SCF_3$, $CH_2SCHF_2$, $CH_2SCCl_3$ or $CH_2SCHCl_2$.

According to a further specific embodiment of formula I, $Q^3$ is $C_1$-$C_5$-alkyl-$CH(=O)$, $C_1$-$C_{15}$-alkyl-$C(=O)C_1$-$C_6$-alkyl, $C_1$-$C_{15}$-alkyl-$C(=O)O(C_1$-$C_6$-alkyl), $C_1$-$C_{15}$-alkyl-$C(=O)NH(C_1$-$C_6$-alkyl) or $C_1$-$C_{15}$-alkyl-$C(=O)N(C_1$-$C_6$-alkyl)$_2$, especially $CH_2CH(=O)$, $CH_2C(=O)C_1$-$C_6$-alkyl, $CH_2C(=O)O(C_1$-$C_6$-alkyl), $CH_2C(=O)NH(C_1$-$C_6$-alkyl) or $CH_2C(=O)N(C_1$-$C_6$-alkyl)$_2$ wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is $C_1$-$C_{15}$-alkyl-$NH(C_1$-$C_4$-alkyl), $C_1$-$C_{15}$-alkyl-$N(C_1$-$C_4$-alkyl)$_2$, $C_1$-$C_{15}$-alkyl-$NH(C(=O)C_1$-$C_4$-alkyl) or $C_1$-$C_{15}$-alkyl-$N(C(=O)C_1$-$C_4$-alkyl)$_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is $C_1$-$C_{15}$-alkyl-$S(O)$—$C_1$-$C_6$-alkyl, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^3$ is $C_1$-$C_{15}$-alkyl-S(O)$_2$—$C_1$-$C_6$-alkyl, wherein alkyl is CH$_3$, C$_2$H$_5$, n-propyl, i-propyl, n-butyl, i-butyl, tert-butyl, n-pentyl or i-pentyl.

According to a further specific embodiment of formula I, $Q^3$ is $C_1$-$C_5$-alkyl-S(O)$_2$—$C_1$-$C_6$-halogenalkyl, wherein halogenalkyl is CF$_3$ or CHF$_2$ and z is 0, 1, 2 or 3.

According to a further specific embodiment of formula I, $Q^3$ is $C_1$-$C_{15}$-alkyl-S(O)$_2$-aryl, wherein the aryl or phenyl moiety in each case is independently unsubstituted or carry one, two, three, four or five substituents selected from the group consisting of halogen, OH, CN, NO$_2$, SH, NH$_2$, NH(C$_1$-C$_4$-alkyl), N(C$_1$-C$_4$-alkyl)$_2$, NH(C(=O)C$_1$-C$_4$-alkyl), N(C(=O)C$_1$-C$_4$-alkyl)$_2$, NH—SO$_2$—R$^x$, C$_1$-C$_6$-alkyl-thio, C$_1$-C$_4$-alkyl, C$_1$-C$_4$-halogenalkyl, C$_1$-C$_4$-alkoxy, C$_1$-C$_4$-halogenalkoxy and S(O)$_z$—C$_1$-C$_6$-alkyl, in particular F, C, Br, CH$_3$, OCH$_3$, CF$_3$, CHF$_2$, OCHF$_2$, OCF$_3$.

According to a further specific embodiment of formula I, $Q^3$ is $C_1$-$C_{15}$-alkyl-NH—SO$_2$—R$^x$ wherein R$^x$ is $C_1$-$C_4$-alkyl, C$_1$-C$_4$-halogenalkyl, unsubstituted aryl or aryl that is substituted by one, two, three, four or five substituents R$^{x2}$ independently selected from C$_1$-C$_4$-alkyl, halogen, OH, CN, C$_1$-C$_4$-halogenalkyl, C$_1$-C$_4$-alkoxy, or C$_1$-C$_4$-halogenalkoxy, such as CH$_2$NHSO$_2$CF$_3$ or CH$_2$NHSO$_2$CH$_3$.

According to still another embodiment of formula I, $Q^3$ is selected from C$_1$-C$_{15}$-alkyl which is substituted, a saturated three-, four-, five-, six-, seven-, eight-, nine-, or ten-membered carbocycle, in particular three-, four-, five- or six-membered, wherein the carbocycle is unsubstituted or substituted by substituents $Q^{3b}$ as defined below. According to one embodiment thereof, the carbocycle is unsubstituted.

According to one embodiment, $Q^3$ is selected from C$_1$-C$_{15}$-alkyl, especially CH$_2$ which is substituted by a 3-membered saturated carbocycle. According to one embodiment thereof, the carbocycle is unsubstituted, i.e. it does not carry any substituent $Q^3$. According to still another embodiment of formula I, it is substituted by $Q^{3b}$.

According to one embodiment, $Q^3$ is selected from C$_1$-C$_{15}$-alkyl, especially CH$_2$ which is substituted by a 4-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^3$ is selected from C$_1$-C$_{15}$-alkyl, especially CH$_2$ which is substituted by a 5-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to one embodiment, $Q^3$ is selected from C$_1$-C$_{15}$-alkyl, especially CH$_2$ which is substituted by a 6-membered saturated carbocycle. According to one embodiment thereof, the carbocycle is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 4-membered saturated heterocycle which contains 1 or 2 heteroatoms, in particular 1 heteroatom, from the group consisting of N, O and S, as ring members. According to one embodiment, the heterocycle contains one O as heteroatom. For example, the formed heterocycle is oxetane. According to one embodiment thereof, the heterocycle is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heterocycle which contains 1, 2 or 3, in particular 1 or 2, heteroatoms from the group consisting of N, O and S, as ring members. According to one embodiment, the heterocycle contains one O as heteroatom. According to one embodiment thereof, the heterocycle is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 6-membered saturated heterocycle which contains 1, 2 or 3, in particular 1 or 2, heteroatoms from the group consisting of N, O and S as ring members. According to one embodiment thereof, the heterocycle is unsubstituted, i.e. it does not carry any substituent $Q^{3b}$. According to still another embodiment of formula I, it is substituted by $Q^{3b}$. According to one specific embodiment thereof, said 6-membered saturated heterocycle contains 1 or 2, in particular 1, heteroatom(s) O. According to one embodiment thereof, the respective 6-membered heterocycle is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heterocycle which contains one N as ring member and optionally one or two groups CH$_2$ are replaced by C(=O).

According to a further specific embodiment of formula I, $Q^3$ is C$_1$-C$_{15}$-alkyl, especially CH$_2$ substituted by a 5-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heteroaryl which contains one N as ring member. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heteroaryl which contains two N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heteroaryl which contains three N as ring members. According to one embodiment thereof, the heteroaryl is unsubstituted, i.e. it does not carry any substituent $Q^{3b}$. According to still another embodiment of formula I, it is substituted by $Q^{3b}$. According to one specific embodiment thereof, said 5-membered saturated heterocycle contains 1 or 2, in particular 1, heteroatom(s) O.

According to a further specific embodiment of formula I, $Q^3$ is C$_1$-C$_{15}$-alkyl, especially CH$_2$ substituted by a 5-membered saturated heteroaryl which contains one S as ring member. According to one embodiment thereof, the heteroaryl is unsubstituted, i.e. it does not carry any substituent $Q^{34b}$. According to still another embodiment of formula I, it is substituted by $Q^{3b}$.

According to a further specific embodiment of formula I, $Q^3$ is C$_1$-C$_{15}$-alkyl, especially CH$_2$ substituted by a 5-membered saturated heteroaryl which contains one S and one N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 5-membered saturated heteroaryl which contains one S and two N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 5-membered saturated heteroaryl which contains one oxygen and one N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 5-membered saturated heteroaryl which contains one oxygen and two N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 6-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 6-membered saturated heteroaryl which one N as ring member. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 6-membered saturated heteroaryl which two N as ring members. According to one embodiment thereof, the heteroaryl is unsubstituted, i.e. it does not carry any substituent $Q^{3b}$. According to still another embodiment of formula I, it is substituted by $Q^{3b}$.

According to a further specific embodiment of formula I, $Q^3$ is $C_1$-$C_{15}$-alkyl, especially $CH_2$ substituted by a 10-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{3b}$. According to still another embodiment of formula I, it is substituted by $Q^{3b}$. According to one specific embodiment thereof, said 10-membered saturated heterocycle contains 1 or 2, in particular 1, heteroatom(s) N.

According to a further specific embodiment of formula I, $Q^3$ is $C_1$-$C_{15}$-alkyl, especially $CH_2$ substituted by a 10-membered saturated heteroaryl which one N as ring members. According to one embodiment thereof, the heteroaryl is unsubstituted, i.e. it does not carry any substituent $Q^{3b}$. According to still another embodiment of formula I, it is substituted by $Q^{3b}$.

According to still another embodiment of formula I, $Q^3$ is $CH_2$ substituted by a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $Q^3$ is $CH_2$ substituted by a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to one preferred embodiment, $Q^{3c}$ is in each case independently selected from OH, CN, $NO_2$, $NH_2$, $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, $CH(=O)$, $C(=O)C_1$-$C_6$-alkyl, $C(=O)O(C_1$-$C_6$-alkyl), $C(=O)NH(C_1$-$C_6$-alkyl) or $CR'=NOR''$.

According to one preferred embodiment, $Q^{3c}$ is in each case independently selected from OH, CN, $CH(=O)$, $C(=O)C_1$-$C_6$-alkyl, $C(=O)O(C_1$-$C_6$-alkyl), $C(=O)NH(C_1$-$C_6$-alkyl) such as CN, CHO, $C(O)CH_3$, $C(O)O(CH_3)$, $CO_2NH(CH_3)$ or $CO_2N(CH_3)_2$.

According to one preferred embodiment, $Q^{3c}$ is in each case independently selected from $C_1$-$C_6$-halogenalkylthio, $S(O)$—$C_1$-$C_6$-alkyl, $S(O)_2$—$C_1$-$C_6$-alkyl, $S(O)_2$—$C_1$-$C_6$-halogenalkyl, $S(O)_z$-aryl, such as $SCH_3$, $SO_2CH_3$, $SO_2Ph$.

According to one preferred embodiment, $Q^{3c}$ is in each case independently selected from $NH(C_1$-$C_4$-alkyl), $N(C_1$-$C_4$-alkyl)$_2$, $NH(C(=O)C_1$-$C_4$-alkyl), $N(C(=O)C_1$-$C_4$-alkyl)$_2$, $NH$—$SO_2$—$R^x$, such as $NH(CH_3)$ $N(CH_3)_2$ or $NHSO_2CH_3$, $NHSO_2CF_3$.

According to one preferred embodiment, $Q^{3c}$ is in each case independently selected from $C_3$-$C_6$-cycloalkyl, $C_3$-$C_6$-halogencycloalkyl, such as cyclopropyl or fully or partially halogenated cyclopropyl.

According to one preferred embodiment, $Q^{3c}$ is in each case independently selected $C_1$-$C_6$-halogenalkoxy, such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to one preferred embodiment, $Q^{3c}$ is in each case independently selected from heterocycle, wherein the heterocycle is a saturated, two $CH_2$ groups are replaced by $C(=O)$ and contains one N as a ring member.

According to one prefer embodiment, $Q^3$ is unsubstituted 5- or 6-membered heteroaryl. According to still a further embodiment, $R^4$ is 5- or 6-membered heteroaryl substituted by halogen selected from the group consisting of F, C, Br, $CH_3$, $CHF_2$, $OCH_3$, $OCHF_2$, $OCF_3$, CN or $SO_2CH_3$.

According to one preferred embodiment, $Q^{3c}$ is in each case independently selected from OH, CN, $C_3$-$C_6$-cycloalkyl, $C_3$-$C_6$-halogencycloalkyl and heterocycle, wherein the heterocycle is a saturated and contains one N as a ring member.

According to one preferred embodiment, $Q^{3c}$ is in each case independently selected from OH, CN, $C_3$-$C_6$-cycloalkyl, $C_3$-$C_6$-halogencycloalkyl and heterocycle, wherein the heterocycle is a saturated, one $CH_2$ group is replaced by $C(=O)$ and contains one N as a ring member.

According to one preferred embodiment, $Q^{3c}$ is in each case independently selected from OH, CN, $C_3$-$C_6$-cycloalkyl, $C_3$-$C_6$-halogencycloalkyl and heterocycle, wherein the heretocyclocycle is a saturated, two $CH_2$ groups are replaced by $C(=O)$ and contains one N as a ring member. Particularly preferred embodiments of $Q^3$ according to the invention are in Table Q3 below, wherein each line of lines Q3-1 to Q3-163 corresponds to one particular embodiment of the invention, wherein Q3-1 to Q3-163 are also in any combination with one another a preferred embodiment of the present invention:

| No. | Q³ |
|---|---|
| Q3-1 | CF₃ |
| Q3-2 | CHF₂ |
| Q3-3 | CH₂CH₂OCH₃ |
| Q3-4 | CH₂OCH₂F |
| Q3-5 | CH₂OCHF₂ |
| Q3-6 | CH₂OCF₃ |
| Q3-7 | CH₂OCF₂CHF₂ |
| Q3-8 | CH₂SOMe |
| Q3-9 | CH₂SO₂Me |
| Q3-10 | CH₂NMe₂ |
| Q3-11 | CH₂NSO₂CF₃ |
| Q3-12 | CH₂NSO₂CH₃ |
| Q3-13 | CH₂cPr |
| Q3-14 | C₆H₅ |
| Q3-15 | —CH₂—C₆H₅ |
| Q3-16 | —CH₂—C₆H₄-4-F |
| Q3-17 | —CH₂—C₆H₄-4-CH₃ |
| Q3-18 | —CH₂—C₆H₄-3-CH₃ |
| Q3-19 | —CH₂—C₆H₄-2-CH₃ |
| Q3-20 | —CH(CH₃)—C₆H₅ |
| Q3-21 | CH(CH₃)—C₆H₄-4-F |
| Q3-22 | CH(CH₃)—C₆H₄-4-CH₃ |
| Q3-23 | CH(CH₃)—C₆H₄-3-CH₃ |
| Q3-24 | CH(CH₃)—C₆H₄-2-CH₃ |
| Q3-25 | [structure: #—CH₂—C≡CH] |
| Q3-26 | [structure: #—CH₂—C≡C—Cl] |
| Q3-27 | [structure: #—CH₂—C≡C—CH₃] |
| Q3-28 | [structure: #—CH₂—C≡C-cyclopropyl] |
| Q3-29 | [structure: #—CH₂—C≡C—CF₃] |
| Q3-30 | [structure: #—CH₂—CH=CH₂] |
| Q3-31 | [structure: #—CH₂—C(Cl)=CCl₂] |
| Q3-32 | [structure: #—CH₂—CH=CCl₂] |
| Q3-33 | [structure: #—CH₂—CH=CF₂] |
| Q3-34 | [structure: #—CH₂—C(F)=CF₂] |
| Q3-35 | 2-py |
| Q3-36 | 3-py |
| Q3-37 | [structure: 1-phenyl-pyrazol-3-yl] |
| Q3-38 | [structure: 1,2,4-triazol-1-yl] |
| Q3-39 | [structure: #—CH₂-(1,2,4-triazol-1-yl)] |
| Q3-40 | [structure: #—CH₂-(pyridin-2-yl)] |
| Q3-41 | [structure: #—CH₂-(6-fluoropyridin-2-yl)] |
| Q3-42 | [structure: #—CH₂-(6-chloropyridin-2-yl)] |
| Q3-43 | [structure: #—CH₂-(6-bromopyridin-2-yl)] |
| Q3-44 | [structure: #—CH₂-(6-methylpyridin-2-yl)] |
| Q3-45 | [structure: #—CH₂-(6-trifluoromethylpyridin-2-yl)] |
| Q3-46 | [structure: #—CH₂-(5-fluoropyridin-2-yl)] |

-continued
| No. | Q³ |
|---|---|
| Q3-47 | 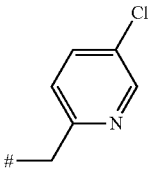 |
| Q3-48 | 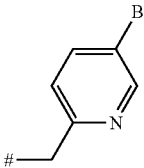 |
| Q3-49 | 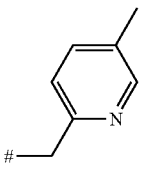 |
| Q3-50 | 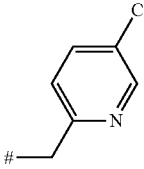 |
| Q3-51 | 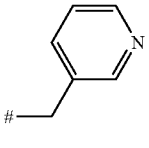 |
| Q3-52 | 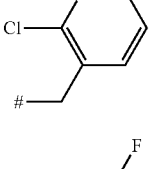 |
| Q3-53 | 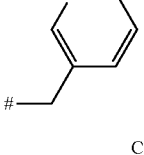 |
| Q3-54 | 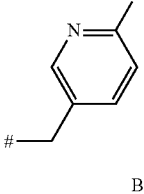 |
| Q3-55 | 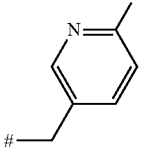 |
-continued
| No. | Q³ |
|---|---|
| Q3-56 | 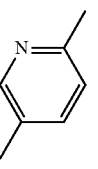 |
| Q3-57 | 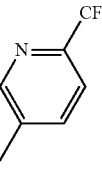 |
| Q3-58 | 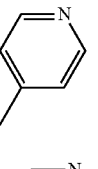 |
| Q3-59 | 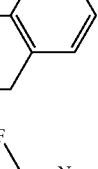 |
| Q3-60 | 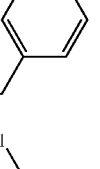 |
| Q3-61 | 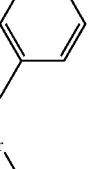 |
| Q3-62 | 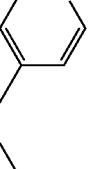 |
| Q3-63 | 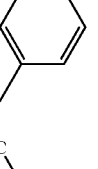 |
| Q3-64 | 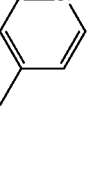 |

-continued
| No. | Q³ |
|---|---|
| Q3-65 | 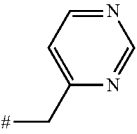 |
| Q3-66 | 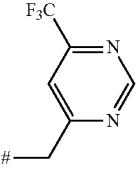 |
| Q3-67 | 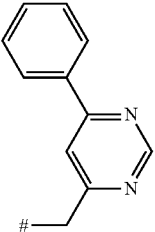 |
| Q3-68 | 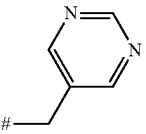 |
| Q3-69 | 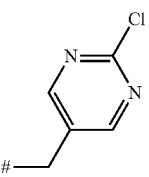 |
| Q3-70 | 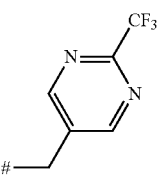 |
| Q3-71 | 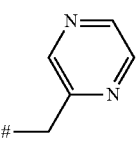 |
| Q3-72 | 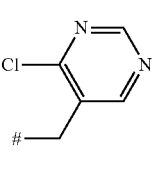 |
| Q3-73 | 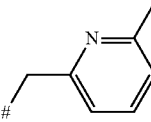 |
-continued
| No. | Q³ |
|---|---|
| Q3-74 | 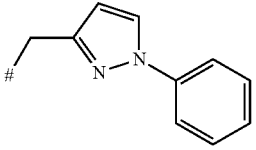 |
| Q3-75 | 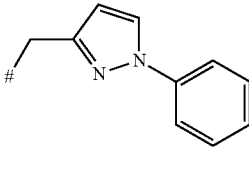 |
| Q3-76 | 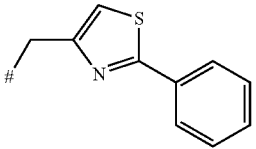 |
| Q3-77 | 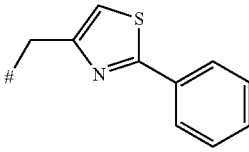 |
| Q3-78 | 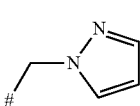 |
| Q3-79 | 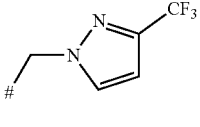 |
| Q3-80 | 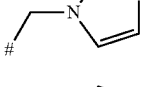 |
| Q3-81 | 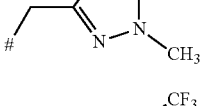 |
| Q3-82 | 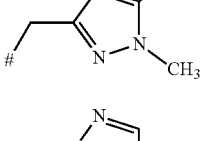 |
| Q3-83 | 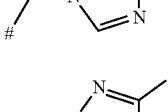 |
| Q3-84 | 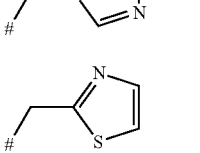 |
| Q3-85 |  |

| No. | Q³ |
|---|---|
| Q3-86 | 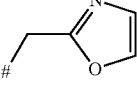 |
| Q3-87 | 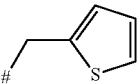 |
| Q3-88 | 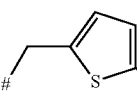 |
| Q3-89 | 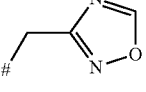 |
| Q3-90 | 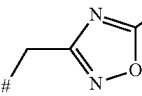 |
| Q3-91 | COCH₃ |
| Q3-92 | COCH₂CH₃ |
| Q3-93 | COCH₂CH₂CH₃ |
| Q3-94 | CO(CH₂)₃CH₃ |
| Q3-95 | CO(CH₂)₄CH₃ |
| Q3-96 | CO(CH₂)₅CH₃ |
| Q3-97 | CO(CH₂)₆CH₃ |
| Q3-98 | COCCl₃ |
| Q3-99 | COCH₂Cl |
| Q3-100 | COCH₂—N(CH₃)₂ |
| Q3-101 | COPh |
| Q3-102 | COCH₂Ph |
| Q3-103 | COCH₂Ph-4-F |
| Q3-104 | COCH₂Ph-4-CH₃ |
| Q3-105 | COCH₂Ph-3-CH₃ |
| Q3-106 | COCH₂Ph-2-CH₃ |
| Q3-107 | COCH(CH₃)Ph |
| Q3-108 | COCH(CH₃)4-F |
| Q3-109 | COCH(CH₃)-4-CH₃ |
| Q3-110 | COCH(CH₃)-3-CH₃ |
| Q3-111 | COCH(CH₃)-3-CH₃ |
| Q3-112 | 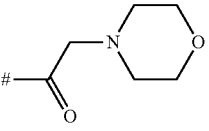 |
| Q3-113 | 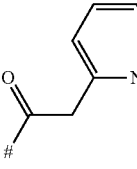 |
| Q3-114 | 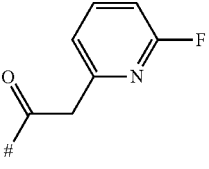 |
| Q3-115 | 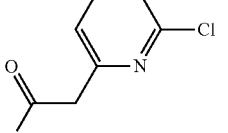 |
| Q3-116 | 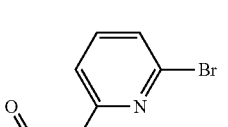 |
| Q3-117 | 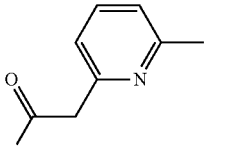 |
| Q3-118 | 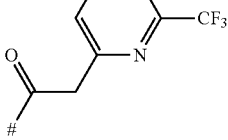 |
| Q3-119 | 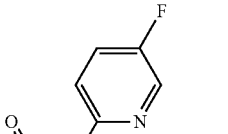 |
| Q3-120 | 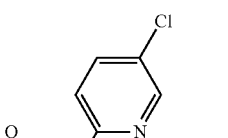 |
| Q3-121 | 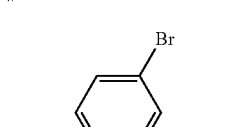 |
| Q3-122 | 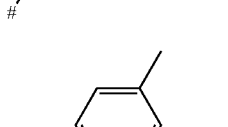 |

-continued

| No. | Q³ |
|---|---|
| Q3-123 | 5-CF₃-pyridin-2-yl-CH₂-C(=O)-# |
| Q3-124 | pyridin-3-yl-CH₂-C(=O)-# |
| Q3-125 | 2-Cl-pyridin-3-yl-CH₂-C(=O)-# |
| Q3-126 | 6-F-pyridin-3-yl-CH₂-C(=O)-# |
| Q3-127 | 6-Cl-pyridin-3-yl-CH₂-C(=O)-# |
| Q3-128 | 6-Br-pyridin-3-yl-CH₂-C(=O)-# |
| Q3-129 | 6-methyl-pyridin-3-yl-CH₂-C(=O)-# |

-continued

| No. | Q³ |
|---|---|
| Q3-130 | 6-CF₃-pyridin-3-yl-CH₂-C(=O)-# |
| Q3-131 | pyridin-4-yl-CH₂-C(=O)-# |
| Q3-132 | 3-Cl-pyridin-4-yl-CH₂-C(=O)-# |
| Q3-133 | 2-F-pyridin-4-yl-CH₂-C(=O)-# |
| Q3-134 | 2-Cl-pyridin-4-yl-CH₂-C(=O)-# |
| Q3-135 | 2-Br-pyridin-4-yl-CH₂-C(=O)-# |
| Q3-136 | 2-methyl-pyridin-4-yl-CH₂-C(=O)-# |

-continued
| No. | Q³ |
|---|---|
| Q3-137 | 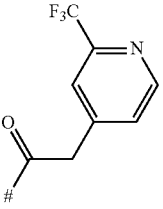 |
| Q3-138 | 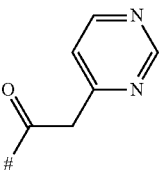 |
| Q3-139 | 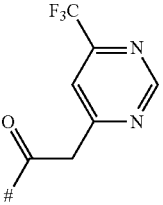 |
| Q3-140 | 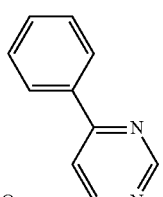 |
| Q3-141 | 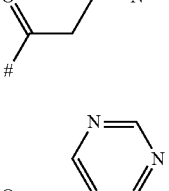 |
| Q3-142 | 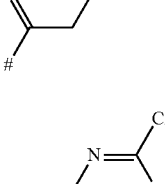 |
| Q3-143 | 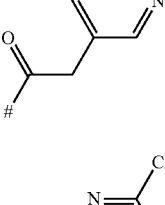 |
-continued
| No. | Q³ |
|---|---|
| Q3-144 | 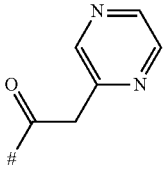 |
| Q3-145 | 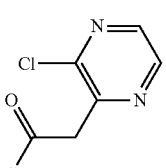 |
| Q3-146 | 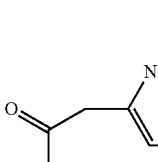 |
| Q3-147 | 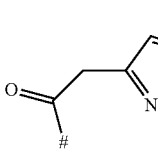 |
| Q3-148 | 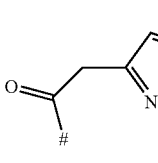 |
| Q3-149 | 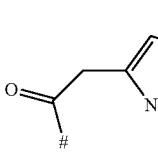 |
| Q3-150 | 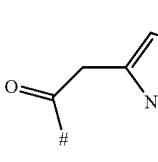 |
| Q3-151 | 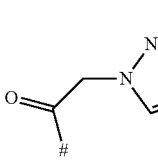 |
| Q3-152 | 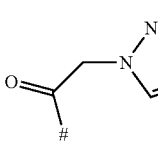 |

| No. | Q³ |
|---|---|
| Q3-153 | 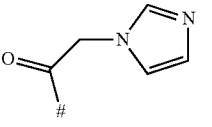 |
| Q3-154 | 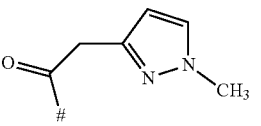 |
| Q3-155 | 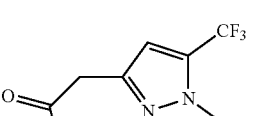 |
| Q3-156 | 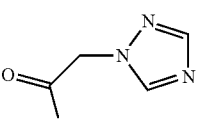 |
| Q3-157 | 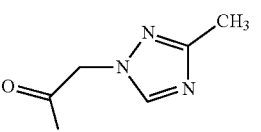 |
| Q3-158 | 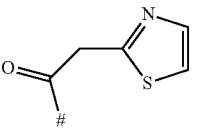 |
| Q3-159 | 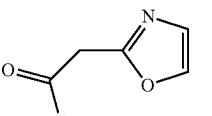 |
| Q3-160 | 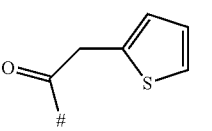 |
| Q3-161 | 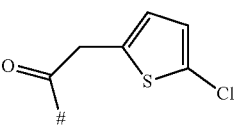 |
| Q3-162 | 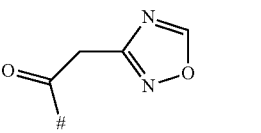 |
| Q3-163 | 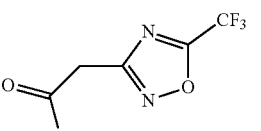 |

$Q^4$ is in each case independently selected from hydrogen, OH, CH(O), C(O)$C_1$-$C_6$-alkyl, C(=O)$C_2$-$C_6$-alkenyl, C(=O)$C_3$-$C_6$-cycloalkyl, C(=O)O($C_1$-$C_6$-alkyl), C(=O)O($C_2$-$C_6$-alkenyl), C(=O)O($C_2$-$C_6$-alkynyl), C(=O)O($C_3$-$C_6$-cycloalkyl), C(=O)NH($C_1$-$C_6$-alkyl), C(=O)NH($C_2$-$C_6$-alkenyl), C(=O)NH($C_2$-$C_6$-alkynyl), C(=O) NH($C_3$-$C_6$-cycloalkyl), C(=O)N($C_1$-$C_6$-alkyl)$_2$, C(=O)N($C_2$-$C_6$-alkenyl)$_2$, C(=O)N($C_2$-$C_6$-alkynyl)$_2$, C(=O)N($C_3$-$C_6$-cycloalkyl)$_2$, CH(=S), C(=S)$C_1$-$C_6$-alkyl, C(=S)$C_2$-$C_6$-alkenyl, C(=S)$C_2$-$C_6$-alkynyl, C(=S)$C_3$-$C_6$-cycloalkyl, C(=S)O($C_1$-$C_6$-alkyl), C(=S)O($C_2$-$C_6$-alkenyl), C(=S)O($C_2$-$C_6$-alkynyl), C(=S)O($C_3$-$C_6$-cycloalkyl), C(=S)NH ($C_1$-$C_6$-alkyl), C(=S)NH($C_2$-$C_6$-alkenyl), C(=S)NH($C_2$-$C_6$-alkynyl), C(=S)NH($C_3$-$C_6$-cycloalkyl), C(=S)N($C_1$-$C_6$-alkyl)$_2$, C(=S)N($C_2$-$C_6$-alkenyl)$_2$, C(=S)N($C_2$-$C_6$-alkynyl)$_2$, C(=S)N($C_3$-$C_6$-cycloalkyl)$_2$, $C_1$-$C_6$-alkyl, $C_1$-$C_4$-halogenalkyl, $C_3$-$C_6$-cycloalkyl, $C_3$-$C_6$-halogencycloalkyl, $C_1$-$C_4$-alkoxy, $C_1$-$C_4$-halogenalkoxy, OR, $C_1$-$C_6$-alkylthio, $C_1$-$C_6$-halogenalkylthio, $C_2$-$C_6$-alkenyl, $C_2$-$C_6$-halogenalkenyl $C_2$-$C_6$-alkynyl, $C_2$-$C_6$-halogenalkynyl, S(O)m-$C_1$-$C_6$-alkyl, S(O)m-$C_1$-$C_6$-halogenalkyl, S(O)m-$C_1$-$C_6$-alkoxy, S(O)$_m$—$C_2$-$C_6$-alkenyl, S(O)$_m$—$C_2$-$C_6$-alkynyl, S(O)m-aryl, $SO_2$—NH($C_1$-$C_6$-alkyl), $SO_2$—NH($C_1$-$C_6$-halogenalkyl), $SO_2$—NH-aryl, tri-($C_1$-$C_6$ alkyl)silyl and di-($C_1$-$C_6$ alkoxy)phosphoryl), five- or six-membered heteroaryl and aryl; wherein the heteroaryl contains one, two or three heteroatoms selected from N, O and S; wherein the aryl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy; wherein n and $R^Y$ is $C_1$-$C_6$-alkyl, $C_1$-$C_6$-halogenalkyl, $C_2$-$C_6$-alkenyl, $C_2$-$C_6$-halogenalkenyl, $C_1$-$C_6$-alkynyl, $C_2$-$C_6$-halogenalkynyl, $C_3$-$C_6$-cycloalkyl, $C_3$-$C_6$-halogencycloalkyl, phenyl and phenyl-$C_1$-$C_6$-alkyl; wherein the phenyl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy;

$Q^{4a}$ is the substituent of the acyclic moieties of $Q^4$. The acyclic moieties of $Q^4$ are not further substituted or carry one, two, three or up to the maximum possible number of identical or different groups $Q^{4a}$ which independently of one another are selected from halogen, OH, CN, $C_1$-$C_6$-alkoxy, $C_3$-$C_6$-cycloalkyl, $C_3$-$C_6$-cycloalkenyl, $C_3$-$C_6$-halogencycloalkyl, $C_3$-$C_6$-halogencycloalkenyl, $C_1$-$C_4$-halogenalkoxy, $C_1$-$C_6$-alkylthio, five- or six-membered heteroaryl, aryl and phenoxy, wherein the heteroaryl, aryl and phenoxy group is unsubstituted or carries one, two, three, four or five substituents selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

$Q^{4b}$ is the substituent of carbocyclic, phenyl, heterocyclic and heteroaryl moieties of $Q^4$. The carbocyclic, phenyl, heterocyclic and heteroaryl moieties of $Q^4$ are not further substituted or carry one, two, three, four, five or up to the maximum number of identical or different groups $Q^{4b}$ which independently of one another are selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment of formula I, $Q^4$ is H.
According to still another embodiment of formula I, $Q^4$ is OH.
According to a further specific embodiment of formula I, $Q^4$ is CH(=O).

According to a further specific embodiment of formula I, $Q^4$ is $C(=O)C_1$-$C_6$-alkyl, $C(=O)O(C_1$-$C_6$-alkyl), $C(=O)NH(C_1$-$C_6$-alkyl) or $C(=O)N(C_1$-$C_6$-alkyl)$_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^4$ is $C(=O)C_2$-$C_6$-alkenyl, $C(=O)O(C_2$-$C_6$-alkenyl), $C(=O)NH(C_2$-$C_6$-alkenyl) or $C(=O)N(C_2$-$C_6$-alkenyl)$_2$), wherein alkenyl is $CH=CH_2$, $CH_2CH=CH_2$.

According to a further specific embodiment of formula I, $Q^4$ is $C(=O)C_2$-$C_6$-alkynyl, $C(=O)O(C_2$-$C_6$-alkynyl), $C(=O)NH(C_2$-$C_6$-alkynyl) or $C(=O)N(C_2$-$C_6$-alkynyl)$_2$, wherein alkynyl is $C\equiv CH$, $CH_2C$ CH.

According to a further specific embodiment of formula I, $Q^4$ is $C(=O)C_3$-$C_6$-cycloalkyl, $C(=O)O(C_3$-$C_6$-cycloalkyl), $C(=O)NH(C_3$-$C_6$-cycloalkyl) or $C(=O)N(C_3$-$C_6$-cycloalkyl)$_2$, wherein cycloalkyl is cyclopropyl ($C_3H_7$) or cyclobutyl ($C_4H_9$).

According to a further specific embodiment of formula I, $Q^4$ is $CH(=S)$.

According to a further specific embodiment of formula I, $Q^4$ is $C(=S)C_1$-$C_6$-alkyl, $C(=S)O(C_1$-$C_6$-alkyl), $C(=S)NH(C_1$-$C_6$-alkyl) or $C(=S)N(C_1$-$C_6$-alkyl)$_2$, wherein alkyl is $CH_3$, $C_2H_5$, n-propyl, i-propyl, n-butyl, i-butyl, tert-butyl, n-pentyl or i-pentyl.

According to a further specific embodiment of formula I, $Q^4$ is $C(=S)C_2$-$C_6$-alkenyl, $C(=S)O(C_2$-$C_6$-alkenyl), $C(=S)NH(C_2$-$C_6$-alkenyl) or $C(=S)N(C_2$-$C_6$-alkenyl)$_2$, wherein alkenyl is $CH=CH_2$, $CH_2CH=CH_2$.

According to a further specific embodiment of formula I, $Q^4$ is $C(=S)O(C_2$-$C_6$-alkynyl), $C(=S)NH(C_2$-$C_6$-alkynyl) or $C(=S)N(C_2$-$C_6$-alkynyl), wherein alkynyl is $C\equiv CH$, $CH_2C\equiv CH$.

According to a further specific embodiment of formula I, $Q^4$ is $C(=S)C_3$-$C_6$-cycloalkyl, $C(=S)O(C_3$-$C_6$-cycloalkyl) or $C(=S)N(C_3$-$C_6$-cycloalkyl)$_2$, wherein cycloalkyl is cyclopropyl ($C_3H_7$) or cyclobutyl ($C_4H_9$).

According to still another embodiment of formula I, $Q^4$ is $C_1$-$C_6$-alkyl, such as $CH_3$, $C_2H_5$, n-propyl, i-propyl, n-butyl, i-butyl, tert-butyl, n-pentyl or i-pentyl.

According to still another embodiment of formula I, $Q^4$ is $C_1$-$C_6$-alkyl, in particular $C_1$-$C_4$-alkyl, such as $CH_3$, $C_2H$, n-propyl, i-propyl.

According to still another embodiment of formula I, $Q^4$ is $C_1$-$C_6$-halogenalkyl, in particular $C_1$-$C_4$-halogenalkyl, such as $CF_3$, $CCl_3$, $FCH_2$, $ClCH_2$, $F_2CH$, $C_2CH$, $CF_3CH_2$, $CCl_3CH_2$ or $CF_2CHF_2$.

According to still another embodiment of formula I $Q^4$ is $C_3$-$C_6$-cycloalkyl, in particular cyclopropyl.

According to still another embodiment of formula I, $Q^4$ is $C_3$-$C_6$-halogencycloalkyl. In a special embodiment $Q^{41}$ is fully or partially halogenated cyclopropyl, such as 1-F-cyclopropyl, 1-Cl-cyclopropyl, 1,1-$F_2$-cyclopropyl, 1,1-$Cl_2$-cyclopropyl.

According to still another embodiment of formula I, $Q^4$ is $C_1$-$C_4$-alkoxy and $C_1$-$C_4$-halogenalkoxy, in particular $C_1$-$C_3$-alkoxy, $C_1$-$C_3$-halogenalkoxy, such as $CH_2OCH_3$, $CH_2OCF_3$ or $CH_2OCHF_2$.

According to a further specific embodiment of formula I, $Q^4$ is OR wherein R is $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_3$-$C_6$-cycloalkyl, $C_3$-$C_6$-halogencycloalkyl, phenyl and phenyl-$C_1$-$C_6$-alkyl; wherein the phenyl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy;

According to a further specific embodiment of formula I, $Q^4$ is OR wherein R is $C_1$-$C_6$-alkyl, in particular $C_1$-$C_4$-alkyl, more specifically $C_1$-$C_2$-alkyl. $Q^4$ is such as $OCH_3$ or $OCH_2CH_3$.

According to a further specific embodiment of formula I, $Q^4$ is OR wherein R is $C_1$-$C_6$-halogenalkyl, in particular $C_1$-$C_4$-halogenalkyl, more specifically $C_1$-$C_2$-halogenalkyl. $Q^4$ is such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment of formula I, $Q^4$ is OR wherein R $C_2$-$C_6$-alkenyl, in particular $C_2$-$C_4$-alkenyl, more specifically $C_1$-$C_2$-alkenyl. $Q^4$ is such as $OCH=CH_2$, $OCH_2CH=CH_2$.

According to a further specific embodiment of formula I, $Q^4$ is OR wherein R $C_2$-$C_6$-alkynyl, in particular $C_2$-$C_6$-alkynyl, in particular $C_2$-$C_4$-alkynyl, more specifically $C_1$-$C_2$-alkynyl. $Q^4$ is such as $OC\equiv CH$ According to still another embodiment of formula I, $Q^4$ is $OR^Y$, wherein R is $C_3$-$C_6$-halogencycloalkyl. In a special embodiment $R^1$ is fully or partially halogenated cyclopropyl.

According to still another embodiment of formula I, $Q^4$ is $OR^Y$ wherein $R^Y$ and phenyl; wherein the phenyl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy.

According to still another embodiment of formula I, $Q^4$ is OR wherein R phenyl-$C_1$-$C_6$-alkyl, such as phenyl-$CH_2$, herein the phenyl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy. $Q^4$ is such as $OCH_2Ph$.

According to still a further embodiment of formula I, $Q^4$ is $C_2$-$C_6$-alkenyl, in particular $C_2$-$C_4$-alkenyl, such as $CH=CH_2$, $C(CH_3)=CH_2$, $CH_2CH=CH_2$.

According to a further specific embodiment of formula I, $Q^4$ is $C_2$-$C_6$-halogenalkenyl, in particular $C_2$-$C_4$-halogenalkenyl, more specifically $C_2$-$C_3$-halogenalkenyl such as $CH=CHF$, $CH=CHCl$, $CH=CF_2$, $CH=CCl_2$, $CH_2CH=CHF$, $CH_2CH=CHCl$, $CH_2CH=CF_2$, $CH_2CH=CCl_2$, $CF_2CH=CF_2$, $CCl_2CH=CCl_2$, $CF_2CF=CF_2$, $CCl_2CCl=CCl_2$.

According to still a further embodiment of formula I, $Q^4$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$, $CH_2C\equiv CH$.

According to still another embodiment of formula I, $Q^4$ is $S(O)n$-$C_1$-$C_6$-alkyl such as $SCH_3$, $S(=O)$ $CH_3$, $S(O)_2CH_3$.

According to still another embodiment of formula I, $Q^4$ is $S(O)n$-$C_1$-$C_6$-halogenalkyl such as $SCF_3$, $S(=O)CF_3$, $S(O)_2CF_3$, $SCHF_2$, $S(=O)CHF_2$, $S(O)_2CHF_2$.

According to still another embodiment of formula I, $Q^4$ is $S(O)n$-aryl such as S-phenyl, $S(=O)$ phenyl, $S(O)_2$phenyl, wherein the phenyl group is unsubstituted or carries one, two, three, four or five substituents $R^{78a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

According to still another embodiment of formula I, $Q^4$ is $S(O)n$-$C_2$-$C_6$-alkenyl such as $SCH=CH_2$, $S(=O)CH=CH_2$, $S(O)_2CH=CH_2$, $SCH_2CH=CH_2$, $S(=O)CH_2CH=CH_2$, $S(O)_2CH_2CH=CH_2$.

According to still another embodiment of formula I, $Q^4$ is $S(O)n$-$C_2$-$C_6$-alkynyl such as $SC\equiv CH$, $S(=O)C\equiv CH$, $S(O)_2C\equiv CH$, $SCH_2C\equiv CH$, $S(=O)CH_2C\equiv CH$, $S(O)_2CH_2C\equiv CH$.

According to still another embodiment of formula I, $Q^4$ is $SO_2$—$NH(C_1$-$C_6$-alkyl), is $C_1$-$C_6$-alkyl, in particular $C_1$-$C_4$- alkyl, more specifically $C_1$-$C_2$-alkyl. $Q^4$ is such as $SO_2NHCH_3$ or $SO_2NHCH_2CH_3$.

According to still another embodiment of formula I, $Q^4$ is $SO_2$—$NH(C_1$-$C_6$-halogenalkyl), wherein $C_1$-$C_6$-halogenalkyl, in particular $C_1$-$C_4$-halogenalkyl, more specifically $C_1$-$C_2$-halogenalkyl. $Q^4$ is such as $SO_2NHCF_3$, $SO_2NHCHF_2$, $SO_2NHCH_2F$, $SO_2NHCCl_3$, $SO_2NHCHCl_2$ or $SO_2NHCH_2Cl$, in particular $SO_2NHCF_3$, $SO_2NHCHF_2$, $SO_2NHCCl_3$ or $SO_2NHCHCl_2$.

According to still another embodiment of formula I, $Q^4$ is $SO_2$—NHaryl, wherein the aryl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy. $Q^4$ is such as $SO_2NHPh$.

According to still another embodiment of formula I, $Q^4$ is tri-($C_1$-$C_6$ alkyl)silyl, in particular $C_1$-$C_4$-alkyl, such as $CH_3$. or $C_2H_5$. $Q^4$ is such as $OSi(CH_3)_3$ According to still another embodiment of formula I, $Q^4$ is di-($C_1$-$C_6$ alkoxy)phosphoryl), in particular $C_1$-$C_4$-alkoxy, such as $OCH_3$. or $OC_2H_5$. $Q^4$ is such as $OPO(OCH_3)_2$.

According to still another embodiment of formula I, $Q^4$ is phenyl-$C_1$-$C_6$-alkyl, such as phenyl-$CH_2$, wherein the phenyl moiety in each case is unsubstituted or substituted by one, two or three identical or different groups $Q^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, C, Br, $CH_3$, $OCH_3$, $CF_3$ and $OCF_3$.

According to still another embodiment of formula I, $Q^4$ is aryl, in particular phenyl, wherein the aryl or phenyl moiety in each case is unsubstituted or substituted by identical or different groups $Q^{4b}$ which independently of one another are selected from halogen, $C_1$-$C_2$-alkyl, $C_1$-$C_2$-alkoxy, $C_1$-$C_2$-halogenalkyl and $C_1$-$C_2$-halogenalkoxy, in particular F, C, Br, $CH_3$, $OCH_3$, $CF_3$ and $OCF_3$. According to one embodiment, $Q^4$ is unsubstituted phenyl. According to another embodiment, $Q^4$ is phenyl, that is substituted by one, two or three, in particular one, halogen, in particular selected from F, Cl and Br, more specifically selected from F and Cl.

According to still another embodiment of formula I, $Q^4$ is a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $Q^4$ is a 6-membered heteroaryl such as pyri-din-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to still another embodiment of formula I, $Q^4$ is in each case independently selected from H, halogen, OH, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, $C_3$-$C_6$-alkenyloxy, $C_3$-$C_6$-alkynyloxy and $C_3$-$C_6$-cycloalkyl wherein the acyclic moieties of $Q^4$ are unsubstituted or substituted with identical or different groups $Q^4$ as defined and preferably defined herein, and wherein the carbocyclic, phenyl and heteroaryl moieties of $Q^4$ are unsubstituted or substituted with identical or different groups $Q^{4b}$ as defined and preferably defined herein.

According to still another embodiment of formula I, $Q^4$ is in each case independently selected from H, halogen, OH, CN, $C_1$-$C_6$-alkyl, $C_2$-$C_6$-alkenyl, $C_2$-$C_6$-alkynyl, $C_1$-$C_6$-alkoxy, $C_3$-$C_6$-alkenyloxy, $C_3$-$C_6$-alkynyloxy and $C_3$-$C_6$-cycloalkyl, wherein the acyclic moieties of $Q^4$ are unsubstituted or substituted with identical or different groups $Q^4$ as defined and preferably defined herein, and wherein the cycloalkyl moieties of $Q^4$ are unsubstituted or substituted with identical or different groups $Q^{4b}$ as defined and preferably defined herein.

According to still another embodiment of formula I, $Q^4$ is in each case independently selected from H and $OR^Y$, wherein R is most preferably $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, phenyl and phenyl-$C_1$-$C_6$-alkyl; wherein the phenyl groups are unsubstituted or carry one, two, three, four or five substituents selected from the group consisting of CN, halogen, OH, $C_1$-$C_4$-alkyl, $C_1$-$C_4$-halogenalkyl, $C_1$-$C_4$-alkoxy and $C_1$-$C_4$-halogenalkoxy.

According to still another embodiment of formula I, $Q^4$ is in each case independently selected from H and $OR^Y$, wherein R is most preferably $C_2$-$C_6$-alkenyl, $C_2$-$C_6$-alkynyl, phenyl and phenyl-$C_1$-$C_6$-alkyl; wherein the phenyl groups are unsubstituted or carry one, two, three, four or five substituents selected from the group consisting of CN, halogen, $C_1$-$C_4$-alkyl, $C_1$-$C_4$-halogenalkyl, $C_1$-$C_4$-alkoxy and $C_1$-$C_4$-halogenalkoxy.

According to still another embodiment of formula I, $Q^4$ is in each case independently selected from H, CH(=O), C(=O)$C_1$-$C_6$-alkyl, C(=O)O($C_1$-$C_6$-alkyl) and C(=O)NH($C_1$-$C_6$-alkyl), C(=O)N($C_1$-$C_6$-alkyl), C(=O)$C_2$-$C_6$-alkenyl, C(=O)O($C_2$-$C_6$-alkenyl), C(=O)NH($C_2$-$C_6$-alkenyl), C(=O)N($C_2$-$C_6$-alkenyl), C(=O)$C_2$-$C_6$-alkynyl, C(=O)O($C_2$-$C_6$-alkynyl), C(=O)NH($C_2$-$C_6$-alkynyl), C(=O)N($C_2$-$C_6$-alkynyl)$_2$C(=O)$C_3$-$C_6$-cycloalkyl, C(=O)O($C_3$-$C_6$-cycloalkyl), C(=O)NH($C_3$-$C_6$-cycloalkyl) and C(=O)N($C_3$-$C_6$-cycloalkyl)$_2$, wherein the acyclic moieties of $Q^4$ are unsubstituted or substituted with identical or different groups $Q^4$ as defined and preferably defined herein, and wherein the cycloalkyl moieties of $Q^4$ are unsubstituted or substituted with identical or different groups $Q^{4b}$ as defined and preferably defined herein.

According to still another embodiment of formula I, $Q^4$ is in each case independently selected from H, C(=O)$C_1$-$C_6$-alkyl, C(=O)O($C_1$-$C_6$-alkyl), C(=O)NH($C_1$-$C_6$-alkyl), C(=O)N($C_1$-$C_6$-alkyl), C(=O)$C_2$-$C_6$-alkenyl, C(=O)O($C_2$-$C_6$-alkenyl), C(=O)NH($C_2$-$C_6$-alkenyl), C(=O)N($C_2$-$C_6$-alkenyl), wherein the acyclic moieties of $Q^4$ are unsubstituted or substituted with identical or different groups $Q^4$ as defined and preferably defined herein, and wherein the cycloalkyl moieties of $Q^4$ are unsubstituted or substituted with identical or different groups $Q^{4b}$ as defined and preferably defined herein.

According to still another embodiment of formula I, $Q^4$ is in each case independently selected from H, S(O)n-$C_1$-$C_6$-alkyl, S(O)$_n$—$C_1$-$C_6$-halogenalkyl, S(O)$_n$—$C_1$-$C_6$-alkoxy, S(O)$_n$—$C_2$-$C_6$-alkenyl, S(O)$_n$—$C_2$-$C_6$-alkynyl, S(O)$_n$aryl, wherein the acyclic moieties of $Q^4$ are unsubstituted or substituted with identical or different groups $Q^4$ as defined and preferably defined herein, and wherein the aryl moieties of $Q^4$ are unsubstituted or substituted with identical or different groups $Q^{4b}$ as defined and preferably defined herein.

According to still another embodiment of formula I, $Q^4$ is in each case independently selected from H, $SO_2$—NH($C_1$-$C_6$-alkyl), $SO_2$—NH($C_1$-$C_6$-halogenalkyl), $SO_2$—NHphenyl, wherein the acyclic moieties of $Q^4$ are unsubstituted or substituted with identical or different groups $Q^4$ as defined and preferably defined herein, and wherein the aryl moieties of $Q^4$ are unsubstituted or substituted with identical or different groups $Q^{4b}$ as defined and preferably defined herein.

According to still another embodiment of formula I, $Q^4$ is in each case independently selected from H, $C_1$-$C_6$-alkyl, $C(=O)C_1$-$C_6$-alkyl, $C(=O)O(C_1$-$C_6$-alkyl), $S(O)n$-$C_1$-$C_6$-alkyl, $S(O)_n$aryl, wherein the acyclic moieties of $Q^4$ are unsubstituted or substituted with identical or different groups $Q^4$ as defined and preferably defined herein, and wherein the aryl moieties of $Q^4$ are unsubstituted or substituted with identical or different groups $Q^{4b}$ as defined and preferably defined herein.

According to still another embodiment of formula I, $Q^4$ is in each case independently selected from H, $C(=O)C_1$-$C_6$-alkyl, $C(=O)OC_1$-$C_6$-alkyl, $C(=O)NHC_1$-$C_6$-alkyl, $S(O)_2$—$C_1$-$C_6$-alkyl, $S(O)_2$-aryl, $SO_2$—$NH(C_1$-$C_6$-alkyl), $OR^Y$, or $C_1$-$C_4$-alkyl; wherein $R^Y$ is $C_1$-$C_6$-alkyl, $C_1$-$C_6$-halogenalkyl, $C_2$-$C_6$-alkenyl or $C_2$-$C_6$-alkynyl.

According to one embodiment $Q^{4a}$ is independently selected from halogen, $C_1$-$C_6$-alkoxy, $C_3$-$C_6$-cycloalkyl, $C_3$-$C_6$-halogencycloalkyl and $C_1$-$C_4$-halogenalkoxy. Specifically, $Q^{4a}$ is independently selected from F, C, Br, I, $C_1$-$C_2$-alkoxy, cyclopropyl, 1-F-cyclopropyl, 1-Cl-cyclopropyl, 1,1-$F_2$-cyclopropyl, 1,1-$Cl_2$-cyclopropyl and $C_1$-$C_2$-halogenalkoxy.

According to still another embodiment of formula I, $Q^{4a}$ is independently halogen, in particular selected from F, Cl, Br and I, more specifically F, Cl and Br.

$Q^{4b}$ are the possible substituents for the cycloalkyl, heteroaryl and phenyl moieties of $Q^4$. $Q^{4b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment thereof $Q^{4b}$ is independently selected from halogen, CN, $C_1$-$C_4$-alkyl, $C_1$-$C_4$-alkoxy, $C_1$-$C_4$-halogenalkyl and $C_1$-$C_4$-halogenalkoxy, in particular halogen, $C_1$-$C_4$-alkyl and $C_1$-$C_4$-alkoxy. Specifically, $Q^{4b}$ is independently selected from F, Cl, CN, $CH_3$, $CHF_2$, $CF_3OCH_3$ and halogenmethoxy.

Particularly preferred embodiments of $Q^4$ according to the invention are in Table Q4 below, wherein each line of lines Q4-1 to Q4-50 corresponds to one particular embodiment of the invention, wherein Q4-1 to Q4-50 are also in any combination with one another a preferred embodiment of the present invention. The connection point to the carbon atom, to which $Q^4$ is bound is marked with "#" in the drawings.

TABLE Q4

| No. | $Q^4$ |
| --- | --- |
| P12-1 | H |
| P12-2 | $CH_3$ |
| P12-3 | $CH_2F$ |
| P12-4 | $CHF_2$ |
| P12-5 | $CF_3$ |
| P12-6 | $C_2H_5$ |
| P12-7 | $C_3H_7$ |
| P12-8 | $CH(CH_3)_2$ |
| P12-9 | $CH_2CH_2CH_3$ |
| P12-10 | $CH_2CH_2CH_2CH_3$ |
| P12-11 | $CH_2CH(CH_3)_2$ |
| P12-12 | $C(CH_3)_3$ |
| P12-13 | $CH_2CH_2CH_2CH_2CH_3$ |
| P12-14 | $CH=CH_2$ |
| P12-15 | $CH_2CH=CH_2$ |

TABLE Q4-continued

| No. | $Q^4$ |
| --- | --- |
| P12-16 | $C\equiv CH$ |
| P12-17 | $CH_2C\equiv CH$ |
| P12-18 | $CH_2CH_2CH(CH_3)_2$ |
| P12-19 | OH |
| P12-20 | $OCH_3$ |
| P12-21 | $OCHF_2$ |
| P12-22 | $OC_2H_5$ |
| P12-23 | $OCH_2OCH_3$ |
| P12-24 | $OCH_2Ph$ |
| P12-25 | $OCH_2CH=CH_2$ |
| P12-26 | $C(O)CH_3$ |
| P12-27 | $C(O)OCH_3$ |
| P12-28 | $C(O)OCH_2CH_3$ |
| P12-29 | $C(O)OCH(CH_3)_2$ |
| P12-30 | $C(O)OC(CH_3)_3$ |
| P12-31 | $CO-NH_2$ |
| P12-32 | $CO-NH(CH_3)$ |
| P12-33 | $CO-N(CH_3)_2$ |
| P12-34 | $SO_2H$ |
| P12-35 | $SO_2-CH_3$ |
| P12-36 | $SO-CH_3$ |
| P12-37 | $S-CH_3$ |
| P12-38 | $SO_2NHCH_3$ |
| P12-39 | $SO_2NHCF_3$ |
| P12-40 | $SO_2NHPh$ |
| P12-41 | $SO_2Ph$ |
| P12-42 | $SO_2C_6H_4$-4-$CH_3$ |
| P12-43 | $Si(CH_3)_3$ |
| P12-44 | $PO(OCH_3)_2$ |
| P12-45 |  |
| P12-46 | 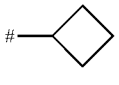 |
| P12-47 | 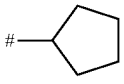 |
| P12-48 | 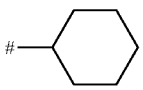 |
| P12-49 | 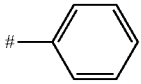 |
| P12-50 | 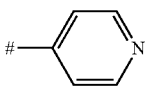 |

Particular embodiments of the compounds I are the following compounds: I-A, I-B, I-C, I-D, I-E, I-F; II-A, II-B, II-C, II-D, II-E, II-F. In these formulae, the substituents $Q^1$, $Q^2$ and $Q^3$ are independently as defined in claim 1 or preferably defined below:

I-A
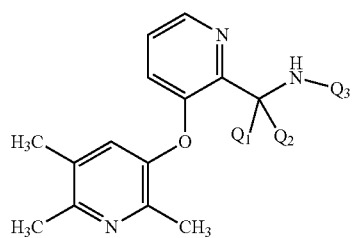
I-B
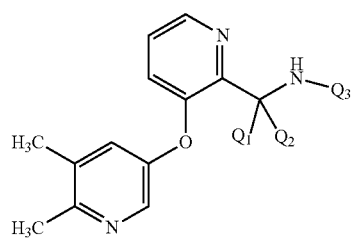
I-C
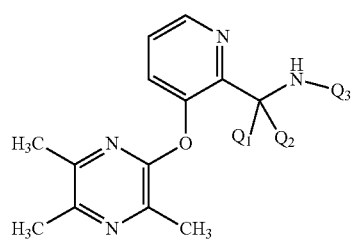
I-D
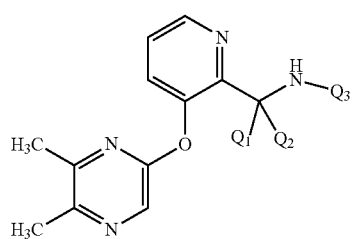
I-E
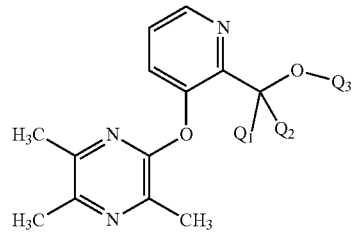
I-F
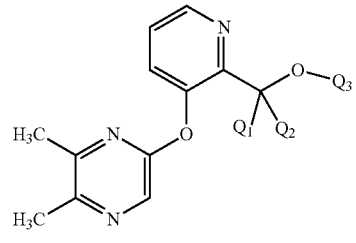
II-A
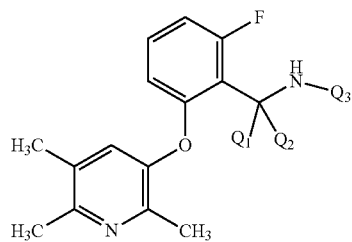
II-B
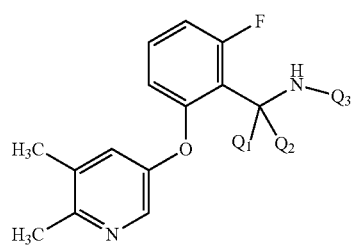
II-C
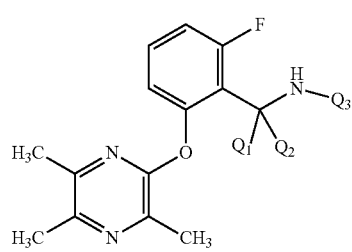
II-D
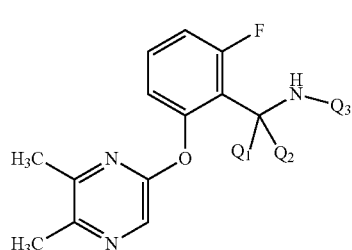
II-E
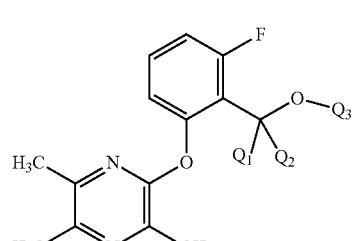
II-F
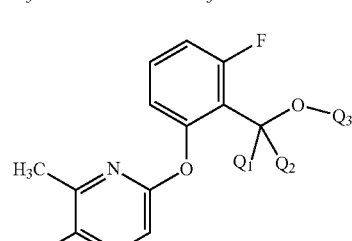
Table 1-1 Compounds of the formula I-A, I-B, I-C, I-D, I-E, I-F in which the meaning for the combination of $Q^1$, $Q^2$ and $Q^3$ for each individual compound corresponds in each case to one line of Table A (compounds I-A.1-1.A-1 to I-A.1-1.A-874, I-B.1-1.A-1 to I-B.1-1.A-874, I-C.1-1.A-1 to I-C.1-1.A-874, I-D.1-1.A-1 to I-D.1-1.A-874, I-E.1-1.A-1 to I-E.1-1.A-874, I-F.1-1.A-1 to I-F.1-1.A-874).

Table 2-1 Compounds of the formula II-A, II-B, II-C, II-D, II-E, II-F in which the meaning for the combination of $Q^1$, $Q^2$ and $Q^3$ for each individual compound corresponds in each case to one line of Table A (compounds II-A.2-1.A-1 to II-A.2-1.A-874, II-B.2-1.A-1 to II-B.2-1.A-874, II-C.2-1.A-1 to II-C.2-1.A-874, II-D.2-1.A-1 to II-D.2-1.A-874, II-E.2-1.A-1 to II-E.2-1.A-874, II-F.2-1.A-1 to II-F.2-1.A-874).

TABLE A

| No. | $Q^3$ | $Q^1$ | $Q^2$ |
|---|---|---|---|
| A-1 | COCH$_3$ | F | F |
| A-2 | COCH$_2$CH$_3$ | F | F |
| A-3 | COCH$_2$CH$_2$CH$_3$ | F | F |
| A-4 | CO(CH$_2$)$_3$CH$_3$ | F | F |
| A-5 | CO(CH$_2$)$_4$CH$_3$ | F | F |
| A-6 | CO(CH$_2$)$_5$CH$_3$ | F | F |
| A-7 | CO(CH$_2$)$_6$CH$_3$ | F | F |
| A-8 | COCCl$_3$ | F | F |
| A-9 | COCH$_2$Cl | F | F |
| A-10 | COCH$_2$-N(CH$_3$)$_2$ | F | F |
| A-11 | COPh | F | F |
| A-12 | COCH$_2$Ph | F | F |
| A-13 | COCH$_2$Ph-4-F | F | F |
| A-14 | COCH$_2$Ph-4-CH$_3$ | F | F |
| A-15 | COCH$_2$Ph-3-CH$_3$ | F | F |
| A-16 | COCH$_2$Ph-2-CH$_3$ | F | F |
| A-17 | COCH(CH$_3$)Ph | F | F |
| A-18 | COCH(CH$_3$)-4-F | F | F |
| A-19 | COCH(CH$_3$)-4-CH$_3$ | F | F |
| A-20 | COCH(CH$_3$)-3-CH$_3$ | F | F |
| A-21 | COCH(CH$_3$)-3-CH$_3$ | F | F |
| A-22 | CF$_3$ | F | F |
| A-23 | CHF$_2$ | F | F |
| A-24 | CH$_2$CH$_2$OCH$_3$ | F | F |
| A-25 | CH$_2$cPr | F | F |
| A-26 | C$_6$H$_5$ | F | F |
| A-27 | CH$_2$—C$_6$H$_5$ | F | F |
| A-28 | CH$_2$—C$_6$H$_4$-4-F | F | F |
| A-29 | CH$_2$—C$_6$H$_4$-4-CH$_3$ | F | F |
| A-30 | CH$_2$—C$_6$H$_4$-3-CH$_3$ | F | F |
| A-31 | CH$_2$—C$_6$H$_4$-2-CH$_3$ | F | F |
| A-32 | CH(CH$_3$)—C$_6$H$_5$ | F | F |
| A-33 | CH(CH$_3$)—C$_6$H$_4$-4-F | F | F |
| A-34 | CH(CH$_3$)—C$_6$H$_4$-4-CH$_3$ | F | F |
| A-35 | CH(CH$_3$)—C$_6$H$_4$-3-CH$_3$ | F | F |
| A-36 | CH(CH$_3$)—C$_6$H$_4$-2-CH$_3$ | F | F |
| A-37 | #–CH$_2$–C≡CH | F | F |
| A-38 | #–CH$_2$–CH=CH$_2$ | F | F |
| A-39 | #–CH$_2$–C(Cl)=CCl$_2$ | F | F |
| A-40 | 2-py | F | F |
| A-41 | 3-py | F | F |
| A-42 | 1-phenylpyrazol-3-ylmethyl | F | F |
| A-43 | 1,2,4-triazol-1-ylmethyl | F | F |
| A-44 | 1,2,4-triazol-1-ylmethyl | F | F |
| A-45 | pyridin-2-ylmethyl | F | F |
| A-46 | 1-phenylpyrazol-3-ylmethyl | F | F |
| A-47 | COCH$_3$ | CF$_3$ | CF$_3$ |
| A-48 | COCH$_2$CH$_3$ | CF$_3$ | CF$_3$ |
| A-49 | COCH$_2$CH$_2$CH$_3$ | CF$_3$ | CF$_3$ |
| A-50 | CO(CH$_2$)$_3$CH$_3$ | CF$_3$ | CF$_3$ |
| A-51 | CO(CH$_2$)$_4$CH$_3$ | CF$_3$ | CF$_3$ |
| A-52 | CO(CH$_2$)$_5$CH$_3$ | CF$_3$ | CF$_3$ |
| A-53 | CO(CH$_2$)$_6$CH$_3$ | CF$_3$ | CF$_3$ |
| A-54 | COCCl$_3$ | CF$_3$ | CF$_3$ |
| A-55 | COCH$_2$Cl | CF$_3$ | CF$_3$ |
| A-56 | COCH$_2$—N(CH$_3$)$_2$ | CF$_3$ | CF$_3$ |
| A-57 | COPh | CF$_3$ | CF$_3$ |
| A-58 | COCH$_2$Ph | CF$_3$ | CF$_3$ |
| A-59 | COCH$_2$Ph-4-F | CF$_3$ | CF$_3$ |
| A-60 | COCH$_2$Ph-4-CH$_3$ | CF$_3$ | CF$_3$ |
| A-61 | COCH$_2$Ph-3-CH$_3$ | CF$_3$ | CF$_3$ |
| A-62 | COCH$_2$Ph-2-CH$_3$ | CF$_3$ | CF$_3$ |
| A-63 | COCH(CH$_3$)Ph | CF$_3$ | CF$_3$ |
| A-64 | COCH(CH$_3$)-4-F | CF$_3$ | CF$_3$ |
| A-65 | COCH(CH$_3$)-4-CH$_3$ | CF$_3$ | CF$_3$ |
| A-66 | COCH(CH$_3$)-3-CH$_3$ | CF$_3$ | CF$_3$ |
| A-67 | COCH(CH$_3$)-3-CH$_3$ | CF$_3$ | CF$_3$ |
| A-68 | CF$_3$ | CF$_3$ | CF$_3$ |
| A-69 | CHF$_2$ | CF$_3$ | CF$_3$ |
| A-70 | CH$_2$CH$_2$OCH$_3$ | CF$_3$ | CF$_3$ |
| A-71 | CH$_2$cPr | CF$_3$ | CF$_3$ |
| A-72 | C$_6$H$_5$ | CF$_3$ | CF$_3$ |
| A-73 | CH$_2$—C$_6$H$_5$ | CF$_3$ | CF$_3$ |
| A-74 | CH$_2$—C$_6$H$_4$-4-F | CF$_3$ | CF$_3$ |
| A-75 | CH$_2$—C$_6$H$_4$-4-CH$_3$ | CF$_3$ | CF$_3$ |
| A-76 | CH$_2$—C$_6$H$_4$-3-CH$_3$ | CF$_3$ | CF$_3$ |
| A-77 | CH$_2$—C$_6$H$_4$-2-CH$_3$ | CF$_3$ | CF$_3$ |
| A-78 | CH(CH$_3$)—C$_6$H$_5$ | CF$_3$ | CF$_3$ |
| A-79 | CH(CH$_3$)—C$_6$H$_4$-4-F | CF$_3$ | CF$_3$ |
| A-80 | CH(CH$_3$)—C$_6$H$_4$-4-CH$_3$ | CF$_3$ | CF$_3$ |
| A-81 | CH(CH$_3$)—C$_6$H$_4$-3-CH$_3$ | CF$_3$ | CF$_3$ |
| A-82 | CH(CH$_3$)—C$_6$H$_4$-2-CH$_3$ | CF$_3$ | CF$_3$ |
| A-83 | #–CH$_2$–C≡CH | CF$_3$ | CF$_3$ |
| A-84 | #–CH$_2$–CH=CH$_2$ | CF$_3$ | CF$_3$ |
| A-85 | #–CH$_2$–C(Cl)=CCl$_2$ | CF$_3$ | CF$_3$ |
| A-86 | 2-py | CF$_3$ | CF$_3$ |
| A-87 | 3-Py | CF$_3$ | CF$_3$ |

TABLE A-continued

| No. | Q³ | Q¹ | Q² |
|---|---|---|---|
| A-88 | 1-phenyl-pyrazol-3-yl (#) | CF₃ | CF₃ |
| A-89 | 1H-1,2,4-triazol-1-yl (#) | CF₃ | CF₃ |
| A-90 | (1,2,4-triazol-1-yl)methyl (#) | CF₃ | CF₃ |
| A-91 | (pyridin-2-yl)methyl (#) | CF₃ | CF₃ |
| A-92 | (1-phenyl-pyrazol-3-yl)methyl (#) | CF₃ | CF₃ |
| A-93 | COCH₃ | C₃H₇ (cyclopropyl) | H |
| A-94 | COCH₂CH₃ | C₃H₇ (cyclopropyl) | H |
| A-95 | COCH₂CH₂CH₃ | C₃H₇ (cyclopropyl) | H |
| A-96 | CO(CH₂)₃CH₃ | C₃H₇ (cyclopropyl) | H |
| A-97 | CO(CH₂)₄CH₃ | C₃H₇ (cyclopropyl) | H |
| A-98 | CO(CH₂)₅CH₃ | C₃H₇ (cyclopropyl) | H |
| A-99 | CO(CH₂)₆CH₃ | C₃H₇ (cyclopropyl) | H |
| A-100 | COCCl₃ | C₃H₇ (cyclopropyl) | H |
| A-101 | COCH₂Cl | C₃H₇ (cyclopropyl) | H |
| A-102 | COCH₂—N(CH₃)₂ | C₃H₇ (cyclopropyl) | H |
| A-103 | COPh | C₃H₇ (cyclopropyl) | H |
| A-104 | COCH₂Ph | C₃H₇ (cyclopropyl) | H |
| A-105 | COCH₂Ph-4-F | C₃H₇ (cyclopropyl) | H |
| A-106 | COCH₂Ph-4-CH₃ | C₃H₇ (cyclopropyl) | H |
| A-107 | COCH₂Ph-3-CH₃ | C₃H₇ (cyclopropyl) | H |
| A-108 | COCH₂Ph-2-CH₃ | C₃H₇ (cyclopropyl) | H |
| A-109 | COCH(CH₃)Ph | C₃H₇ (cyclopropyl) | H |
| A-110 | COCH(CH₃)-4-F | C₃H₇ (cyclopropyl) | H |
| A-111 | COCH(CH₃)-4-CH₃ | C₃H₇ (cyclopropyl) | H |
| A-112 | COCH(CH₃)-3-CH₃ | C₃H₇ (cyclopropyl) | H |
| A-113 | COCH(CH₃)-3-CH₃ | C₃H₇ (cyclopropyl) | H |
| A-114 | CF₃ | C₃H₇ (cyclopropyl) | H |
| A-115 | CHF₂ | C₃H₇ (cyclopropyl) | H |
| A-116 | CH₂CH₂OCH₃ | C₃H₇ (cyclopropyl) | H |
| A-117 | CH₂cPr | C₃H₇ (cyclopropyl) | H |
| A-118 | C₆H₅ | C₃H₇ (cyclopropyl) | H |
| A-119 | CH₂—C₆H₅ | C₃H₇ (cyclopropyl) | H |
| A-120 | CH₂—C₆H₄-4-F | C₃H₇ (cyclopropyl) | H |
| A-121 | CH₂—C₆H₄-4-CH₃ | C₃H₇ (cyclopropyl) | H |
| A-122 | CH₂—C₆H₄-3-CH₃ | C₃H₇ (cyclopropyl) | H |
| A-123 | CH₂—C₆H₄-2-CH₃ | C₃H₇ (cyclopropyl) | H |
| A-124 | CH(CH₃)—C₆H₅ | C₃H₇ (cyclopropyl) | H |
| A-125 | CH(CH₃)—C₆H₄-4-F | C₃H₇ (cyclopropyl) | H |
| A-126 | CH(CH₃)—C₆H₄-4-CH₃ | C₃H₇ (cyclopropyl) | H |
| A-127 | CH(CH₃)—C₆H₄-3-CH₃ | C₃H₇ (cyclopropyl) | H |
| A-128 | CH(CH₃)—C₆H₄-2-CH₃ | C₃H₇ (cyclopropyl) | H |
| A-129 | CH₂—C≡CH (#) | C₃H₇ (cyclopropyl) | H |
| A-130 | CH₂—CH=CH₂ (#) | C₃H₇ (cyclopropyl) | H |
| A-131 | CH₂—C(Cl)=CCl₂ (#) | C₃H₇ (cyclopropyl) | H |
| A-132 | 2-py | C₃H₇ (cyclopropyl) | H |
| A-133 | 3-Py | C₃H₇ (cyclopropyl) | H |
| A-134 | 1-phenyl-pyrazol-3-yl (#) | C₃H₇ (cyclopropyl) | H |
| A-135 | 1H-1,2,4-triazol-1-yl (#) | C₃H₇ (cyclopropyl) | H |
| A-136 | (1,2,4-triazol-1-yl)methyl (#) | C₃H₇ (cyclopropyl) | H |
| A-137 | (pyridin-2-yl)methyl (#) | C₃H₇ (cyclopropyl) | H |
| A-138 | (1-phenyl-pyrazol-3-yl)methyl (#) | C₃H₇ (cyclopropyl) | H |
| A-139 | COCH₃ | i-C₃H₇ | H |

TABLE A-continued

| No. | Q³ | Q¹ | Q² |
|---|---|---|---|
| A-140 | COCH₂CH₃ | i-C₃H₇ | H |
| A-141 | COCH₂CH₂CH₃ | i-C₃H₇ | H |
| A-142 | CO(CH₂)₃CH₃ | i-C₃H₇ | H |
| A-143 | CO(CH₂)₄CH₃ | i-C₃H₇ | H |
| A-144 | CO(CH₂)₅CH₃ | i-C₃H₇ | H |
| A-145 | CO(CH₂)₆CH₃ | i-C₃H₇ | H |
| A-146 | COCCl₃ | i-C₃H₇ | H |
| A-147 | COCH₂Cl | i-C₃H₇ | H |
| A-148 | COCH₂—N(CH₃)₂ | i-C₃H₇ | H |
| A-149 | COPh | i-C₃H₇ | H |
| A-150 | COCH₂Ph | i-C₃H₇ | H |
| A-151 | COCH₂Ph-4-F | i-C₃H₇ | H |
| A-152 | COCH₂Ph-4-CH₃ | i-C₃H₇ | H |
| A-153 | COCH₂Ph-3-CH₃ | i-C₃H₇ | H |
| A-154 | COCH₂Ph-2-CH₃ | i-C₃H₇ | H |
| A-155 | COCH(CH₃)Ph | i-C₃H₇ | H |
| A-156 | COCH(CH₃)-4-F | i-C₃H₇ | H |
| A-157 | COCH(CH₃)-4-CH₃ | i-C₃H₇ | H |
| A-158 | COCH(CH₃)-3-CH₃ | i-C₃H₇ | H |
| A-159 | COCH(CH₃)-3-CH₃ | i-C₃H₇ | H |
| A-160 | CF₃ | i-C₃H₇ | H |
| A-161 | CHF₂ | i-C₃H₇ | H |
| A-162 | CH₂CH₂OCH₃ | i-C₃H₇ | H |
| A-163 | CH₂cPr | i-C₃H₇ | H |
| A-164 | C₆H₅ | i-C₃H₇ | H |
| A-165 | CH₂—C₆H₅ | i-C₃H₇ | H |
| A-166 | CH₂—C₆H₄-4-F | i-C₃H₇ | H |
| A-167 | CH₂—C₆H₄-4-CH₃ | i-C₃H₇ | H |
| A-168 | CH₂—C₆H₄-3-CH₃ | i-C₃H₇ | H |
| A-169 | CH₂—C₆H₄-2-CH₃ | i-C₃H₇ | H |
| A-170 | CH(CH₃)—C₆H₅ | i-C₃H₇ | H |
| A-171 | CH(CH₃)—C₆H₄-4-F | i-C₃H₇ | H |
| A-172 | CH(CH₃)—C₆H₄-4-CH₃ | i-C₃H₇ | H |
| A-173 | CH(CH₃)—C₆H₄-3-CH₃ | i-C₃H₇ | H |
| A-174 | CH(CH₃)—C₆H₄-2-CH₃ | i-C₃H₇ | H |
| A-175 | #—CH₂—C≡CH | i-C₃H₇ | H |
| A-176 | #—CH₂—CH=CH₂ | i-C₃H₇ | H |
| A-177 | #—CH₂—C(Cl)=CCl₂ | i-C₃H₇ | H |
| A-178 | 2-py | i-C₃H₇ | H |
| A-179 | 3-Py | i-C₃H₇ | H |
| A-180 | 3-(1-phenylpyrazolyl) | i-C₃H₇ | H |
| A-181 | 1-(1,2,4-triazolyl) | i-C₃H₇ | H |
| A-182 | 1-(1,2,4-triazolyl)methyl | i-C₃H₇ | H |
| A-183 | 2-pyridylmethyl | i-C₃H₇ | H |
| A-184 | 3-(1-phenylpyrazolyl)methyl | i-C₃H₇ | H |
| A-185 | COCH₃ | CCH | H |
| A-186 | COCH₂CH₃ | CCH | H |
| A-187 | COCH₂CH₂CH₃ | CCH | H |
| A-188 | CO(CH₂)₃CH₃ | CCH | H |
| A-189 | CO(CH₂)₄CH₃ | CCH | H |
| A-190 | CO(CH₂)₅CH₃ | CCH | H |
| A-191 | CO(CH₂)₆CH₃ | CCH | H |
| A-192 | COCCl₃ | CCH | H |
| A-193 | COCH₂Cl | CCH | H |
| A-194 | COCH₂—N(CH₃)₂ | CCH | H |
| A-195 | COPh | CCH | H |
| A-196 | COCH₂Ph | CCH | H |
| A-197 | COCH₂Ph-4-F | CCH | H |
| A-198 | COCH₂Ph-4-CH₃ | CCH | H |
| A-199 | COCH₂Ph-3-CH₃ | CCH | H |
| A-200 | COCH₂Ph-2-CH₃ | CCH | H |
| A-201 | COCH(CH₃)Ph | CCH | H |
| A-202 | COCH(CH₃)-4-F | CCH | H |
| A-203 | COCH(CH₃)-4-CH₃ | CCH | H |
| A-204 | COCH(CH₃)-3-CH₃ | CCH | H |
| A-205 | COCH(CH₃)-3-CH₃ | CCH | H |
| A-206 | CF₃ | CCH | H |
| A-207 | CHF₂ | CCH | H |
| A-208 | CH₂CH₂OCH₃ | CCH | H |
| A-209 | CH₂cPr | CCH | H |
| A-210 | C₆H₅ | CCH | H |
| A-211 | CH₂—C₆H₅ | CCH | H |
| A-212 | CH₂—C₆H₄-4-F | CCH | H |
| A-213 | CH₂—C₆H₄-4-CH₃ | CCH | H |
| A-214 | CH₂—C₆H₄-3-CH₃ | CCH | H |
| A-215 | CH₂—C₆H₄-2-CH₃ | CCH | H |
| A-216 | CH(CH₃)—C₆H₅ | CCH | H |
| A-217 | CH(CH₃)—C₆H₄-4-F | CCH | H |
| A-218 | CH(CH₃)—C₆H₄-4-CH₃ | CCH | H |
| A-219 | CH(CH₃)—C₆H₄-3-CH₃ | CCH | H |
| A-220 | CH(CH₃)—C₆H₄-2-CH₃ | CCH | H |
| A-221 | #—CH₂—C≡CH | CCH | H |
| A-222 | #—CH₂—CH=CH₂ | CCH | H |
| A-223 | #—CH₂—C(Cl)=CCl₂ | CCH | H |
| A-224 | 2-py | CCH | H |
| A-225 | 3-Py | CCH | H |
| A-226 | 3-(1-phenylpyrazolyl) | CCH | H |
| A-227 | 1-(1,2,4-triazolyl) | CCH | H |

TABLE A-continued

| No. | Q³ | Q¹ | Q² |
|---|---|---|---|
| A-228 | (1-CH2-1,2,4-triazole) | CCH | H |
| A-229 | (2-CH2-pyridine) | CCH | H |
| A-230 | (1-phenyl-pyrazol-3-yl-CH2) | CCH | H |
| A-231 | COCH₃ | CH=CH₂ | H |
| A-232 | COCH₂CH₃ | CH=CH₂ | H |
| A-233 | COCH₂CH₂CH₃ | CH=CH₂ | H |
| A-234 | CO(CH₂)₃CH₃ | CH=CH₂ | H |
| A-235 | CO(CH₂)₄CH₃ | CH=CH₂ | H |
| A-236 | CO(CH₂)₅CH₃ | CH=CH₂ | H |
| A-237 | CO(CH₂)₆CH₃ | CH=CH₂ | H |
| A-238 | COCCl₃ | CH=CH₂ | H |
| A-239 | COCH₂Cl | CH=CH₂ | H |
| A-240 | COCH₂—N(CH₃)₂ | CH=CH₂ | H |
| A-241 | COPh | CH=CH₂ | H |
| A-242 | COCH₂Ph | CH=CH₂ | H |
| A-243 | COCH₂Ph-4-F | CH=CH₂ | H |
| A-244 | COCH₂Ph-4-CH₃ | CH=CH₂ | H |
| A-245 | COCH₂Ph-3-CH₃ | CH=CH₂ | H |
| A-246 | COCH₂Ph-2-CH₃ | CH=CH₂ | H |
| A-247 | COCH(CH₃)Ph | CH=CH₂ | H |
| A-248 | COCH(CH₃)-4-F | CH=CH₂ | H |
| A-249 | COCH(CH₃)-4-CH₃ | CH=CH₂ | H |
| A-250 | COCH(CH₃)-3-CH₃ | CH=CH₂ | H |
| A-251 | COCH(CH₃)-3-CH₃ | CH=CH₂ | H |
| A-252 | CF₃ | CH=CH₂ | H |
| A-253 | CHF₂ | CH=CH₂ | H |
| A-254 | CH₂CH₂OCH₃ | CH=CH₂ | H |
| A-255 | CH₂cPr | CH=CH₂ | H |
| A-256 | C₆H₅ | CH=CH₂ | H |
| A-257 | CH₂—C₆H₅ | CH=CH₂ | H |
| A-258 | CH₂—C₆H₄-4-F | CH=CH₂ | H |
| A-259 | CH₂—C₆H₄-4-CH₃ | CH=CH₂ | H |
| A-260 | CH₂—C₆H₄-3-CH₃ | CH=CH₂ | H |
| A-261 | CH₂—C₆H₄-2-CH₃ | CH=CH₂ | H |
| A-262 | CH(CH₃)—C₆H₅ | CH=CH₂ | H |
| A-263 | CH(CH₃)—C₆H₄-4-F | CH=CH₂ | H |
| A-264 | CH(CH₃)—C₆H₄-4-CH₃ | CH=CH₂ | H |
| A-265 | CH(CH₃)—C₆H₄-3-CH₃ | CH=CH₂ | H |
| A-266 | CH(CH₃)—C₆H₄-2-CH₃ | CH=CH₂ | H |
| A-267 | (CH₂-C≡CH) | CH=CH₂ | H |
| A-268 | (CH₂-CH=CH₂) | CH=CH₂ | H |
| A-269 | (CH₂-C(Cl)=CCl₂) | CH=CH₂ | H |
| A-270 | 2-py | CH=CH₂ | H |
| A-271 | 3-Py | CH=CH₂ | H |
| A-272 | (1-phenyl-pyrazol-3-yl) | CH=CH₂ | H |
| A-273 | (1,2,4-triazol-1-yl) | CH=CH₂ | H |
| A-274 | (1-CH2-1,2,4-triazole) | CH=CH₂ | H |
| A-275 | (2-CH2-pyridine) | CH=CH₂ | H |
| A-276 | (1-phenyl-pyrazol-3-yl-CH2) | CH=CH₂ | H |
| A-277 | COCH₃ | CH₂CH=CH₂ | H |
| A-278 | COCH₂CH₃ | CH₂CH=CH₂ | H |
| A-279 | COCH₂CH₂CH₃ | CH₂CH=CH₂ | H |
| A-280 | CO(CH₂)₃CH₃ | CH₂CH=CH₂ | H |
| A-281 | CO(CH₂)₄CH₃ | CH₂CH=CH₂ | H |
| A-282 | CO(CH₂)₅CH₃ | CH₂CH=CH₂ | H |
| A-283 | CO(CH₂)₆CH₃ | CH₂CH=CH₂ | H |
| A-284 | COCCl₃ | CH₂CH=CH₂ | H |
| A-285 | COCH₂Cl | CH₂CH=CH₂ | H |
| A-286 | COCH₂—N(CH₃)₂ | CH₂CH=CH₂ | H |
| A-287 | COPh | CH₂CH=CH₂ | H |
| A-288 | COCH₂Ph | CH₂CH=CH₂ | H |
| A-289 | COCH₂Ph-4-F | CH₂CH=CH₂ | H |
| A-290 | COCH₂Ph-4-CH₃ | CH₂CH=CH₂ | H |
| A-291 | COCH₂Ph-3-CH₃ | CH₂CH=CH₂ | H |
| A-292 | COCH₂Ph-2-CH₃ | CH₂CH=CH₂ | H |
| A-293 | COCH(CH₃)Ph | CH₂CH=CH₂ | H |
| A-294 | COCH(CH₃)-4-F | CH₂CH=CH₂ | H |
| A-295 | COCH(CH₃)-4-CH₃ | CH₂CH=CH₂ | H |
| A-296 | COCH(CH₃)-3-CH₃ | CH₂CH=CH₂ | H |
| A-297 | COCH(CH₃)-3-CH₃ | CH₂CH=CH₂ | H |
| A-298 | CF₃ | CH₂CH=CH₂ | H |
| A-299 | CHF₂ | CH₂CH=CH₂ | H |
| A-300 | CH₂CH₂OCH₃ | CH₂CH=CH₂ | H |
| A-301 | CH₂cPr | CH₂CH=CH₂ | H |
| A-302 | C₆H₅ | CH₂CH=CH₂ | H |
| A-303 | CH₂—C₆H₅ | CH₂CH=CH₂ | H |
| A-304 | CH₂—C₆H₄-4-F | CH₂CH=CH₂ | H |
| A-305 | CH₂—C₆H₄-4-CH₃ | CH₂CH=CH₂ | H |
| A-306 | CH₂—C₆H₄-3-CH₃ | CH₂CH=CH₂ | H |
| A-307 | CH₂—C₆H₄-2-CH₃ | CH₂CH=CH₂ | H |
| A-308 | CH(CH₃)—C₆H₅ | CH₂CH=CH₂ | H |
| A-309 | CH(CH₃)—C₆H₄-4-F | CH₂CH=CH₂ | H |
| A-310 | CH(CH₃)—C₆H₄-4-CH₃ | CH₂CH=CH₂ | H |
| A-311 | CH(CH₃)—C₆H₄-3-CH₃ | CH₂CH=CH₂ | H |
| A-312 | CH(CH₃)—C₆H₄-2-CH₃ | CH₂CH=CH₂ | H |
| A-313 | (CH₂-C≡CH) | CH₂CH=CH₂ | H |
| A-314 | (CH₂-CH=CH₂) | CH₂CH=CH₂ | H |

TABLE A-continued

| No. | Q³ | Q¹ | Q² |
|---|---|---|---|
| A-315 | 1,2,3-trichloroallyl (CH₂–C(Cl)=CCl₂ via #CH₂–C(Cl)=CCl₂) | CH₂CH=CH₂ | H |
| A-316 | 2-py | CH₂CH=CH₂ | H |
| A-317 | 3-Py | CH₂CH=CH₂ | H |
| A-318 | 1-phenyl-1H-pyrazol-3-yl (attached at #) | CH₂CH=CH₂ | H |
| A-319 | 1H-1,2,4-triazol-1-yl (attached at #) | CH₂CH=CH₂ | H |
| A-320 | (1H-1,2,4-triazol-1-yl)methyl (attached at #) | CH₂CH=CH₂ | H |
| A-321 | pyridin-2-ylmethyl (attached at #) | CH₂CH=CH₂ | H |
| A-322 | (1-phenyl-1H-pyrazol-3-yl)methyl (attached at #) | CH₂CH=CH₂ | H |
| A-323 | COCH₃ | CN | H |
| A-324 | COCH₂CH₃ | CN | H |
| A-325 | COCH₂CH₂CH₃ | CN | H |
| A-326 | CO(CH₂)₃CH₃ | CN | H |
| A-327 | CO(CH₂)₄CH₃ | CN | H |
| A-328 | CO(CH₂)₅CH₃ | CN | H |
| A-329 | CO(CH₂)₆CH₃ | CN | H |
| A-330 | COCCl₃ | CN | H |
| A-331 | COCH₂Cl | CN | H |
| A-332 | COCH₂—N(CH₃)₂ | CN | H |
| A-333 | COPh | CN | H |
| A-334 | COCH₂Ph | CN | H |
| A-335 | COCH₂Ph-4-F | CN | H |
| A-336 | COCH₂Ph-4-CH₃ | CN | H |
| A-337 | COCH₂Ph-3-CH₃ | CN | H |
| A-338 | COCH₂Ph-2-CH₃ | CN | H |
| A-339 | COCH(CH₃)Ph | CN | H |
| A-340 | COCH(CH₃)-4-F | CN | H |
| A-341 | COCH(CH₃)-4-CH₃ | CN | H |
| A-342 | COCH(CH₃)-3-CH₃ | CN | H |
| A-343 | COCH(CH₃)-3-CH₃ | CN | H |
| A-344 | CF₃ | CN | H |
| A-345 | CHF₂ | CN | H |
| A-346 | CH₂CH₂OCH₃ | CN | H |
| A-347 | CH₂cPr | CN | H |
| A-348 | C₆H₅ | CN | H |
| A-349 | CH₂—C₆H₅ | CN | H |
| A-350 | CH₂—C₆H₄-4-F | CN | H |
| A-351 | CH₂—C₆H₄-4-CH₃ | CN | H |
| A-352 | CH₂—C₆H₄-3-CH₃ | CN | H |
| A-353 | CH₂—C₆H₄-2-CH₃ | CN | H |
| A-354 | CH(CH₃)—C₆H₅ | CN | H |
| A-355 | CH(CH₃)—C₆H₄-4-F | CN | H |
| A-356 | CH(CH₃)—C₆H₄-4-CH₃ | CN | H |
| A-357 | CH(CH₃)—C₆H₄-3-CH₃ | CN | H |
| A-358 | CH(CH₃)—C₆H₄-2-CH₃ | CN | H |
| A-359 | propargyl (CH₂–C≡CH, attached at #) | CN | H |
| A-360 | allyl (CH₂–CH=CH₂, attached at #) | CN | H |
| A-361 | 1,2,3-trichloroallyl (attached at #) | CN | H |
| A-362 | 2-py | CN | H |
| A-363 | 3-Py | CN | H |
| A-364 | 1-phenyl-1H-pyrazol-3-yl (attached at #) | CN | H |
| A-365 | 1H-1,2,4-triazol-1-yl (attached at #) | CN | H |
| A-366 | (1H-1,2,4-triazol-1-yl)methyl (attached at #) | CN | H |
| A-367 | pyridin-2-ylmethyl (attached at #) | CN | H |
| A-368 | (1-phenyl-1H-pyrazol-3-yl)methyl (attached at #) | CN | H |
| A-369 | COCH₃ | C₆H₅ | H |
| A-370 | COCH₂CH₃ | C₆H₅ | H |
| A-371 | COCH₂CH₂CH₃ | C₆H₅ | H |
| A-372 | CO(CH₂)₃CH₃ | C₆H₅ | H |
| A-373 | CO(CH₂)₄CH₃ | C₆H₅ | H |
| A-374 | CO(CH₂)₅CH₃ | C₆H₅ | H |
| A-375 | CO(CH₂)₆CH₃ | C₆H₅ | H |
| A-376 | COCCl₃ | C₆H₅ | H |
| A-377 | COCH₂Cl | C₆H₅ | H |
| A-378 | COCH₂—N(CH₃)₂ | C₆H₅ | H |
| A-379 | COPh | C₆H₅ | H |
| A-380 | COCH₂Ph | C₆H₅ | H |
| A-381 | COCH₂Ph-4-F | C₆H₅ | H |
| A-382 | COCH₂Ph-4-CH₃ | C₆H₅ | H |
| A-383 | COCH₂Ph-3-CH₃ | C₆H₅ | H |
| A-384 | COCH₂Ph-2-CH₃ | C₆H₅ | H |
| A-385 | COCH(CH₃)Ph | C₆H₅ | H |
| A-386 | COCH(CH₃)-4-F | C₆H₅ | H |
| A-387 | COCH(CH₃)-4-CH₃ | C₆H₅ | H |
| A-388 | COCH(CH₃)-3-CH₃ | C₆H₅ | H |
| A-389 | COCH(CH₃)-3-CH₃ | C₆H₅ | H |
| A-390 | CF₃ | C₆H₅ | H |
| A-391 | CHF₂ | C₆H₅ | H |
| A-392 | CH₂CH₂OCH₃ | C₆H₅ | H |
| A-393 | CH₂cPr | C₆H₅ | H |

TABLE A-continued

| No. | Q³ | Q¹ | Q² |
|---|---|---|---|
| A-394 | C₆H₅ | C₆H₅ | H |
| A-395 | CH₂—C₆H₅ | C₆H₅ | H |
| A-396 | CH₂—C₆H₄-4-F | C₆H₅ | H |
| A-397 | CH₂—C₆H₄-4-CH₃ | C₆H₅ | H |
| A-398 | CH₂—C₆H₄-3-CH₃ | C₆H₅ | H |
| A-399 | CH₂—C₆H₄-2-CH₃ | C₆H₅ | H |
| A-400 | CH(CH₃)—C₆H₅ | C₆H₅ | H |
| A-401 | CH(CH₃)—C₆H₄-4-F | C₆H₅ | H |
| A-402 | CH(CH₃)—C₆H₄-4-CH₃ | C₆H₅ | H |
| A-403 | CH(CH₃)—C₆H₄-3-CH₃ | C₆H₅ | H |
| A-404 | CH(CH₃)—C₆H₄-2-CH₃ | C₆H₅ | H |
| A-405 | (propargyl) | C₆H₅ | H |
| A-406 | (allyl) | C₆H₅ | H |
| A-407 | (2,3,3-trichloroallyl) | C₆H₅ | H |
| A-408 | 2-py | C₆H₅ | H |
| A-409 | 3-Py | C₆H₅ | H |
| A-410 | (1-phenylpyrazol-3-yl) | C₆H₅ | H |
| A-411 | (1,2,4-triazol-1-yl) | C₆H₅ | H |
| A-412 | (1,2,4-triazol-1-ylmethyl) | C₆H₅ | H |
| A-413 | (pyridin-2-ylmethyl) | C₆H₅ | H |
| A-414 | (1-phenylpyrazol-3-ylmethyl) | C₆H₅ | H |
| A-415 | COCH₃ | CH₂—C₆H₅ | H |
| A-416 | COCH₂CH₃ | CH₂—C₆H₅ | H |
| A-417 | COCH₂CH₂CH₃ | CH₂—C₆H₅ | H |
| A-418 | CO(CH₂)₃CH₃ | CH₂—C₆H₅ | H |
| A-419 | CO(CH₂)₄CH₃ | CH₂—C₆H₅ | H |
| A-420 | CO(CH₂)₅CH₃ | CH₂—C₆H₅ | H |
| A-421 | CO(CH₂)₆CH₃ | CH₂—C₆H₅ | H |
| A-422 | COCCl₃ | CH₂—C₆H₅ | H |
| A-423 | COCH₂Cl | CH₂—C₆H₅ | H |
| A-424 | COCH₂—N(CH₃)₂ | CH₂—C₆H₅ | H |
| A-425 | COPh | CH₂—C₆H₅ | H |
| A-426 | COCH₂Ph | CH₂—C₆H₅ | H |
| A-427 | COCH₂Ph-4-F | CH₂—C₆H₅ | H |
| A-428 | COCH₂Ph-4-CH₃ | CH₂—C₆H₅ | H |
| A-429 | COCH₂Ph-3-CH₃ | CH₂—C₆H₅ | H |
| A-430 | COCH₂Ph-2-CH₃ | CH₂—C₆H₅ | H |
| A-431 | COCH(CH₃)Ph | CH₂—C₆H₅ | H |
| A-432 | COCH(CH₃)-4-F | CH₂—C₆H₅ | H |
| A-433 | COCH(CH₃)-4-CH₃ | CH₂—C₆H₅ | H |
| A-434 | COCH(CH₃)-3-CH₃ | CH₂—C₆H₅ | H |
| A-435 | COCH(CH₃)-3-CH₃ | CH₂—C₆H₅ | H |
| A-436 | CF₃ | CH₂—C₆H₅ | H |
| A-437 | CHF₂ | CH₂—C₆H₅ | H |
| A-438 | CH₂CH₂OCH₃ | CH₂—C₆H₅ | H |
| A-439 | CH₂cPr | CH₂—C₆H₅ | H |
| A-440 | C₆H₅ | CH₂—C₆H₅ | H |
| A-441 | CH₂—C₆H₅ | CH₂—C₆H₅ | H |
| A-442 | CH₂—C₆H₄-4-F | CH₂—C₆H₅ | H |
| A-443 | CH₂—C₆H₄-4-CH₃ | CH₂—C₆H₅ | H |
| A-444 | CH₂—C₆H₄-3-CH₃ | CH₂—C₆H₅ | H |
| A-445 | CH₂—C₆H₄-2-CH₃ | CH₂—C₆H₅ | H |
| A-446 | CH(CH₃)—C₆H₅ | CH₂—C₆H₅ | H |
| A-447 | CH(CH₃)—C₆H₄-4-F | CH₂—C₆H₅ | H |
| A-448 | CH(CH₃)—C₆H₄-4-CH₃ | CH₂—C₆H₅ | H |
| A-449 | CH(CH₃)—C₆H₄-3-CH₃ | CH₂—C₆H₅ | H |
| A-450 | CH(CH₃)—C₆H₄-2-CH₃ | CH₂—C₆H₅ | H |
| A-451 | (propargyl) | CH₂—C₆H₅ | H |
| A-452 | (allyl) | CH₂—C₆H₅ | H |
| A-453 | (2,3,3-trichloroallyl) | CH₂—C₆H₅ | H |
| A-454 | 2-py | CH₂—C₆H₅ | H |
| A-455 | 3-Py | CH₂—C₆H₅ | H |
| A-456 | (1-phenylpyrazol-3-yl) | CH₂—C₆H₅ | H |
| A-457 | (1,2,4-triazol-1-yl) | CH₂—C₆H₅ | H |
| A-458 | (1,2,4-triazol-1-ylmethyl) | CH₂—C₆H₅ | H |
| A-459 | (pyridin-2-ylmethyl) | CH₂—C₆H₅ | H |
| A-460 | (1-phenylpyrazol-3-ylmethyl) | CH₂—C₆H₅ | H |
| A-461 | COCH₃ | C₃H₇ (cyclopropyl) | CH₃ |
| A-462 | COCH₂CH₃ | C₃H₇ (cyclopropyl) | CH₃ |
| A-463 | COCH₂CH₂CH₃ | C₃H₇ (cyclopropyl) | CH₃ |
| A-464 | CO(CH₂)₃CH₃ | C₃H₇ | CH₃ |

TABLE A-continued

| No. | Q³ | Q¹ | Q² |
|---|---|---|---|
| A-465 | CO(CH₂)₄CH₃ | C₃H₇ (cyclopropyl) | CH₃ |
| A-466 | CO(CH₂)₅CH₃ | C₃H₇ (cyclopropyl) | CH₃ |
| A-467 | CO(CH₂)₆CH₃ | C₃H₇ (cyclopropyl) | CH₃ |
| A-468 | COCCl₃ | C₃H₇ (cyclopropyl) | CH₃ |
| A-469 | COCH₂Cl | C₃H₇ (cyclopropyl) | CH₃ |
| A-470 | COCH₂—N(CH₃)₂ | C₃H₇ (cyclopropyl) | CH₃ |
| A-471 | COPh | C₃H₇ (cyclopropyl) | CH₃ |
| A-472 | COCH₂Ph | C₃H₇ (cyclopropyl) | CH₃ |
| A-473 | COCH₂Ph-4-F | C₃H₇ (cyclopropyl) | CH₃ |
| A-474 | COCH₂Ph-4-CH₃ | C₃H₇ (cyclopropyl) | CH₃ |
| A-475 | COCH₂Ph-3-CH₃ | C₃H₇ (cyclopropyl) | CH₃ |
| A-476 | COCH₂Ph-2-CH₃ | C₃H₇ (cyclopropyl) | CH₃ |
| A-477 | COCH(CH₃)Ph | C₃H₇ (cyclopropyl) | CH₃ |
| A-478 | COCH(CH₃)-4-F | C₃H₇ (cyclopropyl) | CH₃ |
| A-479 | COCH(CH₃)-4-CH₃ | C₃H₇ (cyclopropyl) | CH₃ |
| A-480 | COCH(CH₃)-3-CH₃ | C₃H₇ (cyclopropyl) | CH₃ |
| A-481 | COCH(CH₃)-3-CH₃ | C₃H₇ (cyclopropyl) | CH₃ |
| A-482 | CF₃ | C₃H₇ (cyclopropyl) | CH₃ |
| A-483 | CHF₂ | C₃H₇ (cyclopropyl) | CH₃ |
| A-484 | CH₂CH₂OCH₃ | C₃H₇ (cyclopropyl) | CH₃ |
| A-485 | CH₂cPr | C₃H₇ (cyclopropyl) | CH₃ |
| A-486 | C₆H₅ | C₃H₇ (cyclopropyl) | CH₃ |
| A-487 | CH₂—C₆H₅ | C₃H₇ (cyclopropyl) | CH₃ |
| A-488 | CH₂—C₆H₄-4-F | C₃H₇ (cyclopropyl) | CH₃ |
| A-489 | CH₂—C₆H₄-4-CH₃ | C₃H₇ (cyclopropyl) | CH₃ |
| A-490 | CH₂—C₆H₄-3-CH₃ | C₃H₇ (cyclopropyl) | CH₃ |
| A-491 | CH₂—C₆H₄-2-CH₃ | C₃H₇ (cyclopropyl) | CH₃ |
| A-492 | CH(CH₃)—C₆H₅ | C₃H₇ (cyclopropyl) | CH₃ |
| A-493 | CH(CH₃)—C₆H₄-4-F | C₃H₇ (cyclopropyl) | CH₃ |
| A-494 | CH(CH₃)—C₆H₄-4-CH₃ | C₃H₇ (cyclopropyl) | CH₃ |
| A-495 | CH(CH₃)—C₆H₄-3-CH₃ | C₃H₇ (cyclopropyl) | CH₃ |
| A-496 | CH(CH₃)—C₆H₄-2-CH₃ | C₃H₇ (cyclopropyl) | CH₃ |
| A-497 | #–CH₂–C≡CH (propargyl) | C₃H₇ (cyclopropyl) | CH₃ |
| A-498 | #–CH₂–CH=CH₂ (allyl) | C₃H₇ (cyclopropyl) | CH₃ |
| A-499 | #–CH₂–C(Cl)=CCl₂ | C₃H₇ (cyclopropyl) | CH₃ |
| A-500 | 2-py | C₃H₇ (cyclopropyl) | CH₃ |
| A-501 | 3-Py | C₃H₇ (cyclopropyl) | CH₃ |
| A-502 | 1-phenyl-pyrazol-3-yl (#) | C₃H₇ (cyclopropyl) | CH₃ |
| A-503 | 1,2,4-triazol-1-yl (#) | C₃H₇ (cyclopropyl) | CH₃ |
| A-504 | (1,2,4-triazol-1-yl)methyl (#) | C₃H₇ (cyclopropyl) | CH₃ |
| A-505 | (pyridin-2-yl)methyl (#) | C₃H₇ (cyclopropyl) | CH₃ |
| A-506 | (1-phenyl-pyrazol-3-yl)methyl (#) | C₃H₇ (cyclopropyl) | CH₃ |
| A-507 | COCH₃ | i-C₃H₇ | CH₃ |
| A-508 | COCH₂CH₃ | i-C₃H₇ | CH₃ |
| A-509 | COCH₂CH₂CH₃ | i-C₃H₇ | CH₃ |
| A-510 | CO(CH₂)₃CH₃ | i-C₃H₇ | CH₃ |
| A-511 | CO(CH₂)₄CH₃ | i-C₃H₇ | CH₃ |
| A-512 | CO(CH₂)₅CH₃ | i-C₃H₇ | CH₃ |
| A-513 | CO(CH₂)₆CH₃ | i-C₃H₇ | CH₃ |
| A-514 | COCCl₃ | i-C₃H₇ | CH₃ |
| A-515 | COCH₂Cl | i-C₃H₇ | CH₃ |
| A-516 | COCH₂—N(CH₃)₂ | i-C₃H₇ | CH₃ |
| A-517 | COPh | i-C₃H₇ | CH₃ |
| A-518 | COCH₂Ph | i-C₃H₇ | CH₃ |
| A-519 | COCH₂Ph-4-F | i-C₃H₇ | CH₃ |
| A-520 | COCH₂Ph-4-CH₃ | i-C₃H₇ | CH₃ |
| A-521 | COCH₂Ph-3-CH₃ | i-C₃H₇ | CH₃ |
| A-522 | COCH₂Ph-2-CH₃ | i-C₃H₇ | CH₃ |
| A-523 | COCH(CH₃)Ph | i-C₃H₇ | CH₃ |
| A-524 | COCH(CH₃)-4-F | i-C₃H₇ | CH₃ |
| A-525 | COCH(CH₃)-4-CH₃ | i-C₃H₇ | CH₃ |
| A-526 | COCH(CH₃)-3-CH₃ | i-C₃H₇ | CH₃ |
| A-527 | COCH(CH₃)-3-CH₃ | i-C₃H₇ | CH₃ |
| A-528 | CF₃ | i-C₃H₇ | CH₃ |
| A-529 | CHF₂ | i-C₃H₇ | CH₃ |
| A-530 | CH₂CH₂OCH₃ | i-C₃H₇ | CH₃ |
| A-531 | CH₂cPr | i-C₃H₇ | CH₃ |
| A-532 | C₆H₅ | i-C₃H₇ | CH₃ |
| A-533 | CH₂—C₆H₅ | i-C₃H₇ | CH₃ |
| A-534 | CH₂—C₆H₄-4-F | i-C₃H₇ | CH₃ |
| A-535 | CH₂—C₆H₄-4-CH₃ | i-C₃H₇ | CH₃ |
| A-536 | CH₂—C₆H₄-3-CH₃ | i-C₃H₇ | CH₃ |
| A-537 | CH₂—C₆H₄-2-CH₃ | i-C₃H₇ | CH₃ |
| A-538 | CH(CH₃)—C₆H₅ | i-C₃H₇ | CH₃ |
| A-539 | CH(CH₃)—C₆H₄-4-F | i-C₃H₇ | CH₃ |
| A-540 | CH(CH₃)—C₆H₄-4-CH₃ | i-C₃H₇ | CH₃ |
| A-541 | CH(CH₃)—C₆H₄-3-CH₃ | i-C₃H₇ | CH₃ |
| A-542 | CH(CH₃)—C₆H₄-2-CH₃ | i-C₃H₇ | CH₃ |

TABLE A-continued

| No. | Q³ | Q¹ | Q² |
|---|---|---|---|
| A-543 | (but-3-yn-1-yl, # attached) | i-C₃H₇ | CH₃ |
| A-544 | (but-3-en-1-yl, # attached) | i-C₃H₇ | CH₃ |
| A-545 | (2,3,3-trichloroallyl, # attached) | i-C₃H₇ | CH₃ |
| A-546 | 2-py | i-C₃H₇ | CH₃ |
| A-547 | 3-Py | i-C₃H₇ | CH₃ |
| A-548 | (1-phenyl-1H-pyrazol-3-yl, # attached) | i-C₃H₇ | CH₃ |
| A-549 | (1H-1,2,4-triazol-1-yl, # attached) | i-C₃H₇ | CH₃ |
| A-550 | ((1H-1,2,4-triazol-1-yl)methyl, # attached) | i-C₃H₇ | CH₃ |
| A-551 | (pyridin-2-ylmethyl, # attached) | i-C₃H₇ | CH₃ |
| A-552 | ((1-phenyl-1H-pyrazol-3-yl)methyl, # attached) | i-C₃H₇ | CH₃ |
| A-553 | COCH₃ | CH=CH₂ | CH₃ |
| A-554 | COCH₂CH₃ | CH=CH₂ | CH₃ |
| A-555 | COCH₂CH₂CH₃ | CH=CH₂ | CH₃ |
| A-556 | CO(CH₂)₃CH₃ | CH=CH₂ | CH₃ |
| A-557 | CO(CH₂)₄CH₃ | CH=CH₂ | CH₃ |
| A-558 | CO(CH₂)₅CH₃ | CH=CH₂ | CH₃ |
| A-559 | CO(CH₂)₆CH₃ | CH=CH₂ | CH₃ |
| A-560 | COCCl₃ | CH=CH₂ | CH₃ |
| A-561 | COCH₂Cl | CH=CH₂ | CH₃ |
| A-562 | COCH₂—N(CH₃)₂ | CH=CH₂ | CH₃ |
| A-563 | COPh | CH=CH₂ | CH₃ |
| A-564 | COCH₂Ph | CH=CH₂ | CH₃ |
| A-565 | COCH₂Ph-4-F | CH=CH₂ | CH₃ |
| A-566 | COCH₂Ph-4-CH₃ | CH=CH₂ | CH₃ |
| A-567 | COCH₂Ph-3-CH₃ | CH=CH₂ | CH₃ |
| A-568 | COCH₂Ph-2-CH₃ | CH=CH₂ | CH₃ |
| A-569 | COCH(CH₃)Ph | CH=CH₂ | CH₃ |
| A-570 | COCH(CH₃)-4-F | CH=CH₂ | CH₃ |
| A-571 | COCH(CH₃)-4-CH₃ | CH=CH₂ | CH₃ |
| A-572 | COCH(CH₃)-3-CH₃ | CH=CH₂ | CH₃ |
| A-573 | COCH(CH₃)-3-CH₃ | CH=CH₂ | CH₃ |
| A-574 | CF₃ | CH=CH₂ | CH₃ |
| A-575 | CHF₂ | CH=CH₂ | CH₃ |
| A-576 | CH₂CH₂OCH₃ | CH=CH₂ | CH₃ |
| A-577 | CH₂cPr | CH=CH₂ | CH₃ |
| A-578 | C₆H₅ | CH=CH₂ | CH₃ |
| A-579 | CH₂—C₆H₅ | CH=CH₂ | CH₃ |
| A-580 | CH₂—C₆H₄-4-F | CH=CH₂ | CH₃ |
| A-581 | CH₂—C₆H₄-4-CH₃ | CH=CH₂ | CH₃ |
| A-582 | CH₂—C₆H₄-3-CH₃ | CH=CH₂ | CH₃ |
| A-583 | CH₂—C₆H₄-2-CH₃ | CH=CH₂ | CH₃ |
| A-584 | CH(CH₃)—C₆H₅ | CH=CH₂ | CH₃ |
| A-585 | CH(CH₃)—C₆H₄-4-F | CH=CH₂ | CH₃ |
| A-586 | CH(CH₃)—C₆H₄-4-CH₃ | CH=CH₂ | CH₃ |
| A-587 | CH(CH₃)—C₆H₄-3-CH₃ | CH=CH₂ | CH₃ |
| A-588 | CH(CH₃)—C₆H₄-2-CH₃ | CH=CH₂ | CH₃ |
| A-589 | (but-3-yn-1-yl, # attached) | CH=CH₂ | CH₃ |
| A-590 | (but-3-en-1-yl, # attached) | CH=CH₂ | CH₃ |
| A-591 | (2,3,3-trichloroallyl, # attached) | CH=CH₂ | CH₃ |
| A-592 | 2-py | CH=CH₂ | CH₃ |
| A-593 | 3-Py | CH=CH₂ | CH₃ |
| A-594 | (1-phenyl-1H-pyrazol-3-yl, # attached) | CH=CH₂ | CH₃ |
| A-595 | (1H-1,2,4-triazol-1-yl, # attached) | CH=CH₂ | CH₃ |
| A-596 | ((1H-1,2,4-triazol-1-yl)methyl, # attached) | CH=CH₂ | CH₃ |
| A-597 | (pyridin-2-ylmethyl, # attached) | CH=CH₂ | CH₃ |
| A-598 | ((1-phenyl-1H-pyrazol-3-yl)methyl, # attached) | CH=CH₂ | CH₃ |
| A-599 | COCH₃ | CH₂CH=CH₂ | CH₃ |
| A-600 | COCH₂CH₃ | CH₂CH=CH₂ | CH₃ |
| A-601 | COCH₂CH₂CH₃ | CH₂CH=CH₂ | CH₃ |
| A-602 | CO(CH₂)₃CH₃ | CH₂CH=CH₂ | CH₃ |
| A-603 | CO(CH₂)₄CH₃ | CH₂CH=CH₂ | CH₃ |
| A-604 | CO(CH₂)₅CH₃ | CH₂CH=CH₂ | CH₃ |
| A-605 | CO(CH₂)₆CH₃ | CH₂CH=CH₂ | CH₃ |
| A-606 | COCCl₃ | CH₂CH=CH₂ | CH₃ |
| A-607 | COCH₂Cl | CH₂CH=CH₂ | CH₃ |
| A-608 | COCH₂—N(CH₃)₂ | CH₂CH=CH₂ | CH₃ |
| A-609 | COPh | CH₂CH=CH₂ | CH₃ |
| A-610 | COCH₂Ph | CH₂CH=CH₂ | CH₃ |
| A-611 | COCH₂Ph-4-F | CH₂CH=CH₂ | CH₃ |
| A-612 | COCH₂Ph-4-CH₃ | CH₂CH=CH₂ | CH₃ |
| A-613 | COCH₂Ph-3-CH₃ | CH₂CH=CH₂ | CH₃ |
| A-614 | COCH₂Ph-2-CH₃ | CH₂CH=CH₂ | CH₃ |
| A-615 | COCH(CH₃)Ph | CH₂CH=CH₂ | CH₃ |
| A-616 | COCH(CH₃)-4-F | CH₂CH=CH₂ | CH₃ |
| A-617 | COCH(CH₃)-4-CH₃ | CH₂CH=CH₂ | CH₃ |

TABLE A-continued

| No. | Q³ | Q¹ | Q² |
|---|---|---|---|
| A-618 | COCH(CH₃)-3-CH₃ | CH₂CH=CH₂ | CH₃ |
| A-619 | COCH(CH₃)-3-CH₃ | CH₂CH=CH₂ | CH₃ |
| A-620 | CF₃ | CH₂CH=CH₂ | CH₃ |
| A-621 | CHF₂ | CH₂CH=CH₂ | CH₃ |
| A-622 | CH₂CH₂OCH₃ | CH₂CH=CH₂ | CH₃ |
| A-623 | CH₂cPr | CH₂CH=CH₂ | CH₃ |
| A-624 | C₆H₅ | CH₂CH=CH₂ | CH₃ |
| A-625 | CH₂—C₆H₅ | CH₂CH=CH₂ | CH₃ |
| A-626 | CH₂—C₆H₄-4-F | CH₂CH=CH₂ | CH₃ |
| A-627 | CH₂—C₆H₄-4-CH₃ | CH₂CH=CH₂ | CH₃ |
| A-628 | CH₂—C₆H₄-3-CH₃ | CH₂CH=CH₂ | CH₃ |
| A-629 | CH₂—C₆H₄-2-CH₃ | CH₂CH=CH₂ | CH₃ |
| A-630 | CH(CH₃)—C₆H₅ | CH₂CH=CH₂ | CH₃ |
| A-631 | CH(CH₃)—C₆H₄-4-F | CH₂CH=CH₂ | CH₃ |
| A-632 | CH(CH₃)—C₆H₄-4-CH₃ | CH₂CH=CH₂ | CH₃ |
| A-633 | CH(CH₃)—C₆H₄-3-CH₃ | CH₂CH=CH₂ | CH₃ |
| A-634 | CH(CH₃)—C₆H₄-2-CH₃ | CH₂CH=CH₂ | CH₃ |
| A-635 | #–CH₂–C≡CH | CH₂CH=CH₂ | CH₃ |
| A-636 | #–CH₂–CH=CH₂ | CH₂CH=CH₂ | CH₃ |
| A-637 | #–CH₂–C(Cl)=CCl₂ | CH₂CH=CH₂ | CH₃ |
| A-638 | 2-py | CH₂CH=CH₂ | CH₃ |
| A-639 | 3-Py | CH₂CH=CH₂ | CH₃ |
| A-640 | 1-phenyl-pyrazol-3-yl | CH₂CH=CH₂ | CH₃ |
| A-641 | 1,2,4-triazol-1-yl | CH₂CH=CH₂ | CH₃ |
| A-642 | (1,2,4-triazol-1-yl)methyl | CH₂CH=CH₂ | CH₃ |
| A-643 | (pyridin-2-yl)methyl | CH₂CH=CH₂ | CH₃ |
| A-644 | (1-phenyl-pyrazol-3-yl)methyl | CH₂CH=CH₂ | CH₃ |
| A-645 | COCH₃ | C₆H₅ | CH₃ |
| A-646 | COCH₂CH₃ | C₆H₅ | CH₃ |
| A-647 | COCH₂CH₂CH₃ | C₆H₅ | CH₃ |
| A-648 | CO(CH₂)₃CH₃ | C₆H₅ | CH₃ |
| A-649 | CO(CH₂)₄CH₃ | C₆H₅ | CH₃ |
| A-650 | CO(CH₂)₅CH₃ | C₆H₅ | CH₃ |
| A-651 | CO(CH₂)₆CH₃ | C₆H₅ | CH₃ |
| A-652 | COCCl₃ | C₆H₅ | CH₃ |
| A-653 | COCH₂Cl | C₆H₅ | CH₃ |
| A-654 | COCH₂—N(CH₃)₂ | C₆H₅ | CH₃ |
| A-655 | COPh | C₆H₅ | CH₃ |
| A-656 | COCH₂Ph | C₆H₅ | CH₃ |
| A-657 | COCH₂Ph-4-F | C₆H₅ | CH₃ |
| A-658 | COCH₂Ph-4-CH₃ | C₆H₅ | CH₃ |
| A-659 | COCH₂Ph-3-CH₃ | C₆H₅ | CH₃ |
| A-660 | COCH₂Ph-2-CH₃ | C₆H₅ | CH₃ |
| A-661 | COCH(CH₃)Ph | C₆H₅ | CH₃ |
| A-662 | COCH(CH₃)-4-F | C₆H₅ | CH₃ |
| A-663 | COCH(CH₃)-4-CH₃ | C₆H₅ | CH₃ |
| A-664 | COCH(CH₃)-3-CH₃ | C₆H₅ | CH₃ |
| A-665 | COCH(CH₃)-3-CH₃ | C₆H₅ | CH₃ |
| A-666 | CF₃ | C₆H₅ | CH₃ |
| A-667 | CHF₂ | C₆H₅ | CH₃ |
| A-668 | CH₂CH₂OCH₃ | C₆H₅ | CH₃ |
| A-669 | CH₂cPr | C₆H₅ | CH₃ |
| A-670 | C₆H₅ | C₆H₅ | CH₃ |
| A-671 | CH₂—C₆H₅ | C₆H₅ | CH₃ |
| A-672 | CH₂—C₆H₄-4-F | C₆H₅ | CH₃ |
| A-673 | CH₂—C₆H₄-4-CH₃ | C₆H₅ | CH₃ |
| A-674 | CH₂—C₆H₄-3-CH₃ | C₆H₅ | CH₃ |
| A-675 | CH₂—C₆H₄-2-CH₃ | C₆H₅ | CH₃ |
| A-676 | CH(CH₃)—C₆H₅ | C₆H₅ | CH₃ |
| A-677 | CH(CH₃)—C₆H₄-4-F | C₆H₅ | CH₃ |
| A-678 | CH(CH₃)—C₆H₄-4-CH₃ | C₆H₅ | CH₃ |
| A-679 | CH(CH₃)—C₆H₄-3-CH₃ | C₆H₅ | CH₃ |
| A-680 | CH(CH₃)—C₆H₄-2-CH₃ | C₆H₅ | CH₃ |
| A-681 | #–CH₂–C≡CH | C₆H₅ | CH₃ |
| A-682 | #–CH₂–CH=CH₂ | C₆H₅ | CH₃ |
| A-683 | #–CH₂–C(Cl)=CCl₂ | C₆H₅ | CH₃ |
| A-684 | 2-py | C₆H₅ | CH₃ |
| A-685 | 3-py | C₆H₅ | CH₃ |
| A-686 | 1-phenyl-pyrazol-3-yl | C₆H₅ | CH₃ |
| A-687 | 1,2,4-triazol-1-yl | C₆H₅ | CH₃ |
| A-688 | (1,2,4-triazol-1-yl)methyl | C₆H₅ | CH₃ |
| A-689 | (pyridin-2-yl)methyl | C₆H₅ | CH₃ |
| A-690 | (1-phenyl-pyrazol-3-yl)methyl | C₆H₅ | CH₃ |
| A-691 | COCH₃ | CH₂C₆H₅ | CH₃ |

TABLE A-continued

| No. | Q³ | Q¹ | Q² |
|---|---|---|---|
| A-692 | COCH₂CH₃ | CH₂C₆H₅ | CH₃ |
| A-693 | COCH₂CH₂CH₃ | CH₂C₆H₅ | CH₃ |
| A-694 | CO(CH₂)₃CH₃ | CH₂C₆H₅ | CH₃ |
| A-695 | CO(CH₂)₄CH₃ | CH₂C₆H₅ | CH₃ |
| A-696 | CO(CH₂)₅CH₃ | CH₂C₆H₅ | CH₃ |
| A-697 | CO(CH₂)₆CH₃ | CH₂C₆H₅ | CH₃ |
| A-698 | COCCl₃ | CH₂C₆H₅ | CH₃ |
| A-699 | COCH₂Cl | CH₂C₆H₅ | CH₃ |
| A-700 | COCH₂—N(CH₃)₂ | CH₂C₆H₅ | CH₃ |
| A-701 | COPh | CH₂C₆H₅ | CH₃ |
| A-702 | COCH₂Ph | CH₂C₆H₅ | CH₃ |
| A-703 | COCH₂Ph-4-F | CH₂C₆H₅ | CH₃ |
| A-704 | COCH₂Ph-4-CH₃ | CH₂C₆H₅ | CH₃ |
| A-705 | COCH₂Ph-3-CH₃ | CH₂C₆H₅ | CH₃ |
| A-706 | COCH₂Ph-2-CH₃ | CH₂C₆H₅ | CH₃ |
| A-707 | COCH(CH₃)Ph | CH₂C₆H₅ | CH₃ |
| A-708 | COCH(CH₃)-4-F | CH₂C₆H₅ | CH₃ |
| A-709 | COCH(CH₃)-4-CH₃ | CH₂C₆H₅ | CH₃ |
| A-710 | COCH(CH₃)-3-CH₃ | CH₂C₆H₅ | CH₃ |
| A-711 | COCH(CH₃)-3-CH₃ | CH₂C₆H₅ | CH₃ |
| A-712 | CF₃ | CH₂C₆H₅ | CH₃ |
| A-713 | CHF₂ | CH₂C₆H₅ | CH₃ |
| A-714 | CH₂CH₂OCH₃ | CH₂C₆H₅ | CH₃ |
| A-715 | CH₂cPr | CH₂C₆H₅ | CH₃ |
| A-716 | C₆H₅ | CH₂C₆H₅ | CH₃ |
| A-717 | CH₂—C₆H₅ | CH₂C₆H₅ | CH₃ |
| A-718 | CH₂—C₆H₄-4-F | CH₂C₆H₅ | CH₃ |
| A-719 | CH₂—C₆H₄-4-CH₃ | CH₂C₆H₅ | CH₃ |
| A-720 | CH₂—C₆H₄-3-CH₃ | CH₂C₆H₅ | CH₃ |
| A-721 | CH₂—C₆H₄-2-CH₃ | CH₂C₆H₅ | CH₃ |
| A-722 | CH(CH₃)—C₆H₅ | CH₂C₆H₅ | CH₃ |
| A-723 | CH(CH₃)—C₆H₄-4-F | CH₂C₆H₅ | CH₃ |
| A-724 | CH(CH₃)—C₆H₄-4-CH₃ | CH₂C₆H₅ | CH₃ |
| A-725 | CH(CH₃)—C₆H₄-3-CH₃ | CH₂C₆H₅ | CH₃ |
| A-726 | CH(CH₃)—C₆H₄-2-CH₃ | CH₂C₆H₅ | CH₃ |
| A-727 | 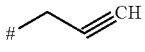 | CH₂C₆H₅ | CH₃ |
| A-728 | 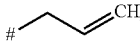 | CH₂C₆H₅ | CH₃ |
| A-729 | 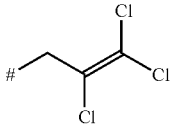 | CH₂C₆H₅ | CH₃ |
| A-730 | 2-py | CH₂C₆H₅ | CH₃ |
| A-731 | 3-py | CH₂C₆H₅ | CH₃ |
| A-732 | 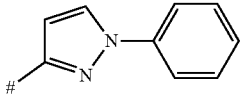 | CH₂C₆H₅ | CH₃ |
| A-733 | 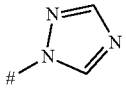 | CH₂C₆H₅ | CH₃ |
| A-734 | 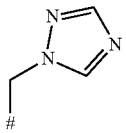 | CH₂C₆H₅ | CH₃ |
| A-735 | 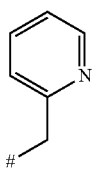 | CH₂C₆H₅ | CH₃ |
| A-736 | 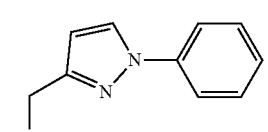 | CH₂C₆H₅ | CH₃ |
| A-737 | COCH₃ |  | |
| A-738 | COCH₂CH₃ | 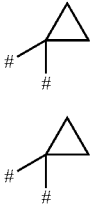 | |
| A-739 | COCH₂CH₂CH₃ |  | |
| A-740 | CO(CH₂)₃CH₃ |  | |
| A-741 | CO(CH₂)₄CH₃ |  | |
| A-742 | CO(CH₂)₅CH₃ | 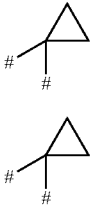 | |
| A-743 | CO(CH₂)₆CH₃ |  | |
| A-744 | COCCl₃ | 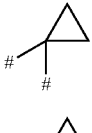 | |
| A-745 | COCH₂Cl |  | |
| A-746 | COCH₂—N(CH₃)₂ | | |
| A-747 | COPh | | |
| A-748 | COCH₂Ph | | |
| A-749 | COCH₂Ph-4-F |  | |

TABLE A-continued
| No. | Q³ | Q¹ | Q² |
|---|---|---|---|
| A-750 | COCH₂Ph-4-CH₃ | |  |
| A-751 | COCH₂Ph-3-CH₃ | |  |
| A-752 | COCH₂Ph-2-CH₃ | |  |
| A-753 | COCH(CH₃)Ph | |  |
| A-754 | COCH(CH₃)-4-F | | 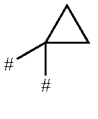 |
| A-755 | COCH(CH₃)-4-CH₃ | |  |
| A-756 | COCH(CH₃)-3-CH₃ | |  |
| A-757 | COCH(CH₃)-3-CH₃ | | 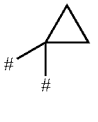 |
| A-758 | CF₃ | | 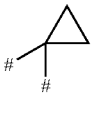 |
| A-759 | CHF₂ | | 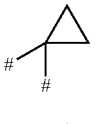 |
| A-760 | CH₂CH₂OCH₃ | | 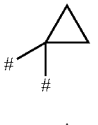 |
| A-761 | CH₂cPr | | 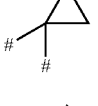 |
| A-762 | C₆H₅ | | 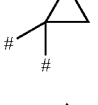 |
| A-763 | CH₂—C₆H₅ | | 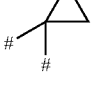 |
TABLE A-continued
| No. | Q³ | Q¹ | Q² |
|---|---|---|---|
| A-764 | CH₂—C₆H₄-4-F | |  |
| A-765 | CH₂—C₆H₄-4-CH₃ | |  |
| A-766 | CH₂—C₆H₄-3-CH₃ | |  |
| A-767 | CH₂—C₆H₄-2-CH₃ | |  |
| A-768 | CH(CH₃)—C₆H₅ | |  |
| A-769 | CH(CH₃)—C₆H₄-4-F | | 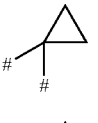 |
| A-770 | CH(CH₃)—C₆H₄-4-CH₃ | |  |
| A-771 | CH(CH₃)—C₆H₄-3-CH₃ | | 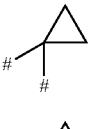 |
| A-772 | CH(CH₃)—C₆H₄-2-CH₃ | | 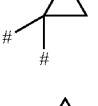 |
| A-773 | 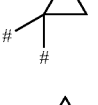 | | |
| A-774 | 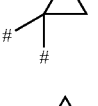 | | |
| A-775 |  | | |
| A-776 | 2-py | |  |
| A-777 | 3-py | |  |

TABLE A-continued

| No. | Q³ | Q¹ | Q² |
|---|---|---|---|
| A-778 | 3-(1-phenyl-1H-pyrazol-3-yl), # attached | | 1-methylcyclopropyl, # |
| A-779 | 1H-1,2,4-triazol-1-yl, # | | 1-methylcyclopropyl, # |
| A-780 | (1H-1,2,4-triazol-1-yl)methyl, # | | 1-methylcyclopropyl, # |
| A-781 | (pyridin-2-yl)methyl, # | | 1-methylcyclopropyl, # |
| A-782 | (1-phenyl-1H-pyrazol-3-yl)methyl, # | | 1-methylcyclopropyl, # |
| A-783 | COCH₃ | | 2-methyloxiran-2-yl, # |
| A-784 | COCH₂CH₃ | | 2-methyloxiran-2-yl, # |
| A-785 | COCH₂CH₂CH₃ | | 2-methyloxiran-2-yl, # |
| A-786 | CO(CH₂)₃CH₃ | | 2-methyloxiran-2-yl, # |
| A-787 | CO(CH₂)₄CH₃ | | 2-methyloxiran-2-yl, # |
| A-788 | CO(CH₂)₅CH₃ | | 2-methyloxiran-2-yl, # |
| A-789 | CO(CH₂)₆CH₃ | | 2-methyloxiran-2-yl, # |
| A-790 | COCCl₃ | | 2-methyloxiran-2-yl, # |
| A-791 | COCH₂Cl | | 2-methyloxiran-2-yl, # |
| A-792 | COCH₂—N(CH₃)₂ | | 2-methyloxiran-2-yl, # |
| A-793 | COPh | | 2-methyloxiran-2-yl, # |
| A-794 | COCH₂Ph | | 2-methyloxiran-2-yl, # |
| A-795 | COCH₂Ph-4-F | | 2-methyloxiran-2-yl, # |
| A-796 | COCH₂Ph-4-CH₃ | | 2-methyloxiran-2-yl, # |
| A-797 | COCH₂Ph-3-CH₃ | | 2-methyloxiran-2-yl, # |
| A-798 | COCH₂Ph-2-CH₃ | | 2-methyloxiran-2-yl, # |
| A-799 | COCH(CH₃)Ph | | 2-methyloxiran-2-yl, # |
| A-800 | COCH(CH₃)-4-F | | 2-methyloxiran-2-yl, # |
| A-801 | COCH(CH₃)-4-CH₃ | | 2-methyloxiran-2-yl, # |
| A-802 | COCH(CH₃)-3-CH₃ | | 2-methyloxiran-2-yl, # |

TABLE A-continued

| No. | Q³ | Q¹ | Q² |
|---|---|---|---|
| A-803 | COCH(CH₃)-3-CH₃ | | 2-methyloxiranyl |
| A-804 | CF₃ | | 2-methyloxiranyl |
| A-805 | CHF₂ | | 2-methyloxiranyl |
| A-806 | CH₂CH₂OCH₃ | | 2-methyloxiranyl |
| A-807 | CH₂cPr | | 2-methyloxiranyl |
| A-808 | C₆H₅ | | 2-methyloxiranyl |
| A-809 | CH₂—C₆H₅ | | 2-methyloxiranyl |
| A-810 | CH₂—C₆H₄-4-F | | 2-methyloxiranyl |
| A-811 | CH₂—C₆H₄-4-CH₃ | | 2-methyloxiranyl |
| A-812 | CH₂—C₆H₄-3-CH₃ | | 2-methyloxiranyl |
| A-813 | CH₂—C₆H₄-2-CH₃ | | 2-methyloxiranyl |
| A-814 | CH(CH₃)—C₆H₅ | | 2-methyloxiranyl |
| A-815 | CH(CH₃)—C₆H₄-4-F | | 2-methyloxiranyl |
| A-816 | CH(CH₃)—C₆H₄-4-CH₃ | | 2-methyloxiranyl |
| A-817 | CH(CH₃)—C₆H₄-3-CH₃ | | 2-methyloxiranyl |
| A-818 | CH(CH₃)—C₆H₄-2-CH₃ | | 2-methyloxiranyl |
| A-819 | CH₂—C≡CH | | 2-methyloxiranyl |
| A-820 | CH₂—CH=CH₂ | | 2-methyloxiranyl |
| A-821 | CH₂—C(Cl)=CCl₂ | | 2-methyloxiranyl |
| A-822 | 2-py | | 2-methyloxiranyl |
| A-823 | 3-py | | 2-methyloxiranyl |
| A-824 | 1-phenyl-3H-pyrazol-3-yl | | 2-methyloxiranyl |
| A-825 | 1H-1,2,4-triazol-1-yl | | 2-methyloxiranyl |
| A-826 | CH₂-(1H-1,2,4-triazol-1-yl) | | 2-methyloxiranyl |
| A-827 | CH₂-(pyridin-2-yl) | | 2-methyloxiranyl |

TABLE A-continued
| No. | Q³ | Q¹ | Q² |
|---|---|---|---|
| A-828 | 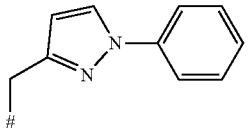 | |  |
| A-829 | COCH₃ | | 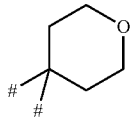 |
| A-830 | COCH₂CH₃ | | 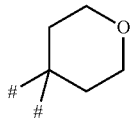 |
| A-831 | COCH₂CH₂CH₃ | | 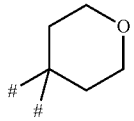 |
| A-832 | CO(CH₂)₃CH₃ | | 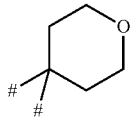 |
| A-833 | CO(CH₂)₄CH₃ | | 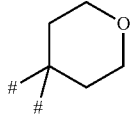 |
| A-834 | CO(CH₂)₅CH₃ | | 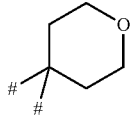 |
| A-835 | CO(CH₂)₆CH₃ | | 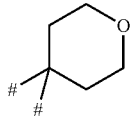 |
| A-836 | COCCl₃ | | 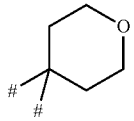 |
| A-837 | COCH₂Cl | | 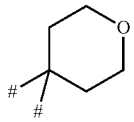 |
| A-838 | COCH₂—N(CH₃)₂ | | 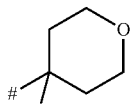 |
TABLE A-continued
| No. | Q³ | Q¹ | Q² |
|---|---|---|---|
| A-839 | COPh | | 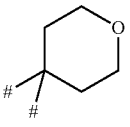 |
| A-840 | COCH₂Ph | | 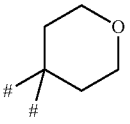 |
| A-841 | COCH₂Ph-4-F | | 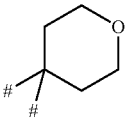 |
| A-842 | COCH₂Ph-4-CH₃ | | 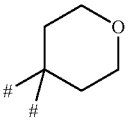 |
| A-843 | COCH₂Ph-3-CH₃ | | 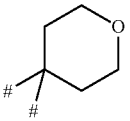 |
| A-844 | COCH₂Ph-2-CH₃ | | 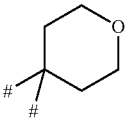 |
| A-845 | COCH(CH₃)Ph | | 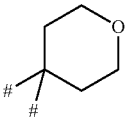 |
| A-846 | COCH(CH₃)-4-F | | 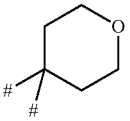 |
| A-847 | COCH(CH₃)-4-CH₃ | | 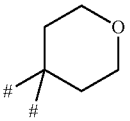 |
| A-848 | COCH(CH₃)-3-CH₃ | | 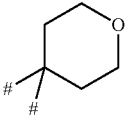 |
| A-849 | COCH(CH₃)-3-CH₃ | | 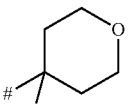 |

TABLE A-continued

| No. | Q³ | Q¹ | Q² |
|---|---|---|---|
| A-850 | CF₃ | | tetrahydropyran-4-yl |
| A-851 | CHF₂ | | tetrahydropyran-4-yl |
| A-852 | CH₂CH₂OCH₃ | | tetrahydropyran-4-yl |
| A-853 | CH₂cPr | | tetrahydropyran-4-yl |
| A-854 | C₆H₅ | | tetrahydropyran-4-yl |
| A-855 | CH₂—C₆H₅ | | tetrahydropyran-4-yl |
| A-856 | CH₂—C₆H₄-4-F | | tetrahydropyran-4-yl |
| A-857 | CH₂—C₆H₄-4-CH₃ | | tetrahydropyran-4-yl |
| A-858 | CH₂—C₆H₄-3-CH₃ | | tetrahydropyran-4-yl |
| A-859 | CH₂—C₆H₄-2-CH₃ | | tetrahydropyran-4-yl |
| A-860 | CH(CH₃)—C₆H₅ | | tetrahydropyran-4-yl |
| A-861 | CH(CH₃)—C₆H₄-4-F | | tetrahydropyran-4-yl |
| A-862 | CH(CH₃)—C₆H₄-4-CH₃ | | tetrahydropyran-4-yl |
| A-863 | CH(CH₃)—C₆H₄-3-CH₃ | | tetrahydropyran-4-yl |
| A-864 | CH(CH₃)—C₆H₄-2-CH₃ | | tetrahydropyran-4-yl |
| A-865 | propargyl (#-CH₂-C≡CH) | | tetrahydropyran-4-yl |
| A-866 | allyl (#-CH₂-CH=CH₂) | | tetrahydropyran-4-yl |
| A-867 | #-CH₂-C(Cl)=CCl₂ | | tetrahydropyran-4-yl |
| A-868 | 2-py | | tetrahydropyran-4-yl |
| A-869 | 3-py | | tetrahydropyran-4-yl |
| A-870 | 1-phenyl-pyrazol-3-yl | | tetrahydropyran-4-yl |
| A-871 | 1,2,4-triazol-1-yl | | tetrahydropyran-4-yl |

TABLE A-continued
| No. | Q³ | Q¹ | Q² |
|-----|-----|-----|-----|
| A-872 | 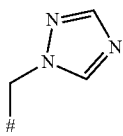 | | 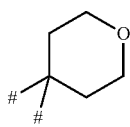 |
| A-873 | 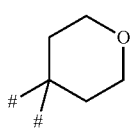 | | 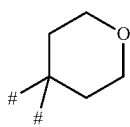 |
| A-874 | 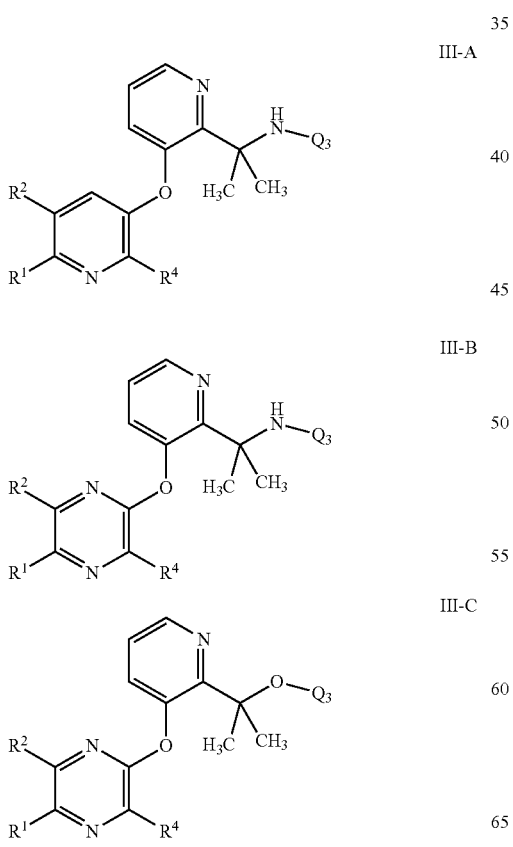 | | |
Particular embodiments of the compounds I are the following compounds: III-A, III-B, III-C, III-D, III-E, III-F, III-G, III-H, III-I; IV-A, IV-B, IV-C, IV-D, IV-E, IV-F, IV-G, IV-H, IV-I. In these formulae, the substituents $R^1$, $R^2$, $R^4$ and $Q^3$ are independently as defined in claim 1 or preferably defined below:

-continued

IV-A 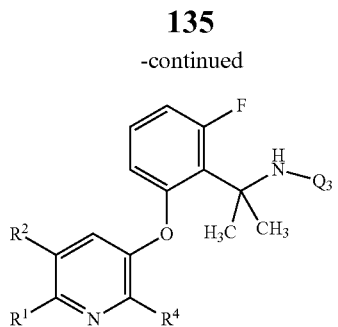

IV-B 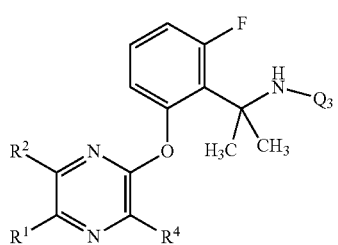

IV-C 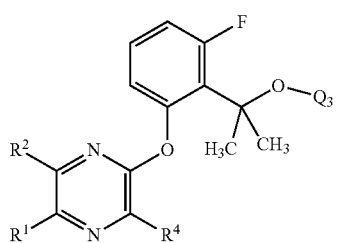

IV-D 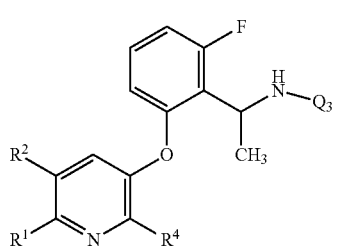

IV-E 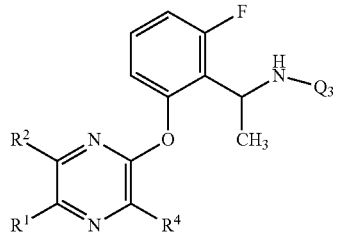

IV-F 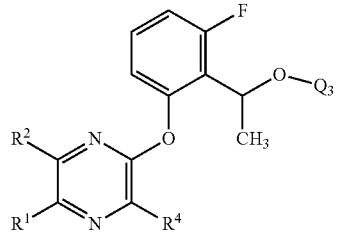

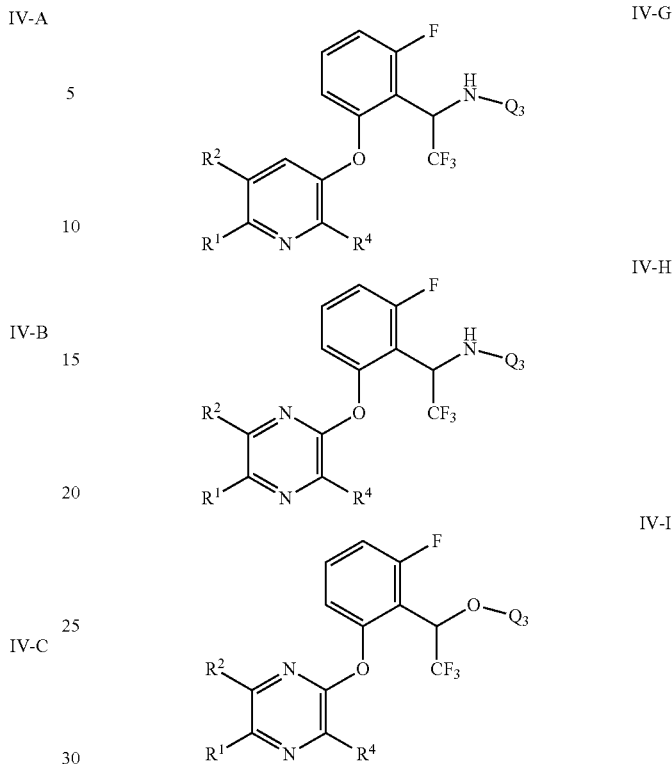

Table 3-1 Compounds of the formula III-A, III-B, III-C, II-D, II-E, III-F, II-G, III-H, III-I in which the meaning for the combination of $Q^1$, $Q^2$ and $Q^3$ for each individual compound corresponds in each case to one line of Table B (compounds III-A.3-1.B-1 to III-A.3-1.B-230, III-B.3-1.B-1 to III-B.3-1.B-230, III-C.3-1.B-1 to III-C.3-1.B-230, III-D.3-1.B-1 to III-D.3-1.B-230, III-E.3-1.B-1 to III-E.3-1.B-230, III-F.3-1.B-1 to III-F.3-1.B-230, III-G.3-1.B-1 to III-G.3-1.B-230, III-H.3-1.B-1 to III-H.3-1.B-230, III-I.3-1B-1 to III-I.3-1.B-230).

Table 4-1 Compounds of the formula IV-A, IV-B, IV-C, IV-D, IV-E, IV-F, IV-G, IV-H, IV-I in which the meaning for the combination of $Q^1$, $Q^2$ and $Q^3$ for each individual compound corresponds in each case to one line of Table B (compounds IV-A.4-1.B-1 to IV-A.4-1.B-230, IV-B.4-1.B-1 to IV-B.4-1.B-230, IV-C.4-1.B-1 to IV-C.4-1.B-230, IV-D.4-1.B-1 to IV-D.4-1.B-230, IV-E.4-1.B-1 to IV-E.4-1.B-230, IV-F.4-1.B-1 to IV-F.4-1.B-230, IV-G.4-1.B-1 to IV-G.4-1.B-230, IV-H.4-1.B-1 to IV-H.4-1.B-230, IV-I.4-1.B-1 to IV-I.4-1.B-230).

TABLE B

| No. | $Q^3$ | $R^1$ | $R^2$ | $R^4$ |
|---|---|---|---|---|
| B-1 | $COCH_3$ | $CH_3$ | $CH_3$ | H |
| B-2 | $COCH_2CH_3$ | $CH_3$ | $CH_3$ | H |
| B-3 | $COCH_2CH_2CH_3$ | $CH_3$ | $CH_3$ | H |
| B-4 | $CO(CH_2)_3CH_3$ | $CH_3$ | $CH_3$ | H |
| B-5 | $CO(CH_2)_4CH_3$ | $CH_3$ | $CH_3$ | H |
| B-6 | $CO(CH_2)_5CH_3$ | $CH_3$ | $CH_3$ | H |
| B-7 | $CO(CH_2)_6CH_3$ | $CH_3$ | $CH_3$ | H |
| B-8 | $COCCl_3$ | $CH_3$ | $CH_3$ | H |
| B-9 | $COCH_2Cl$ | $CH_3$ | $CH_3$ | H |
| B-10 | $COCH_2-N(CH_3)_2$ | $CH_3$ | $CH_3$ | H |
| B-11 | $COPh$ | $CH_3$ | $CH_3$ | H |
| B-12 | $COCH_2Ph$ | $CH_3$ | $CH_3$ | H |

TABLE B-continued

| No. | Q³ | R¹ | R² | R⁴ |
|---|---|---|---|---|
| B-13 | COCH₂Ph-4-F | CH₃ | CH₃ | H |
| B-14 | COCH₂Ph-4-CH₃ | CH₃ | CH₃ | H |
| B-15 | COCH₂Ph-3-CH₃ | CH₃ | CH₃ | H |
| B-16 | COCH₂Ph-2-CH₃ | CH₃ | CH₃ | H |
| B-17 | COCH(CH₃)Ph | CH₃ | CH₃ | H |
| B-18 | COCH(CH₃)-4-F | CH₃ | CH₃ | H |
| B-19 | COCH(CH₃)-4-CH₃ | CH₃ | CH₃ | H |
| B-20 | COCH(CH₃)-3-CH₃ | CH₃ | CH₃ | H |
| B-21 | COCH(CH₃)-3-CH₃ | CH₃ | CH₃ | H |
| B-22 | CF₃ | CH₃ | CH₃ | H |
| B-23 | CHF₂ | CH₃ | CH₃ | H |
| B-24 | CH₂CH₂OCH₃ | CH₃ | CH₃ | H |
| B-25 | CH₂cPr | CH₃ | CH₃ | H |
| B-26 | C₆H₅ | CH₃ | CH₃ | H |
| B-27 | CH₂—C₆H₅ | CH₃ | CH₃ | H |
| B-28 | CH₂—C₆H₄-4-F | CH₃ | CH₃ | H |
| B-29 | CH₂—C₆H₄-4-CH₃ | CH₃ | CH₃ | H |
| B-30 | CH₂—C₆H₄-3-CH₃ | CH₃ | CH₃ | H |
| B-31 | CH₂—C₆H₄-2-CH₃ | CH₃ | CH₃ | H |
| B-32 | CH(CH₃)—C₆H₅ | CH₃ | CH₃ | H |
| B-33 | CH(CH₃)—C₆H₄-4-F | CH₃ | CH₃ | H |
| B-34 | CH(CH₃)—C₆H₄-4-CH₃ | CH₃ | CH₃ | H |
| B-35 | CH(CH₃)—C₆H₄-3-CH₃ | CH₃ | CH₃ | H |
| B-36 | CH(CH₃)—C₆H₄-2-CH₃ | CH₃ | CH₃ | H |
| B-37 | 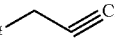 | CH₃ | CH₃ | H |
| B-38 | 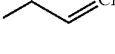 | CH₃ | CH₃ | H |
| B-39 | 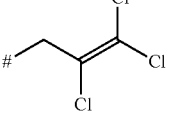 | CH₃ | CH₃ | H |
| B-40 | 2-py | CH₃ | CH₃ | H |
| B-41 | 3-py | CH₃ | CH₃ | H |
| B-42 | 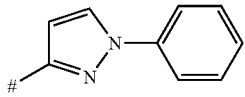 | CH₃ | CH₃ | H |
| B-43 | 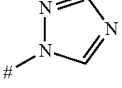 | CH₃ | CH₃ | H |
| B-44 | 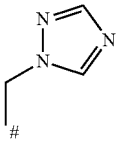 | CH₃ | CH₃ | H |
| B-45 | 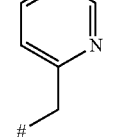 | CH₃ | CH₃ | H |
| B-46 | 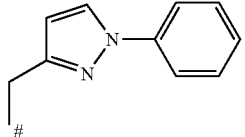 | CH₃ | CH₃ | H |
| B-47 | COCH₃ | CH₃ | CH₃ | CH₃ |
| B-48 | COCH₂CH₃ | CH₃ | CH₃ | CH₃ |
| B-49 | COCH₂CH₂CH₃ | CH₃ | CH₃ | CH₃ |
| B-50 | CO(CH₂)₃CH₃ | CH₃ | CH₃ | CH₃ |
| B-51 | CO(CH₂)₄CH₃ | CH₃ | CH₃ | CH₃ |
| B-52 | CO(CH₂)₅CH₃ | CH₃ | CH₃ | CH₃ |
| B-53 | CO(CH₂)₆CH₃ | CH₃ | CH₃ | CH₃ |
| B-54 | COCCl₃ | CH₃ | CH₃ | CH₃ |
| B-55 | COCH₂Cl | CH₃ | CH₃ | CH₃ |
| B-56 | COCH₂—N(CH₃)₂ | CH₃ | CH₃ | CH₃ |
| B-57 | COPh | CH₃ | CH₃ | CH₃ |
| B-58 | COCH₂Ph | CH₃ | CH₃ | CH₃ |
| B-59 | COCH₂Ph-4-F | CH₃ | CH₃ | CH₃ |
| B-60 | COCH₂Ph-4-CH₃ | CH₃ | CH₃ | CH₃ |
| B-61 | COCH₂Ph-3-CH₃ | CH₃ | CH₃ | CH₃ |
| B-62 | COCH₂Ph-2-CH₃ | CH₃ | CH₃ | CH₃ |
| B-63 | COCH(CH₃)Ph | CH₃ | CH₃ | CH₃ |
| B-64 | COCH(CH₃)-4-F | CH₃ | CH₃ | CH₃ |
| B-65 | COCH(CH₃)-4-CH₃ | CH₃ | CH₃ | CH₃ |
| B-66 | COCH(CH₃)-3-CH₃ | CH₃ | CH₃ | CH₃ |
| B-67 | COCH(CH₃)-3-CH₃ | CH₃ | CH₃ | CH₃ |
| B-68 | CF₃ | CH₃ | CH₃ | CH₃ |
| B-69 | CHF₂ | CH₃ | CH₃ | CH₃ |
| B-70 | CH₂CH₂OCH₃ | CH₃ | CH₃ | CH₃ |
| B-71 | CH₂cPr | CH₃ | CH₃ | CH₃ |
| B-72 | C₆H₅ | CH₃ | CH₃ | CH₃ |
| B-73 | CH₂—C₆H₅ | CH₃ | CH₃ | CH₃ |
| B-74 | CH₂—C₆H₄-4-F | CH₃ | CH₃ | CH₃ |
| B-75 | CH₂—C₆H₄-4-CH₃ | CH₃ | CH₃ | CH₃ |
| B-76 | CH₂—C₆H₄-3-CH₃ | CH₃ | CH₃ | CH₃ |
| B-77 | CH₂—C₆H₄-2-CH₃ | CH₃ | CH₃ | CH₃ |
| B-78 | CH(CH₃)—C₆H₅ | CH₃ | CH₃ | CH₃ |
| B-79 | CH(CH₃)—C₆H₄-4-F | CH₃ | CH₃ | CH₃ |
| B-80 | CH(CH₃)—C₆H₄-4-CH₃ | CH₃ | CH₃ | CH₃ |
| B-81 | CH(CH₃)—C₆H₄-3-CH₃ | CH₃ | CH₃ | CH₃ |
| B-82 | CH(CH₃)—C₆H₄-2-CH₃ | CH₃ | CH₃ | CH₃ |
| B-83 | 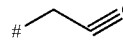 | CH₃ | CH₃ | CH₃ |
| B-84 | 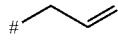 | CH₃ | CH₃ | CH₃ |
| B-85 | 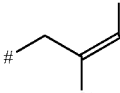 | CH₃ | CH₃ | CH₃ |
| B-86 | 2-py | CH₃ | CH₃ | CH₃ |
| B-87 | 3-py | CH₃ | CH₃ | CH₃ |
| B-88 | 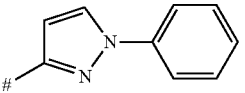 | CH₃ | CH₃ | CH₃ |
| B-89 | 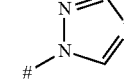 | CH₃ | CH₃ | CH₃ |
| B-90 | 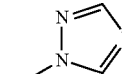 | CH₃ | CH₃ | CH₃ |

TABLE B-continued

| No. | Q³ | R¹ | R² | R⁴ |
|---|---|---|---|---|
| B-91 | 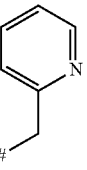 | CH₃ | CH₃ | CH₃ |
| B-92 | 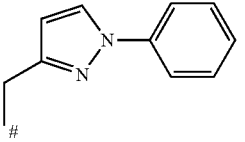 | CH₃ | CH₃ | CH₃ |
| B-93 | COCH₃ | CH₃ | CHF₂ | H |
| B-94 | COCH₂CH₃ | CH₃ | CHF₂ | H |
| B-95 | COCH₂CH₂CH₃ | CH₃ | CHF₂ | H |
| B-96 | CO(CH₂)₃CH₃ | CH₃ | CHF₂ | H |
| B-97 | CO(CH₂)₄CH₃ | CH₃ | CHF₂ | H |
| B-98 | CO(CH₂)₅CH₃ | CH₃ | CHF₂ | H |
| B-99 | CO(CH₂)₆CH₃ | CH₃ | CHF₂ | H |
| B-100 | COCCl₃ | CH₃ | CHF₂ | H |
| B-101 | COCH₂Cl | CH₃ | CHF₂ | H |
| B-102 | COCH₂—N(CH₃)₂ | CH₃ | CHF₂ | H |
| B-103 | COPh | CH₃ | CHF₂ | H |
| B-104 | COCH₂Ph | CH₃ | CHF₂ | H |
| B-105 | COCH₂Ph-4-F | CH₃ | CHF₂ | H |
| B-106 | COCH₂Ph-4-CH₃ | CH₃ | CHF₂ | H |
| B-107 | COCH₂Ph-3-CH₃ | CH₃ | CHF₂ | H |
| B-108 | COCH₂Ph-2-CH₃ | CH₃ | CHF₂ | H |
| B-109 | COCH(CH₃)Ph | CH₃ | CHF₂ | H |
| B-110 | COCH(CH₃)-4-F | CH₃ | CHF₂ | H |
| B-111 | COCH(CH₃)-4-CH₃ | CH₃ | CHF₂ | H |
| B-112 | COCH(CH₃)-3-CH₃ | CH₃ | CHF₂ | H |
| B-113 | COCH(CH₃)-3-CH₃ | CH₃ | CHF₂ | H |
| B-114 | CF₃ | CH₃ | CHF₂ | H |
| B-115 | CHF₂ | CH₃ | CHF₂ | H |
| B-116 | CH₂CH₂OCH₃ | CH₃ | CHF₂ | H |
| B-117 | CH₂cPr | CH₃ | CHF₂ | H |
| B-118 | C₆H₅ | CH₃ | CHF₂ | H |
| B-119 | CH₂—C₆H₅ | CH₃ | CHF₂ | H |
| B-120 | CH₂—C₆H₄-4-F | CH₃ | CHF₂ | H |
| B-121 | CH₂—C₆H₄-4-CH₃ | CH₃ | CHF₂ | H |
| B-122 | CH₂—C₆H₄-3-CH₃ | CH₃ | CHF₂ | H |
| B-123 | CH₂—C₆H₄-2-CH₃ | CH₃ | CHF₂ | H |
| B-124 | CH(CH₃)—C₆H₅ | CH₃ | CHF₂ | H |
| B-125 | CH(CH₃)—C₆H₄-4-F | CH₃ | CHF₂ | H |
| B-126 | CH(CH₃)—C₆H₄-4-CH₃ | CH₃ | CHF₂ | H |
| B-127 | CH(CH₃)—C₆H₄-3-CH₃ | CH₃ | CHF₂ | H |
| B-128 | CH(CH₃)—C₆H₄-2-CH₃ | CH₃ | CHF₂ | H |
| B-129 | 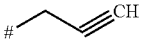 | CH₃ | CHF₂ | H |
| B-130 | 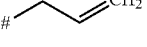 | CH₃ | CHF₂ | H |
| B-131 | 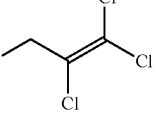 | CH₃ | CHF₂ | H |
| B-132 | 2-py | CH₃ | CHF₂ | H |
| B-133 | 3-Py | CH₃ | CHF₂ | H |
| B-134 | 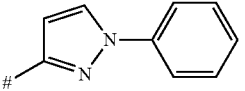 | CH₃ | CHF₂ | H |
| B-135 | 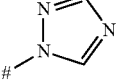 | CH₃ | CHF₂ | H |
| B-136 | 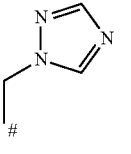 | CH₃ | CHF₂ | H |
| B-137 | 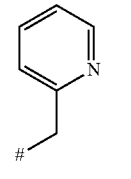 | CH₃ | CHF₂ | H |
| B-138 | 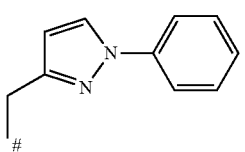 | CH₃ | CHF₂ | H |
| B-139 | COCH₃ | CH₃ | OCH₃ | H |
| B-140 | COCH₂CH₃ | CH₃ | OCH₃ | H |
| B-141 | COCH₂CH₂CH₃ | CH₃ | OCH₃ | H |
| B-142 | CO(CH₂)₃CH₃ | CH₃ | OCH₃ | H |
| B-143 | CO(CH₂)₄CH₃ | CH₃ | OCH₃ | H |
| B-144 | CO(CH₂)₅CH₃ | CH₃ | OCH₃ | H |
| B-145 | CO(CH₂)₆CH₃ | CH₃ | OCH₃ | H |
| B-146 | COCCl₃ | CH₃ | OCH₃ | H |
| B-147 | COCH₂Cl | CH₃ | OCH₃ | H |
| B-148 | COCH₂—N(CH₃)₂ | CH₃ | OCH₃ | H |
| B-149 | COPh | CH₃ | OCH₃ | H |
| B-150 | COCH₂Ph | CH₃ | OCH₃ | H |
| B-151 | COCH₂Ph-4-F | CH₃ | OCH₃ | H |
| B-152 | COCH₂Ph-4-CH₃ | CH₃ | OCH₃ | H |
| B-153 | COCH₂Ph-3-CH₃ | CH₃ | OCH₃ | H |
| B-154 | COCH₂Ph-2-CH₃ | CH₃ | OCH₃ | H |
| B-155 | COCH(CH₃)Ph | CH₃ | OCH₃ | H |
| B-156 | COCH(CH₃)-4-F | CH₃ | OCH₃ | H |
| B-157 | COCH(CH₃)-4-CH₃ | CH₃ | OCH₃ | H |
| B-158 | COCH(CH₃)-3-CH₃ | CH₃ | OCH₃ | H |
| B-159 | COCH(CH₃)-3-CH₃ | CH₃ | OCH₃ | H |
| B-160 | CF₃ | CH₃ | OCH₃ | H |
| B-161 | CHF₂ | CH₃ | OCH₃ | H |
| B-162 | CH₂CH₂OCH₃ | CH₃ | OCH₃ | H |
| B-163 | CH₂cPr | CH₃ | OCH₃ | H |
| B-164 | C₆H₅ | CH₃ | OCH₃ | H |
| B-165 | CH₂—C₆H₅ | CH₃ | OCH₃ | H |
| B-166 | CH₂—C₆H₄-4-F | CH₃ | OCH₃ | H |
| B-167 | CH₂—C₆H₄-4-CH₃ | CH₃ | OCH₃ | H |
| B-168 | CH₂—C₆H₄-3-CH₃ | CH₃ | OCH₃ | H |
| B-169 | CH₂—C₆H₄-2-CH₃ | CH₃ | OCH₃ | H |
| B-170 | CH(CH₃)—C₆H₅ | CH₃ | OCH₃ | H |
| B-171 | CH(CH₃)—C₆H₄-4-F | CH₃ | OCH₃ | H |
| B-172 | CH(CH₃)—C₆H₄-4-CH₃ | CH₃ | OCH₃ | H |
| B-173 | CH(CH₃)—C₆H₄-3-CH₃ | CH₃ | OCH₃ | H |
| B-174 | CH(CH₃)—C₆H₄-2-CH₃ | CH₃ | OCH₃ | H |
| B-175 |  | CH₃ | OCH₃ | H |
| B-176 | 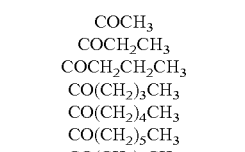 | CH₃ | OCH₃ | H |

TABLE B-continued

| No. | Q³ | R¹ | R² | R⁴ |
|---|---|---|---|---|
| B-177 | (2,3-dichloro-3-chloroallyl: CH₂-C(Cl)=CCl₂) | CH₃ | OCH₃ | H |
| B-178 | 2-py | CH₃ | OCH₃ | H |
| B-179 | 3-py | CH₃ | OCH₃ | H |
| B-180 | 1-phenyl-1H-pyrazol-3-ylmethyl | CH₃ | OCH₃ | H |
| B-181 | 1H-1,2,4-triazol-1-ylmethyl | CH₃ | OCH₃ | H |
| B-182 | 1-ethyl-1H-1,2,4-triazol-... | CH₃ | OCH₃ | H |
| B-183 | (pyridin-2-yl)methyl | CH₃ | OCH₃ | H |
| B-184 | 3-ethyl-1-phenyl-1H-pyrazol-5-ylmethyl | CH₃ | OCH₃ | H |
| B-185 | COCH₃ | OCH₃ | CHF₂ | H |
| B-186 | COCH₂CH₃ | OCH₃ | CHF₂ | H |
| B-187 | COCH₂CH₂CH₃ | OCH₃ | CHF₂ | H |
| B-188 | CO(CH₂)₃CH₃ | OCH₃ | CHF₂ | H |
| B-189 | CO(CH₂)₄CH₃ | OCH₃ | CHF₂ | H |
| B-190 | CO(CH₂)₅CH₃ | OCH₃ | CHF₂ | H |
| B-191 | CO(CH₂)₆CH₃ | OCH₃ | CHF₂ | H |
| B-192 | COCCl₃ | OCH₃ | CHF₂ | H |
| B-193 | COCH₂Cl | OCH₃ | CHF₂ | H |
| B-194 | COCH₂—N(CH₃)₂ | OCH₃ | CHF₂ | H |
| B-195 | COPh | OCH₃ | CHF₂ | H |
| B-196 | COCH₂Ph | OCH₃ | CHF₂ | H |
| B-197 | COCH₂Ph-4-F | OCH₃ | CHF₂ | H |
| B-198 | COCH₂Ph-4-CH₃ | OCH₃ | CHF₂ | H |
| B-199 | COCH₂Ph-3-CH₃ | OCH₃ | CHF₂ | H |
| B-200 | COCH₂Ph-2-CH₃ | OCH₃ | CHF₂ | H |
| B-201 | COCH(CH₃)Ph | OCH₃ | CHF₂ | H |
| B-202 | COCH(CH₃)-4-F | OCH₃ | CHF₂ | H |
| B-203 | COCH(CH₃)-4-CH₃ | OCH₃ | CHF₂ | H |
| B-204 | COCH(CH₃)-3-CH₃ | OCH₃ | CHF₂ | H |
| B-205 | COCH(CH₃)-3-CH₃ | OCH₃ | CHF₂ | H |
| B-206 | CF₃ | OCH₃ | CHF₂ | H |
| B-207 | CHF₂ | OCH₃ | CHF₂ | H |
| B-208 | CH₂CH₂OCH₃ | OCH₃ | CHF₂ | H |
| B-209 | CH₂cPr | OCH₃ | CHF₂ | H |
| B-210 | C₆H₅ | OCH₃ | CHF₂ | H |
| B-211 | CH₂—C₆H₅ | OCH₃ | CHF₂ | H |
| B-212 | CH₂—C₆H₄-4-F | OCH₃ | CHF₂ | H |
| B-213 | CH₂—C₆H₄-4-CH₃ | OCH₃ | CHF₂ | H |
| B-214 | CH₂—C₆H₄-3-CH₃ | OCH₃ | CHF₂ | H |
| B-215 | CH₂—C₆H₄-2-CH₃ | OCH₃ | CHF₂ | H |
| B-216 | CH(CH₃)—C₆H₅ | OCH₃ | CHF₂ | H |
| B-217 | CH(CH₃)—C₆H₄-4-F | OCH₃ | CHF₂ | H |
| B-218 | CH(CH₃)—C₆H₄-4-CH₃ | OCH₃ | CHF₂ | H |
| B-219 | CH(CH₃)—C₆H₄-3-CH₃ | OCH₃ | CHF₂ | H |
| B-220 | CH(CH₃)—C₆H₄-2-CH₃ | OCH₃ | CHF₂ | H |
| B-221 | propargyl (CH₂—C≡CH) | OCH₃ | CHF₂ | H |
| B-222 | allyl (CH₂—CH=CH₂) | OCH₃ | CHF₂ | H |
| B-223 | (2,3-dichloro-3-chloroallyl: CH₂-C(Cl)=CCl₂) | OCH₃ | CHF₂ | H |
| B-224 | 2-py | OCH₃ | CHF₂ | H |
| B-225 | 3-py | OCH₃ | CHF₂ | H |
| B-226 | 1-phenyl-1H-pyrazol-3-ylmethyl | OCH₃ | CHF₂ | H |
| B-227 | 1H-1,2,4-triazol-1-ylmethyl | OCH₃ | CHF₂ | H |
| B-228 | 1-ethyl-1H-1,2,4-triazol-... | OCH₃ | CHF₂ | H |
| B-229 | (pyridin-2-yl)methyl | OCH₃ | CHF₂ | H |
| B-230 | 3-ethyl-1-phenyl-1H-pyrazol-5-ylmethyl | OCH₃ | CHF₂ | H |

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, *Zygomycetes*, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grapejuice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as b-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink®

(corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard, Protecta, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera© rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchil*) and rice; *Cladosporium* spp. on tomatoes (e. g. *C. fulvum*. leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes* black dot), beans (e. g. *C. lindemuthianum*) and soybeans (e. g. *C. truncatum* or *C. gloeosporioides*); *Corticium* spp., e. g. *C. sasakii*(sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri* teleomorph: *Neonectria liriodendri* Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis* tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysihe* spp. (powdery mildew) on sugar beets (*E. betae*), vegetables (e. g. *E. pisi*), such as cucurbits (e. g. *E. cichoracearum*), cabbages, rape (e. g. *E. crucferarum*); *Eutypa lata* (*Eutypa* canker or dieback, anamorph: *Cytosporna lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasillense* each causing sudden death syndrome on soybeans, and *F. verticillloides* on corn; *Gaeumannomyces graminis* (take-all) on cereals (e. g. wheat or barley) and corn; *Gibberella* spp. on cereals (e. g. *G. zeae*) and rice (e. g. *G. fujkuro* Bakanae disease); *Glomerella clingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Coch-*

*liobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructcola* and *M. fructgena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici; Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. trachephila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brasscae* (club root) on cabbage, rape, radish and other plants; Plasmopara spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyes pot, teleomorph: *Tapesia yallundae*) on cereals, e. g. wheat or barley; *Pseudoperonospora* (downy mildew) on various plants, e. g. *P. cubensison* cucurbits or *P. humili* on hop; *Pseudopezicua tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora*(anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ulitimum* or *P. aphanidermatum*); *Ramularia* spp., e. g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. relliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occuita* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis* corn smut) and sugar cane; *Venturia* spp. (scab) on apples (e. g. *V. inaequalls*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicllum* spp., *Trichoderma* spp., *Alternara* spp., *Paecilomyces* spp. and *Zygomycetes* such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid di-methyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pesticidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

Biopesticides have been defined as a form of pesticides based on microorganisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multi-cellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and LS), form part of such kit, it must be taken care that choice and amounts of the components (e.g. chemical pesticides) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration Inhibitors

Inhibitors of complex III at Q site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)ox-ylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chloro-phenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-1-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38);

inhibitors of complex III at Q$_i$ site: cyazofamid (A.2.1), amisulbrom (A.2.2), [(6,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), 3-(difluoromethyl)-1-methyl-N-(1,1,3-trimethylindan-4-yl) pyrazole-4-carboxamide (A.3.22), 3-(trifluoromethyl)-1-methyl-N-(1,1,3-trimethylindan-4-yl)pyrazole-4-carboxamide (A.3.23), 1,3-dimethyl-N-(1,1,3-trimethylindan-4-yl)pyrazole-4-carboxamide (A.3.24), 3-(trifluoromethyl)-1,5-dimethyl-N-(1,1,3-trimethylindan-4-yl)pyrazole-4-carboxamide (A.3.25), 1,3,5-trimethyl-N-(1,1,3-trimethylindan-4-yl)pyrazole-4-carboxamide (A.3.26), 3-(difluoromethyl)-1,5-dimethyl-N-(1,1,3-trimethylindan-4-yl)pyrazole-4-carboxamide (A.3.27), 3-(difluoromethyl)-N-(7-fluoro-1,1,3-trimethyl-indan-4-yl)-1-methyl-pyrazole-4-carboxamide (A.3.28), N-[(5-chloro-2-isopropyl-phenyl)methyl]-N-cyclopropyl-5-fluoro-1,3-dimethyl-pyrazole-4-carboxamide (A.3.29), methyl (E)-2-[2-[(5-cyano-2-methyl-phenoxy)methyl]phenyl]-3-methoxy-prop-2-enoate (A.3.30), N-[(5-chloro-2-isopropyl-phenyl)methyl]-N-cyclopropyl-3-(difluoromethyl)-5-fluoro-1-methyl-pyrazole-4-carboxamide (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl) pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl] pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)

C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), ipfentrifluconazole, (B.1.37), mefentrifluconazole (B.1.38), 2-(chloromethyl)-2-methyl-5-(p-tolylmethyl)-1-(1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyri-dines and piperazines: fenarimol (B.1.49), pyrifenox (B.1.50), triforine (B.1.51), [3-(4-chloro-2-fluoro-phenyl)-5-(2,4-difluorophenyl)isoxazol-4-yl]-(3-pyridyl) methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);
Inhibitors of 3-keto reductase: fenhexamid (B.3.1);
Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D.1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N-eth-yl-2-[(3-ethynyl-8-methyl-6-quinolyl) oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acids: propamocarb (G.4.1);

inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclo-propyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoro-methyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl] acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5-yl]-2-prop-2-ynyloxy-acetamide (K.1.36), 3-[5-(4-chloro-phenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynylN-[6-[[(Z)-[(1-methyltetrazol-5-yl)-phenyl-methylene]amino]oxymethyl]-2-pyridyl]carbamate (K.1.43),2-[2-[(7,8-difluoro-2-methyl-3-quinolyl)oxy]-6-fluoro-phenyl]pro-pan-2-ol (K.1.44),2-[2-fluoro-6-[(8-fluoro-2-methyl-3-quinolyl)oxy]phen-yl]propan-2-ol (K.1.45), quinofumelin (K.1.47),9-fluoro-2,2-dimethyl-5-(3-quinolyl)-3H-1,4-benzoxazepine (K.1.49), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox(K.1.52), N'-(2,5-dimethyl-4-phenoxy-phenyl)-N-ethyl-N-methyl-formamidine (K.1.53);

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex B. solisalsi B. subtilis, B. subtilis* var. *amyloliquefaciens, Candida oleophila, C. saitoana, Clavibacter michiganensis*(bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei Paenibacillus polymyxa, Pantoea vagans, Penicillium bilaiae, Phlebiopsis ggantea, Pseudomonas* sp., *Pseudomonas chlorophis, Pseudozyma flocculosa, Pichia anomala, Pythium oigandrum, Sphaerodes mycoparasitica, Streptomyces griseoviridis, S. lydicus, S. violaceusniger Talaromyces flavus, Trichoderma asperelloides, T. aspereum, T. atroviride, T. fertile, T. gamsil T. harmatum, T. harzianum, T. polysporum, T. stromaticum, T. vrens, T. viride, Typhula phacorrhiza, Ulocladium oudemansi, Verticilium dahlia*, zucchini yellow mosaic virus (avirulent strain);

L2) Biochemical pesticides with fungicidal, bactericidal, viricidal and/or plant defense activator activity: harpin protein, *Reynoutria sachallnensis* extract;

L3) Microbial pesticides with insecticidal, acaricidal, molluscidal and/or nematicidal activity: *Agrobacterium radiobacter Bacillus cereus, B. firmus, B. thuringiensis, B. thuringiensis* ssp. *aizawai B. t.* ssp. *israelensis, B. t.* ssp. *gaeriae, B. t.* ssp. *kurstaki B. t.* ssp. *tenebrionis, Beauveria bassiana, B. brongniartil Burkholderia* spp., *Chromobacterium subtsugae, Cydia pomonella* granulovirus (CpGV), *Cryptophlebia leucotreta* granulovirus (CrleGV), *Flavobacterium* spp., *Hellcoverpa armigera* nucleopolyhedrovirus (HearNPV), *Helicoverpa zea* nucleopolyhedrovirus (HzNPV), *Hellcoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi; Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. fetiae, S. kraussei Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl-jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. braslense, A. lipoferum, A. irakense, A. halopraeferens, Bradyrhizobium* spp., *B. ekanil B. japonicum, B. liaoningense, B. lupini, Deftia acidovorans, Glomus intraradices, Mesorhzobium* spp., *Rhizobium leguminosarum* bv. *phaseoli R. l.* bv. *trifoli R. l.* bv. *viciae, R. tropic, Sinorhizobium melioti,*

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides from Classes N.1 to N.15

N.1 Lipid biosynthesis inhibitors: alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-chloro-4-cyclo, propyl-2'-fluoro[1,1'-biphenyl]-3-yl)-5-hydroxy-2,2,6,6-tetramethyl-2H-pyran-3(6H)-one (CAS 1312337-72-6); 4-(2',4'-dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(acetyloxy)-4-(2',4'-dichloro-4-cyclopropyl-[1,1'-biphenyl]-3-yl)-3,6-dihydro-2,2,6,6-tetramethyl-2H-pyran-3-one; 5-(acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-dichloro-4-ethyl,[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

N.2 ALS inhibitors: amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuronmethyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl, tritosulfuron, imazamethabenz, imazamethabenz-methyl, imazamox, imazapic, imazapyr, imazaquin, imazethapyr; cloransulam, cloransulam-methyl, diclosulam, flumetsulam, florasulam, metosulam, penoxsulam, pyrimisulfan and pyroxsulam; bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methyl¬ethyl ester (CAS 420138-41-6), 4-[[[2-[(4,6-dimethoxy-2-pyrimidinyl)oxy]phenyl]¬methyl]amino]-benzoic acid propyl ester (CAS 420138-40-5), N-(4-bromo-phenyl)-2-[(4,6-dimethoxy-2-pyrimidinyl)oxy] benzenemethanamine (CAS 420138-01-8); flucarbazone, flucarbazone-sodium, propoxycarbazone, propoxycarbazone-sodium, thiencarbazone, thiencarbazone-methyl; triafamone;

N.3 Photosynthesis inhibitors: amicarbazone; chlorotriazine; ametryn, atrazine, chloridazone, cyanazine, desmetryn, dimethametryn, hexazinone, metribuzin, prometon, prometryn, propazine, simazine, simetryn, terbumeton, terbuthylazin, terbutryn, trietazin; chlorbromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron, thiadiazuron, desmedipham, karbutilat, phenmedipham, phenmediphamethyl, bromofenoxim, bromoxynil and its salts and esters, ioxynil and its salts and esters, bromacil, lenacil, terbacil, bentazon, bentazon-sodium, pyridate, pyridafol, pentanochlor, propanil; diquat, diquat-dibromide, paraquat, paraquat-dichloride, paraquat-dimetilsulfate;

N.4 protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlormethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6), N-ethyl-3-(2,6-dichloro-4-tri-fluoro-methylphenoxy)-5-methyl-1H-pyrazole-1-carboxamide (CAS 452098-92-9), N tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethyl, phenoxy)-5-methyl-1H-pyrazole-1-carboxamide (CAS 452099-05-7), N tetrahydro¬furfuryl-3-(2-chloro-6-fluoro-4-trifluoro¬methylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoro, methyl-3-(2,2,7-tri-fluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

N.5 Bleacher herbicides: beflubutamid, diflufenican, fluridone, flurochloridone, flurtamone, norflurazon, picolinafen, 4-(3-trifluoromethyl¬phenoxy)-2-(4-trifluoromethylphenyl)¬pyrimidine (CAS 180608-33-7);

benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone; aclonifen, amitrole, flumeturon;

N.6 EPSP synthase inhibitors: glyphosate, glyphosate-isopropylammonium, glyposate-potassium, glyphosate-trimesium (sulfosate);

N.7 Glutamine synthase inhibitors: bilanaphos (bialaphos), bilanaphos-sodium, glufosinate, glufosinate-P, glufosinate-ammonium;

N.8 DHP synthase inhibitors: asulam;

N.9 Mitosis inhibitors: benfluralin, butralin, dinitramine, ethalfluralin, fluchloralin, oryzalin, pendimethalin, prodiamine, trifluralin; amiprophos, amiprophos-methyl, butamiphos; chlorthal, chlorthal-dimethyl, dithiopyr, thiazopyr, propyzamide, tebutam; carbetamide, chlorpropham, flamprop, flamprop-isopropyl, flamprop-methyl, flamprop-M-isopropyl, flamprop-M-methyl, propham;

N.10 VLCFA inhibitors: acetochlor, alachlor, butachlor, dimethachlor, dimethenamid, dimethenamid-P, metazachlor, metolachlor, metolachlor-S, pethoxamid, pretilachlor, propachlor, propisochlor, thenylchlor, flufenacet, mefenacet, diphenamid, naproanilide, napropamide, napropamide-M, fentrazamide, anilofos, cafenstrole, fenoxasulfone, ipfencarbazone, piperophos, pyroxasulfone, isoxazoline compounds of the formulae II.1, II.2, II.3, II.4, II.5, II.6, II.7, II.8 and II.9

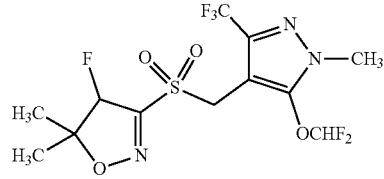

II.1

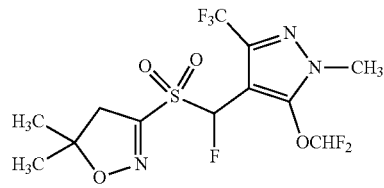

II.2

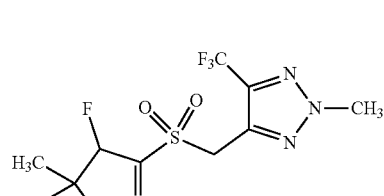

II.3

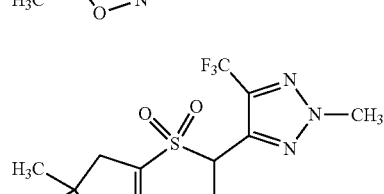

II.4

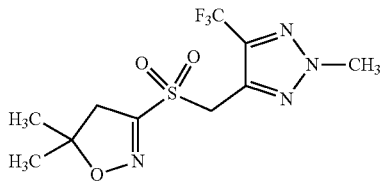

II.5

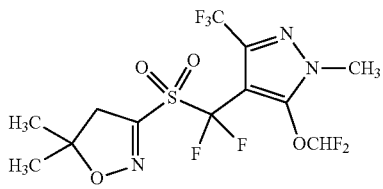

II.6

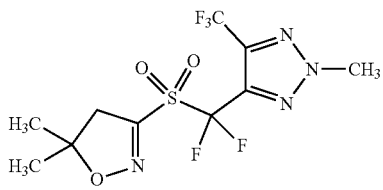

II.7

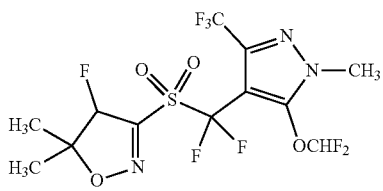

II.8

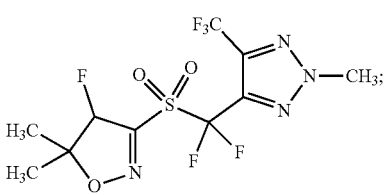

II.9

N.11 Cellulose biosynthesis inhibitors: chlorthiamid, dichlobenil, flupoxam, indaziflam, isoxaben, triaziflam, 1-cyclohexyl-5-pentafluorphenyloxy-14-[1,2,4,6]thiatriazin-3-ylamine (CAS 175899-01-1);

N.12 Decoupler herbicides: dinoseb, dinoterb, DNOC and its salts;

N.13 Auxinic herbicides: 2,4-D and its salts and esters, clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxy-phenyl)-5-fluoropyridine-2-carboxylic acid, benzyl 4-amino-3-chloro-6-(4-chloro-2-fluoro-3-methoxyphenyl)-5-fluoropyridine-2-carboxylate (CAS 1390661-72-9);

N.14 Auxin transport inhibitors: diflufenzopyr, diflufenzopyr-sodium, naptalam and naptalam-sodium;

N.15 Other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, tridiphane;

O) Insecticides from Classes 0.1 to 0.29

O.1 Acetylcholine esterase (AChE) inhibitors: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

O.2 GABA-gated chloride channel antagonists: endosulfan, chlordane; ethiprole, fipronil, flufiprole, pyrafluprole, pyriprole;

O.3 Sodium channel modulators: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; DDT, methoxychlor;

O.4 Nicotinic acetylcholine receptor agonists (nAChR): acetamiprid, clothianidin, cycloxaprid, dinotefuran, imidacloprid, nitenpyram, thiacloprid, thiamethoxam; (2E)-1-[(6-chloropyridin-3-yl)methyl]-N'-nitro-2-pentylidenehydrazinecarboximidamide; 1-[(6-chloropyridin-3-yl)methyl]-7-methyl-8-nitro-5-propoxy-1,2,3,5,6,7-hexahydroimidazo[1,2-a]pyridine; nicotine;

O.5 Nicotinic acetylcholine receptor allosteric activators: spinosad, spinetoram;

O.6 Chloride channel activators: abamectin, emamectin benzoate, ivermectin, lepimectin, milbemectin;

O.7 Juvenile hormone mimics: hydroprene, kinoprene, methoprene; fenoxycarb, pyriproxyfen;

O.8 miscellaneous non-specific (multi-site) inhibitors: methyl bromide and other alkyl halides; chloropicrin, sulfuryl fluoride, borax, tartar emetic;

O.9 Selective homopteran feeding blockers: pymetrozine, flonicamid;

O.10 Mite growth inhibitors: clofentezine, hexythiazox, diflovidazin; etoxazole;

O.11 Microbial disruptors of insect midgut membranes: *Bacillus thuringiensis, Bacillus sphaericus* and the insecticdal proteins they produce: *Bacillus thuringiensis* subsp. *israelensis, Bacillus sphaericus, Bacillus thuringiensis* subsp. *aizawai, Bacillus thuringiensis* subsp. *kurstaki, Bacillus thuringiensis* subsp. *tenebrionis*, the Bt crop proteins: Cry1Ab, Cry1Ac, Cry1Fa, Cry2Ab, mCry3A, Cry3Ab, Cry3Bb, Cry34/35Ab1;

O.12 Inhibitors of mitochondrial ATP synthase: diafenthiuron; azocyclotin, cyhexatin, fenbutatin oxide, propargite, tetradifon;

O.13 Uncouplers of oxidative phosphorylation via disruption of the proton gradient: chlorfenapyr, DNOC, sulfluramid;

O.14 Nicotinic acetylcholine receptor (nAChR) channel blockers: bensultap, cartap hydrochloride, thiocyclam, thiosultap sodium;

O.15 Inhibitors of the chitin biosynthesis type 0: bistrifluron, chlorfluazuron, diflubenzuron, flucycloxuron, flufenoxuron, hexaflumuron, lufenuron, novaluron, noviflumuron, teflubenzuron, triflumuron;

O.16 Inhibitors of the chitin biosynthesis type 1: buprofezin;

O.17 Moulting disruptors: cyromazine;

O.18 Ecdyson receptor agonists: methoxyfenozide, tebufenozide, halofenozide, fufenozide, chromafenozide;

O.19 Octopamin receptor agonists: amitraz;

O.20 Mitochondrial complex III electron transport inhibitors: hydramethylnon, acequinocyl, fluacrypyrim;

O.21 Mitochondrial complex I electron transport inhibitors: fenazaquin, fenpyroximate, pyrimidifen, pyridaben, tebufenpyrad, tolfenpyrad; rotenone;

O.22 Voltage-dependent sodium channel blockers: indoxacarb, metaflumizone, 2-[2-(4-cyano-phenyl)-1-[3-(trifluoromethyl)phenyl]ethylidene]-N-[4-(difluoromethoxy)phenyl]-hydrazinecarboxamide, N-(3-chloro-2-methylphenyl)-2-[(4-chlorophenyl)-4-[methyl(methylsulfonyl)-amino]phenyl]methylene]-hydrazinecarboxamide;

O.23 Inhibitors of the of acetyl CoA carboxylase: spirodiclofen, spiromesifen, spirotetramat;

O.24 Mitochondrial complex IV electron transport inhibitors: aluminium phosphide, calcium phosphide, phosphine, zinc phosphide, cyanide;

O.25 Mitochondrial complex II electron transport inhibitors: cyenopyrafen, cyflumetofen;

O.26 Ryanodine receptor-modulators: flubendiamide, chlorantraniliprole, cyantraniliprole, cyclaniliprole, tetraniliprole; (R)-3-chloro-N1-{2-methyl-4-[1,2,2,2-tetrafluoro-1-(trifluoromethyl)-ethyl]phenyl}-N2-(1-methyl-2-methylsulfonylethyl)phthalamide, (S)-3-chloro-N1-{2-methyl-4-[1,2,2,2-tetrafluoro-1-(trifluoromethyl)ethyl]phenyl}-N2-(1-methyl-2-methylsulfonylethyl)-phthalamide, methyl-2-[3,5-dibromo-2-({[3-bromo-1-(3-chloropyridin-2-yl)-1H-pyrazol-5-yl]-carbonyl}amino)benzoyl]-1,2-dimethylhydrazinecarboxylate; N-[4,6-dichloro-2-[(diethyl-lambda-4-sulfanylidene)carbamoyl]-phenyl]-2-(3-chloro-2-pyridyl)-5-(trifluoromethyl) pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3- carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; N-[2-(5-amino-1,3,4-thiadiazol-2-yl)-4-chloro-6-methylphenyl]-3-bromo-1-(3-chloro-2-pyridinyl)-1H-pyrazole-5-carboxamide; 3-chloro-1-(3-chloro-2-pyridinyl)-N-[2,4-dichloro-6-[[(1-cyano-1-methylethyl)amino]carbonyl]phenyl]-1H-pyrazole-5-carboxamide; 3-bromo-N-[2,4-dichloro-6-(methylcarbamoyl)phenyl]-1-(3,5-dichloro-2-pyridyl)-1H-pyrazole-5-carboxamide; N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; cyhalodiamide;

O.27. insecticidal active compounds of unknown or uncertain mode of action: afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 1-[2-fluoro-4-methyl-5-[(2,2,2-trifluoroethyl)sulfinyl]phenyl]-3-(trifluoromethyl)-1H-1,2,4-triazole-5-amine, *Bacillus firmus*; (E/Z)—N-[1-[(6-chloro-3-pyridyl)methyl]-2-pyridylidene]-2,2,2-trifluoro-acetamide; (E/Z)—N-[1-[(6-chloro-5-fluoro-3-pyridyl)methyl]-2-pyridylidene]-2,2,2-trifluoro-acetamide; (E/Z)-2,2,2-trifluoro-N-[1-[(6-fluoro-3-pyridyl)methyl]-2-pyridylidene]acetamide; (E/Z)—N-[1-[(6-bromo-3-pyridyl)methyl]-2-pyridylidene]-2,2,2-trifluoro-acetamide; (E/Z)—N-[1-[1-(6-chloro-3-pyridyl)ethyl]-2-pyridylidene]-2,2,2-trifluoro-acetamide; (E/Z)—N-[1-[(6-chloro-3-pyridyl)methyl]-2-pyridylidene]-2,2-difluoro-acetamide; (E/Z)-2-chloro-N-[1-[(6-chloro-3-pyridyl)methyl]-2-pyridylidene]-2,2-difluoro-acetamide; (E/Z)—N-[1-[(2-chloropyrimidin-5-yl)methyl]-2-pyridylidene]-2,2,2-trifluoro-acetamide; (E/Z)—N-[1-[(6-chloro-3-pyridyl)methyl]-2-pyridylidene]-2,2,3,3,3-pentafluoro-propanamide.); N-[1-[(6-chloro-3-pyridyl)methyl]-2-pyridylidene]-2,2,2-trifluoro-thioacetamide; N-[1-[(6-chloro-3-pyridyl)methyl]-2-pyridylidene]-2,2,2-trifluoro-N'-isopropyl-acetamidine; fluazaindolizine; 4-[5-(3,5-dichlorophenyl)-5-(trifluoromethyl)-4H-isoxazol-3-yl]-2-methyl-N-(1-oxothietan-3-yl)benzamide; fluxametamide; 5-[3-[2,6-dichloro-4-(3,3-dichloroallyloxy)phenoxy]propoxy]-1H-pyrazole; 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; N-[3-[[[2-bromo-4-[1,2,2,2-tetra-fluoro-1-(trifluoromethyl)ethyl]-6-(trifluoromethyl)phenyl]amino]carbonyl]-2-fluorophenyl]-4-fluoro-N-methyl-benzamide; 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; 4-cyano-N-[2-cyano-5-[[2,6-dichloro-4-[1,2,2,3,3,3-hexafluoro-1-(trifluoromethyl)propyl]phenyl]carbamoyl]-2-methyl-benzamide; 4-cyano-N-[2-cyano-5-[[2,6-dichloro-4-[1,2,2,2-tetrafluoro-1-(trifluoromethyl)ethyl]phenyl]carbamoyl]-2-methyl-benzamide; N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; 2-(1,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine; 2-[6-[2-(3-pyridinyl)-5-thiazolyl]-2-pyridinyl]-pyrimidine; N-methylsulfonyl-6-[2-(3-pyridyl)thiazol-5-yl]pyridine-2-carboxamide; N-methylsulfonyl-6-[2-(3-pyridyl)thiazol-5-yl]pyridine-2-carboxamide; N-ethyl-N-[4-methyl-2-(3-pyridyl)thiazol-5-yl]-3-methylthio-propanamide; N-methyl-N-[4-methyl-2-(3-pyridyl)thiazol-5-yl]-3-methylthio-propanamide; N,2-dimethyl-N-[4-methyl-2-(3-pyridyl)thiazol-5-yl]-3-methylthio-propanamide; N-ethyl-2-methyl-N-[4-methyl-2-(3-pyridyl)thiazol-5-yl]-3-methylthio-propanamide; N-[4-chloro-2-(3-pyridyl)thiazol-5-yl]-N-ethyl-2-methyl-3-methylthio-propanamide; N-[4-chloro-2-(3-pyridyl)thiazol-5-yl]-N,2-dimethyl-3-methylthio-propanamide; N-[4-chloro-2-(3-pyridyl)thiazol-5-yl]-N-methyl-3-methyl-thio-propanamide; N-[4-chloro-2-(3-pyridyl)thiazol-5-yl]-N-ethyl-3-methylthio-propanamide; 1-[(6-chloro-3-pyridinyl)methyl]-1,2,3,5,6,7-hexahydro-5-methoxy-7-methyl-8-nitro-imidazo[1,2-a]pyridine; 1-[(6-chloropyridin-3-yl)methyl]-7-methyl-8-nitro-1,2,3,5,6,7-hexahydroimidazo[1,2-a]pyridin-5-ol; 1-isopropyl-N,5-dimethyl-N-pyridazin-4-yl-pyrazole-4-carboxamide; 1-(1,2-dimethylpropyl)-N-ethyl-5-methyl-N-pyridazin-4-yl-pyrazole-4-carboxamide; N,5-di-methyl-N-pyridazin-4-yl-1-(2,2,2-trifluoro-1-methyl-ethyl)pyrazole-4-carboxamide; 1-[1-(1-cyanocyclopropyl)ethyl]-N-ethyl-5-methyl-N-pyridazin-4-yl-pyrazole-4-carboxamide; N-ethyl-1-(2-fluoro-1-methyl-propyl)-5-methyl-N-pyridazin-4-yl-pyrazole-4-carboxamide; 1-(1,2-di-methylpropyl)-N,5-dimethyl-N-pyridazin-4-yl-pyrazole-4-carboxamide; 1-[1-(1-cyanocyclopropyl)ethyl]-N,5-dimethyl-N-pyridazin-4-yl-pyrazole-4-carboxamide; N-methyl-1-(2-fluoro-1-methyl-propyl)-5-methyl-N-pyridazin-4-yl-pyrazole-4-carboxamide; 1-(4,4-difluorocyclohexyl)-N-ethyl-5-methyl-N-pyridazin-4-yl-pyrazole-4-carboxamide; 1-(4,4-difluorocyclohexyl)-N,5-dimethyl-N-pyridazin-4-yl-pyrazole-4-carboxamide, N-(1-methylethyl)-2-(3-pyridinyl)-2H-indazole-4-carboxamide; N-cyclopropyl-2-(3-pyridinyl)-2H-indazole-4-carboxamide; N-cyclohexyl-2-(3-pyridinyl)-2H-indazole-4-carboxamide; 2-(3-pyridinyl)-N-(2,2,2-trifluoroethyl)-2H-indazole-4-carboxamide; 2-(3-pyridinyl)-N-[(tetrahydro-2-furanyl)methyl]-2H-indazole-5-carboxamide; methyl 2-[[2-(3-pyridinyl)-2H-indazol-5-yl]carbonyl]hydrazinecarboxylate; N-[(2,2-difluorocyclopropyl)methyl]-2-(3-pyridinyl)-2H-indazole-5-carboxamide; N-(2,2-difluoropropyl)-2-(3-pyridinyl)-2H-indazole-5-carboxamide; 2-(3-pyridinyl)-N-(2-pyrimidinyl-methyl)-2H-indazole-5-carboxamide; N-[(5-methyl-2-pyrazinyl)methyl]-2-(3-pyridinyl)-2H-indazole-5-carboxamide, N-[3-chloro-1-(3-pyridyl)pyrazol-4-yl]-N-ethyl-3-(3,3,3-trifluoro-propylsulfanyl)propanamide; N-[3-chloro-1-(3-pyridyl)pyrazol-4-yl]-N-ethyl-3-(3,3,3-trifluoro-propylsulfinyl)propanamide; N-[3-chloro-1-(3-pyridyl)pyrazol-4-yl]-3-[(2,2-difluoro-cyclopropyl)methylsulfanyl]-N-ethyl-propanamide; N-[3-chloro-1-(3-pyridyl)pyrazol-4-yl]-3-[(2,2-difluoro-cyclopropyl)methylsulfinyl]-N-ethyl-propanamide; sarolaner, lotilaner.

The active substances referred to as component 2, their preparation and their activity e. g. against harmful fungi is known; these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1028125; EP-A1035122; EP-A1201648; EP-A1122 244, JP 2002316902; DE19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide II is applied as last treatment.

According to the invention, the solid material (dry matter) of the biopesticides (with the exception of oils such as Neem oil) are considered as active components (e. g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as Steinemema feltiae.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to further embodiments of the mixtures and compositions, the weight ratio of the component 1) and the component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to further embodiments of the mixtures and compositions, the weight ratio of the component 1) and the component 2) usually is in the range of from 10:1 to 1:20,000, often in the range of from 1:1 to 1:10,000, regularly in the range of from 1:5 to 1:5,000, preferably in the range of from 1:10 to 1:5,000, more preferably in the range of from 1:30 to 1:2,000, even more preferably in the range of from 1:100 to 1:2,000 to and in particular in the range of from 1:100 to 1:1,000.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

When mixtures comprising microbial pesticides are employed in crop protection, the application rates preferably range from about $1 \times 10^6$ to $5 \times 10^{16}$ (or more) CFU/ha, preferably from about $1 \times 10^8$ to about $1 \times 10^{13}$ CFU/ha, and even more preferably from about $1 \times 10^9$ to $5 \times 10^{15}$ CFU/ha and particularly preferred even more preferably from $1 \times 10^{12}$ to $5 \times 10^{14}$ CFU/ha. In the case of (entomopathogenic) nematodes as microbial pesticides (e. g. *Steinernema feltiae*), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e. g. in the form of eggs, juvenile or any other live stages, preferably in an infetive juvenile stage) per ha.

When mixtures comprising microbial pesticides are employed in seed treatment, the application rates with respect to plant propagation material preferably range from about $1 \times 10^6$ to $1 \times 10^{12}$ (or more) CFU/seed. Preferably, the concentration is about $1 \times 10^6$ to about $1 \times 10^9$ CFU/seed. In the case of the microbial pesticides II, the application rates with respect to plant propagation material also preferably range from about $1 \times 10^7$ to $1 \times 10^{14}$ (or more) CFU per 100 kg of seed, preferably from $1 \times 10^9$ to about $1 \times 10^{12}$ CFU per 100 kg of seed.

Preference is also given to mixtures comprising as component 2) at least one active substance selected from inhibitors of complex III at $Q_o$ site in group A), more preferably selected from compounds (A.1.1), (A.1.4), (A.1.8), (A.1.9), (A.1.10), (A.1.12), (A.1.13), (A.1.14), (A.1.17), (A.1.21), (A.1.24), (A.1.25), (A.1.26), (A.1.27), (A.1.30), (A.1.31), (A.1.32), (A.1.34) and (A.1.35); particularly selected from (A.1.1), (A.1.4), (A.1.8), (A.1.9), (A.1.13), (A.1.14), (A.1.17), (A.1.24), (A.1.25), (A.1.26), (A.1.27), (A.1.30), (A.1.31), (A.1.32), (A.1.34) and (A.1.35).

Preference is also given to mixtures comprising as component 2) at least one active substance selected from inhibitors of complex III at $Q_i$ site in group A), more preferably selected from compounds (A.2.1), (A.2.3) and (A.2.4); particularly selected from (A.2.3) and (A.2.4).

Preference is also given to mixtures comprising as component 2) at least one active substance selected from inhibitors of complex II in group A), more preferably selected from compounds (A.3.2), (A.3.3), (A.3.4), (A.3.7), (A.3.9), (A.3.11), (A.3.12), (A.3.15), (A.3.16), (A.3.17), (A.3.18), (A.3.19), (A.3.20), (A.3.21), (A.3.22), (A.3.23), (A.3.24), (A.3.25), (A.3.27), (A.3.28), (A.3.29), (A.3.31), (A.3.32), (A.3.33), (A.3.34), (A.3.35), (A.3.36), (A.3.37), (A.3.38) and (A.3.39); particularly selected from (A.3.2), (A.3.3), (A.3.4), (A.3.7), (A.3.9), (A.3.12), (A.3.15), (A.3.17), (A.3.19), (A.3.22), (A.3.23), (A.3.24), (A.3.25), (A.3.27), (A.3.29), (A.3.31), (A.3.32), (A.3.33), (A.3.34), (A.3.35), (A.3.36), (A.3.37), (A.3.38) and (A.3.39).

Preference is also given to mixtures comprising as component 2) at least one active substance selected from other respiration inhibitors in group A), more preferably selected from compounds (A.4.5) and (A.4.11); in particular (A.4.11).

Preference is also given to mixtures comprising as component 2) at least one active substance selected from C14 demethylase inhibitors in group B), more preferably selected from compounds (B.1.4), (B.1.5), (B.1.8), (B.1.10), (B.1.11), (B.1.12), (B.1.13), (B.1.17), (B.1.18), (B.1.21), (B.1.22), (B.1.23), (B.1.25), (B.1.26), (B.1.29), (B.1.34), (B.1.37), (B.1.38), (B.1.43) and (B.1.46); particularly selected from (B.1.5), (B.1.8), (B.1.10), (B.1.17), (B.1.22), (B.1.23), (B.1.25), (B.1.33), (B.1.34), (B.1.37), (B.138), (B.1.43) and (B.1.46).

Preference is also given to mixtures comprising as component 2) at least one active substance selected from Delta14-reductase inhibitors in group B), more preferably selected from compounds (B.2.4), (B.2.5), (B.2.6) and (B.2.8); in particular (B.2.4).

Preference is also given to mixtures comprising as component 2) at least one active substance selected from phenylamides and acyl amino acid fungicides in group C), more preferably selected from compounds (C.1.1), (C.1.2), (C.1.4) and (C.1.5); particularly selected from (C.1.1) and (C.1.4).

Preference is also given to mixtures comprising as component 2) at least one active substance selected from other nucleic acid synthesis inhibitors in group C), more preferably selected from compounds (C.2.6), (C.2.7) and (C.2.8).

Preference is also given to mixtures comprising as component 2) at least one active substance selected from group D), more preferably selected from compounds (D.1.1), (D.1.2), (D.1.5), (D.2.4) and (D.2.6); particularly selected from (D.1.2), (D.1.5) and (D.2.6).

Preference is also given to mixtures comprising as component 2) at least one active substance selected from group E), more preferably selected from compounds (E.1.1), (E.1.3), (E.2.2) and (E.2.3); in particular (E.1.3).

Preference is also given to mixtures comprising as component 2) at least one active substance selected from group F), more preferably selected from compounds (F.1.2), (F.1.4) and (F.1.5).

Preference is also given to mixtures comprising as component 2) at least one active substance selected from group G), more preferably selected from compounds (G.3.1), (G.3.3), (G.3.6), (G.5.1), (G.5.2), (G.5.3), (G.5.4), (G.5.5), (G.5.6), G.5.7), (G.5.8), (G.5.9), (G.5.10) and (G.5.11); particularly selected from (G.3.1), (G.5.1), (G.5.2) and (G.5.3).

Preference is also given to mixtures comprising as component 2) at least one active substance selected from group H), more preferably selected from compounds (H.2.2), (H.2.3), (H.2.5), (H.2.7), (H.2.8), (H.3.2), (H.3.4), (H.3.5), (H.4.9) and (H.4.10); particularly selected from (H.2.2), (H.2.5), (H.3.2), (H.4.9) and (H.4.10).

Preference is also given to mixtures comprising as component 2) at least one active substance selected from group I), more preferably selected from compounds (I.2.2) and (I.2.5).

Preference is also given to mixtures comprising as component 2) at least one active substance selected from group J), more preferably selected from compounds (J.1.2), (J.1.5), (J.1.8), (J.1.11) and (J.1.12); in particular (J.1.5).

Preference is also given to mixtures comprising as component 2) at least one active substance selected from group K), more preferably selected from compounds (K.1.41), (K.1.42), (K.1.44), (K.1.45), (K.1.47) and (K.1.49); particularly selected from (K.1.41), (K.1.44), (K.1.45), (K.1.47) and (K.1.49).

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection are referred to in literature, registered and/or are commercially available: mixtures of *Aureobasidium pullulans* DSM 14940 and DSM 14941 isolated in 1989 in Konstanz, Germany (e. g. blastospores in Blossom-Protect® from bio-ferm GmbH, Austria), *Azospirillum brasilense* Sp245 originally isolated in wheat region of South Brazil (Passo Fundo) at least prior to 1980 (BR 11005; e. g. GELFIX® Gramineas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or Simbiose-Maíz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e. g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e. g. RhizoVital® 42 from AbiTEP GmbH, Germany), *B. amyloliquefaciens* ssp. *plantarum* MB1600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. amyloliquefaciens* spp. *plantarum* QST-713 isolated from peach orchard in 1995 in California, U.S.A. (NRRL B-21661; e. g. Serenade® MAX from Bayer Crop Science LP, USA), *B. amyloliquefaciens* spp. *plantarum* TJ1000 isolated in 1992 in South Dakoda, U.S.A. (also called 1BE; ATCC BAA-390; CA 2471555 A1; e. g. QuickRoots™ from TJ Technologies, Watertown, S. Dak., USA), *B. firmus* CNCM 1-1582, a variant of parental strain EIP-N1 (CNCM 1-1556) isolated from soil of central plain area of Israel (WO 2009/126473, U.S. Pat. No. 6,406, 690; e. g. Votivo® from Bayer CropScience LP, USA), *B. pumilus* GHA 180 isolated from apple tree rhizosphere in Mexico (IDAC 260707-01; e. g. PRO-MIX® BX from Premier Horticulture, Quebec, Canada), *B. pumilus* INR-7 otherwise referred to as BU-F22 and BU-F33 isolated at least before 1993 from cucumber infested by *Erwnia trachephila* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e. g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wis., U.S.A., in 1987 (also called ABG-6346; ATCC SD-1372; e. g. Xen-Tari® from BioFa AG, Munsingen, Germany), *B. t.* ssp. *kurstaki* ABTS-351 identical to HD-1 isolated in 1967 from diseased Pink Bollworm black larvae in Brownsville, Tex., U.S.A. (ATCC SD-1275; e. g. Dipel® DF from Valent BioSciences, IL, USA), *B. t.* ssp. *kurstaki* SB4 isolated from *E. saccharina* larval cadavers (NRRL B-50753; e. g. Beta Pro® from BASF Agricultural Specialities (Pty) Ltd., South Africa), *B. t.* ssp. *tenebrionis* NB-176-1, a mutant of strain NB-125, a wild type strain isolated in 1982 from a dead pupa of the beetle *Tenebrio molitor* (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *B. bassiana* PPRI 5339 isolated from the larva of the tortoise beetle *Conchyloctenia punctata* (NRRL 50757; e. g. BroadBand® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e. g. GELFIX 5 from BASF Agricultural Specialties Ltd., Brazil), *B. japonicum* 532c isolated from Wisconsin field in U.S.A.

(Nitragin 61A152; Can. J. Plant. Sci. 70, 661-666, 1990; e. g. in Rhizoflo®, Histick, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); Burkho/der/a sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Hellcoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Hellcoverpa zea* single capsid nucleopolyhedrovirus (HzSNPV) (e. g. Gemstar® from Certis LLC, USA), *Hellcoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Fla., U.S.A. (ATCC 20874; Biocontrol Science Technol. 22(7), 747-761, 2012; e. g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecllomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaii*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutra sachalinenss* extract (EP 0307510 B1; e. g. Regalia® SC from Marrone BioInnovations, Davis, Calif., USA or Milsana® from BioFa AG, Germany), *Steinernema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e. g. Trichoplus® from BASF Agricultural Specialities (Pty) Ltd., South Africa), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA).

According to one embodiment of the inventive mixtures, the at least one pesticide II is selected from the groups L1) to L5):

L1) Microbial pesticides with fungicidal, bactericidal, viricidal and/or plant defense activator activity: *Aureobasidium pullulans* DSM 14940 and DSM 14941 (L1.1), *Bacillus amyloliquefaciens* AP-188 (0.1.2), *B. amyloliquefaciens* ssp. *plantarum* D747 (L.1.3), *B. amyloliquefaciens* ssp. *plantarum* FZB24 (L.1.4), *B. amyloliquefaciens* ssp. *plantarum* FZB42 (L.1.5), *B. amyloliquefaciens* ssp. *plantarum* MB1600 (L.1.6), *B. amyloliquefaciens* ssp. *plantarum* QST-713 (L.1.7), *B. amyloliquefaciens* ssp. *plantarum* TJ1000 (L.1.8), *B. pumilus* GB34 (L.1.9), *B. pumilus* GHA 180 (L.1.10), *B. pumilus* INR-7 (L.1.11), *B. pumilus* KFP9F (L.1.12), *B. pumilus* QST 2808 (L.1.13), *B. simplex* ABU 288 (L.1.14), *B. subtilis* FB17 (L.1.15), *Coniothyrium minitans* CON/M/91-08 (L.1.16), *Metschnikowia fructicola* NRRL Y-30752 (L.1.17), *Paenibacillus alvei* NAS6G6 (L.1.18), *Penicillium bilaiae* ATCC 22348 (L.1.19), *P. bilaiae* ATCC 20851 (L.1.20), *Penicillium bilaiae* ATCC 18309 (L.1.21), *Streptomyces microflavus* NRRL B-50550 (L.1.22), *Trichoderma asperelloides* JM41R (L.1.23), *T. harzianum* T-22 (L.1.24);

L2) Biochemical pesticides with fungicidal, bactericidal, viricidal and/or plant defense activator activity: harpin protein (L.2.1), *Reynoutria sachalinensis* extract (L.2.2);

L3) Microbial pesticides with insecticidal, acaricidal, molluscidal and/or nematicidal activity: *Bacillus firmus* I-1582 (L.3.1); *B. thuringiensis* ssp. *aizawai* ABTS-1857 (L.3.2), *B. t.* ssp. *kurstaki* ABTS-351 (L.3.3), *B. t.* ssp. *kurstaki* SB4 (L.3.4), *B. t.* ssp. *tenebrionis* NB-176-1 (L.3.5), *Beauveria bassiana* GHA (L.3.6), *B. bassiana* JW-1 (L.3.7), *B. bassiana* PPRI 5339 (L.3.8), Burkho/der/a sp. A396 (L.3.9), *Hellcoverpa armigera* nucleopolyhedrovirus (HearNPV) (L.3.10), *Hellcoverpa zea* nucleopolyhedrovirus (HzNPV) ABA-NPV-U (L.3.11), *Hellcoverpa zea* single capsid nucleopolyhedrovirus (HzSNPV) (L.3.12), *Heterohabditis bacteriophora* (L.3.13), *Isaria fumosorosea* Apopka-97 (L.3.14), *Metarhizium anisopllae* var. *anisopllae* F52 (L.3.15), *Paecllomyces lilacinus* 251 (L.3.16), *Pasteuria nishizawae* Pn1 (L.3.17), *Steinernema carpocapsae* (L.3.18), *S. feltiae* (L.3.19);

L4) Biochemical pesticides with insecticidal, acaricidal, molluscidal, pheromone and/or nematicidal activity: cis-jasmone (L.4.1), methyljasmonate (L.4.2), Quillay extract (L.4.3);

L5) Microbial pesticides with plant stress reducing, plant growth regulator, plant growth promoting and/or yield enhancing activity: *Azospirillum brasilense* Ab-V5 and Ab-V6 (L.5.1), *A. brasilense* Sp245 (L.5.2), *Bradyrhzobium elkani* SEMIA 587 (L.5.3), *B. elkani* SEMIA 5019 (L.5.4), *B. japonicum* 532c (L.5.5), *B. japoncum* E-109 (L.5.6), *B. japoncum* SEMIA 5079 (L.5.7), *B. japonicum* SEMIA 5080 (L.5.8).

The present invention furthermore relates to agrochemical compositions comprising a mixture of XXX (component 1) and at least one biopesticide selected from the group L) (component 2), in particular at least one biopesticide selected from the groups L1) and L2), as described above, and if desired at least one suitable auxiliary.

The present invention furthermore relates to agrochemical compositions comprising a mixture of XXX (component 1) and at least one biopesticide selected from the group L) (component 2), in particular at least one biopesticide selected from the groups L3) and L4), as described above, and if desired at least one suitable auxiliary.

Preference is also given to mixtures comprising as pesticide II (component 2) a biopesticide selected from the groups L1), L3) and L5), preferably selected from strains denoted above as (L1.2), (L.1.3), (L.1.4), (L.1.5), (L1.6), (L.1.7), (L1.8), (L.1.10), (L.1.11), (L.1.12), (L.1.13), (L.1.14), (L.1.15), (L.1.17), (L.1.18), (L.1.19), (L.1.20), (L.1.21), (L.3.1); (L.3.9), (L.3.16), (L.3.17), (L.5.1), (L.5.2), (L.5.3), (L.5.4), (L.5.5), (L.5.6), (L.5.7), (L.5.8), (L.4.2), and (L.4.1); even more preferably selected from (L.1.2), (L.1.6), (L.1.7), (L.1.8), (L.1.11), (L.1.12), (L.1.13), (L.1.14), (L.1.15), (L.1.18), (L.1.19), (L.1.20), (L.1.21), (L.3.1); (L.3.9), (L.3.16), (L.3.17), (L.5.1), (L.5.2), (L.5.5), (L.5.6); (L.4.2), and (L.4.1). These mixtures are particularly suitable for treatment of propagation materials, i. e. seed treatment purposes and likewise for soil treatment. These seed treatment mixtures are particularly suitable for crops such as cereals, corn and leguminous plants such as soybean.

Preference is also given to mixtures comprising as pesticide II (component 2) a biopesticide selected from the groups L1), L3) and L5), preferably selected from strains denoted above as (L.1.22), (L.1.23), (L.1.24), (L.2.2); (L.3.2), (L.3.3), (L.3.4), (L.3.5), (L.3.6), (L.3.7), (L.3.8), (L.3.10), (L.3.11), (L.3.12), (L.3.13), (L.3.14), (L.3.15), (L.3.18), (L.3.19); (L.4.2), even more preferably selected from (L.1.2), (L.1.7), (L.1.11), (L.1.13), (L.1.14), (L.1.15), (L.1.18), (L.1.23), (L.3.3), (L.3.4), (L.3.6), (L.3.7), (L.3.8), (L.3.10), (L.3.11), (L.3.12), (L.3.15), and (L.4.2). These mixtures are particularly suitable for foliar treatment. These mixtures for foliar treatment are particularly suitable for vegetables, fruits, vines, cereals, corn, leguminous crops such as soybeans.

The mixtures of active substances can be prepared as compositions comprising besides the active ingredients at least one inert ingredient (auxiliary) by usual means, e. g. by the means given for the compositions of compounds I. Concerning usual ingredients of such compositions reference is made to the explanations given for the compositions containing compounds I.

According to one embodiment, the microbial pesticides selected from groups L1), L3) and L5) embrace not only the isolated, pure cultures of the respective microorganism as defined herein, but also its cell-free extract, its suspensions in a whole broth culture or as a metabolite-containing culture medium or a purified metabolite obtained from a whole broth culture of the microorganism.

When living microorganisms, such as pesticides II from groups L1), L3) and L5), form part of the compositions, such compositions can be prepared as compositions comprising besides the active ingredients at least one auxiliary by usual means (e. g. H. D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions, capsules, pastes, pastilles, wettable powders or dusts, pressings, granules, insecticidal articles, as well as gel formulations. Herein, it has to be taken into account that each formulation type or choice of auxiliary should not influence the viability of the microorganism during storage of the composition and when finally applied to the soil, plant or plant propagation material. Suitable formulations are e. g. mentioned in WO 2008/002371, U.S. Pat. Nos. 6,955,912, 5,422,107.

SYNTHESIS EXAMPLE

With due modification of the starting compounds, the procedures shown in the synthesis examples below were used to obtain further compounds I. The resulting compounds, together with physical data, are listed in Table I below.

HPLC-MS: HPLC-column Kinetex XB C18 1.7µ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

1. Synthesis of 2-[2-[(5,6-dimethyl-3-pyridyl)oxy]-6-fluoro-phenyl]-N,2-dimethyl-propanamide (I-1)

To a solution of 2-[2-[(5,6-dimethyl-3-pyridyl)oxy]-6-fluoro-phenyl]propan-2-ol (1.07 g, 3.9 mmol) in acetic acid (15 mL), acetonitrile (3 mL) and sulfuric acid (3 mL) were added at rt. The reaction was stirred for 2 h at 70° C., then ice was added and the reaction mixture was quenchend with NaOH to pH>10. The aqueous phase was extracted with ethyl acetate, the organic phase was washed with water, dried over $Na_2SO_4$, concentrated. The crude was purified via HPLC (water/acetonitrile) to yield 101 mg (8%) of the title compound as a colorless oil.

$^1$H-NMR (CDCl$_3$, δ in ppm): 8.2 (s, 1H); 7.1 (td, 1H); 7.0 (s, 1H); 6.8 (td, 1H); 6.5 (d, 1H); 5.9 (br s, 1H); 2.5 (s, 3H); 2.3 (s, 3H); 1.8 (s, 6H); 1.7 (s, 3H),

2. Synthesis of 5-[2-(1-benzyloxy-1-methyl-ethyl)-3-fluoro-phenoxy]-2,3-dimethyl-pyrazine (I-3)

$^1$H-NMR (CDCl$_3$, δ in ppm): 8.0 (s, 1H); 7.4-7.2 (m, 4H); 7.2 (m, 2H); 7.0 (td, 1H); 6.8 (d, 1H); 5.9 (q, 1H); 4.4 (d, 1H), 4.3 (d, 1H), 2.4 (s, 3H); 2.3 (s, 3H); 1.6 (d, 3H).

TABLE 1

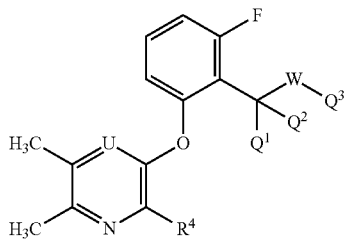

| No. | U | R4 | Q1 | Q2 | W | Q3 | Mp [° C.] | HPLC-MS ($R_t$ [min], $M^+ + H$) |
|---|---|---|---|---|---|---|---|---|
| I-1 | CH | H | $CH_3$ | $CH_3$ | N | $COCH_3$ | | 0.722 min; $M^+ + H = 317$ |
| I-2 | N | H | $CH_3$ | H | O | $CH_2Ph$ | 70 | 1.329 min; $M^+ + H = 353.2$ |
| I-3 | N | $CH_3$ | $CH_3$ | H | O | $CH_2Ph$ | | 1.62 min; $M^+ + H = 367.1$ |
| I-4 | N | $CH_3$ | $CF_3$ | H | O | $CH_2C_6H_4$-4-F | | 1.405 min; $M^+ + H = 438.39$ |
| I-5 | CH | H | $CH_3$ | $CH_3$ | N | $COC_6H_4$-4-F | | 0.881 min; $M^+ + H = 397$ |
| I-6 | CH | H | $CH_3$ | $CH_3$ | N | $COC_6H_4$-4-Cl | | 0.918 min; $M^+ + H = 413$ |
| I-7 | CH | H | $CH_3$ | $CH_3$ | N | $COCH_2OC_6H_4$-4-F | | 0.932 min; $M^+ + H = 427$ |
| I-8 | CH | H | $CH_3$ | $CH_3$ | N | $COCH_2Cl$ | | 0.787 min; $M^+ + H = 351$ |
| I-9 | CH | H | $CH_3$ | $CH_3$ | N | $CO(CH_2)_2CH_3$ | | 0.825 min; $M^+ + H = 345.1$ |
| I-10 | CH | H | $CH_3$ | $CH_3$ | N | $CO(CH_2)_4CH_3$ | | 0.945 min; $M^+ + H = 373.1$ |
| I-11 | CH | H | $CH_3$ | $CH_3$ | N | $CO(CH_2)_3CH_3$ | | 0.896 min; $M^+ + H = 359.0$ |
| I-12 | CH | H | $CH_3$ | $CH_3$ | N | $COCH_2CH_3$ | | 0.789 min; $M^+ + H = 331.2$ |
| I-13 | CH | H | $CH_3$ | $CH_3$ | N | $COCH_2$-morpholine | 155 | 0.665 min; $M^+ + H = 402.2$ |
| I-14 | N | $CH_3$ | $CH_3$ | $CH_3$ | O | $CH_2Ph$ | | 1.381 min; $M^+ + H = 381.1$ |
| I-15 | N | $CH_3$ | $CF_3$ | H | O | $CH(CH_3)C_6H_4$-4-F | | 1.420 min $M^+ + H = 453.1$ |

II. Biological Trials

Microtest

The active compounds were formulated separately as a stock solution having a concentration of 10000 ppm in dimethyl sulfoxide.

Example 1—Activity Against the Grey Mold *Botytis Cinerea* in the Microtiterplate Test The stock solutions were mixed according to the ratio, pipetted onto a micro titer plate (MTP) and diluted with water to the stated concentrations. A spore suspension of *Botrci cinerea* in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-2, I-3, I-5, I-14 and I-15 respectively, showed up to at most 6% growth of the pathogen.

Example 2—Activity Against *Fusarium culmorum* in the Microtiterplate Test

The stock solutions were mixed according to the ratio, pipetted onto a micro titer plate (MTP) and diluted with water to the stated concentrations. A spore suspension of *Fusarium culmorum* in an aqueous biomalt or yeast-bacto-peptone-sodiumacetate solution was then added. The plates were placed in a water vapor-saturated chamber at a temperature of 18° C. Using an absorption photometer, the MTPs were measured at 405 nm 7 days after the inoculation.

In this test, the samples which had been treated with 31 ppm of the active substance from examples 1-2, I-3, I-14 and I-15 respectively, showed up to at most 17% growth of the pathogen.

Example 3—Activity Against Rice Blast *Pyricularia oryzae* in the Microtiterplate Test The stock solutions were mixed according to the ratio, pipetted onto a micro titer plate (MTP) and diluted with water to the stated concentrations. A spore suspension of *Pyricularia oryzae* in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-2, I-3, I-4, I-5, I-6, I-7, I-8, I-9, I-10, I-11, I-12, I-13, I-14 and I-15 respectively, showed up to at most 13% growth of the pathogen.

The measured parameters were compared to the growth of the active compound-free control variant (100%) and the fungus-free and active compound-free blank value to determine the relative growth in % of the pathogens in the respective active compounds.

The invention claimed is:
1. A compound of formula I

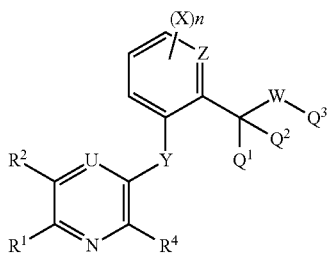

wherein
$R^1$ is $C_1$-$C_6$-alkyl;
$R^2$ is $C_1$-$C_6$-alkyl;
U is N or $CR^3$;
$R^3$ is H and $C_1$-$C_6$-alkyl;
$R^4$ is selected from H and $C_1$-$C_6$-alkyl;
Y is O
Z is $CR^5$;
$R^5$ is H;
X is halogen;
n is 1;
$Q^1$ is selected from $C_1$-$C_6$-alkyl and $C_1$-$C_6$-halogenalkyl;
$Q^2$ is selected from H and $C_1$-$C_6$-alkyl;
W is O or $NQ^4$;
$Q^3$ is selected from substituted $C_1$-$C_{15}$-alkyl, C(=O)$C_1$-$C_{15}$-alkyl, and C(=O)aryl
wherein the aliphatic moieties of $Q^3$ except for substituted $C_1$-$C_{15}$-alkyl moieties are unsubstituted or substituted with identical or different groups $Q^{3a}$ which independently of one another are selected from:
$Q^{3a}$ halogen, $C_1$-$C_6$-alkoxy, and phenyl; and wherein the phenyl groups are unsubstituted or substituted with 1, 2, 3, 4 or 5 substituents $Q^{311a}$ selected from the group consisting of halogen;
wherein the aryl moieties of $Q^3$ are unsubstituted or substituted with 1, 2, 3, 4, 5 or up to the maximum number of identical or different groups $Q^{3b}$ which independently of one another are selected from:
$Q^{3b}$ halogen and phenyl wherein the phenyl groups are unsubstituted or substituted with 1, 2, 3, 4 or 5 substituents $Q^{31b}$ selected from the group consisting of halogen
$Q^4$ is hydrogen;
with the proviso that if
U is $CR^3$
W cannot be O or $S(O)_m$
and of an agriculturally acceptable salt thereof.

2. The compound of claim 1, wherein U is N and W is O.
3. The compound of claim 1, wherein U is N and W is $NQ^4$.
4. The compound of claim 1, wherein U is $CR^3$ and W is $NQ^4$,
wherein $R^3$ is H.
5. A composition comprising one compound of claim 1, an N-oxide or an agriculturally acceptable salt thereof.
6. A method for combating phytopathogenic fungi, comprising treating the fungi or the materials, plants, the soil or seeds to be protected against fungal attack with an effective amount of at least one compound of claim 1.

* * * * *